(12) United States Patent
De Kreij et al.

(10) Patent No.: US 8,278,062 B2
(45) Date of Patent: *Oct. 2, 2012

(54) METHOD OF USING LIPID ACYLTRANSFERASE

(75) Inventors: Arno De Kreij, Papendrecht (NL); Susan Mampusti Madrid, Vedbaek (DK); Jørn Dalgaard Mikkelsen, Hvidovre (DK); Jørn Borch Søe, Tilst (DK)

(73) Assignee: DuPont Nutrition Biosciences ApS, Copenhagen (DK)

( * ) Notice: Subject to any disclaimer, the term of this patent is extended or adjusted under 35 U.S.C. 154(b) by 580 days.

This patent is subject to a terminal disclaimer.

(21) Appl. No.: 12/400,268

(22) Filed: Mar. 9, 2009

(65) Prior Publication Data

US 2010/0285525 A1    Nov. 11, 2010

Related U.S. Application Data

(60) Division of application No. 11/182,480, filed on Jul. 15, 2005, now Pat. No. 7,638,293, which is a continuation-in-part of application No. PCT/IB2004/000575, filed on Jan. 15, 2004.

(60) Provisional application No. 60/489,441, filed on Jul. 23, 2003.

(30) Foreign Application Priority Data

| Jan. 14, 2003 | (GB) | 0301117.8 |
|---|---|---|
| Jan. 17, 2003 | (GB) | 0301118.6 |
| Jan. 17, 2003 | (GB) | 0301119.4 |
| Jan. 17, 2003 | (GB) | 0301120.2 |
| Jan. 17, 2003 | (GB) | 0301121.0 |
| Jan. 17, 2003 | (GB) | 0301122.8 |
| Dec. 24, 2003 | (GB) | 0330016.7 |

(51) Int. Cl.
C12Q 1/48 (2006.01)
C12N 9/10 (2006.01)

(52) U.S. Cl. ......... 435/15; 435/193

(58) Field of Classification Search .......... 435/15, 435/193

See application file for complete search history.

(56) References Cited

U.S. PATENT DOCUMENTS

| 2,888,385 A | 5/1959 | Grandel |
|---|---|---|
| 3,260,606 A | 7/1966 | Azuma |
| 3,368,903 A | 2/1968 | Johnson |
| 3,520,702 A | 7/1970 | Menzi |
| 3,634,195 A | 1/1972 | Melachouris |
| 3,652,397 A | 3/1972 | Pardun |
| 3,677,902 A | 7/1972 | Aunstrup |
| 3,817,837 A | 6/1974 | Rubenstein et al. |
| 3,850,752 A | 11/1974 | Schuurs et al. |
| 3,852,260 A | 12/1974 | Knutsen |
| 3,939,350 A | 2/1976 | Kronick et al. |
| 3,973,042 A | 8/1976 | Kosikowski |
| 3,996,345 A | 12/1976 | Ullman et al. |
| 4,034,124 A | 7/1977 | Van Dam |
| 4,065,580 A | 12/1977 | Feldman |
| 4,160,848 A | 7/1979 | Vidal |
| 4,202,941 A | 5/1980 | Terada |
| 4,275,149 A | 6/1981 | Litman et al. |
| 4,277,437 A | 7/1981 | Maggio |
| 4,366,241 A | 12/1982 | Tom et al. |
| 4,399,218 A | 8/1983 | Gauhl |
| 4,567,046 A | 1/1986 | Inoue et al. |
| 4,683,202 A | 7/1987 | Mullis |
| 4,689,297 A | 8/1987 | Good |
| 4,707,291 A | 11/1987 | Thom |
| 4,707,364 A | 11/1987 | Barach |
| 4,708,876 A | 11/1987 | Yokoyama |
| 4,798,793 A | 1/1989 | Eigtved |
| 4,808,417 A | 2/1989 | Masuda |
| 4,810,414 A | 3/1989 | Huge-Jensen |
| 4,814,331 A | 3/1989 | Kerkenaar |
| 4,816,567 A | 3/1989 | Cabilly et al. |
| 4,818,695 A | 4/1989 | Eigtved |
| 4,826,767 A | 5/1989 | Hansen |
| 4,865,866 A | 9/1989 | Moore |
| 4,904,483 A | 2/1990 | Christensen |

(Continued)

FOREIGN PATENT DOCUMENTS

AR        249546         12/1996

(Continued)

OTHER PUBLICATIONS

"Definition of Recombined Milk", International Dairy Federation Bulletin Document 1979, No. 116, p. 5.
Stryer, Biochemistry, $2^{nd}$ Edition, 1981, WH Freeman & Co., San Francisco.
Verenium Corporation leaflet Purifine® Enzyme Jan. 2008.
Brumlik, et al.; "Identification of the Catalytic Triad of the Lipase/Acyltransferase from *Aeromonas hydrophila*"; Journal of Bacteriology (1996); vol. 178(7); pp. 2060-2064.
Hilton, et al.; "Purification and Spectral Study of a Microbial Fatty Acyltransferase: Activation by Limited Proteolysis"; American Chemical Society (1990); vol. 29; pp. 9072-9078.
Mason, Kenneth; "Use of Lipolytic Enzyme from *Areomonas* in Detergents"; Research Disclosure (1996); No. 390; pp. 661-662.
Nerland, et al.; "The nucleotide sequence of the gene encoding GCAT from *Areomonas salmonicida* ssp. *salmonicida*" Journal of Fish Diseases (1996); vol. 19; pp. 145-150.

(Continued)

Primary Examiner — Tekchand Saidha
(74) Attorney, Agent, or Firm — Vedder Price P.C.; Thomas J. Kowalski; Smitha B. Uthaman

(57) ABSTRACT

A method of producing one or more of a carbohydrate ester, a protein ester, a protein subunit ester or a hydroxyl acid ester, which method comprises admixing an acyl donor, an acyl acceptor and water to produce a high water environment comprising 5-98% water, wherein said acyl donor is a lipid substrate selected from one or more of the group consisting of a phospholipid, a lysophospholipid, a triacylglyceride, a diglyceride, a glycolipid or a lysoglycolipid and said acyl acceptor is selected from one ore more of the group consisting of a carbohydrate, a protein, a protein subunit, or a hydroxyl acid; and contacting the admixture with a lipid acyltransferase, such that said lipid acyl transferase catalyses one or both of the following reactions: alcoholysis or transesterification.

12 Claims, 44 Drawing Sheets

U.S. PATENT DOCUMENTS

| | | | |
|---|---|---|---|
| 4,916,064 A | 4/1990 | Derez |
| 5,112,624 A | 5/1992 | Johna |
| 5,213,968 A | 5/1993 | Castle |
| 5,219,733 A | 6/1993 | Myojo |
| 5,219,744 A | 6/1993 | Kurashige |
| 5,232,846 A | 8/1993 | Takeda |
| 5,264,367 A | 11/1993 | Aalrust |
| 5,273,898 A | 12/1993 | Ishii |
| 5,288,619 A | 2/1994 | Brown |
| 5,290,694 A | 3/1994 | Nakanishi |
| 5,310,679 A | 5/1994 | Artiss et al. |
| 5,378,623 A | 1/1995 | Hattori |
| 5,523,237 A | 6/1996 | Budtz |
| 5,536,661 A | 7/1996 | Boel |
| 5,558,781 A | 9/1996 | Buchold |
| 5,650,188 A | 7/1997 | Gaubert |
| 5,674,707 A | 10/1997 | Hintz et al. |
| 5,677,160 A | 10/1997 | Oester |
| 5,695,802 A | 12/1997 | Van Den Ouweland |
| 5,716,654 A | 2/1998 | Groenendaal |
| 5,741,665 A | 4/1998 | Kato et al. |
| 5,763,383 A | 6/1998 | Hashida |
| 5,766,912 A | 6/1998 | Boel |
| 5,776,741 A | 7/1998 | Pedersen |
| 5,814,501 A | 9/1998 | Becker |
| 5,821,102 A | 10/1998 | Berka |
| 5,824,354 A | 10/1998 | Ritter et al. |
| 5,827,719 A | 10/1998 | Sandal |
| 5,830,736 A | 11/1998 | Oxenboll |
| 5,834,280 A | 11/1998 | Oxenboll |
| 5,856,163 A | 1/1999 | Hashida |
| 5,863,759 A | 1/1999 | Boel |
| 5,869,438 A | 2/1999 | Svendsen |
| 5,874,558 A | 2/1999 | Boel |
| 5,879,920 A | 3/1999 | Dale |
| 5,892,013 A | 4/1999 | Svendsen |
| 5,914,306 A | 6/1999 | Svendsen |
| 5,916,619 A | 6/1999 | Miyazaki |
| 5,919,746 A | 7/1999 | Hirayama |
| 5,929,017 A | 7/1999 | Gormsen |
| 5,965,384 A | 10/1999 | Boel |
| 5,965,422 A | 10/1999 | Loffler |
| 5,976,855 A | 11/1999 | Svendsen |
| 5,989,599 A | 11/1999 | Chmiel |
| 5,990,069 A | 11/1999 | Andre |
| 6,001,586 A | 12/1999 | Schellenberger |
| 6,001,640 A | 12/1999 | Loeffler |
| 6,020,180 A | 2/2000 | Svendsen |
| 6,066,482 A | 5/2000 | Steffens et al. |
| 6,074,863 A | 6/2000 | Svendsen |
| 6,103,505 A | 8/2000 | Clausen |
| 6,110,508 A | 8/2000 | Olesen |
| 6,140,094 A | 10/2000 | Loffler |
| 6,143,543 A | 11/2000 | Michelsen |
| 6,143,545 A | 11/2000 | Clausen |
| 6,146,869 A | 11/2000 | Harris |
| 6,156,548 A | 12/2000 | Christensen |
| 6,180,406 B1 | 1/2001 | Stemmer |
| 6,254,645 B1 | 7/2001 | Kellis |
| 6,254,903 B1 | 7/2001 | Schuster et al. |
| 6,344,328 B1 | 2/2002 | Short |
| 6,350,604 B1 | 2/2002 | Hirayama |
| 6,358,543 B1 | 3/2002 | Soe |
| 6,361,974 B1 | 3/2002 | Short |
| 6,365,204 B1 | 4/2002 | Spendler et al. |
| 6,432,898 B1 | 8/2002 | Rey |
| 6,495,357 B1 | 12/2002 | Fuglsang |
| 6,506,588 B2 | 1/2003 | Tsutsumi |
| 6,509,182 B2 | 1/2003 | Tsutsumi |
| 6,511,837 B2 | 1/2003 | Tsutsumi |
| 6,514,739 B1 | 2/2003 | Udagawa |
| 6,558,715 B1 | 5/2003 | Rey |
| 6,582,942 B1 | 6/2003 | Christensen |
| 6,624,129 B1 | 9/2003 | Borch |
| 6,645,749 B2 | 11/2003 | Vind |
| 6,682,922 B2 | 1/2004 | Berka |
| 6,686,189 B2 | 2/2004 | Rey |
| 6,726,942 B2 | 4/2004 | Soe et al. |
| 6,730,346 B2 | 5/2004 | Rey |
| 6,815,190 B1 | 11/2004 | Abo |
| 6,852,346 B2 | 2/2005 | Søe |
| 6,866,837 B2 | 3/2005 | Reubi et al. |
| 6,936,289 B2 | 8/2005 | Olsen et al. |
| 6,964,944 B1 | 11/2005 | Callisen et al. |
| 6,967,035 B2 | 11/2005 | Bojsen et al. |
| 7,226,771 B2 | 6/2007 | Gramatikova et al. |
| 7,638,293 B2 * | 12/2009 | De Kreij et al. .............. 435/15 |
| 7,718,204 B2 | 5/2010 | Soe et al. |
| 2001/0055635 A1 | 12/2001 | Spendler et al. |
| 2002/0098536 A1 | 7/2002 | Norinobu |
| 2002/0110854 A1 | 8/2002 | Tsutsumi |
| 2002/0142434 A1 | 10/2002 | Tsutsumi |
| 2002/0168746 A1 | 11/2002 | Tsutsumi |
| 2002/0182734 A1 | 12/2002 | Diaz-Torres |
| 2003/0003561 A1 | 1/2003 | Vind |
| 2003/0028923 A1 | 2/2003 | Lardizabal |
| 2003/0040450 A1 | 2/2003 | Rey |
| 2003/0074695 A1 | 4/2003 | Farese |
| 2003/0100092 A1 | 5/2003 | Berka |
| 2003/0119164 A1 | 6/2003 | Udagawa |
| 2003/0148495 A1 | 8/2003 | Hastrup |
| 2003/0180418 A1 | 9/2003 | Rey |
| 2003/0185939 A1 | 10/2003 | Nielsen |
| 2003/0215544 A1 | 11/2003 | Nielsen |
| 2004/0005399 A1 | 1/2004 | Chakrabarti |
| 2004/0142441 A1 | 7/2004 | Weiss et al. |
| 2004/0235106 A1 | 11/2004 | Kapeller-Libermann |
| 2005/0059130 A1 | 3/2005 | Bojsen et al. |
| 2005/0059131 A1 | 3/2005 | Bisgard-Frantzen |
| 2005/0118697 A1 | 6/2005 | Budolfsen |
| 2005/0142647 A1 | 6/2005 | Wassell |
| 2006/0040357 A1 | 2/2006 | Bandaru et al. |
| 2006/0075518 A1 | 4/2006 | Yaver et al. |
| 2006/0141457 A1 | 6/2006 | Lindqvist et al. |
| 2007/0026106 A1 | 2/2007 | Kreij et al. |
| 2007/0122525 A1 | 5/2007 | Kreij |
| 2007/0207247 A1 * | 9/2007 | Budolfsen et al. ............ 426/549 |
| 2008/0063783 A1 | 3/2008 | Kreij et al. |
| 2008/0070287 A1 | 3/2008 | Soe et al. |
| 2008/0131936 A1 | 6/2008 | Miasnikov et al. |
| 2008/0187643 A1 | 8/2008 | Horlacher |

FOREIGN PATENT DOCUMENTS

| | | |
|---|---|---|
| AR | P000105426 | 10/2000 |
| AR | P040101441 | 4/2004 |
| AT | 110 768 | 8/1987 |
| AU | 570720 | 9/1984 |
| AU | 723031 | 4/1998 |
| AU | 199742798 | 4/1998 |
| AU | 754470 | 11/1999 |
| BR | 8404421-7 | 4/1984 |
| CA | 1 270 781 | 6/1990 |
| CA | 1270781 | 6/1990 |
| CA | 2012723 | 9/1990 |
| CA | 2134597 | 10/1994 |
| CA | 2224143 | 12/1996 |
| CA | 2 403 025 | 4/2004 |
| CA | 2403025 | 4/2004 |
| CN | 101200754 | 12/2007 |
| DE | 2817087 | 11/1978 |
| DE | 19620649 | 11/1997 |
| DE | 69129988 | 3/1999 |
| DE | 69330066 | 10/2001 |
| DE | 10018787 | 5/2002 |
| DE | 69527835 | 4/2003 |
| DE | 69528070 | 6/2003 |
| DE | 69904161 | 7/2003 |
| DE | 69716711 | 9/2003 |
| DE | 69333065 | 4/2004 |
| DE | 69531538 | 6/2004 |
| DE | 69819782 | 9/2004 |
| DK | 3106.200 | 1/1989 |
| DK | 157560 | 1/1990 |
| DK | PA0888/92 | 7/1992 |
| DK | 0217/94 | 2/1994 |
| DK | PA0830/95 | 7/1995 |
| DK | PA1096/95 | 9/1995 |

| | | | | | |
|---|---|---|---|---|---|
| DK | 152763 | 3/1998 | EP | 1108360 | 6/2001 |
| DK | PA0543/98 | 4/1998 | EP | 1138763 | 10/2001 |
| DK | PA199801572 | 11/1998 | EP | 1145637 | 10/2001 |
| DK | PA5677000 | 12/1998 | EP | 0191217 | 2/2002 |
| DK | PA199801604 | 12/1998 | EP | 0869167 | 2/2002 |
| DK | PA199901736 | 12/1999 | EP | 1 193 314 | 4/2002 |
| DK | PA200000989 | 6/2000 | EP | 1193314 | 4/2002 |
| DK | PA200000991 | 6/2000 | EP | 0746618 | 8/2002 |
| DK | PA200100285 | 2/2001 | EP | 1233676 | 8/2002 |
| DK | PA200100843 | 5/2001 | EP | 0648263 | 9/2002 |
| DK | EP659049 | 6/2001 | EP | 0784674 | 9/2002 |
| DK | EP0784674 | 11/2002 | EP | 1073339 | 11/2002 |
| DK | EP0869167 | 1/2003 | EP | 1275711 | 1/2003 |
| DK | EP1073339 | 1/2003 | EP | 1285969 | 2/2003 |
| DK | PA200300634 | 4/2003 | EP | 1298205 | 4/2003 |
| DK | EP0746608 | 10/2003 | EP | 0635053 | 6/2003 |
| DK | EP1042458 | 3/2004 | EP | 0675944 | 6/2003 |
| EP | 0064855 | 11/1982 | EP | 0817838 | 6/2003 |
| EP | 0010296 | 12/1982 | EP | 1280919 | 6/2003 |
| EP | 0109244 | 5/1984 | EP | 0746608 | 8/2003 |
| EP | 0130064 | 1/1985 | EP | 0851913 | 5/2004 |
| EP | 0140542 | 5/1985 | EP | 1262562 | 6/2004 |
| EP | 0167309 | 1/1986 | EP | 1433852 | 6/2004 |
| EP | 0171995 | 2/1986 | EP | 0977869 | 7/2004 |
| EP | 0205208 | 12/1986 | EP | 01624047 A1 | 8/2004 |
| EP | 0206390 | 12/1986 | EP | 0743017 | 9/2004 |
| EP | 0214761 | 3/1987 | EP | 0675949 | 10/2004 |
| EP | 0257388 | 3/1988 | EP | 0880590 | 10/2004 |
| EP | 0260573 | 3/1988 | EP | 0897423 | 10/2004 |
| EP | 0334462 | 9/1989 | EP | 1466980 | 10/2004 |
| EP | 0195311 | 6/1990 | EP | 0839186 | 11/2004 |
| EP | 0375102 | 6/1990 | EP | 1162889 | 2/2005 |
| EP | 0426211 | 5/1991 | EP | 1532863 | 5/2005 |
| EP | 0445692 | 9/1991 | EP | 1559788 | 8/2005 |
| EP | 0449375 | 10/1991 | EP | 1363506 | 11/2005 |
| EP | 0468731 | 1/1992 | EP | 01624047 A1 | 2/2006 |
| EP | 0493045 | 7/1992 | EP | 01624047 B1 | 10/2006 |
| EP | 0583265 | 10/1992 | EP | 1762622 | 3/2007 |
| EP | 0513709 | 11/1992 | EP | 1788080 | 5/2007 |
| EP | 0542351 | 5/1993 | ES | 535608 | 9/1984 |
| EP | 0558112 | 9/1993 | ES | 535602 | 10/1984 |
| EP | 0258068 | 11/1993 | ES | 535609 | 3/1985 |
| EP | 0238023 | 12/1993 | GB | 1086550 | 10/1967 |
| EP | 0575133 | 12/1993 | GB | 1 275 711 | 5/1972 |
| EP | 0580252 | 1/1994 | GB | 1442418 | 7/1976 |
| EP | 0 258 068 | 8/1994 | GB | 1577933 | 10/1980 |
| EP | 0258068 | 8/1994 | GB | 2264429 | 9/1993 |
| EP | 0622446 | 11/1994 | GB | 0028701.1 | 11/2000 |
| EP | 0652289 | 5/1995 | GB | 2358784 | 8/2001 |
| EP | 0654527 | 5/1995 | GB | 0301117.8 | 1/2003 |
| EP | 0396162 | 9/1995 | GB | 0301118.6 | 1/2003 |
| EP | 0 758 377 | 11/1995 | GB | 0301119.4 | 1/2003 |
| EP | 0687414 | 12/1995 | GB | 0301120.2 | 1/2003 |
| EP | 0585988 | 3/1996 | GB | 0301121.0 | 1/2003 |
| EP | 0 375 102 | 4/1996 | GB | 0301122.8 | 1/2003 |
| EP | 0721981 | 7/1996 | GB | 2379165 | 3/2003 |
| EP | 0752008 | 1/1997 | GB | 2267033 | 11/2003 |
| EP | 0 140 542 | 2/1997 | GB | 0330016.7 | 12/2003 |
| EP | 0776604 | 6/1997 | JP | 59183881 | 4/1960 |
| EP | 0531104 | 8/1997 | JP | 480116612 | 5/1973 |
| EP | 0808903 | 11/1997 | JP | 55131340 | 10/1980 |
| EP | 0682116 | 12/1997 | JP | 57-189638 | 11/1982 |
| EP | 0812910 | 12/1997 | JP | 57-189637 | 12/1982 |
| EP | 0305216 | 3/1998 | JP | 59088040 | 5/1984 |
| EP | 0847701 | 6/1998 | JP | 60078529 | 5/1985 |
| EP | 0548228 | 8/1998 | JP | 62118883 | 11/1985 |
| EP | 0866796 | 9/1998 | JP | 63042691 | 8/1986 |
| EP | 0702712 | 12/1998 | JP | 62061590 | 3/1987 |
| EP | 0882797 | 12/1998 | JP | 62285749 | 12/1987 |
| EP | 0897667 | 2/1999 | JP | 63068697 | 3/1988 |
| EP | 0913092 | 5/1999 | JP | 10203974 | 8/1988 |
| EP | 0913468 | 5/1999 | JP | 1252294 | 10/1989 |
| EP | 0321811 | 12/1999 | JP | 2-49593 | 2/1990 |
| EP | 1131416 | 6/2000 | JP | 2-153997 | 6/1990 |
| EP | 0739985 | 11/2000 | JP | 04075592 | 3/1992 |
| EP | 1057415 | 12/2000 | JP | 6014773 | 3/1992 |
| EP | 1071734 | 1/2001 | JP | 4121186 | 4/1992 |
| EP | 0659049 | 3/2001 | JP | 15626492 | 6/1992 |
| EP | 1103606 | 5/2001 | JP | 04200339 | 7/1992 |

| | | | | | |
|---|---|---|---|---|---|
| JP | 4300839 | 10/1992 | WO | 97/27276 | 7/1997 |
| JP | 4327536 | 11/1992 | WO | 97/41212 | 11/1997 |
| JP | 04-370055 | 12/1992 | WO | 97/41735 | 11/1997 |
| JP | 5211852 | 8/1993 | WO | 97/41736 | 11/1997 |
| JP | 6345800 | 12/1994 | WO | WO 98/00029 | 1/1998 |
| JP | 07-079687 | 3/1995 | WO | 98/08939 | 3/1998 |
| JP | 8268882 | 4/1995 | WO | 98/14594 | 4/1998 |
| JP | 7231788 | 9/1995 | WO | WO 98/13479 | 4/1998 |
| JP | 7330794 | 12/1995 | WO | WO 98/16112 | 4/1998 |
| JP | 8143457 | 6/1996 | WO | 98/18912 | 5/1998 |
| JP | 8266213 | 10/1996 | WO | 98/26057 | 6/1998 |
| JP | 9040689 | 2/1997 | WO | WO 98/23162 | 6/1998 |
| JP | 10155493 | 6/1998 | WO | 98/31790 | 7/1998 |
| JP | 10155493 A | 6/1998 | WO | WO 98/31790 | 7/1998 |
| JP | 11-228986 | 8/1999 | WO | 98/41623 | 9/1998 |
| JP | 11290078 | 10/1999 | WO | 98/44804 | 10/1998 |
| JP | 2000226335 | 8/2000 | WO | 98/45453 | 10/1998 |
| JP | 03/024096 | 7/2001 | WO | 98/50532 | 11/1998 |
| JP | 3553958 | 5/2004 | WO | 98/51163 | 11/1998 |
| KR | 93-700773 | 3/1993 | WO | 98/59028 | 12/1998 |
| KR | 94-10252 | 10/1994 | WO | 99/33964 | 7/1999 |
| KR | 95-700043 | 1/1995 | WO | 99/34011 | 7/1999 |
| KR | 95-702583 | 6/1995 | WO | 99/37782 | 7/1999 |
| KR | 96-704602 | 8/1996 | WO | 99/42566 | 8/1999 |
| KR | 2001-7012115 | 9/2001 | WO | 99/50399 | 10/1999 |
| KR | 2003-7008997 | 10/2003 | WO | 99/53001 | 10/1999 |
| NL | 0784674 | 12/2002 | WO | 99/53769 | 10/1999 |
| NL | 0869167 | 1/2003 | WO | WO 9953769 | 10/1999 |
| NL | 1073339 | 2/2003 | WO | 99/55883 | 11/1999 |
| NL | 0746608 | 11/2003 | WO | 00/05396 | 2/2000 |
| PH | 31068 | 11/1984 | WO | WO 00/05396 | 2/2000 |
| RU | 2140751 | 6/1997 | WO | WO 00/23461 | 4/2000 |
| RU | 2235775 | 11/1999 | WO | 00/28044 | 5/2000 |
| RU | 2001117497 | 6/2001 | WO | 00/32758 | 6/2000 |
| TR | 200101551 | 12/1999 | WO | 00/34450 | 6/2000 |
| WO | 88/02775 | 4/1988 | WO | 00/36114 | 6/2000 |
| WO | 88/03365 | 5/1988 | WO | WO 00/32758 | 6/2000 |
| WO | 89/01969 | 3/1989 | WO | 00/43036 | 7/2000 |
| WO | 89/06803 | 7/1989 | WO | 00/49164 | 8/2000 |
| WO | 91/00920 | 1/1991 | WO | 00/58517 | 10/2000 |
| WO | 91/06661 | 5/1991 | WO | 00/59307 | 10/2000 |
| WO | WO 91/06661 | 5/1991 | WO | 00/60063 | 10/2000 |
| WO | 91/14772 | 10/1991 | WO | 00/61771 | 10/2000 |
| WO | WO 91/17243 | 11/1991 | WO | 00/71808 | 11/2000 |
| WO | 92/05249 | 4/1992 | WO | 00/75295 | 12/2000 |
| WO | 92/14830 | 9/1992 | WO | WO 00/75295 | 12/2000 |
| WO | 92/18645 | 10/1992 | WO | 01/16308 | 3/2001 |
| WO | 93/01285 | 1/1993 | WO | 01/27251 | 4/2001 |
| WO | 93/11249 | 6/1993 | WO | 01/29222 | 4/2001 |
| WO | 93/12812 | 7/1993 | WO | 01/34835 | 5/2001 |
| WO | 94/01541 | 1/1994 | WO | WO 01/39544 | 5/2001 |
| WO | 94/04035 | 3/1994 | WO | 01/39602 | 6/2001 |
| WO | 94/14940 | 7/1994 | WO | 01/42433 | 6/2001 |
| WO | 94/14951 | 7/1994 | WO | 01/47363 | 7/2001 |
| WO | 94/26883 | 11/1994 | WO | 01/66711 | 9/2001 |
| WO | 95/06720 | 3/1995 | WO | 01/78524 | 10/2001 |
| WO | 95/09909 | 4/1995 | WO | WO 01/75083 | 10/2001 |
| WO | 95/22606 | 8/1995 | WO | 01/83559 | 11/2001 |
| WO | 95/22615 | 8/1995 | WO | 01/83770 | 11/2001 |
| WO | 95/22625 | 8/1995 | WO | 01/92502 | 12/2001 |
| WO | 95/29996 | 11/1995 | WO | 02/00852 | 1/2002 |
| WO | 95/30744 | 11/1995 | WO | 02/03805 | 1/2002 |
| WO | WO 95/29996 | 11/1995 | WO | 02/06457 | 1/2002 |
| WO | 96/09772 | 4/1996 | WO | WO 02/06508 | 1/2002 |
| WO | 96/13578 | 5/1996 | WO | 02/14490 | 2/2002 |
| WO | 96/13579 | 5/1996 | WO | 02/24881 | 3/2002 |
| WO | 96/13580 | 5/1996 | WO | 02/30207 | 4/2002 |
| WO | 96/27002 | 9/1996 | WO | WO 02/39828 | 5/2002 |
| WO | 96/28542 | 9/1996 | WO | 02/055679 | 7/2002 |
| WO | 96/30502 | 10/1996 | WO | 02/062973 | 8/2002 |
| WO | 96/32472 | 10/1996 | WO | 02/065854 | 8/2002 |
| WO | 96/39851 | 12/1996 | WO | 02/066622 | 8/2002 |
| WO | 97/04079 | 2/1997 | WO | 02/094123 | 11/2002 |
| WO | 97/05219 | 2/1997 | WO | 03/020923 | 3/2003 |
| WO | 97/07202 | 2/1997 | WO | WO 03/020923 | 3/2003 |
| WO | 97/07205 | 2/1997 | WO | WO 03/020941 | 3/2003 |
| WO | 97/11083 | 3/1997 | WO | 03/040091 | 5/2003 |
| WO | 97/14713 | 4/1997 | WO | 03/060112 | 7/2003 |
| WO | 97/27237 | 7/1997 | WO | 03/070013 | 8/2003 |

| | | |
|---|---|---|
| WO | 03/089260 | 10/2003 |
| WO | 03/097825 | 11/2003 |
| WO | WO 03/097835 | 11/2003 |
| WO | 03/099016 | 12/2003 |
| WO | 03/100044 | 12/2003 |
| WO | 03/102118 | 12/2003 |
| WO | WO 03/100044 | 12/2003 |
| WO | 2004/004467 | 1/2004 |
| WO | 2004/018660 | 3/2004 |
| WO | 2004/053039 | 6/2004 |
| WO | 2004/053152 | 6/2004 |
| WO | 2004/059075 | 7/2004 |
| WO | 2004/064537 | 8/2004 |
| WO | 2004/064987 | 8/2004 |
| WO | WO 2004/064537 | 8/2004 |
| WO | WO 2004/084638 | 10/2004 |
| WO | 2004/097012 | 11/2004 |
| WO | 2004/111216 | 12/2004 |
| WO | 2005/003339 | 1/2005 |
| WO | 2005/005977 | 1/2005 |
| WO | 2005/056782 | 6/2005 |
| WO | 2005/066347 | 7/2005 |
| WO | 2005/066351 | 7/2005 |
| WO | 2005/080540 | 9/2005 |
| WO | 2005/087918 | 9/2005 |
| WO | WO 2005/111203 | 11/2005 |
| WO | 2006/008508 | 1/2006 |
| WO | 2006/008653 | 1/2006 |
| WO | 2006/032279 | 3/2006 |
| WO | WO 2006/031699 | 3/2006 |
| WO | WO 2006/045354 | 5/2006 |
| WO | WO 2006/066590 | 6/2006 |
| WO | WO 2008/003420 | 1/2008 |
| WO | WO 2008/036863 | 3/2008 |
| WO | WO 2008/090395 | 7/2008 |
| WO | WO 2008/094847 | 8/2008 |
| WO | WO 2008/094847 A1 | 8/2008 |
| WO | WO 2009/002480 | 12/2008 |
| WO | WO 2009/024736 | 2/2009 |
| WO | WO 2009/024862 | 2/2009 |
| WO | WO 2009/081094 | 7/2009 |

OTHER PUBLICATIONS

Upton, et al.; "A New Family of Lipolytic Enzymes"; Tibs Trends in Biochemical Science, Elsevier Publication (1995); vol. 20 (5); pp. 178-179.
Patent Abstract of Canada; Publication No. CA 805618; Publication Date Feb. 4, 1969.
Patent Abstracts of Japan; Publication No. 04-370055; Publication Date Dec. 22, 1992.
Patent Abstracts of Japan; Publication No. 07-079687; Publication Date Mar. 28, 1995.
Patent Abstracts of Japan; Publication No. 48-16612; Publication Date May 23, 1973 (Equivalent to JP 73016612).
Patent Abstracts of Japan; Publication No. 2003-524386; Publication Date Aug. 19, 2003.
Arskog et al., "Baking performance of prior art lipases from *Candida cylindracea* and *Aspergillus foeditus* and their activity of galactoplipids in dough", Novozymes Report, Jul. 18, 2005.
Arskog et al., "Baking performance of prior art lipases from Humicola lanuginose, Aspergillus tubigensis, Rhizopus delemar and Rhizomucor miehei, and their activity on galactoplipids in dough" Novozymes Report, Jul. 17, 2005.
Briand et al., "Substrate Specificity of the Lipase from Candid parapsilosis" Lipids, vol. 30, No. 8, 1995.
Chica et al., "Semi-rational approaches to engineering enzyme activity: combining the benefits of directed evolution and rational design", Current Opinion in Biotechnology, vol. 16, pp. 378-384; 2005.
Garcia et al., "Analysis and Modeling of the Ferulic Acid Oxidation by a Glucose Oxidase-Peroxidase Association. Comparison with a Hexose Oxidase-Peroxidase Association" J. Agric. Food Chem. vol. 52, pp. 3946-3953; 2004.
Garzillo et al., "Production purification and characterization of glucose oxidase from *Penicillium variabile* P16", Biotechnol. Appl. Biochem., vol. 22, pp. 169-178, 1995.

Seffernick et al., "Melamine Deaminase and Atrazine Chlorohydolase: 98 Percent Identical but Functionally Different", Journal of Bacteriology, vol. 183, No. 8, pp. 2405-2410; Apr. 2001.
Seino et al., "Enzymatic Synthesis of Carbohydrate Esters of Fatty Acid (1) Esterification of Sucrose, Glucose, Fructose and Sorbitol", JAOCS, vol. 61, No. 11, Nov. 1984.
Witkowski et al., "Conversion of a β-Ketoacyl Synthase to a Malonyl Decarboxylase by Replacement of the Active-Site Cysteine with Glutamine", Biochemistry, vol. 38, pp. 11643-11650, 1999.
Richardson, Toby H., et al., "A Novel, High Performance Enzyme for Starch Liquefaction", The Journal of Biological Chemistry, vol. 277, No. 29, Issue of Jul. 19, pp. 25501-26507, 2002.
Roberts et al. (1992) Gene 122(1), 155-61.
Roberts, et al.; "Extracellular Lipase Production by Fungi from Sunflower Seed"; Mycologia(1987); vol. 79(2); pp. 265-273.
Robertson et al, Journal of Biological Chemistry, 1994, 2146-2150.
Rodrigues, et al.;"Short Communication: Bioseparations with Permeable Particles"; Journal of Chromatography & Biomedical Applications(1995); vol. 655; pp. 233-240.
Rogalska, Ewa, et al., "Stereoselective Hydrolysis of Triglycerides by Animal and Microbial Lipases", Chirality, vol. 5, pp. 24-30, 1993.
Rose, et al.;"CODEHOP (Consensus-Degenerate Hybrid Oligonucleotide Primer) PCR primer design"; Nucleic Acids Research(2003); vol. 31(13); pp. 3763-3766.
Rousseau, Derick, et al., "Tailoring the Textural Attributes of Butter Fat/Canola Oil Blends via Rhizopus arrhizus Lipase-Catalyzed Interesterification. 2. Modifications of Physical Properties", J. Agric. Food Chem., vol. 1998, vol. 46, pp. 2375-2381.
Rydel, Timothy J. et al., "The Crystal Structure, Mutagenesis and Activity Studies Reveal that Patatin Is a Lipid Acyl Hydrolase with a Ser-Asp Catalytic Dyad", Biochemistry, 2003, vol. 42, pp. 6696-6708.
Sahsah, Y., et al., "Enzymatic degradation of polar lipids in Vigna unguiculata leaves and influence of drought stress", Physiologia Plantarum, vol. 104, pp. 577-586, 1998.
Sahsah, Y., et al., "Purification and characterization of a soluble lipolytic acylhydrolase from Cowpea (vigna unguiculata L.) leaves", Biochimica et Biophysica Acta, vol. 1215, pp. 66-73, 1994.
Saiki R.K. et al Science (1988) 239, pp. 487-491.
Sakai, Norio, et al., "Human glactocerebrosidase gene: promoter analysis of the 5'-flanking region and structural organization", Biochimica et Biophysica Acta, vol. 1395, pp. 62-67, 1998.
Sakaki T et al, Advanced Research on Plant Lipids, Proceedings of the International Symposium on Plant Lipids, 15th, Okazaki, Japan, May 12-17, 2002 (2003) p. 291-294, Publisher Kluwer Academic Publishers.
Sambrook et al, Chapters 1, 7, 9, 11, 12 and 13—Molecular Cloning a laboratory manual, Cold Spring Harbor Laboratory Press (1989).
Sambrook, J., et al. "A Laboratory Manual, Second Edition", Plasmid Vectors, 1989.
Sanchez et al., "Solution and Interface Aggregation States of Crotalus atrox Venom Phospholipase A2 by Two-Photon Excitation Fluorescence Correlation Spectroscopy", Biochemistry, 2001, vol. 40, pp. 6903-6911.
Sarney Douglas B. et al, "Enzymatic Synthesis of Sorbitan Esters Using a Low-Boiling-Point Azeotrope as Reaction Solvent", Biotechnology and Bioengineering, 1997, vol. 54(4).
Saxena, et al.; "Purification Strategies for Microbial Lipases"; Journal of Microbilogical Methods (2003); pp. 1-18.
Scheib et al.; "Stereoselectivity of Mucorales lipases toward triradylglycerols—A simple solution to a complex problem"; Protein Science (1999); vol. 8; pp. 215-221.
Schiller, Jurgen, et al., "Lipid analysis of human spermatozoa and seminal plasma by MALDI-TOF mass spectrometry and NMR spectroscopy—effects of freezing and thawing" Chemistry and Physics of Lipids, vol. 106, 2000, pp. 145-156.
Scopes, Robert K., "Section 8.4: Ultrafiltration" in *Protein Purification Principles and Practice, Third Edition* (1994) Springer-Verlag, New York, p. 267-9.
Sequence alignment of the nucleotide sequences of SEQ ID No. 2 of EP'167 and SEQ ID No. 7 of D20 and the amino acid sequences of SEQ ID No. 2 of EP'167 and SEQ ID No. 8 of D20.

Shillcock, Julian C., et al., "Equilibrium structure and lateral stress distribution of amphiphilic bilayers from dissipative particle dynamics simulations", Journal of Chemical Physics, vol. 117, No. 10, Sep. 8, 2002.
Shimada et al, J. of Bioscience and Bioengineering vol. 91, No. 6, 529-538 (2001).
Shimada et al, J. of Fermentation and Bioengineering vol. 75, No. 5, 349-352 (1993).
Shimada et al, JAOCS vol. 71, No. 9, (Sep. 1994).
Shin, et al.; "Butyl-Toyopearl 650 as a New Hydrophobic Adsorbent for Water-Soluable Enzyme Proteins"; Analytical Biochemistry(1984); vol. 138; pp. 259-261.
Shogren, M.D., et al., "Functional (Breadmaking) and Biochemical Properties of Wheat Flour Components. I. Solubilizing Gluten and Flour Protein", Cereal Chemistry, vol. 46, No. 2, Mar. 1969.
Si, Joan Qi; "New Enzymes for the Baking Industry"; Food Tech Europe (1996) pp. 60-64.
Sias B et al, Biochemistry, (2004), vol. 43(31), p. 10138-48.
Siew W.L. & Ng W.L. (1999) Influence of diglycerides on crystalisation of palm oil, in Journal of Science of Food and Agriculture 79:722-726.
Siew W.L. & Ng W.L. (2000) Differential scanning thermograms of palm oil triglycerides in the presence of diglycerides, in Journal of Oil Palm Research 12:107.
Siew W.L. (2001) Understanding the Interactions of Diacylglycerols with oil for better product performance, paper presented at the 2001 PIPOC International Palm Oil Congress—Chemistry and Technology Conference Aug. 20-23, 2001, Kuala Lumpur, Malaysia.
Skovgaard, et al.;"Comparison of Intra- and extracelluar isozyme banding patterns of *Fusarium Oxysporum*"; Mycol. Res. (1998); vol. 102(9); pp. 1077-1084.
Slotboom et al Chem. Phys. Lipids 4 (1970) 15-29.
Smith, George P.; "The Progeny of sexual PCR"; Nature; vol. 370; No. 18; Aug. 4, 1994.
Smith, Timothy L., et al., "The promoter of the glucoamylase-encoding gene of Aspergillus niger functions in Ustilago maydis", Gene. 88, 259-262, 1990.
Solares, Laura F., et al., "Enzymatic resolution of new carbonate intermediates for the synthesis of (S)-(+)-zopiclone", Tetrahedron: Asymmetry, vol. 13, 2002, pp. 2577-2582.
Sols and De Le Fuente, "On the substrate specificity of glucose oxidase", Biochem et Biophysica Acta (1957) 24:206-7.
Sonntag N.O.V. (1982a) Glycerolysis of Fats and methyl esters—status, review and critique, in Journal of American Oil Chemist Society 59:795-802A.
Soragni, Elisabetta, et al., "A nutrient-regulated, dual localization phospholipase A2 in the symbiotic fungus" The EMBO Journal, vol. 20, No. 18, pp. 5079-5090, 2001.
Sosland, Josh, "Alive and kicking", Milling & Baking News, Feb. 24, 2004.
Soumanou, Mohamed M., et al., "Two-Step Enzymatic Reaction for the Synthesis of Pure Structured Triacylglycerides", JAOCS, vol. 75, No. 6, 1998.
Spendler, et al., "Functionality and mechanism of a new 2nd generation lipase for baking industry"—Abstract. 2001 AACC Annual Meeting; Symposia at Charlotte, NC. Oct. 14-18, 2001.
Spradlin J E, Biocatalysis in Agric. Technol., ACS Symposium, 389(3), 24-43 (1989).
Sreekrishna K et al (1988) J Basic Microbiol. 28(4), 265-78.
Stadler et al., "Understanding Lipase Action and Selectivity", CCACAA, vol. 68, No. 3, pp. 649-674, 1995.
Steinstraesser, et al., "Activity of Novispirin G10 against Pseudomonas aeruginosa In Vitro and in Infected Burns", Antimicrobial Agents and Chemotherapy, Jun. 2002, vol. 46, No. 6, pp. 1837-1844.
Stemmer, Willem P.C.; "DNA shuffling by random fragmentation and reassembly: In vitro recombination for molecular evolution"; Proc. Natl. Acad. Sci. USA, vol. 91, pp. 10747-10751; Oct. 1994.
Stemmer, Willem P.C.; "Rapid evolution of a protein in vitro by DNA shuffling"; Affymax Research Institute, Nature, vol. 370, Aug. 4, 1994.
Sternberg, M., "Purification of Industrial Enzymes with Polyacrylic Acids", Process Biochemistry, Sep. 1976.
Strickland, James A., et al., "Inhibition of Diabrotica Larval Growth by Patatin, the Lipid Acyl Hydrolase from Potato Tubers", Plant Physiol, vol. 109, pp. 667-674, 1995.
Sudbery et al (1988) Biochem Soc Trans. 16(6), 1081-3.
Sugatani, Junko, et al., "Studies of a Phospholipase B from Penicillium Notatum Substrate Specificity and Properties of Active Site", Biochimica et Biophysica Acta, vol. 620, 1980, pp. 372-386.
Sugimoto et al., Agric. Biol. Chem. 47(6), 1201-1206 (1983).
Sugiyama et al., "Molecular cloning of a second phospholipase B gene, caPLB2 from Candida albicans", Medical Mycology, vol. 37, 1999.
Svendsen, A. "Engineered lipases for practical use", INFORM (1994) 5(5):619-623.
Svendsen, Allan, "Lipase protein engineering" Biochimica et Biophysica Acta, vol. 1543, 2000, pp. 223-238.
Svendsen, Allan, et al., "Biochemical properties of cloned lipases from the Pseudomonas family", Biochimica et Biophysica Acta, vol. 1259, 1995, pp. 9-17.
Sweigard, James A., et al., "Cloning and analysis of CUT1, a cutinase gene from Magnaporthe grisea", Mol. Gen. Genet., 232:174-182, 1992.
Swinkels et at (1993) Antonie van Leeuwenhoek 64, 187-201.
Sztajer H et al Acta Biotechnol, vol. 8, 1988, pp. 169-175.
Talker-Huiber, Cynthia Z., et al., "Esterase EstE from Xanthomonas vesicatoria (Xv_EstE) is an outer membrane protein capable of hydrolyzing long-chain polar esters", Appl. Microbiol Biotechnol, 61:479-487, 2003.
Terasaki, Masaru, et al., "Glycerolipid Acyl Hydrolase Activity in the Brown Alga Cladosiphon okamuranus Tokida", Biosci. Biotechnol. Biochem., vol. 67, No. 9, pp. 1986-1989, 2003.
The New Enzyme Operatives, Ingredient Technology, 50, Aug. 1997.
Thommy L-G; Carlson, "Law and Order in Wheat Flour Dough; Colloidal Aspects of the Wheat Flour Dough and its Lipid and Protein Constitutents in Aqueous Media", Fortroligt, Lund 1981.
Thornton et at 1988 Biochem. Et Biophys. Acta. 959, 153-159.
Tiss, Aly, et al., "Effects of Gum Arabic on Lipase Interfacial Binding and Activity", Analytical Biochemistry, vol. 294, pp. 36-43, 2001.
Toida J et al, Bioscience, Biotechnology, and Biochemistry, Jul. 1995, vol. 59, No. 7, pp. 1199-1203.
Tombs and Blake, Biochim. Biophys (1982) 700:81-89.
Topakas, E., et al. "Purification and characterization of a feruloyl esterase from Fusarium oxysporum catalyzing esterification of phenolic acids in ternary water—organic solvent mixtures", Journal of Biotechnology, vol. 102, 2003, pp. 33-44.
Torossian and Bell (Biotechnol. Appl. Biochem., 1991, 13:205-211.
Tsao et al. (1973) J Supramol Struct. 1(6), 490-7.
Tsuneo Yamane et al., "Glycerolysis of Fat by Lipase", Laboratory of Bioreaction Engineering, vol. 35, No. 8, 1986.
Tsychiya, Atsushi, et al., "Cloning and nucleotide sequence of the mono- and diacylglycerol lipase gene (mdlB) of Aspergillus oryzae", FEMS Microbiology Letters, vol. 143, pp. 63-67, 1996.
Turnbull, K.M., et al., "Early expression of grain hardness in the developing wheat endosperm", Planta, 2003, vol. 216, pp. 699-706.
Turner, Nigel A., et al., "At what temperature can enzymes maintain their catalytic activity?", Enzyme and Microbial Technology, vol. 27, 2000, pp. 108-113.
Turner, Progress in Industrial Microbiology, Martinelli and Kinghorn (eds.), Elsevier, Amsterdam, 1994, 29:641-666.
Unknown, *Studies on Lipase* (1964) p. 21.
Uppenberg, Jonas, et al., "Crystallographic and Molecular-Modeling Studies of Lipase B from Candida antarctia Reveal a Stereospecificity Pocket for Secondary alcohols", Biochemistry, 1995, vol. 34, pp. 16838-16851.
Uppenberg, Jonas, et al., "The Sequence, crystal structure determination and refinement of two crystal forms of lipase B from Candida antarctica", Structure 1994, vol. 2, No. 4.
Upton C et al TIBS Trends in Biochemical Sciences, Elsevier Publication (1995), vol. 20, pp. 178-179.
USDA, "Production of an Industrially Useful Fungal Lipase by a Genetically Altered Strain of *E. coli*", New Technology.
Uusitalo et al. (1991) J Biotechnol. 17(1), 35-49.
Uwajima T et al, Agricultural and Biological Chemistry, 43(12), pp. 2633-2634, 1979.

Uwajima T et al, Agricultural and Biological Chemistry, 44(9), pp. 2039-2045, 1980.

Uwajima T et al, Methods in Enzymology, 89(41), pp. 243-248.

Vaidehi, et al.; "Lipase Activity of Some Fungi Isolated from Groundnut"; Current Science (1984); vol. 53(23); p. 1253.

van Binsbergen, Jan, et al., "Substitution of PHE-5 and ILE-9, Amino Acids Involved in the Active Site of Phospholipase A2 (PLA), and Chemical Modification of Enzymatically Generated (LYS-6)-PLA.", Proceedings of the 20th European Peptide Symposium, Sep. 4-9, 1988, University of Tubingen.

van Gemeren, I.A., et al., "Expression and Secretion of Defined Cutinase Variants by Aspergillus awamori" Applied and Environmental Microbiology, vol. 64, No. 8, pp. 2794-2799, Aug. 1998.

van Kampen, M.D., et al., "The phospholipase activity of Staphylococcus hyicus lipase strongly depends on a single Ser to Val mutation", Chemistry and Physics of Lipids, vol. 93, 1998, pp. 39-45.

van Oort, Maarten G et al, Biochemistry 1989 9278-9285.

Vaysse et al J. of Biotechnology 53 (1997) 41-46.

Villenueva, Inform, vol. 8, No. 6, Jun. 1997.

Vujaklija, Dušica, et al., "A novel streptomycete lipase: cloning, sequencing and high-level expression of the Streptomyces rimosus Gds (L)-lipase gene", Arch. Microbiol, vol. 178, pp. 124-130, 2002.

Wahnelt S.V., Meusel D, & Tülsner M, (1991) Zur kenntnis des diglyceride influsses auf das kristallisationsverhalten von Fetten, in Fat Science Technology 4:117-121.

Waninge, Rianne, et al., "Milk membrane lipid vesicle structures studied with Cryo-TEM", Colloids and Surfaces B: Biointerfaces 31 (2003), pp. 257-264.

Warmuth et al, 1992, Bio Forum 9, 282-283.

Watanabe et al. Bio sci Biochem 63(5) 820-826, 1999.

Watanabe, Yasuo et al., "Cloning and sequencing of phospholipase B gene from the yeast Torulaspora delbrueckii", FEMS Microbiology Letters, vol. 124, 1994, pp. 29-34.

Webb EC, Enzyme Nomenclature, 1992, p. 310.

Weber et al. J Agric Food Chem 1985, 33, 1093-1096.

Wen-Chen Suen et al., "Improved activity and thermostability of Candida antarctica lipase B by DNA family shuffling", Protein Engineering, Design & Selection, vol. 17, No. 2, pp. 133-140, 2004.

West S.; "Olive and Other Edible Oils"; Industrial Enzymology (1996); pp. 295-299.

Whitaker, John R., et al., "Biocatalysis in Agricultural Biotechnology", ACS Symposium Series.

Whitehead, Michael, et al., "Transformation of a nitrate reductase deficient mutant of Penicillium chrysogenum with the corresponding Aspergillus niger and A. nidulans niaD genes", Mol Gen Genet, 216: 408-411, 1989.

Wilhelm et al., "A Novel Lipolytic Enzyme Located in the Outer Membrane of Pseudomonas aeruginosa", Journal of Bacteriology, vol. 181, No. 22, Nov. 1999, pp. 6977-6986.

Winnacker, Chapter 11, pp. 424-431 in From genes to clones: introduction to gene technology, VCH (1987).

Winnacker, E. "Chapter 11: Identification of Recombinant DNA" in *From Genes to Clones: Introduction to Gene Technology*, 1987 John Wiley & Sons.

Winther, Ole, et al., "Teaching computers to fold proteins", Physical Review, vol. 70, No. 030903, 2004.

Withers-Martinez, Chrislaine, et al., "A pancreatic lipase with a phospholipase A1 activity: crystal structure of a chimeric pancreatic lipase-related protein 2 from guinea pig", Structure, 1996, vol. 4, No. 11.

Witt, Wolfgang et al., "Secretion of Phospholipase B From Saccharomyces Cerevisiae", Biochimica et Biophysica Acta, vol. 795, 1984, pp. 117-124.

Wood et al., Eds., "Biomass, Part B, Lignin, Pectin, and Chitin", Methods in Enzymology (1988) vol. 161, Academic Press, San Diego.

Xu, Jun, et al., "Intron requirement for AFP gene expression in Trichoderma viride", Microbiology, 2003, vol. 149, pp. 3093-3097.

Yamaguchi et al, 1991, Gene 103:61-67.

Yamane et al., "High-Yield Diacylglycerol Formation by Solid-Phase Enzymatic Glycerolysis of Hydrogenated Beef Tallow", JAOCS, vol. 71, No. 3, Mar. 1994.

Yamauchi, Asao et al., "Evolvability of random polypetides through functional selection within a small library", Protein Engineering, vol. 15, No. 7, pp. 619-626, 2002.

Yang, Baokang, et al., "Control of Lipase-Mediated Glycerolysis Reactions with Butteroil in Dual Liquid Phase Media Devoid of Organic Solvent", J. Agric. Food Chem., 1993, vol. 41, pp. 1905-1909.

Zaks, Aleksey, et al., "Enzyme-catalyzed processes in organic solvents", Proc. Natl. Acad. Sci. USA, vol. 82, pp. 3192-3196, May 1985.

Zaks, Aleksey, et al., "The Effect of Water on Enzyme Action in Organic Media", The Journal of Biological Chemistry, vol. 263, No. 17, Issue of Jun. 15, pp. 8017-8021, 1988.

Zangenbert, Niels Honberg, et al., "A dynamic in vitro lipolysis model 1. Controlling the rate of lipolysis by continuous addition of calcium", European Journal of Pharmaceutical Sciences, vol. 14, 2001, pp. 115-122.

Zangenbert, Niels Honberg, et al., "A dynamic in vitro lipolysis model II. Evaluation of the model", European Journal of Pharmaceutical Sciences, vol. 14, 2001, pp. 237-244.

Zhang, Hong, et al., "Modification of Margarine Fats by Enzymatic Interesterification: Evaluation of a Solid-Fat-Content-Based Exponential Model with Two Groups of Oil Blends", JAOCS, vol. 81, No. 1, 2004.

Acker, L. "Die Lipide des Getreides, ihre Zusammense and inre Bedeutung", Getreide Mehl Brot (1974) 28:181-187.

Adamzcak, Marek, et al., "Application of Enzymatic Glycerolysis for Production of Monoglycerides from Waste Fats", Polish Journal of Food and Nutrition Science, Mar. 1994.

Adhikari, B., et al., "Stickiness in Foods: A Review of Mechanisms and Test Methods", International Journal of Food Properties, vol. 4, No. 1, 2001.

Agarwal et al., "Lipase Activity of Some Fungi Isolated from Groundnut", Current Science, Dec. 5, 1984, vol. 53, No. 23.

Aires-Barros et at (1994) Isolation and purification of lipases, Cambridge Unversity Press.

Aisaka, Kazuo et al., "Production of Lipoprotein Lipase and Lipase by Rhizopus japonicu", Agri. Biol. Chem., vol. 43, No. 10, pp. 2125-2129, 1979.

Akoh, Casimir C., et al., "GDSL family of serine esterases/lipases" Progress in Lipid Research, vol. 43, 2004, pp. 534-552.

Allan Svendsen et al., "Biochemical properties of cloned lipases from the Pseudomonas family", Biochimica et Biophysica Acta, vol. 1259, 1995, pp. 9-17.

Al-Obaidy, K A, Dissertation Abstracts International B (1987) vol. 47(9) 3597, order No. DA8624641, pp. 266.

Amano Enzyme Inc. (2004). Http://www.amano-enzyme.co.jp/english/productuse/oil_fat.html. Dato 21.06.04.

Amano Enzymes "Enzymes for Gastrointestinal Digestion" Oct. 1997.

Amano Enzymes, Amano Enzyme Europe Ltd, Sep. 1994.

Amin, Neelam S., et al., "Direct transformation of site-saturation libraries in Bacillus subtilis", BioTechniques, Dec. 2003, 35:1134-1140.

Andersson, L., et al., "Hydrolysis of galactolipids by human pancreatic lipolytic enzymes and duidenal contents", Journal of Lipid Research, 1995, vol. 36, pp. 1392-1400.

Andreas Sander, Eberhand Eilers, Andrea Heilemann, Edith von Kreis.Fett/lipid 99 (1997) Nr. 4, 115-120.

An-I Yeh et al., "Effects of Oxido-reductants on rheological properties of wheat flour dough and comparison with some characteristics of extruded noodles", Cereal Chemistry, 1999, vol. 76, No. 5, pp. 614-620.

Archer, David B., et al., "Proteolytic degradation of heterologous proteins expressed in Aspergillus Niger", Biotechnology Letter, vol. 14, No. 5, May 1992, pp. 357-362.

Arcos J.A. et al, "Quantative Enzymatic Production of 6.O-Acylglucose Esters", Biotechnology and Bioengineering 1998 57(5).

Arpigny Jean Louis et al, "Bacterial lipolytic enzymes: Classification and properties", Biochemical Journal, vol. 343, No. 1, Oct. 1, 1999, pp. 177-183, XP002375631.

August C.A.P.A. et al. "The use of genetic engineering to obtain efficient production of porcine pancreatic phospholipase A2", Biochimica et Biophysica Acta, vol. 1089, 1991, pp. 345-351.
Ausubel, Frederick M., et al., "Short Protocols in Molecular Biology—A Compendium of Methods from Current Protocols in Molecular Biology", 1995, John Wiley & Sons, Inc.
Bachmatova, I., et al., "Lipase of Pseudomonas mendocina 3121-1 and its Substrate Specificty", Biologija, 1995.
Balcao V.M., Pavia A.L. Malcata F.X., Enzyme Microb Technhol, May 1, 1996; 18(6):392-416.
Balcao, Victor M and Malcata F. Xavier (1998), Biotechnology Advances, vol. 16, No. 2, pp. 309-341.
Ballance, D.J., et al., "Transformation of Aspergillus Nidulans by the orotidine-5'-phosphate decarboxylase gene of neurospora crassa", Biochemical and biophysical Research Communications, vol. 112, No. 1, 1983, pp. 284-289.
Ballance, Molecular Industrial Mycology, Systems and Applications for Filamentous Fungi, Leong and Berka (eds.), Marcel Dekker Inc, New York 1991, pp. 1-29.
Barbesgaard, Peder et al Applied Microbiology and Biotechnology (1992) 36: 569-572.
Barnes, P.J., "Lipids in Cereal Technology", Food and Science Technology, Academic Press, 1983.
Basrl, M., et al., "Amidination of Lipase with Hyrdophobic Imidoesters", JAOCS, vol. 69, No. 6, Jun. 1992.
Bateman A and Haft DH (2002) Brief Bioinform 3, 236-245.
Bateman A et al, (2002) Nucleic Acids Res. 30, 276-280.
Bekkers et al, The use of genetic engineering to obtain efficient production of porcine pancreatic phospholipase A2 by Saccharomyces cerevisiae, (1991) Biochim Biophys Acta 1089(3), 345-51.
Bengtsson Olivecrona Gunilla et al. Phospholipase activity of milk lipoprotein lipase, Methods in Enzymology, vol. 197, 1991.
Bentley S D et al, Complete genome sequence of the model actinomycete Streptomyces coelicolor A3(2), Nature vol. 417, 2002, pp. 141-147.
Berger K.G. (1990) Recent developments in palm oil. In Oleagineux 45:437-443.
Berks, Ben C., "A common export pathway for proteins binding complex redox cofactors?" Molecular Microbiology, 1996, vol. 22, pp. 393-404.
Beucage S.L. et al, (1981) Tetrahedron Letters 22, p. 1859-1869.
Bilyk, Alexander, et al., "Lipase-catalyzed triglyceride Hydrolysis in Organic Solvent", pp. 320-323, JAOCS, vol. 68, No. 5, May 1991.
Birch et al., "Evidence of Multiple Extracellular Phospholipase Activities of Aspergillus fumigatus", Infection and Immunity, Mar. 1996, vol. 64, No. 3, 1996.
Birgitte Hugh-Jensen et al., "Rhizomucor miehei Triglyceride Lipase is Processed and Secreted from Transformed Aspergillus oryzae", Lipids, vol. 24, No. 9, 1989.
Biswas, et al., "Interfacial Behavior of Wheat Puroindolines: Study of Adsorption at the Air-Water Interface from Surface Tension Measurement Using Wilhelmy Plate Method", Journal of Colloid and Interface Science, vol. 244, pp. 245-253, 2001.
Bjorkling, F., et al., "Lipase Catalyzed Organic Synthesis", S. Servie (ed.), Microbial Reagents in Organic Synthesis, pp. 249-260, 1992.
Bjorkling, Frederik, et al., "Lipase Catalyzed Synthesis of Perozycarboxylic Acids and Lipase Mediated Oxidations", Tetrahedron, vol. 48, No. 22, pp. 4587-4592, 1992.
Bjorkling, Frederik, et al., "Lipase—mediated Formation of Peroxycarboxylic acids used in Catalytic Epoxidation of Alkenes", J. Chem. Soc., Chemical Communications, Issue 19, 1990.
Bjurlin et al. Identification of carboxylesterase activities of commercial triacylglycerol hydrolase (lipase) preparations, Eur. J. Lipid Sci. Technol. 104 (2002) 143-155.
Blain JA et al, The Nature of Mycelial Lipolytic enzymes in filamentous fungi, Fems Microbiol. Lett., 1978, vol. 3, 85-87.
Blecker et al, Improved emulsifying and foaming of whey proteins after enzymic fat hydrolysis, (1997) J Food Science, vol. 62, No. 1.
Blumenthal, Cynthia Z., "Production of toxic metabolites in Aspergillus niger, Aspergillus oryzae, and Trichoderma reesei: justification of mycotoxin testing in food grade enzyme preparations derived from the three fungi", Regulatory Toxicology and Pharmacology, vol. 39, 2004, p. 214-228.
Boel, Esper, et al.; "Rhizomucor miehei Triglyceride Lipase is Synthesized as a Precursor"; Novo Research Institute; vol. 23; No. 7; Jul. 1988.
Bornscheuer U T et al, Trends in Biotechnology, Elsevier Publications, Cambridge GB, vol. 20, No. 10, Oct. 1, 2002, pp. 433-437.
Bornscheuer, Uwe T., "Lipase-catalyzed syntheses of monoacylglycerols", Enzyme and Microbiol Technology, vol. 17, pp. 578-586, 1995.
Brady, Leo, et al., "A serine protease triad forms the catalytic centre of a triacylglycerol lipase", Nature, vol. 343, 1990.
Brockerhoff, Hans, et al., "Lipolytic Enzymes", Academic Press, 1974.
Brumlik, Michael J., et al., "Identification of the Catalytic Triad of the Lipase/Acyltransferase from *Aeromonas hydrophila*", Journal of Bacteriology, Apr. 1996, vol. 178, No. 7, pp. 2060-2064.
Brzozowski, A.M., et al., "A model for interfacial activation in lipases from the structure of a fungal lipase-inhibitor complex", Nature, vol. 351, 1991.
Buckley J. Thomas et al, Journal of Biological Chemistry, vol. 257, No. 6, pp. 3320-3325, 1982.
Buckley, Biochemistry 1983, 22, 5490-5493.
Bulkacz J et al, Biochim. Biophys. Acta (1981) vol. 664, pp. 148-155.
Bulletin of the IDF 294: 1994.
Burdge, Graham C., et al., "A method for separation of phosphatidylcholine, triacylglycerol, non-esterified fatty acids and cholesterol esters from plasma by solid-phase extraction", British Journal of Nutrition, 2000, vol. 84, pp. 281-787.
Butcher, Bronwyn G., et al., Microbiology, 2002, vol. 148, pp. 3983-3992.
Buxton et al, Gene, 1985, 37:207-214.
Carriere et al, "Pancreatic Lipase Structure—Function Relationships by Domain Exchange", American Chemical Society—Biochemistry (1997), 36, pp. 239-248.
Corriére, Frédéric, et al., "Structural basis for the substrate selectivity of pancreatic lipases and some related proteins", Biochemica et Biophysica Acta, vol. 1376, pp. 417-432, 1998.
Caruthers MH et at (1980) Nuc Acids Res Symp Ser 215-23.
Casimir C A et al Progress in Lipid Research, 2004, pp. 534-552.
Castello, Phillippe, et al., "Effect of exogenous lipase on dough lipids during mixing of wheat flours", Cereal Chemistry, 1998, vol. 75, No. 5, pp. 595-601.
Castello, Phillippe, et al., "Effects of mixing conditions and wheat flour dough composition on lipid hydrolysis and oxidation levels in the presence of exogenous lipase", Cereal Chemistry, 1999, vol. 76, No. 4. pp. 476-482.
Chakravarti DN et al, Biol. Abstracts, 1981, vol. 72, abstract No. 012592.
Cheng Cheng et al., "Transformation of Trichoderma viride using the Neurospora crassa pyr4 gene and its use in the expression of a Taka-amylase A gene from Aspergillus oryzae", Curr. Genet., 18: 453-456, 1990.
Christensen et al, "A new and simple method to immobilise lipases by means of granulation", 1998 Nachwachsende Rohstoff 10, 98-105.
Christie, William et al., "New Procedures for Rapid Screening of Leaf Lipid Components from Arabidopsis", Phytochemical Analysis, vol. 9, pp. 53-57, 1998.
Christophersen, Claus, et al., "Enzymatic Characterisation of Novamyl a Thermostable α-Amylase", Starch/Sturke, vol. 50, 1998.
Chung O K et al, "Defatted and Reconstituted wheat flours. VI. Response to shortening addition and Lipid Removal in Flours that vary in Bread-making Quality" Cereal Chemistry (1980), vol. 57(2), p. 111-117.
Chung OK et al, "Recent Research on Wheat Lipids" Bakers Digest Oct. 1981.
Ciuffreda, Pierangela, et al., "Spectrophotometric Assay of Lipase Activity: A New 40nitrophenyl Ester of a Dialkylglycerol Suitable as a Chromogenic Substrate of Pseudomonas cepacia Lipase", Biocatalysis and Biotransformation, vol. 21, No. 3, pp. 123-127, 2003.
Claesson et al., "Techniques for measuring surface forces", Advances in Colloid and Interface Science, vol. 67, 1996, pp. 119-183.

Clausen, Kim, "Enzymatic oil-degumming by a novel microbial phospholipase", European Journal of Lipid Science and Technology, vol. 103, 2001, pp. 333-340.

Clausen, Kim, "New enzyme for degumming", Oils and Fats International, vol. 17, No. 4, Jun. 2001, pp. 24-25.

Collar C, et al, "Lipid binding fresh and stored formulated wheat breads. Relationships with dough and bread technological performance", Lab de Cereales Inst de Agroquimica y Tec de Alimentos, CSIC, Food Science and Technology International 2001, vol. 7(6), p. 501-510.

Colombo, Diego, et al., "Optically Pure 1-0- and 3-0-β-D-Glucosylk- and Galactosyl-sn-glycerols through Lipase-catalyzed Transformations", Tetrahedron Letters, vol. 36, No. 27, pp. 2865-4868, 1995.

Conference May 6-8, 1999 in Santorini, Greece—Lipases & Lipids Structure, Function and Biotechnological Applications—Slides presented by Charlotte Poulsen.

Cordle et al, "The hydrophobic surface of colipase influences lipase activity at an oil-water interface", Journal of Lipid Research, vol. 39 (1998), 1759-1767.

Coteron, A., et al., "Reactions of Olive Oil and Glycerol over Immobilized Lipases", JAOCS, vol. 75, No. 5, 1998.

Council Directive of Dec. 21, 1988 (89/107/EEC).

Council Regulation (EC) No. 2991/94 5/12/94 Official Journal of the European Communities, Sep. 12, 1994, No. L316/2-7.

Creveld, Lucia D, et al., "Identification of Functional and Unfolding Motions of Cutinase as Obtained from Molecular Dynamics Computer Simulations", Proteins: Structure, Function, and Genetics, 33:253-264, 1998.

Cromie, Susan. Psychrotrophs and their Enzyme residues in cheese milk, The Australian Journal of Dairy Technology, vol. 47, Nov. 1992.

Cui et al., "Purification and characterization of an intracellular carboxylesterase from Arthrobacter viscosus NRRL B-1973", Enzyme and Microbial Technology, vol. 24, pp. 200-208, 1999.

Daboussi et al, Heterologous expression of the Aspergillus nidulans regulatory gene nirA in Fusarium oxysporum, (1991) Gene 109(1), 155-60.

Daboussi et al., "Transformation of seven species of filamentous fungi using the nitrate reductase gene of Aspergillus nidulans", Curr. Genet., 15:453-456, 1989.

Daftary, R.D., et al., "Functional Bread-Making Properties of Wheat Flour Lipids", Food Technology, vol. 22, No. 237, Mar. 1968-1979.

Dahlquist, Anders, et al., "Phospholipid: diacylglycerol acyltransferase: An enzyme that catalyzes the acyl-CoA-independent formation of triacylglycerol in yeast and plants", PNAS, vol. 97, No. 12, pp. 6487-6492, 2000.

Dalrymple, Brian D., et al., "Three Neocallimastic patriciarum esterases associated with the degradation of complex polysaccharides are members of a new family of hydrolases", Microbiology, vol. 142, pp. 2605-2614, 1997.

Danisco, "Unique Chance for Better Bread" *Direct, A Newsletter from Danisco Ingredients* (1996).

Darnell et al., Eds., "Synthetic Peptide and Nucleotide Sequences: Their Use in Isolating and Identifying Genes", in *Molecular Cell Biology*, Chapter 6, Manipulating Macromolecules, 1990, Scientific American Books, Baltimore.

Database accession No. P10480—& Database UniProt 'Online!, Jul. 1, 1989.

Database accession No. Q44268—& Database UniProt 'Online! Nov. 1, 1996.

Database accession No. Q9F7Y6 Database UniProt 'Online!, Mar. 1, 2001.

Database FSTA International Food Information Service (IFIS), Frankfurt/Main, De Mine Y:"Application of the enzymatic methods to the determination of contaminated yolk in egg white." XP002077295 see abstract & Food Research International, vol. 29, No. 1, 19976, pp. 81-84.

Database FSTA International Food Information Service (IFIS), Frankfurt/Main, De Nicolas J:"Action of oxidoreductases in breadmaking. Maturation of soft wheat flours and kneading of doughs." XP002077286 see abstract & Annales De Technologie Agricole, vol. 28, No. 4, 1979, pp. 445-468.

Database FSTA International Food Information Service (IFIS), Frankfurt/Main, De Qi Si J: "New enzymes for the baking industry" XP002077284 see abstract & Food Tech Europe vol. 3, No. 1, 1996, pp. 60-64, Novo Nordisk Ferment Ltd.

Database FSTA International Food Information Service (IFIS), Frankfurt/Main, De Weipert D:"Rheologie von Roggenteigen. II. Der einfluss der enzyme unterschiedlicher spezifitat auf das rheologische verhalten des teiges." XP002077285 see abstract & Getreide, Mehl Und Brot, vol. 26, No. 10, 1972, pp. 275-280.

Database UNIPROTKB Jun. 1, 2003, S. Omura et al: "putative secreted hydrolase from streptomyces avermitilis" XP002376340 retrieved from EBI, HINXTON, UK Database accession No. Q828T4 abstract.

Database UNIPROTKB May 1, 2000, S.D. Bentley et al: "Putative Secreted Hydrolase from Streptomyces coelicolor" XP002376339 retrieved from EBI, HINXTON, UK Database accession No. Q9S2A5 abstract.

Davies, Progress in Industrial Microbiology, Martinelli and Kinghorn (eds.), Elsevier, Amsterdam 1994, 29:525-560.

De Haas GH et al, "Purification and Properties of Phospholipase A from Porcine Pancreas" Biochim. Biophys. ACTA, 1968, vol. 139, pp. 103-117.

Delcros, Jean-Francois, et al., "Effect of mixing conditions on the behavior of lipoxygenase, peroxidase, and catalase in wheat flour doughs", Cereal Chemistry, 1998, vol. 75, No. 1, pp. 85-93.

Dellaporta, et al.; "A Plant DNA Minipreparation Version II"; Plant Molecular Biology Reporter(1983); vol. 1(4); pp. 19-21.

Derewenda et al, "The crystal and molecular structure of the Rhizomuxor miehei Triacylglyceride Lipase at 1•9 Å Resolution", J. Mol. Biol. 1992, 227:818-839.

Derewenda, Urszula, et al., "Catalysis at the Interface: The Anatomy of a Conformational Change in a Triglyceride Lipase", Biochemistry, vol. 31, pp. 1532-1541, 1992.

Direct, A Newsletter from Danisco Ingredients, Sep. 1996.

Directive 2000/36/EC. Http://europa.ea.int/scadplus/leg/en/lvb/121122b.htm. Dato: 16.06.04.

Drost-Lustenberger, Cornelia, et al., "Lipopan F BG-application and mechanism of a new lipase for bread baking", Cereal Food, 2003.

Drost-Lustenberger, Cornelia, et al., "Lipopan F BG-unlocking the natural strengthening potential in dough", Cereal Food, 2004.

Duan, Rui Dong, Fat Digestion and Absorption (2000), p. 25-46, publisher AOCS Press, Champaign III CODEN 69ACBA Conference; general review written in English.

Dubreil, Laurence, et al., "Localization of Puroinoline-a and Lipids in Bread Dough Using Confocal Scanning Laser Microscopy", J. Agric. Food Chem., 2002, vol. 50, pp. 6078-6085.

Ducancel, Frederic, et al., "Complete amino acid sequence of a PLA2 from the tiger snake Notechis scutatus scutatus as deduced from a complementary DNA", Nucleic Acids Research, vol. 16, No. 18, 1988.

Dugi KA et al, "Human hepatic and lipoprotein lipase: the loop covering the catalytic site mediates lipase substrate specificity", Journal of Biological Chemistry (1995), vol. 270, pp. 25, 396—pp. 25, 401.

Dugruix (Edited by) Crystallization of Nucleic Acids and Proteins A Practical Approach.

Dutilh & Groger, "Improvement of Product Attributes of Mayonnaise by Enzymic Hydrolysis of Egg Yolk with Phospholipase A2", 1981 J. Sci. Food Agric. 32, 451-458.

Dybdal, L., et al., "Enzymes in Cereals Processing".

Eddine et al, "Cloning and expression analysis of NhL1, a gene encoding an extracellular lipase from the fungal pea pathogen Nextria haematococca MP VI (Fusarium solani f. sp. pisi) that is expressed in planta", Mol. Genet. Genomics (2001) 265: 215-224.

EFEMA Index of Food Emulsifiers Jan. 2004, 4th Edition.

Ellaiah et al., "Production of lipase by immobilized cells of Aspergillus niger", Process Biochemistry, vol. 39, 2004, pp. 525-528.

Elyk, Alexander, et al., "Lipase-Catalyzed ", JAOCS, vol. 08, No. 5, May 1991, pp. 320-323.

Engelhorn and Raab, "Rapid Electroblotting of Small DNA Fragments from Polyacrylamide Gels", Biotechniques (1991) 11(5): 594-6.

Engelhorn et al., "Rapid Electroblotting of Small DNA Fragments from Polyacrylamide Gels"; Biotechniques(1991); vol. 11(5); pp. 594-596.
Enzymes in food processing (3rd Ed.), Academic press 1993.
EPO, Mobay Chemical Corporation—Decision of the Technical Board of Appeal 3.3.1 dated Jul. 1, 1982, *Official Journal EPO*, Oct. 1982, pp. 394-402.
Ettinger, William F. et al., "Structure of Cutinase Gene, cDNA, and the Derived Amino Acid Sequence from Phytopathogenic Fungi", Biochemistry, vol. 26, pp. 7883-7892, 1987.
Euromonitor International, "The World Market for Dairy Products—Introduction, Executive Summary, Operating Environment, World Market Overview, Key Trends and Developments" in *Euromonitor, Strategy 2000*, Feb. 2001.
European Parliament and Council Directive No. 95/2/EC of Feb. 20, 1995 on food additives other than colours and sweeteners.
European Parliament and Council Directive No. 98/72/EC of Oct. 15, 1998 amending Directive 95/2/EC on food additives other than colours and sweeteners.
Eurpean Journal of Biochemistry, vol. 166, 1987, Published by Springer International on behalf of the Federation of European Biochemical Societies.
Ezra, David, et al., "Coronamycins, peptide antibiotics produced by a verticillate Streptomyces sp. (MSU-2110) endophytic on Monstera sp.", Microbiology, 2004, vol. 150, p. 785-793.
Fauvel, et al.; "Purification of Two Lipases With High Phospholipase A, Activity from Guinea-Pig Pancreas"; Biochimica et Biophysica Acta(1981); vol. 663; pp. 446-456.
Fernandez-Garcia et al., "The use of lipolytic and proteolytic enzymees in the manufacture of manchego type cheese from ovine and bovine milk", 1994 J. Dairy Sci. 77: 2139-2149.
Fernandez-Lafuente, Roberto, et al., The coimmobilization of D-amino acid oxidase and catalase enables the quantitative transformation of D-amino acids (D-phenylalanine) into α-keto acids (phenylpyruvic acid), Enzyme and Microbial Technology, vol. 23, pp. 28-33, 1998.
Ferrer et al, 2000, J. Chem. Technol. Biotechnol. 75, 569-576.
Finizym Technical Information, Novo Enzymes, 1981.
Fødevarenubusteriet (2003). Bekendtgørelse om indhold af transfedtsyrer l olier og fedtstoffer. Bekendtgørelse nr. 160 af Nov. 3, 2003.
Forman, Todd, "Enzymes Used in Bread Baking: An Application Update", Technical Bulletin, vol. XXVI, Issue 10, Oct. 2004.
Fox, et al.; "Isolation and some Properties of Extracellular Heat-Stable Lipases: from *Pseudomonas fluorescens* Strain AFT 36"; Journal of Dairy Research (1988); vol. 50; pp. 77-89.
Frenken N. et al (1992) Appl. Envir. Microbiol. 58 3787-3791.
Frohman, et al.;"Rapid Production of Full-Length cDNAs from Rare transcripts: Amplification using a single gene-specific oligonucleotide primer"; Proc. Natl. Acad. Sci. USA (1988); vol. 85; pp. 8998-9002.
Frost & Sullivan, U.S. Market for Enzymes for food Applications.
Fugman, Douglas A et al Biochemica et Biophysica acia 795 (1984) 191-195.
Galliard T and Dennis S (1974) Phytochemistry vol. 13, pp. 1731-1735.
Galliard, "The Enzymic Breakdown of Lipids in Potato Tuber by Phospholipid- and Galactolipid-Acyl Hydrolase Activities and by Lipoxygenase", Phytochemistry, 1970, vol. 9, pp. 1725-1734.
Gan, Z. et al., "Rapid Communication—Antisera agains: Wheat Diacylgalactosylglycerol (MGDG) and Diacyldigalactosylglycerol (DGDG)", Journal of Cereal Science, vol. 18, pp. 207-210, 1993.
Ganghro AB & Dahot MU, Sci Int. (Lahore), 1992, vol. 4, pp. 169-172.
Gemel, Joanna et al., "Comparison of galactolipase activity and free fatty acid levels in chloroplasts of chill-sensitive and chill resistant plants", European Journal of Biochemistry, vol. 166, 1987.
Geus et al (1987) Nucleic Acids Research 15(9) p. 3743-3759.
Gilbert, E. Jane, et al., "Purification and properties of extracellular lipase from Pseudomonal aeruginosa EF2", Journal of General Microbiology, 1991, vol. 137, pp. 2223-2229.
Gillian, B., Turgeon et al., "Cochliobolus heterostrophus using the Aspergillus nidulans amdS gene", Mol Gen Genet, 201: 450-453, 1985.
Goodey et al, Yeast Biotechnology, Berry et al (eds.), Allen and Unwin, London 1987, pp. 401-429.
Graille J, Lipid Technology, vol. 5, No. 1, 1993, pp. 11-16.
GRAS Notification dated Apr. 11, 2001 by Novozymes for Lecitase$^R$ and Lipopan™ F.
Greenough et al (1996) Food Chem Toxicology 34:161-166 and PubMed abstract in respect thereof.
Greenough R J et al, Food and Chemical Toxicology, vol. 34(2), 1996, pp. 161-166.
Haas and Berka, 1991, Gene, 109:107-113.
Haas, et al., "Enzymatic Phosphatidylcholine Hydrolysis in Organic Solvents: An Examination of Selected Commercially Available Lipases", JAOCS, vol. 71, No. 5, May 1994, pp. 483-490.
Haas, et al.; "Lipases of the Genera *Rhizopus* and *Rhizomucor*: Versatile Catalysts in Nature and the Laboratory"; Food Biotechnology Micro-organisims (1995); pp. 549-588.
Haggag H F et al. Egypt J Food Sci vol. 22, No. 1 pp. 99-107 (1994).
Hansen, Chr., Danisco and Novozymes, Apr. 3, 2002, Food Ingredients day, R&D—the main ingredients for growth.
Hara, et al.; "Comparative Study of Comercially Available Lipases in Hydrolysis Reaction of Phosphatidylcholine"; JAOCS (1997); vol. 74; No. 9, pp. 1129-1132.
Hawker, Kim L., et al., "Heterologous expression and regulation of the Neurospora crassa nit-4 pathway-specific regularlory gene for nitrate assimilation in Aspergillus nidulans", Gene., vol. 100, pp. 237-240, 1991.
Helmsing, "Purification and Properties of Galactolipase", Biochim., Biophys., Acta, vol. 178, pp. 519-533, 1969.
Henderson, H.E., et al., "Structure-function relationships of lipoprotein lipase: mutation analysis and mutagenesis of the loop region", Journal of Lipid Research, vol. 34, 1993, pp. 1593-1602.
Henke, Erik, et al., "Activity of Lipases and Esterases towards Tertiary Alcohols: Insights into Structure-Function Relationships", Angew. Chem. Int. Ed., 2002, vol. 41, No. 17.
Hernquist L & Anjou K (1993) Diglycerides as a stabilizer of the β'-crystal form in margarines and fats, in Fette Seifen Anstrichmittel 2:64-66.
Hernquist L. Herslof B. Larsson K & Podlaha O. (1981) Polymorphism of rapeseed oil with low content of erucic acid and possibilities to stabilize the β'-crystal form in fats, in Journal of Science and Food Agriculture 32:1197-1202.
Hilton S et al, Biochemistry vol. 29, No. 38, 1990, pp. 9072-9078.
Hilton S, Buckley JT, J Biol Chem. Jan. 15, 1991; 266(2): 997-1000.
Hirayama O et al, Biochim Biophys Acta. 1975, vol. 384(1), p. 127-37.
Hjorth, Annegrethe, et al., "A Structional Domain (the lid) Found in Pancreatic Lipases is Absent in the Guinea Pic (Phospho) lipase", Biochemistry, vol. 32, pp. 4702-4704, 1993.
Höfelmann et al, J. Food Sci., 1985, 50:1721-1731.
Holmquist et al., "Lipases from Rhizomucor miehei and Humicola lanuginosa: Modification of the Lid covering the active site alters enantioselectivity", Journal of Protein Chemistry, vol. 12, No. 6, 1993.
Holmquist et al., "Probing a Functional Role of Glu87 and Trp89 in the Lid of Humicola lanuginosa Lipase through Transesterification Reactions in Organic Solvent", Journal of Protein Chemistry, 1995, vol. 14, No. 4, pp. 217-224.
Holmquist et al., "Trp89 in the Lid of Humicola lanuginosa Lipase is Important for Efficient Hydrolysis of Tributyrin", Lipids, vol. 29, No. 9, 1994.
Horn T et al, (1980) Nuc Acids Res Symp Ser 225-232.
Hoshino, et al.; "Calcium Ion Regulates the Release of Lipase of *Fusarium oxysporum*"; J. Biochem (1991); vol. 110; pp. 457-461.
Hoshino, et al.; "Purification and Some Characteristics of Extracellular Lipase from *Fusarium oxysporum f. sp. lini*"; Biosci. Biotech. Biochem (1992); pp. 660-664.
Hoshino, Tamotsu, et al., "Purfication and Some Characteristics of Extracellular Lipase from Fusarium oxysporum", Biosci. Biotech. Biochem., vol. 56, No. 4, pp. 660-664, 1992.

Hossen, Monjur and Hernandez, Ernesto, Lipids, vol. 39, Aug. 2004, pp. 777-782.
Hou Ching T, Journal of Industrial Microbiology, vol. 13, No. 4, 1994, pp. 242-248.
Hübner et al., "Interactions at the lipid-water interface", Chemistry and physics of Lipids, vol. 96, 1998, pp. 99-123.
Hugh-Jensen, Birgitte, et al., "Rhizomucor miehei Triglyceride Lipase is Processed and Secreted from Transformed Aspergillus oryzae", Lipids, vol. 24, No. 9, pp., 1989.
Humum et al., "Enzyme Catalysed Synthesis in Ambient Temperature Ionic Liquids", Biocatalysis and Biotransformation, vol. 19, pp. 331-338.
Icard-Verniere, Christele, et al., "Effects of mixing conditions on pasta dough development on biochemical changes", Cereal Chemistry, 1999, vol. 76, No. 4, pp. 558-565.
Igrejas, Gilberto, et al., "Genetic and Environmental Effects on Puroindoline-a and Puroindoline-b Content and their Relationship to Technological Properties in French Bread Wheats", Journal of Cereal Science, vol. 34, 2001, pp. 37-47.
Ikeda H et al, Nature Biotech, vol. 21, 2003, p. 526-531.
Industrial enzymology (2nd Ed.), The Macmillan press 1996.
Ishihara et al Biochimica et Biophysica Acta 388 (1975) 413-422.
Isobe and Nokihara, Febs. Lett., 1993, 320:101-106.
Isobe K et al, Journal of Molecular Catalysis B: Enzymatic 1 (1995), pp. 37-43.
Iwai and Tsujisaka (in Lipases, Borgström and Brockman (eds.), Elsevier, Amsterdam, 1984, pp. 443-468.
Izco et al. Adv Food Sci vol. 21 N 3/4, (10-116) 1999.
Jacob, Jules S., et al., "The Effects of Galactolipid Depletion on the Structure of a Photosynthetic Membrane", The Journal of Cell Biology, vol. 103, Oct. 1986, pp. 1337-1347.
Jacobsberg B. & Oh C.H. (1976) Studies in Palm Oil Crystallisation, in Journal of the American Oil Chemist Society 53:609-616.
jan-Willem F. A. Simons et al., "Cloning, purification and characterisation of the lipase from Staphylococcus epidermidis", Eur. J. Biochem., vol. 253, pp. 675-683, 1998.
Jeng-yen Lin, Matthew, "Wheat Polar Lipids—A Theseis Submitted to the Graduate Faculty of the North Dakota State University of Agriculture and Applied Science", May 1972.
Joerger et al., "Alteration of Chain Length Selectivity of a Rhizopus delemar Lipase through Site-Directed Mutagenesis", Lipids, vol. 29, No. 6, 1994, pp. 377-384.
Jong et al.; "American Type Culture Collection Catalogue of Filamentous FUNGI"; Eighteenth edition (1991).
Joshi, et al.; "Specificity of Fungal Lipase in Hydrolytic Cleavage of Oil"; Acta Microbiologica Hungarica (1987); vol. 34(2); pp. 111-114.
Joshi, Sunita, et al., "Specificity of Lipase isolated from Fusarium oxysporum", Department of Chemistry, Indian Institute of Technology, vol. 25, No. 1 & 2, pp. 76-78.
Juffer, A.H., et al., "Adsorption of Proteins onto Charged Surfaces: A Monte Carlo Approach with Explicit Ions", Journal of Computational Chemistry, vol. 17, No. 16, pp. 1783-1803, 1996.
Jurgens, Catharina, et al., "Directed evolution of a (βα)8-barrel enzyme to catalyze related reactions in two different metabolic pathways", PNAS, Aug. 29, 2000, vol. 97, No. 18, pp. 9925-9930.
Kaniuga Z, Acta Biochim Pol. (1997), vol. 44(1), p. 21-35.
Kapur J & Sood ML, J. Parasit., 1986, vol. 72, pp. 346-347.
Kasai, Naoya, et al., "Chiral C3 epoxides and halophydrins: Their preparation and synthetic application", Journal of Molecular Catalysis B: Enzymatic, vol. 4, 1998, pp. 237-252.
Kasai, Naoya, et al., "Optically Active Chlorohydrins as Chiral C3 and C4 Building Units: Microbial Resolution and Synthetic Applications", Chirality, vol. 10, pp. 682-692.
Kawamura and Doi, J. of Bacteriology Oct. 1984, p. 442-444.
Keller, R.C.A., et al., "Competitive Adsorption Behaviour of Wheat Flour Components and Emulsifiers at an Air-Water Interface", Journal of Cereal Science, vol. 25, 1997, pp. 175-183.
Keum J S et al. Korean J Dairy Sci 15 (2): 103-117 1993.
Kim, Hyung Kwoun, et al., Expression and characterization of Ca2+-independent lipase from Bacillus pumilus B26, Biochimica et Biophysica Acta, vol. 1583, 2002, pp. 205-212.

Kim, Myo-Jeong, et al., "Thermal Inactivation Kinetics and Application of Phospho and Galactolipid-Degrading Enzymes for Evaluation of Quality Changes in Frozen Vegetables", J. Agric. Food Chem., 2001, vol. 49, pp. 2241-2248.
Kimura, Yoshiharu, et al., "Application of Immobilized Lipase to Hydrolysis of Triacylglyceride", Eur J. Appl Microbiol Biotechnol, 1983, vol. 17, pp. 107-112.
King et al, Molecular and Cell Biology of Yeasts, Walton and Yarronton (eds.), Blackie, Glasgow, 1989, pp. 107-133.
Kirk, Ole, et al., "Fatty Acid Specificity in Lipase-Catalyzed Synthesis of Glucoside Esters" Biocatalysis, 1992, vol. 6, pp. 127-134.
Klein, Robert R., et al., "Altered Acyl Chain Length Specificity of Rhizopus delemar Lipase Through Mutagenesis and Molecular Modeling", Lipids, 1997, vol. 32, No. 2, pp. 123-130.
Klein, Robert R., et al., "Additive Effects of Acyl-Binding Site Mutations on the Fatty Acid Selectivity of Rhizopus delemar Lipase", JAOCS, vol. 74, No. 11, 1997.
Kocak et al, Milchwissenschaft 51(1), 1996.
Kochubei et al Role of lipids in the organization of the closest surroundings of the reaction centers(1976) Institute of Plant Physiology.
Kochubei S M et al, Biophysics (1981), vol. 26(2), p. 299-304.
Kochubei S M et al, Mol Biol (Mosk) (1975), vol. 9(2), (p. 190-3) p. 150-153.
Kochubei SM et al, Mol Biol (Mosk) (1978),(vol. 1, p. 47-54) p. 32-37.
Kolkovski et al (1991) Fish Nutrition in Practice, Biarritz (France), Jun. 24-27.
Kostal, Jan, et al., "Enhanced Arsenic Accumulation in Engineered Bacterial Cells Expressing ArsR", Applied and Environmental Microbiology, Aug. 2004, pp. 4582-4587.
Kouker, et al., "Specific and Sensitive Plate Assay for Bacterial Lipases"; Applied and Environmental Microbiology (1987); vol. 53(1); pp. 211-213.
Krishna, Sajja Hari, et al., "Enantioselective transesterification of a tertiary alcohol by lipase A from Candida antarctica", Tetrahedron: Asymmetry, vol. 13, 2002, pp. 2693-2696.
Kristensen A.C.J. (2004) Preparation of margarine and spreads by enzyme-generated emulsifiers. Master thesis, The Royal Veterinary and Agricultural University, Frederiksberg, Copenhagen.
Krog, Cereal Foods World, The American Association of Cereal Chemists, p. 10, Jan. 1979, vol. 24, No. 1, pp. 10-11.
Krupa, Zbigniew et al., "Requirement of Galactolipids for Photosystem J Activity in Lyophilized Spinach Chloroplasts", Biochimica et Biophysica Acta, 408, pp. 26-34, 1975.
Kuipers, Oscar P., et al., "Enhanced Activity and Altered Specificity of Phospholipase A2 by Deletion of a Surface Loop", Science, vol. 244, 1989.
Kunze, Hans, et al., "On the mechanism of lysophospholipase activity of secretory phospholipase A2 (EC 3.1.1.4): deacylation of monoacylphosphoglycerides by intrinsic sn-1 specificity and Ph-dependent acyl migration in combination with sn-2 specificity", Biochimica et Biophysica Acta, vol. 1346, 1997, pp. 86-92.
Kuwabara, et al., "Purification and Some Properties of Water-soluble Phospholipase B from Torulaspora delbrueckii", J. Biochem., vol. 104, pp. 236-241, 1988.
Kuwabara, et al., "Purification and Some Properties of Water-soluble Phospholipase", Agric. Biol. Chem., vol. 52, No. 10, pp. 2451-2458, 1988.
Kweon et al., "Phospholipid Hydolysate and Antistaling Amylase Effects on Retrogradation of Starch in Bread", Journal of Food Science, vol. 59, No. 5, 1994.
Larsen N G et al, Journal of Cereal Science (1990), vol. 12(2), p. 155-164.
Lecointe et al Biotechnology Letters, vol. 18, No. 8 (August) pp. 869-874.
Lee, Keun Hyeung, et al., "Identification and characterization of the antimicrobial peptide corresponding to C-terminal B-sheet domain of tenecin 1, an antibacterial protein of larvae of Tenebrio molitor", Biochem. J., 1996, vol. 334, pp. 99-105.
Leggio, Leila Lo, et al., "The 1.62 A structure of Thermoascus aurantiacus endoglucanase: completing the structural picture of subfamilies in glycoside hydrolase family 5", FEBS Letters, vol. 523, 2002, pp. 103-108.

Leidich et al., "Cloning and Disruption of caPLB1, a Phospholipase B Gene Involved in the Pathogenicity of Candida albicans", The Journal of Biological Chemistry, vol. 273, No. 40, oo. 26078-26086, 1998.

Li, W., et al., "Surface properties and locations of gluten proteins and lipids revealed using confocal scanning laser microscopy in bread dough", Journal of Cereal Science, vol. 39, 2004, pp. 403-411.

Lih-ling Wang et al, J Agric. Food. Chem. (1993), 41, 1000-1005.

Lima, Vera L.M., et al., "Lecithin-cholesterol acyltransferase (LCAT) as a plasma glycoprotein: an overview", Carbohydrate Polymers, vol. 55, 2004, pp. 179-191.

Lin M J Y et al, Cereal Chemistry (1974), vol. 51(1), p. 34-45.

Lin S et al, Enzyme and Microbial Technology 18 (1996), pp. 383-387.

Lipase A "Amano" 6 Assay Note and Product Specification from Armano Pharmaceutical Co Ltd Nagoya Japan, Dec. 16, 1985.

Lipase A "Amano" 6 Assay Note and Product Specification from Armano Pharmaceutical Co Ltd Nagoya Japan, Aug. 27, 1985.

Lipase A "Amano" 6 product sheet, Apr. 1, 1999.

Lipase SP677 as a Baking Enzyme, from Novo Nordisk, Denmark, Mar. 17, 1994.

Lipopan F: Keep the quality—cut your costs 2000 Novozymes A/S. www.enzymes.novo.dk/cgl-bin/bvisapi.dll/biotimes/one_article. jsp?id=16947&lang=en&t=b1.

Litthauer, Derek, et al., "Pseudomonas luteola lipase: A new member of the 320-residue Pseudomonas lipase family", Enzyme and Microbial Technology, vol. 30, pp. 209-215, 2002.

Llustenberger, Cornelia, et al., "Application of Noopazyme in Asian Noodles and Non-Durum Pasta", Cereal Food, 2002-18584-01, p. 1, vol. 11.

Llustenberger, Cornelia, et al., "Enzymes in Frozen Dough and Parbaked Bread", Cereal Food, 2001-17056-01, p. 1, vol. 19.

Longhi, Sonia, et al., "Atomic Resolution (1.0 Å) Crystal Structure of Fusarium solani Cutinase: Stereochemical Analysis" J. Mol. Biol. vol. 268, pp. 779-799, 1997.

Lozano et al., "Over-stabilization of Candida antarctica lipase B by ionic liquids in ester synthesis", Biotechnology Letters, vol. 23, pp. 1529-1533, 2001.

Luzi, Paola et al, Genomics (1995), vol. 26(2), p. 407-9.

Madsen J.S. & Qvist K.B. (1997) J. Food Sci. 62, 579-582.

Mao, Cungui, et al., "Cloning and Characterization of a Saccharomyces cerevisiae Alkaline Ceramidase with Specificity for Dihydroceramide", The Journal of Biological Chemistry, vol. 275, No. 40, 2000, pp. 31369-31378.

Maria Teres Neves Petersen, PhD, "Total Internal Reflection Fluorescence Flow System with Electrochemical Control", TIRF-EC Flow System, Sep. 2002.

Marion D et al—Chapter 6, pp. 131-p. 167 of "Interactions the Keys to Cereal Quality" 1998 ISBN 0 913250-99-6 (ed. Hamer & Hoseney).

Marion D et al pp. 245-260 of Wheat Structure Biochemistry & Functionality (ed Schofield JP) ISBN 085404777-8 published in 2000—(It states that it is the Proceedings of Conference organised by Royal Soc of Chemistry Food Chemistry Group held on Apr. 10-12, 1995, in Reading, UK. However, it is unclear why there was such a delay).

Marsh, Derek, et al., "Derivatised lipids in membranes. Physicochemical aspexts of N-biotinyl phosphatidylethanolamines and N-acyl ethanolamines", Chemistry and Physics of Lipids, vol. 105, 2000, pp. 43-69.

Martinelle et al., "The Role of Glu87 and Trp89 in the lid of Humicola lanuginosa lipase", Protein Engineering, vol. 9, No. 6, 1996, pp. 519-524.

Martinez, Chrislaine, et al., "Engineering cysteine mutants to obtain crystallographic phases with a cutinase from Fusarium solani pisi", Protein Engineering, vol. 6, No. 2, pp. 157-165, 1993.

Martinez, Diego, et al., "Genome sequence of the lignocellulose degrading fungus Phanerochaete chrysosporium strain RP78", Nature Biology, May 2, 2004.

Mase at al., "Purification and Characterization of a new Lipase from Fusarium sp. TM-30", Biosci. Biotech. Biochem., vol. 59, No. 9, pp. 1771-1772, 1995.

Mason, Research Disclosure, Kenneth Mason Publications, Westbourne GB No. 390, Oct. 1996, pp. 661-662.

Masuda, Naoko, et al., "Primary structure of protein moiety of Penicillium notatum phospholipase B deduced from the Cdna", Eur. J. Biochem., vol. 202, pp. 783-787, 1991.

Matos AR, Lipid Catabolism: Lipid Degradation, 2000, p. 779-781.

Matos, A.R., et al., "A patatin-like protein with galactolipase activity is induced by drought stress in Vigna unguiculata leaves", Biochemical Society Transactions, vol. 28, part 6, 2000.

Matos, AR et al, Febs Letters, 491 (2001) p. 188-192.

Matsuda H et al, Biochim Biophys Acta, (1979), vol. 573(1), p. 155-65.

Matsuoka, et al.; "Purification and properties of a Phospholipase C That has High Activity toward Sphingomyelin from *Aspergillus Saitoi*"; Biotiechonology and Applied Biochemistry (1987); vol. 9, pp. 401-409.

Matthes et al, (1984) EMBO J. 3, p. 801-805.

Max-Planck-Institut fur Kohlenforschung et al., "Controlling the enantioselectivity of enzymes by directed evolution: Practical and theoretical ramifications".

McAuley, Katherine E., et al., "Structure of a feruloyl esterase from Aspergillus niger", Acta Crystallographica, Section D, pp. 878-887, 2004.

McCoy M G et al, Journal of Lipid Research (2002), vol. 43, pp. 921-929.

McNeill G.P. & Berger R.G. (1993) Enzymatic glycerolysis of palm oil fractions and palm oil based model mixture: Relationship between fatty acid composition and monoglyceride yield, in Food Biotechnology 7: 75-87.

McNeill, Gerald P., et al., "High-Yield Enzymatic Glycerolysis of Fats and Oils", JAOCS, vol. 68, No. 1, Jan. 1991.

McNeill, Gerald P., et al., "Selective Distribution of Saturated Fatty Acids into the Monoglyceride Fraction During Enzymatic Glycerolysis", JAOCS, vol. 69, No. 11, Nov. 1992.

Memo: From Charlotte Johanson?, "Short introduction/ status on Ferulic Acid Esterases and Acetyl Xylan Esterases", Jan. 9, 2004.

Meyer, V., et al., "Transcriptional regulation of the Antifungal Protein in Aspergillus giganteus", Mol Genet Genomics, 2002, vol. 266, pp. 747-757.

Michalski et al., "Photosynthetic apparatus in chilling-sensitive plants. VII. Comparison of the effect of galactolipase treatment of chloroplasts and cold-dark storage of leaves on photosynthetic electron flow", Biochimica et Biophysica Acta, vol. 589, pp. 84-99, 1980.

Mielgo, I., et al., "Covalent immobilisation of manganese peroxidases (MnP) from Phanerochaete chrysosporium and Bjerkandera sp. BOS55", Enzyme and Microbial Technology, vol. 32, 2003, pp. 769-775.

Miller, Byron S., et al., "A Comparison of Cereal, Fungal, and Bacterial Alpha-Amylases as Supplements for Breadmaking", Food Technology, Jan. 1953.

Mine Y, Food Research International, 29(1), 1996, pp. 81-84.

Ministerio da Ciencia e Tecnologia, *Diario Oficial da Uniao*, Jul. 15, 2003.

Mogensen, Jesper E., et al., "Activation, Inhibition, and Destabilization of Thermomyces lanuginosus Lipase by Detergents", Biochemistry, vol. 44, pp. 1719-1730, 2005.

Molecular Biological Methods for Bacillus—Chapter 3 (Ed. C.R. Harwood and S.M. Cutting) 1990, John Wiley and Sons Ltd, Chichester, UK.

Mølgaard, Anne, et al., "Rhamnogalacturonan acetylesterase elucidates the structure and function of a new family of hydrolases", Structure, vol. 9, No. 4, 2000.

Molochnaya Promyshlennost 1980 No. 11 21-25, 47—abstract from Food Sci & Tech Abs.

Monographs for Emulsifiers for Foods, EFEMA Nov. 1985 2nd Edition.

Moore, Charles M., et al., "Metal ion homeostasis in Bacillus subtilis", Current Opinion in Microbiology, 2005, vol. 8, pp. 188-195.

Morgan, Keith R., et al., "Stalling in Starch Breads: The Effect of Antistaling α-Amylase", Starch/Stärke, vol. 49, 1997, pp. 59-66.

Morgan-Jones, Gareth; "Notes on Coelomycetes.II. Concerning the Fusicoccum Anamorph of Botryosphaneria Ribis"; vol. Xxxx, pp. 117-125; Oct.-Dec. 1987.

Morinaga et al Biotechnology (1984) 2, p. 636-639.

Morten, T. & A., Letter, Rodovre, Jul. 2004.

Mukherjee, Kumar D. et al., "Enrichment of y-linolenic acid from fungal oil by lipase-catalysed reactions", Appl. Microbiol Biotechnol (1991), vol. 35, pp. 579-584.

Murakami, Nobutoshi, et al., "Enzymatic Transformation of Glyceroglycolipids into sn-1 and sn-2 Lysoglyceroglycolipids by use of Rhizopus arrhizus Lipase", Tetrahedron, vol. 50, No. 7, pp. 1993-2002, 1994.

Mustranta, Annikka, et al., "Comparison of Lipases and Phosphlipases in the Hydrolysis of Phospholipids", Process Biochemistry, vol. 30, No. 5, pp. 393-401, 1995.

Nagano, et al.; "Cloning and Nucleotide Sequence of cDNA Encoding a Lipase from *Fusarium keteroporum*"; J. Biochem (1994); vol. 116; pp. 535-540.

Nagao et al, J. Biochem 124, 1124-1129, 1998.

Nagao et al, J. of Bioscience and Bioengineering vol. 89, No. 5, 446-450, 2000.

Nagao et al, J. of Molecular Catalysis B: Enzymatic 17 (2002) 125-132.

Nagao et al, JAOCS vol. 78, No. 2, 2001.

Nagao, Toshihiro et al., "Cloning and Nucleotide Sequence of CDNA Encoding a Lipase from Fusarium heterosporum", J. Biochem., vol. 116, pp. 535-540, 1994.

Nagao, Toshihiro et al., "Expression of Lipase cDNA from Fusarium heterosporum by Saccharomyces cereviisiae: High-Level Production and Purification", Journal of Fermentation and Bioengineering, 1996, vol. 81, No. 6, pp. 488-492.

Nagodawlthana et al., "Enzymes in Food Processing", Third Edition, 1993, Academic Press, Inc.

National Research Council (U.S.) Committee on Specifications of the Food Chemicals Codex, "Lipase Activity" in *Food Chemicals Codex* (1981) National Academy Press, Washington, D.C. pp. 492-493.

Needleman & Wunsch (1970), J. of Molecular Biology 48, 443-453.

Nelson and Long, Analytical Biochemistry (1989), 180, p. 147-151.

Nerland A H, Journal of Fish Diseases, vol. 19, No. 2, 1996, pp. 145-150.

Ness, Jon. E., et al., "DNA shuffling of subgenomic sequences of subtilisin" Nature Biotechnology, vol. 17, Sep. 1999.

Nestle Research Center, Brochure for "Food Colloids 2006" in Montreux, Switzerland, Apr. 23-26, 2006.

Neugnot Virginie et al, European Journal of Biochemistry, 2002, vol. 269, pp. 1734-1745.

Newport, G., et al., "KEX2 Influences Candida albicans Proteinase Secretion and Hyphal Formation", The Journal of Biological Chemistry, 1997, vol. 272, No. 46, pp. 28954-28961.

Nicolas, Anne, et al., "Contribution of Cutinase Serine 42 Side Chain to the Stabilization of the Oxyanion Transition State", Biochemistry, vol. 35, pp. 398-410, 1996.

Nierle W et al, Fette Seifen Anstrichmittel (1981), vol. 83(10), p. 391-395.

Nierle, W., et al., "Versuche zur Verlangerung der Haltbarkeit von Dartoffelprodukten", Chem. Mikrobiol. Technol. Lebensm., 1975, vol. 3, pp. 172-175.

Nobutoshi M et al, Tetrahedron Letters (1991), vol. 31(1), p. 1331-4.

Novozymes data dated Jul. 17, 2005 entitled "Baking performance of prior art lipases from *Humicola lanuginosa, Aspergillus tubigensis, Rhizopus delemar* and *Rhizomucor miehei*, and their activity on galactolipids in dough".

Novozymes Memo—Test of lipases for EP1193314B1, Jul. 6, 2005.

Novozymes Report 2002 Annual Report.

Novozymes, "Biowhitening—a new concept for steamed bread", *BioTimes*, Jan. 2005.

Novozymes, "Breakthrough: Less Fattening Fried Food" *BioTimes*, Jun. 2001, No. 2.

Novozymes, "Enzymes for dough strengthening", 2001.

Novozymes, "Lipopan F BG—application and mechanism of a new lipase for bread baking" (Draft) *Cereal Food* (2003) (Author: Drost-Lustenberger, C. et al.).

Novozymes, "Product Sheet for Lipopan F BG", *Cereal Food*, (2001).

Novozymes, "Product Sheet for Lipopan FS BG", *Cereal Food* (2002).

Novozymes, "Product Sheet for Lipopan S BG", *Cereal Food* (2002).

Novozymes, "Revolutionizing baking", *BioTimes* (2002) pp. 6-7.

Novozymes, "Strong sales for lipase that makes dough stronger" *BioTimes*, Dec. 2003.

Novozymes, "The perfect roll every time for steers", *BioTimes*, Sep. 2003.

Novozymes, "The value of innovation", *BioTimes*, Mar. 2004.

Novozymes, "The vital role of technical service in baking", *BioTimes*, Jun. 2004.

Ohm, J.B., et al., "Relationships of Free Lipids with Quality Factors in Hard Winter Wheat Flours", Cereal Chem., vol. 79, No. 2, pp. 274-278, 2002.

Ohta, S. at al., "Application of Enzymatic Modification of Phospholipids on Breadmaking", Abstract from AACC 68th Annual Meeting in Kansas City, MO, Oct. 30-Nov. 3, 1983, published in Cerial Foods World, p. 561.

Ohta, Yoshifumi, et al., "Inhibition and Inactivation of Lipase by Fat Peroxide in the Course of Batch and Continuous Glycerolyses of Fat by Lipase", Agric. Biol. Chem., vol. 53, No. 7, pp. 1885-1890, 1989.

Okiy D.A. (1977) Partial glycerides and palm oil Crystallisation, in Journal of Science and Food Agriculture 28:955.

Okiy D.A. (1978) Interaction of triglycerides and diglycerides of palm oil, in Oleagineux 33:625-628.

Okiy D.A., Wright, W.B., Berger, K.G. & Morton I.D. (1978), The physical properties of modified palm oil, in Journal of Science of Food and Agriculture 29:1061-1068.

Oluwatosin, Yemisi E., et al., "Phenotype: a Possible Role for the Kex2 Endoprotease in Vacuolar Acidification", Molecular and Cellular Biology, 1998, pp. 1534-1543.

Oluwatosin, Yemisi E., at al., "Mutations in the Yeast KEX2 Gene Cause a Vma-Like Phenotype: a Possible Role for the Kex2 Endoprotease in Vacuolar Acidification", Molecular and Cellular Biology, vol. 18, No. 3, pp. 1534-1543, Mar. 1998.

Orberg, Marie-Louise, "Self-assembly Structures Formed by Wheat Polar Lipids and their Interaction with Lipases", Master of Scient Thesis, Apr. 2005.

Orskov, Janne, et al., "Solubilisation of poorly water-soluble drugs during in vitro lipolysis of medium- and long-chain triacylglycerols", European Journal of Pharmaceutical Sciences, vol. 23, 2004. pp. 287-296.

Osman, Mohamed, et al., "Lipolytic activity of Alternaria alternata and Fusarium oxysporum and certain properties of their lipids", Microbios Letters, vol. 39, pp. 131-135, 1988.

O'Sullivan et al, J Plant Physiol, vol. 313, (1987) p. 393-404.

Palomo, Jose M., et al., "Enzymatic production of (3S, 4R)-(−)-4-(4'-fluorophenyl)-6-oxo-piperidin-3-carboxylic acid using a commerical preparation of lipase A from Candida antarctica: the role of a contaminant esterase" Tetrahedron: Asymmetry, vol. 13, 2002, pp. 2653-2659.

Palomo, Jose M., et al., "Enzymatic resolution of (±)-glycidyl butyrate in aquenous media. Strong modulation of the properties of the lipase from Rhizopus oryzae via immobilization techniques", Tetrahedron: Asymmetry, vol. 15, 2004, pp. 1157-1161.

Palomo, Jose M., et al., "Modulation of the enantioselectivity of Candida antarctica B lipase via conformational engineering: kinetic resolution of (±)-α-hydroxy-phenylacetic acid derivatives", Tetrahedron: Asymmetry, vol. 13, 2002, pp. 1337-1345.

Patent Abstracts of Japan vol. 016, No. 528 (C-1001), Oct. 29, 1992 & JP 04 200339 A see abstract.

Patent Abstracts of Japan vol. 095, No. 001, Feb. 28, 1995 & JP 06 296467 A see abstract.

Peelman F, et al, Protein Science Mar. 1998; 7(3): 587-99.

Penninga et al, Biochemistry (1995), 3368-3376.

Persson, Mattias, et al., "Enzymatic fatty acid exchange in digalactosyldiacylglycerol", Chemistry and Physics of Lipids, vol. 104, 2000, pp. 13-21.

Peters, G.H., et al., "Active Serine Involved in the Stabilization of the Active Site Loop in the Humicola lanuginosa Lipase", Biochemistry, 1998, vol. 37, pp. 12375-12383.

Peters, Günther H., et al., "Theoretical Investigation of the Dynamics of the Active Site Lid in Rhizomucor miehei Lipase", Biophysical Journal, vol. 71, 1996, pp. 119-129.

Plijter J and JHGM Mutsaers, The surface rheological properties of dough and the influence of lipase on it, Gist-brocades, Bakery Ingredients Division, Oct. 1994.

Plou et al, J. Biotechnology 92 (2002) 55-66.

Ponte J G, Cereal Chemistry (1969), vol. 46(3), p. 325-29.

Punt and van den Hondel, Meth. Enzym., 1992, 216:447-457.

Pyler, E.J., "Baking Science and Technology Third Edition", vol. 1, 1988.

Pyler, E.J., "Baking Science and Technology Third Edition", vol. II, 1988.

Queener et al. (1994) Ann N Y Acad Sci. 721, 178-93.

Rambosek and Leach, CRC Crit. Rev. Biotechnol., 1987, 6:357-393.

Rapp, Peter, et al., "Formation of extracellular lipases by filamentous fungi, yeasts, and bacteria", Enzyme Microb. Technol., 1992, vol. 14, November.

Rapp, Peter; "Production, regulation, and some properties of lipase activity from *Fusarium Oxysporum* f. sp. *vasinfectum*"; Enzyme and Microbial Technology(1995); vol. 17; pp. 832-838.

Reetz M.T., Jaeger K.E. Chem Phys Lipids. Jun. 1998 ; 93(1-2): 3-14.

Reetz Manfred T, Current Opinion in Chemical Biology, Apr. 2002, vol. 6, No. 2, pp. 145-150.

Reiser J et al. (1990) Adv Biochem Eng Biotechnol. 43, 75-102.

Richardson & Hyslop, pp. 371-476 in Food Chemistry, 1985, second edition, Owen R. Fennema (ed), Manel Dekker, Inc, New York and Basel.

Richardson and Hyslop, "Enzymes: XI—Enzymes Added to Foods During Processing" in *Food Chemistry*, Marcel Dekker, Inc., New York, NY 1985.

Arskog and Joergensen, "Baking performance of prior art lipases from *Candida cylindracea* and *Aspergillus foeditus* and their actiivty on galactolipids in dough", Novozymes Report 2005.

Arskog and Joergensen, "Baking performance of prior art lipases from *Humicola lanuginosa, Aspergillus tubigensis, Rhizopus delemar* and *Rhizomucor miehei*, and their actiivty on galactolipids in dough", Novozymes Report 2005.

U.S. Appl. No. 60/039,791, filed Mar. 4, 1997, Clausen.

U.S. Appl. No. 60/189,780, filed Mar. 16, 2000, Soe.

U.S. Appl. No. 60/489,441, filed Jul. 23, 2003, Kreij.

Larchenkova LP et al. "Effect of starter and souring temperature on reproduction of *E coli* and lactobacili in milk," International Dairy Congress XXI, vol. 1, book 2. Moscow, Jul. 12-16, 1982, Brief Communications, p. 539.

Lecointe, C. et. al. "Ester Synthesis in Aqueous Media in the Presence of Various Lipase," Biotechnology Letters, vol. 18, No. 8, p. 896-874, Aug. 1996.

Lee, Kyung S., et al., The Saccharomyces cerevisiae PLB1 Gene Encodes a Protein Required for Lysophospholipase and Phospholipase B Activity, The Journal of Biological Chemistry, vol. 269, No. 31, Issue of Aug. 5, pp. 19725-19730, NZAS—0418807.

Lipomod L338P Data Sheet, Biocatalysts Limited, Aug. 15, 2003, p. 1-2.

Lipopan F: Keep the quality—cut your costs. Novozymes A/S. http://www.enzymes.novo.dk/cgl-bin/bvisapi.dll/biotimes/one_article.jsp?id=16947&lang=en&t=b1 (2000).

Lustenberger, C. et. al., "Application of lipase in Asian noodles and nondurum pasta." American Association of Cereal Chemists. 2000 Annual Meeting, Kansas City Missouri, Nov. 5-9, 2000.

Lo Y-C et al. Crystal structure of *Escherichia coli* Thioesterase I/ProteaseI/Lysophospholipase L1: Consensus sequence blocks constitute the catalytic center of SGNH-hydrolases through a conserved hydrogen bond network. Journal of Molecular Biology, London, GB, vol. 330, No. 3, 539-551.

Reetz, M. et al., "Controlling the enantioselectivity of enzymes by directed evolution: Practical and theoretical ramifications", PNAS, Apr. 2004, vol. 101, No. 16, p. 5716-5722.

McNeill, Gerald P., et al., "Further Improvements in the Yield of Monoglycerides During Enzymatic Glycerolysis of Fats and Oils", JAOCS, Jan. 1991, vol. 68, No. 1, p. 6-10.

McNeill, Gerald P., et al., "Solid Phase Enzymatic Glycerolysis of Beef Tallow Resulting in a High Yield of Monoglyceride", JAOCS, Nov. 1990, vol. 67, No. 11, p. 779-783.

Meyers, R., "Molecular Biology and Biotechnology: A Comprehensive Desk Reference," VCH Publishers, p. 1-9, (1995).

Mohsen et al., "Specificity of Lipase Produced by Rhyopus Delemar and Its Utilization in Bread Making", Egypt. J Food. Sci. vol. 14, No. 1, pp. 175-182.

Monick, J., "Alcohols: Their Chemistry, Properties and Manufacture," Reinhold Book Corporation, p. 1-7, 1968.

Murakami, Mototake, et al., "Transesterification of Oil by Fatty Acid-Modified Lipase", Technical Research Institute, JAOCS, Jun. 1993, vol. 70, No. 6, p. 571-574.

General Conditions of the company limited by shares N.V. Nederlandsch Octrooibureau Terms and Conditions, Jan. 2004.

Néron, et al., "Effects of lipase and the phosphlipase on the lipids hydrolysis during mixing in correlation with the oxygen consumption by wheat flour dough during kneading" Sep. 20-22, 2004, available at http://www.cnam.fr/biochimie.

Nielsen et al., "Lipases A and B from the yeast Candida antarctica", Research and Development, Novo Nordisk Bioindustry, 1999, p. 49-61.

Nierle, Von W. et al. "Weizenlipide: Funktion and Einflub bei der Verarbeitung des Mehles" with English abstract "Wheat lipids: Function and Effect in Flour Processing", vol. 83, No. 10, p. 391-395, 1981.

Novozymes, "Product Sheet for Lipopan F BG", *Cereal Food*, (2001), p. 1-3.

Novozymes, "Product Sheet for Noopazyme", Cereal Food (2002) p. 1-3.

Novozymes, "Product Sheet for Novozym 27016," Baking (2000), p. 1-6.

Novozymes, "Product Sheet for Novozym 27019," Baking (2000), p. 1-6.

Novozymes, "Product Sheet for Novozym 27080," Cereal Food (2003), p. 1-3.

Novozymes brochure "Enzymes at work" 2004, p. 1-60.

Nylander et al., "Interaction between lipids and lipases A collection of papers presented at the European Meeting on lipid and lipase interaction at Lund University" Sep. 2000.

Ognjenovic Radomir et al, Acceleration of ripening of semi-hard cheese by proteolytic and lipolytic enzymes, Proceedings for Natural Sciences, 1996, vol. 91, p. 5-17.

O'Mahony et al. "Hydrolysis of the lipoprotein fractions of milk by Phospholipase C," Journal of Dairy Science, 1972, vol. 55, No. 4, p. 408-412.

Ostrovskaya L K et al, "Spectral Features of the Action of Galactolipase on Native Forms of Chlorophyll," Dokl Akad Nauk SSSR, (vol. 186(4), p. 961-3) p. 59-61.

Outtrup, Gunther H., et al., "Properties and Application of a Thermostable Maltogenic Amylase Produced by a Strain of Bacillus Modified by Recombinant-DNA Techniques", Starch/Starke, vol. 36, No. 12, pp. 405-411, 2003.

Pariza, Michael, et al., "Evaluating the safety of Microbiol Enzyme Preparations Used in Food Processing: Update for a New Century", Regulatory Toxicology and Pharmacology, vol. 33, pp. 173-186, 2001.

Peters, G.H., et al.; "Essential motions in lipases and their relationship to the biological function", Proceedings of the German Conference on Bioinformatics, GCB '96, Leipzig, Germany, Sep. 30-Oct. 2, 1996, poster, p. 280-282 NZAS—0031438.

Peters, G.H., et al.; "Dynamics of Rhizomucor miehei lipase in a lipid or aqueous environment: Functional role of glycines"; Draft for Biophys. J, Nov. 1996, vol. 71, No. 5, p. 2245-2255 NZAS—0031441.

Harborne J.B. et al. (editors), Phytochemical Dictionary: A Handbook of Bioactive Compounds from Plants, Taylor & Francis, 1993, ISBN 978050667363 Chapter 4, "Sugar Alcohols and Cyclitols", p. 20-23.

Picon et al., "Release of Encapsulated Proeinase from Dehydration-Rehydration Liposomes by a Co-encapsulated Phospholipase," Biotechnology Letters, Oct. 1995, vol. 17, No. 10, pp. 1051-1056.

Poulsen, C.H., et al., "Effect and Functionality of Lipases in Dough and Bread", in Angelino SAGF, Hamer RJ, van Hartingsveldt W, Heidekamp F, van der Lugt JP (editors), First European Symposium on Enzymes and Grain Processing, Zeist, The Netherlands, TNO Nutrition and Food Research Institute, ISBN 90-75202-04-0, p. 204-214. Proceedings of ESEGP-1, Noordwijkerhout, The Netherlands, Dec. 2-4, 1996. NZAS—0158559.

Poulsen, Charlotte, et al. "Purification and Characterization of a Hexose Oxidase with Excellent Strenghening Effects in Bread" Cereal Chem. (1998) vol. 75(1); pp. 51-57.

Roberts et al. (1992) . "Heterologous gene expression in Aspergillus niger: a glucoamylase-porcine pancreatic prophospholipase A2 fusion protein is secreted and processed to yield mature enzyme," Gene 122(1), 155-161.

Saito, Kunihiko, et al., "Phospholipase B from Penicillium notatum", Methods in Enzymology, 1991, vol. 197, p. 446-456 NZAS—0418833.

Sales Range for Baking Improver and Premix Manufacturers from DSM Bakery Ingredients, p. 1.

Schofield, J. David, "Wheat Structure, Biochemistry and Functionality", Department of Food Science and Technology, p. 243-260., Apr. 2000.

Shehata, A. "Manufacture of Blue Cheese by Direct Acidification Methods," p. 1-90. University of Wisconsin, Nov. 30, 2005.

Shillcock, Julian C., et al., "Tension-induced fusion of bilayer membranes and vesicles", Advance Online Publication Feb. 13, 2005, Nat. Mater., 2005, vol. 4, No. 3, p. 225-228 NZAS—0231181.

Si, Joan Qi, "Enzymes, Baking, Bread-Making", Encyclopedia of Bioprocess Technology, Wiley, 1999, ISBN 0471138223 NZAS—0255053, p. 1-18.

Si, Joan Qi, "Synergistic Effect of Enzymes for Breadbaking", Novo Nordisk publication A-06513b, p. 1-18, based on presentation No. 300 at AACC Annual Meeting 1996, Baltimore. Also Encyclopedia of Bioprocess Technology, Wiley, 1999, ISBN 0471138223.

Si, Joan Qi, et al. "Enzymes for bread, noodles and non-durum pasta", Cereal Food 2002 p. 1:3-3:4. Also in Enzymes in Food Technology, RJ Whitehurst & BA Law, Enzymes in Food Technology, Sheffield Academic Press, ISBN 1-84127-223-X, p. 19-54.

Si, Joan Qi, et al., "Novamyl—A true Anti-Staling Enzyme", Cereal Food, Oct. 2001, p. 1-20.

Soe, J.B., "Analyses of Monoglycerides and Other Emulsifiers by Gaschromatography", Fette, Seifen, Anstrichmittel, 1983, 85 Jahrgang, nr. 2, p. 72-76NZNA-0005896.

Tsuchiya, A. et. al., "Cloning and nucleotide sequence of the mono- and diacylglycerol lipase gene (md1B) of Aspergillus oryzae," FEMS Microbiology Letters 143 p. 63-67, (1996).

Uwajima, T. et. al., "Glycerol Oxidase from Aspergillus japonicas," Methods in Enzymology, vol. 89, p. 243-248.

Van Den Berg. G, "Regulatory status and use of lipase in various countries" Bullentin of the IDF 294, p. 19-20, 1994.

van Nieuqenhuyzen W., "Lecithins Open Doors to baked goods", International Food Ingredients, 1998, No. 2, p. 32-36.

EFEMA Index of Food Emulsifiers, "Mono- and diglycerides of fatty acids," Jan. 2004, 4th Edition, p. 1-3 and 51-55.

Efthymiou CC et al., "Development of domestic feta cheese", Journal of Dairy Science 1964, vol. 47, No. 6, p. 593-598.

Vafiades D, "Embracing Enzymes", Food R&D, Dairy Fields ingredient technology section, Mar. 1996 p. 39-44.

Freshzyme™, Novozymes Product Sheet Baking/2000-11814, NZAS—0265916. Mar. 12, 2001, p. 1-3.

Daftary, R. D. et. al "Functional Bread-Making Properties of Wheat Flour Lipids", Food Technology, vol. 22, p. 327-330.

Gist-brocades, Amylase P Information Sheet, (Date Unknown).

Godfrey, Tony, et al., "Industrial Enzymology Second Edition", Macmillan Press, 1996, ISBN 0333594649, Chapter 2.17, Olive and other Edible Oils, p. 299-300.

Hanlin, Richard T., "Illustrated Genera of Ascomycetes"; The American Phytopathological Society, 1992, St Paul, Minnesota, p. 48, 49, 234, 235, 244, 245.

Hedin, Eva M.K., et al., "Selective reduction and chemical modification of oxidized lipase cysteine mutants," Journal of Chemistry, vol. 80 pp. 529-539, 2002.

Humum et al., "Enzyme Catalysed Synthesis in Ambient Temperature Ionic Liquids", Biocatalysis and Biotransformation, 2001, vol. 19, pp. 331-338, NZAS—0215170.

Iwai, Mieko, et al., "Hydrolytic and Esterifying Actions of Crystalline Lipase of Aspergillus Niger", J. Gen. Appl. Microbiol., 1964, vol. 10, No. 1, p. 13-21.

Jensen B et al "Effect and Activity of Lipases in Dough and Bread" (translation), 48th Conference on Baking technology and 3rd Conference on Cake & Pastry Technology, Nov. 4-6, 1997, pp. 67-76.

Jensen, B., et al., "Effekt and Wirksamkeit von Lipasen in Teig und Brot" 48th Conference on Baking technology and 3rd Conference on Cake & Pastry Technology, Nov. 4-6, 1997, pp. 67-76.

Owens J. et. al., "Lecithinase Positive Bacteria in Milk", Process Biochemistry, Jan. 1978, vol. 13, pp. 13-14, 30.

Joshi, Sunita, et al., "Specificity of Lipase isolated from Fusarium oxysporum", Department of Chemistry, Indian Institute of Technology, vol. 25, No. 1 & 2, pp. 76-78, (Jan.-Jun. 1985).

Kasai, Naoya, et al., "Optically Active Chlorohydrins as Chiral C3 and C4 Building Units: Microbial Resolution and Synthetic Applications", Chirality, vol. 10, pp. 682-692, (1998).

Kindstedt et al., "Rapid Quantative test for free oil (Oiling off) in melted Mozzarella cheese," J. Dairy Sci., 1990, vol. 73, p. 867-873.

Kocak et al., Effect of lipase enzyme (palatase A 750 L) on the ripening of tulum cheese, Tr. J. of Agriculture and Forestry, 1995, vol. 19, p. 171-177.

Notification of Reasons for Refusal: JP Application No. 526105, Feb. 12, 2003 (Translation).

Notification of Reasons for Refusal: JP Application No. 526105, Jun. 4, 2002 (Translation).

Written Argument: JP Application No. 97181706.5, (Dec. 9, 1997) (Translation).

Internal Novo Nordisk Ref. No. DK5559215, p. 3-10 (NZAS-0017041-0017048) submitted during litigation.

U.S. Appl. No. 60/083,277, filed Apr. 28, 1998, Spender, Tina, et al.

AACC Method 54-21 Faringograph Method for Flour, from Physical Dough Tests supplied by the British Library, Nov. 3, 1999.

Anderson D, "A Primer in Oils Processing Technology" in Bailey's Industrial Oil and Fat Products, Sixth edition, John Wiley, 2005, vol. 5, chapter 1, p. 1-56. ISBN 978047138401.

Anguita et al, "Purification, Gene Cloning, Amino Acid Sequence Analysis, and Expression of an Extracellular Lipase from an Aeromonas hydrophila Human Isolate", Appl. Environ. Microbiol., vol. 59, No. 8, p. 2411-2417, Aug. 1993.

"AOAC Official method 999.10 (Lead, Cadmium, Zinc, Copper, and Iron in Foods Atomic absorption Spectrophotometry after Microwave Digestion), First Action 1999 NMKL-AOAC Method", AOAC International, pp. 1-3, 2002.

AOCS Introduction to the Processing of Fats and Oils p. 111-16-111-19. Four modules on CD-ROM. American Oil Chemists Society, 2003.

AOCS Method 2c-25 "1997 Moisture and Volatile Matter Air Oven Method" Sampling and Analysis of Commercial Fats and Oils, obtained from The British Library, p. 1, 1997.

AOCS Official Method Ca 20-99: "Analysis of Phosphorus in oil by inductively Coupled Plasma Optical Emission Spectroscopy", Sampling and Analysis of Commercial Fats and Oils, obtained from The British Library, pp. 1-3, 2001.

Archer D.B. & Peberdy, The Molecular Biology of Secreted Enzyme Production by Fungi, Critical Reviews in Biotechnology, 1997, vol. 17, No. 4, p. 273-306.

Arskog and Joergensen, "Baking performance of prior art lipases from *Candida cylindracea* and *Aspergillus foeditus* and their activity on galactolipids in dough", Novozymes Report Jul. 18, 2005, pp. 1-2.

Arskog and Joergensen, "Baking performance of prior art lipases from *Humicola Lanuginosa, Aspergillus tubigensis, Rhizopus delemar* and *Rhizomucor miehei*, and their activity on galactolipids in dough", Novozymes Report Jul. 17, 2005, pp. 1-8.

Aust K., "Applications of lecithin in bakery foods," AIB Research Technical Bulletin, vol. XV, issue 12, Dec. 1993, p. 1-6.

Banas A. et al., "Cellular sterol ester synthesis in plants is performed by an enzyme (Phospholipid: Sterol Acyltransferase) different from the yeast and mammalian Acyl-CoA: Sterol AcylTransferase", Journal of Biological Chemistry, 2005, vol. 280, No. 41, pp. 34626-34634.

Beggs J.D., Transformation of yeast by a replicating hybrid plasmid, Nature (London), 1978, vol. 275, p. 104.

Bessette, "Efficient folding or proteins with multiple disulphide bonds in the *Escherida coli cytoplasm*", Proc. Natl. Acad. Sci. USA, 1999, vol. 96, p. 13703-13708.

Bo Yang et al., "Optimization of Enzymatic Degumming Process for Rapseed Oil," JAOCS, 2006, vol. 83, No. 7, p. 653-658.

Briand et al, "Substrate Specificity of the Lipase from Candida parapsilosis", Lipids, Aug. 1995, vol. 30, No. 8, p. 747-754.

Bru R., López-Nicolás J.M., Garcia-Carmona F., (1995) "Aggregation of polyunsaturated fatty acid in the presence of cyclodextrins", Colloids and Surfaces A: Physiochemical and Engineering Aspects. 97, p. 263-269.

Brunel et al, "High-Level expression of Candida parapsilosis lipase/acyltransferase in Pichia pastoris," J Biotechnology, Jul 1, vol. 111, No. 1, p. 41-50, 2004.

Buchold H. et. al., "Enzymatische Phosphatidentfernung aus Pflanzenolen" Technologies, 1993, vol. 95, No. 8, p. 300-304, ISSN:0931-5985.

Buckley J. Thomas et al., Substrate specificity of bacterial glycerophospholipid: Cholesterol Acyltransferase, Biochemistry, 1982, vol. 21, p. 6699-6703.

Bylund G. (ed), 1995, Dairy Processing Handbook, Chapter 2, p. 17-42, Lund, Sweden.

Bylund G. (ed), 1995, Dairy Processing Handbook, Chapter 9, p. 227-246, Lund, Sweden.

Ceci L.N. et al, Oil recovery and lecithin production using water degumming sludge of crude soybean oils, Journal of the Science of Food and Agriculture, 2008, vol. 88, No. 14, p. 2460-2466.

Cereghino et al., Heterologous protein expression in the methylotrophic yeast *Pichia pastoris*, FEMS Microbiology Review, 2000, vol. 24, No. 1, p. 45-66.

Chica et al, "Semi-rational approaches to engineering enzyme activity: combining the benefits of directed evolution and rational design" Current Opinion in Biotechnology, 2005, vol. 16, p. 378-384.

Christou P., Genetic engineering of crop legumes and cereals: current status and recent advances, Agro-Food-Industry Hi-Tech, Mar./Apr. 1994, p. 17-27.

Davis R.H. and de Serres, Genetic and Microbiological Research Techniques for *Neurospora crassa*, Methods Enzymology, 1971, vol. 17A, p. 79-143.

EC 1.1.3.10 (downloaded—Jul. 12, 2010 from http://www.chem.qmul.ac.uk/iubmb/enzyme/EC1/1/3/10.html).

EC 1.1.3.4 (downloaded—Jul. 12, 2010 from http://www.chem.qmul.ac.uk/iubmb/enzyme/EC1/1/3/4.html).

EC 1.1.3.5 (downloaded—Nov. 16, 2009 from http://www.chem.qmul.ac.uk/iubmb/enzyme/EC1/1/3/5.html).

EC 2.3.1.43 (downloaded Apr. 21, 2009 from http://www.chem.qmul.ac.uk/iubmb/enzyme/EC2/3/1/43.html).

EC 2.4.1.19 (Downloaded Jul. 12, 2010 from http://www.chem.qmul.ac.uk/iubmb/enzyme/EC2/4/1/19.html).

EC 3.1.1.26 (downloaded—Dec. 18, 2008 from http://www.chem.qmul.ac.uldiubmb/enzyme/EC3/1/1/26.html).

EC 3.1.1.3 (downloaded—Dec. 18, 2008 from http://www.chem.qmul.ac.uk/iubmb/enzyme/EC3/1/1/3.html).

EC 3.1.1.32 (downloaded—May 22, 2008 from http://www.chem.qmul.ac.uk/iubmb/enzyme/EC3/1/1/32.html).

EC 3.1.1.4 Phospholipase A2 enzyme Enzyme Entry 1983 (downloaded Apr. 21, 2009 from http://www.chem.qmul.ac.uk/iubmb/enzyme/EC3/1/1/4.html).

EC 3.1.1.5 (downloaded Dec. 18, 2008 from http://www.chem.qmul.ac.uk/iubmb/enzyme/EC3/1/1/5.html).

EC 3.2.1.3 (downloaded Jul. 12, 2010 from http://www.chem.qmul.ac.uk/iubmb/enzyme/EC3/2/1/3.html).

EC 3.2.1.32 (Downloaded Jul. 12, 2010 from http://www.chem.qmul.ac.uk/iubmb/enzyme/EC3/2/1/32.html).

EC 3.2.1.60 (downloaded Apr. 28, 2009 from http://www.chem.qmul.ac.uk/iubmb/enzyme/EC3/2/1/60.html).

Eliasson A-C. and Larssen K., "Chapter 2: Physiochemical Behavior of the Components of Wheat Flour", *Cereals in Breadmaking: a molecular colloidal approach*, Marcel Dekker Inc, 1993, ISBN0824788168, p. 31-45.

Garzillo et al, "Production, Purification, and Characterization of Glucose Oxidase from Penicillium Variable P16," Biotechnol. Appl. Biochem., 1995, vol. 22, p. 169-178.

Genbank accession code NC_003888.1:8327480..8328367 (downloaded Apr. 21, 2009), p. 1.

Genbank accession No. AL646052 (downloaded Apr. 21, 2009), pp. 1-2.

Genbank accession No. AL939131.1:265480..266367 (downloaded Apr. 21, 2009), p. 1.

Genbank accession No. CAC42140 (downloaded Apr. 21, 2009), pp. 1-2.

Genbank accession No. NP_003888.1 (downloaded Apr. 21, 2009), pp. 1.

Genbank accession No. NP_631558.1 (downloaded Apr. 21, 2009), pp. 1-2.

Genbank accession No. P41734 (downloaded Apr. 21, 2009), pp. 1-4.

NCBI Accession No. Z75034 (downloaded Apr. 21, 2009) p. 1-2.

Hammond E.G. et al., "Soybean Oil" in Bailey's Industrial Oil and Fat Products, Sixth edition, John Wiley, 2005, vol. 3, chapter 13, p. 577-653. ISBN 978047138401.

Hinchcliffe E., Kenny E., "Yeast as a vehicle for the expression of heterologous genes", Yeasts, 1993, vol. 5, Anthony H. Rose and J. Stuart Harrison, eds. 2nd edition, Academic Press Ltd.

Hinnen A. et al., Transformation of yeast, Proceedings of the National Academy of Sciences USA, Apr. 1978, vol. 75, No. 4, p. 1929-1933.

Hollenberg C.P. et al., Production of recombinant proteins by methylotrophic yeasts, Current Opinion in Biotechnology Oct. 1997, vol. 8, No. 5, pp. 554-560.

Horwell DC, "The 'peptoid' approach to the design of non-peptide, small molecular agonists and antogonists of neuropeptides", Trends Biotechnol., 1995, vol. 13, No. 4, pp. 132-134.

Hossen, Monjur, "Enzyme catalyzed synthesis of structured phospholipids with conjugated linoleic acid and plant sterols, " A Dissertation by MD Monjur Hossen, May 2005, p. 1-152.

Hui, Bailey's Industrial Oil and Fat Products, 5th edition vol. 2 Edible Oil and Fat Products: Oils and Oilseeds, Wiley Interscience (1996), pp. 513-516. ISBN 0471594261.

International Dairy Federation Bulletin Document 116, 1979, p. 5, "Definition of recombined milk".

Ito H. et al., "Transformation of Intact Yeast Cells Treated with Alkali Cations," J. Bacteriology, 1983, vol. 153, p. 163-168.

Jost R. et. al., "Milk and Dairy Products," Nestle Product Technology Center, 2007, Wiley-VCH, pp. 1-62, Konolfingen, Switzerland.

Kalscheuer et al, "Synthesis of Novel Lipids in Saccharomyces cerevisiae by Heterologous Expression of an Unspecific Bacterial Acyltransferase," Applied and Environmental Microbiology, vol. 70, No. 12, p. 7119-7125, 2004.

Kane, "Effects of rare codon clusters on high-level expression of heterolgous proteins in *E. coli*" Current Opinion Biotechnology, 1995, vol. 6, p. 494-500.

Kimmel, A. et al. "Preparation of cDNA and the Generation of cDNA Libraries: Overview," Methods in Enzymology, 1987, vol. 152, p. 307-316.

LaVallie T.M., 2-Methoxyestradiol Inhibits Proliferation and Induces Apoptosis Independently of Estrogen Receptors α and β, Current Opinion in Biotechnology, 1995, vol. 6, No. 5, pp. 501-506.

Leon et al., "A new approach to study starchy changes occurring the double-baking process and during bread storage," Z. Lebensn. Unters Forsch A, 1997, vol. 204 pp. 316-320.

McIntyre et al., "Distribution of Glycerophospholipid-Cholesterol Acyltransferase in Selected Bacterial Species," Journal of Bacteriology, Jul. 1979, vol. 139, No. pp. 132-136.

NCBI protein accession code AAK84028.1 GI:15082088, (downloaded Dec. 18, 2009), pp. 1-2.

NCBI protein accession code CAB39707.1 GI:4529178, (downloaded Dec. 18, 2009), pp. 1-2.

NCBI protein accession code CAB62724.1 GI:6562793, (downloaded Dec. 18, 2009), pp. 1-2.

NCBI protein accession code CAB88833.1 GI:7635996, (downloaded Dec. 18, 2009), pp. 1-2.
NCBI protein accession code CAB89450.1; GI:7672261, (downloaded Dec. 18, 2009), pp. 1-2.
NCBI protein accession code CAC01477.1 GI:9716139, (downloaded Dec. 18, 2009), pp. 1-2.
NCBI's Genbank database accession number: 1IVN_A; GID:33357066, (downloaded Oct. 14, 2010), pp. 1-2.
Nerland A.H., "Glycerophospholipid-cholesterol acyltransferase precursor", SwissProt, Feb. 11, 2005 XP002318368 citing Nerland, A.H., "The nucleotide sequence of the gene encoding GCAT from Aeromonas salmonicida ssp. Salmonicida," Journal of Fish Diseases, vol. 19, p. 145-150, 1996.
Oil Mill Gazetteer, "Enzymatic Degumming Improves Oil Refilling in China," Jul. 2005 vol. 111, p. 2-4.
Phospholipase C, E.C. 3.1.4.3, (downloaded Sep. 8, 2009 from http://www.chem.qmul.ac.uk/iubmb/enzyme/EC3/1/4/3.html), p. 1.
Poldermans B and Schoppink P, "Controlling the baking process and product quality with enzymes", Cereal Foods World, Mar. 1999, 44 (3), p. 132-135.
Potrykus I., Gene Transfer to Plants: assessment of published approaches and results, Annu. Rev. Plant Physiol. Plant Mol. Biol., 1991, vol. 42, p. 205-225.
PreSens Manual HydroPlate® HP96U and HydroPlate® HP96C, pp. 1-15, Aug. 17, 2004.
Seffernick et al, "Melamine Deaminase and Atrazine Chlorohydrolase: 98 Percent Identical but Functionally Different", Journal of Bacteriology, Apr. 2001, vol. 183, No. 8, p. 2405-2410.
Seino et al, "Enzymatic Synthesis of Carbohydrate Esters of Fatty Acid (10 Esterification of Sucrose, Glucose, Fructose and Sorbitol", J. Am. Oil Chem. Soc., Nov. 1984, vol. 61, No. 11, p. 1761-1765.
Sequence alignment of database accession No. Q44268 (database: UNIProtKB/TrEMBL) with SEQ. ID No. 16, (downloaded Jan. 27, 2009), pp. 1-2.
Sequence alignment of database accession No. Q44268 (database: UNIProtKB/TrEMBL) with SEQ. ID No. 70, (downloaded Jan. 27, 2009), pp. 1-2.
Simon RJ et al.,"Peptoids: a modular approach to drug discovery", Proc. Natl. Acad. Sci. USA, 1992, vol. 89, No. 20, pp. 9367-9371.
Stryer, "Conformation and Dynamics," Biochemistry, 2nd Edition, 1981, WH Freeman & Co., San Francisco, p. 16.
Sutrisno, A. et al, "Expression of a gene Encoding Chitinase (pCA 8 ORF) from Aeromonas sp. No. 10S-24 in *Esxherichia coli* and Enzyme Characterization," Journal of Bioscience and Bioengineering, vol. 91, No. 6, p. 599-602, 2001.
Szuhaj B.F., "Lecithins" in Bailey's Industrial Oil and Fat Products, Sixth edition, John Wiley, 2005, vol. 2, chapter 13, p. 361-456. ISBN 978047138401.
Tanji M.et al., "Lipase hydrolysis of milk fat and its soft fractions", Research Bulletin of Obihiro University, 2001, vol. 22, No. 2, p. 89-94.
Tilden E.B. and Hudson C.S., Preparation and Properties of the Amylases Produced by Bacillus Macerans and Bacillus Polymyxa, J. Bacteriology, 1942, vol. 43, p. 527-544.
Tones C.F. et al., A two steps enzymatic procedure to obtain sterol esters, tocopherols and fatty acid ethyl esters from soybean oil deodorizer distillate, Process Biochemistry, 2007, vol. 42, No. 9, p. 1335-1341.
Trueman L.J., "Heterologous Expression in Yeast," Methods Molecular Biology, vol. 49, p. 341-354 (1995).
Turner G. Vectors for generic manipulation, in Martinelli S.D, Kinghorn J.R. (editors), *Aspergillus*: 50 years on. Progress in industrial microbiology, 1994, vol. 29, p. 641-666.
Verenium Corporation leaflet Purifine® Enzyme"Convert Gums to Oils Significantly Increase Oil Yields no increase in Free Fatty Acids", San Diego, Jan. 2008.
Witkowski et al, "Conversion of a B-Ketoacyl Synthase to a Malonyl Decarboxylase by Replacement of the Active-Site Cysteine with Glutamine," Biochemistry, Sep. 7, 1999, vol. 38, No. 36, p. 11643-11650.
Whitaker, John R., et al., "Biocatalysis in Agricultural Biotechnology", ACS Symposium Series, American Chemical Society, 1989, p. 25-43.

Williams K.R. et al., "Protein Analysis by Integrated Sample Preparation, Chemistry, and Mass Spectrometry", in Molecular Biology and Biotechnology—A Comprehensive Desk Reference, VCH, 1995, ISBN 1-56081-569-8 edited by Meyers R.A., p. 731-737.
Helmerich G. et al., Strukur-Wirkungsbeziehehungen von Phospholipiden in Backwaren, Wirkung von Phospholipiden, Getreide Mehl und Brot, 2003, vol. 57, No. 5, p. 270-273 NZAS—0301096.
Woolley et al., "Lipases their structure, biochemistry and application", Published by the Press syndicate of the University of Cambridge, Cambridge University Press. 1994, p. 242-270.
WPI Acc No. 93-298906(38) and JP05211852 Preparation of low fat content cream—by adding lipase to mixture of fat and water, Nisshin Oil and Fat Corp. Aug. 24, 1993.
Yamano Y et al., Surface activity of lysophosphatidyl choline from soybean, 4th World Surfactants Congress, 1996, p. 24-34.
Yount, Nannette Y., et al., "Multidimensional signatures in antimicrobial peptides," Proceedings of the National Academy of Sciences, vol. 101, No. 19, p. 7363-7368, (2004).
Arbige, Michael A et al, "Novel lipase for cheddar cheese flavor development" Food Technology, vol. 40, 1996 , p. 91-98.
Assignment Document for Enzymatisk detergent additiv, detergent og vaskemetode, executed Aug. 13, 1986 p. 1-3.
Atomi H, et al., "Microbial lipases-from screening to design", In: Barnes PJ, ed. Oils-Fats-Lipids, 21st World Congress Int Soc Fat Res. England: Bridgwater, 1995: pp. 49-50, vol. 1. NZAS-0016055-NZAS-0016056.
Aunstrup, Knud et al., "Production of Microbiol Enzymes", Microbiol Technology, Academic Press, 1979, 2nd edition, vol. 1, chap. 9, p. 281-309.
"Fat Splitting, Esterification, and Interesterification", in Bailey's Industrial Oils and Fat Products, vol. 2, 4th Edition, John Wiley and Sons, New York pp. 97-173, 1982.
Bakezyme PH 800 Product Data Sheet, DSM Bakery ingredients, pp. 1-2. NZAS-0299424-NZAS-0299425, p. 1-2, (Date after Mar. 19, 2002).
Becker T. "Separation and Purification Processes for Recovery of Industrial Enzymes" in R.K. Singh, S.S.H. Rizvi (eds): Bioseparation processes in Foods, Marcel Dekker, New York, pp. 427-445. 1995.
Bieleski R.L., Sugar Alcohols, in Loewus F A & Tanner W (eds), Plant Carbohydrates I. Intercellular Carbohydrates Encyclopedia Plant Physiol. N. S., 1982, 13A, chapter 5, p. 158-192, Springer, Berlin.
Biocatalysts, Limited, Product Sheet for Lipomod(TM) 627P-L627P, published Jan. 9, 2002, Pontypridd UK, p. 1.
Jakobsen, Soren, "Biotekkomet falder hardt til jorden", Borsens, p. 6, Aug. 28, 2002. NZAS-0564031.
Cao, Shu-Gui, et al., "Enzymatic Preparation of Monoglycerides via Glycerolysis of Fats and Oils Catalyzed by Lipase from Pseudomonas Species" National Laboratory of Enzyme Engineering. Monoglycerides, Enzyme Engine, Annals New York Academy of Sciences, 1996, vol. 799, issue 1, p. 670-677.
Castello, P., et al., "Technological and Biochemical effects of exogenous lipases in breadmaking", 2nd European Symposium on enzymes in Grain Processing, Dec. 8-10, 1999, Helsinki, p. 193-199. Published by VTT, Espoo, 2000.
Cloning of rad51 and rad52 homologues from Aspergillus oryzae and the effect of their overexpression on homologous recombination, Novozymes internal document, p. 1-21, Feb. 9, 2001.
Courtin, Christophe M., et al., "Recent Advances in Enzymes in Grain Processing", Laboratory of Food Chemistry, Leuven, Belgium, 2003, ISBN 90-9016671-8, p. 269-274. Sep. 2002.
Danisco, Hexose oxidase—nyt enzym med mange mulingheder (advert). Mar. 15, 1999.
Declaration by Clive Graham Phipps Walter (Dec C) Jul. 4, 2003.
Declaration by Dr Jorn Borch Soe (Dec F) Dec. 2, 2003.
Declaration by Dr Mark Turner (Dec G) Feb. 4, 2005, pp. 1-6.
Declaration by Henrik Pedersen (Dec A) Jul. 7, 2003, pp. 1-3.
Declaration by Henrik Pedersen, Masoud Rajabi Zargahi and Clive Graham Phipps Walter (Dec 2) Feb. 7, 2005, pp. 1-26, D46.
Declaration by Janne Brunstedt (Dec D) Jul. 4, 2003.

Declaration by Kazuko Kato, Henrik Pedersen, Masoud Rajabi Zaghari, Clive Phipps Walter, and Janne Brunstedt (Dec I) Feb. 7, 2005.
Declaration by Kim Borch Oct. 17, 2005.
Declaration by Luise Erlandsen Oct. 21, 2005.
Declaration by Masoud Rajabi Zargahi (Dec B) Jul. 7, 2003.
Declaration by Masoud Rajabi Zargahi (Dec E) Jul. 15, 2003.
Declaration by Tina Spendler Oct. 14, 2005.
Dictionary of Biochemistry and Molecular Biology, Stenesh, J. Second Edition, John Wiley, 1975, p. 16, ISBN 0471840890, p. 1-3.

Dinkci. N, Mucor miehei den elde edilen lipaz, Ege Univeraitesi Ziraat Fakultesi Dergisi Cilt, 37, Saiy 2-3, 2000, p. 141-148.
Directive 2000/36/EC. Http://europa.eu.int/scadplus/leg/en/lvb/121122b.htm. Dato: 16.06.04.
Drost-Lustenberger, Cornelia, et al., "Lipopan F BG-unlocking the natural strengthening potential in dough", Cereal Food, 2004. Novozymes internal draft, p. 1-6.
Dugruix, A. et. al. (1992), "Preparation and handling of biological macromolecules," Oxford University Press, p. 31-39.

* cited by examiner

Figure 1

SEQ ID No. 1

```
  1 ivafGDSlTd geayygdsdg ggwgagladr Ltallrlrar prgvdvfnrg isGrtsdGrl
 61 ivDalvallF laqslglpnL pPYLsqdflr GANFAsagAt Ilptsgpfli QvqFkdfksq
121 vlelrqalgl lqellrllpv ldakspdlvt imiGtNDlit saffgpkste sdrnvsvpef
181 kdnlrqlikr Lrsnngarii vlitlvilnl gplGClPlkl alalassknv dasgclerln
241 eavadfneal relaiskled qlrkdglpdv kgadvpyvDl ysifqdldgi qnpsayvyGF
301 ettkaCCGyG gryNynrvCG naglcnvtak aCnpssylls flfwDgfHps ekGykavAea
361 l
```

Figure 2

SEQ ID No. 2

```
  1 mkkwfvcllg lvaltvqaad srpafsrivm fgdslsdtgk myskmrgylp ssppyyegrf
 61 sngpvwleql tnefpgltia neaeggptav aynkiswnpk yqvinnldye vtqflqkdsf
121 kpddlvilwv gandylaygw nteqdakrvr daisdaanrm vlngakeill fnlpdlgqnp
181 sarsqkvvea ashvsayhnq lllnlarqla ptgmvklfei dkqfaemlrd pqnfglsdqr
241 nacyggsyvw kpfasrsast dsqlsafnpq erlaiagnpl laqavaspma arsastlnce
301 gkmfwdqvhp ttvvhaalse paatfiesqy eflah
```

Figure 3

SEQ ID No. 3

```
  1 mkkwfvcllg lialtvqaad trpafsrivm fgdslsdtgk myskmrgylp ssppyyegrf
 61 sngpvwleql tkqfpgltia neaeggatav aynkiswnpk yqvynnldye vtqflqkdsf
121 kpddlvilwv gandylaygw nteqdakrvr daisdaanrm vlngakqill fnlpdlgqnp
181 sarsqkvvea vshvsayhnk lllnlarqla ptgmvklfei dkqfaemlrd pqnfglsdve
241 npcydggyvw kpfatrsvst drqlsafspq erlaiagnpl laqavaspma rrsasplnce
301 gkmfwdqvhp ttvvhaalse raatfietqy eflahg
```

Figure 4

SEQ ID No. 4

```
  1 mpkpalrrvm tatvaavgtl algltdatah aapaqatptl dyvalgdsys agsgvlpvdp
 61 anllclrsta nyphviadtt garltdvtcg aaqtadftra qypgvapqld algtgtdlvt
121 ltiggndnst finaitacgt agvlsggkgs pckdrhgtsf ddeieantyp alkeallgvr
181 arapharvaa lgypwitpat adpscflklp laagdvpylr aiqahlndav rraaeetgat
241 yvdfsgvsdg hdaceapgtr wiepllfghs lvpvhpnalg errmaehtmd vlgld
```

Figure 5

SEQ ID No. 5

```
  1 mpkpalrrvm tatvaavgtl algltdatah aapaqatptl dyvalgdsys agsgvlpvdp
 61 anllclrsta nyphviadtt garltdvtcg aaqtadftra qypgvapqld algtgtdlvt
121 ltiggndnst finaitacgt agvlsggkgs pckdrhgtsf ddeieantyp alkeallgvr
181 arapharvaa lgypwitpat adpscflklp laagdvpylr aiqahlndav rraaeetgat
241 yvdfsgvsdg hdaceapgtr wiepllfghs lvpvhpnalg errmaehtmd vlgld
```

Figure 6

SEQ ID No. 6

```
  1 mdyekfllfg dsitefafnt rpiedgkdqy algaalvney trkmdilqrg fkgytsrwal
 61 kilpeilkhe snivmatifl gandacsagp qsvplpefid nirqmvslmk syhirpiiig
121 pglvdrekwe kekseeialg yfrtnenfai ysdalaklan eekvpfvaln kafqqeggda
181 wqqlltdglh fsgkgykifh dellkvietf ypqyhpknmq yklkdwrdvl ddgsnims
```

Figure 7A

```
Alignment of pfam00657.6 consensus sequence with P10480
              *->ivafGDSlTdg..............eayygdsdgggwgagladrl
                 iv-fGDSl+d+++  ++ ++  +++++++ +-+s+g  w ++l + +
      P10480  28 IVMFGDSLSDTgkmyskmrgylpssppYYEGRFSNGPVWLEQLTNEF 74 tall...rlrarprgvdvfnrgisGrtsdGrlivDalvallFlaqslglpn
                 + l   +  +++++++++ +n+  +
      P10480  75 PGLTiaNEAEGGPTAVAYNKISWNPK---------------------- 100

LpPYLsgdflrGANFAsagAtIlptsqpfliQvqFkdfksqvlelrqalg
                                                           ++  -+
      P10480 101 ---------------------------------------------YQVINN 106 llqellrllpvldakspdlvtimiGtNDlitsaffgpkstesdrnvsvpe
                 l-+e+ +-l +++ k+ dlv++++G+ND+       -+ +- ++-+-+
      P10480 107 LDYEVTQFLQKDSFKPDDLVILWVGANDY--------LAYGWNTEQDAKR 148 fkdnlrqlikrLrsnngariivlitlvilnlgplGClPlklalalasskn
                 +-d ++-+++r+    nga+         ++++nl+ lG+ P-
      P10480 149 VRDAISDAANRMV-LNGAK-----EILLFNLPDLGQNPS----------- 181 vdasgqlerlneavadfnealrelaiskledqlrkdglpdvkgadvpyvD
                 +l-+ +e -  ++a++n++l +la     +ql+-+g+-+++++d -+-+
      P10480 182 ARSQKVVEAASHVSAYHNQLLLNLA-----RQLAPTGMVKLFEIDKQFAE 226 lysifqdldgiqnpsayv.y....GFe.ttkaCCGyGgr.yNyn.rv.CG
                 +    +g+-+ + + +a+++++     +++ +++a-+-+-+- -N-++r- -+
      P10480 227 MLRDPQNFGLSDQRNACYgGSyvwKPFaSRSASTDSQLSaFNPQeRLaIA 276 nag.l.c.nvtakaC.npssyll.sflfwDgfHpsekGykavAeal<-*
                 +++ l + -+++a++  +s+ ++++++fwD++Hp-   -+a+ e
      P10480 277 GNPLLaQaVASPMAArSASTLNCeGKMFWDQVHPTTVVHAALSEPA    322

Alignment of pfam00657.6 consensus sequence with AAG09804
              *->ivafGDSlTdg..............eayygdsdgggwgagladrl
                 iv-fGDSl+d+++  ++ ++  +++++++ +-+s+g  w ++l + +
     AAG09804  28 IVMFGDSLSDTgkmyskmrgylpssppYYEGRFSNGPVWLEQLTKQF 74 tallrlrarprgvdvfnrgisGrtsdGrlivDalvallFlaqslglpnLp
                 +g+++ n + +G+t
     AAG09804  75 ----------PGLTIANEAEGGAT-------------------- 88

PYLsgdflrGANFAsagAtIlptsgpfliQvqFkdfksqvlelrqa....
                                                      ++++ - ++- +
     AAG09804  89 --------------------------------------AVAYNKISWNpkyq 102

..lgllqellrllpvldakspdlvtimiGtNDlitsaffgpkstesdrnv
                 +-l-+e+ ++ +++ k+ dlv++++G+ND-       -+ +- -+
     AAG09804 103 vyNNLDYEVTQFLQKDSFKPDDLVILWVGANDY--------LAYGWNTEQ 144 svpefkdnlrqlikrLrsnngariivlitlvilnlgplGClPlklalala
                 +-+++-+d ++++++r+    nga+         ++++nl+ lG+ P-
     AAG09804 145 DAKRVRDAISDAANRMV-LNGAK-----QILLFNLPDLGQNPS------- 181 sskavdasgqlerlneavadfnealrelaiskledqlrkdglpdvkgadv
                          -+++ +e +  ++a++n++l +la     -ql+-+g+-+++-+d
     AAG09804 182 ----ARSQKVVEAVSHVSAYHNKLLLNLA-----RQLAPTGMVKLFEIDK 222 pyvDlysifqdldgiqnpsayv.y....GFe.ttkaCCGyGgr.yNyn.r
                 +++-+   +q+++  + ++ +++++    +++ t+-  -++ ++- + --+-r
     AAG09804 223 QFAEMLRDPQNFGLSDVENPCYdGgyvwKPFaTRSVSTDRQLSaFSPQeR 272 v.CGnag.l.c.nvtakaC.npssyll.sflfwDgfHpsekGykavAeal
                 + +-+-+ l + ++++a++ +s+ ++++++fwD-+Hp-   -+a+ e-
     AAG09804 273 LaIAGNPLLaQaVASPMARrSASPLNCeGKMFWDQVHPTTVVHAALSERA 322
                 <-*
```

Figure 7B

```
       AAG09804       -         -

Alignment of pfam00657.6 consensus sequence with NP_631558
                *->ivafGDSlTdgeayygdsdgggwgagladrLtallrlrarprgvdvf
                   +va+GDS ++g         +g +  +++L     + + + ++   +
     NP_631558   42      YVALGDSYSAG---------SGVLPVDPANL----LCLRSTANYPHV  75 nrgisGrtsdGrlivD.a.l.vallFlaqslglpnLpPYLsgdflrGANF
                 +  ++G+-           D  +  + +
     NP_631558   76     IADTTGAR-----LTDvTcGaAQ--------------------------  93

AsagAtIlptsgpfliQvqFkdfksqvlelrqalgllqellrllpvldak
                                          +++      -+ +  -+ +++
     NP_631558   94     ----------------------------TADFTRAQYPGVAPQLDALGT 114 spdlvtimiGtNDl...............itsaffgpkstesdrnvsvp
                 + dlvt+ iG+ND ++   +   + ++ +     +- +  +k   -+ +  +-+
     NP_631558  115     GTDLVTLTIGGNDNstfinaitacgtagvlSGGKGSPCKDRHGTSFDDEI 164 efkdn..lrqlikrLrs.nngariivlitlvilnlg..........pLG
                e  -+- l+-++  +r+++ +ar+ +l  ++i-+-   ++-+    + +    G
     NP_631558  165     EANTYpaLKEALLGVRArAPHARVAALGYPWITPATadpscflklplAAG 214

ClPlklalalassknvdasgclerlneavadfnealrelaiskledqlrk
                P-                         l+ ++a  n a+l    a
     NP_631558  215     DVPY-------------------LRAIQAHLNDAVRRAA---------- 234 dglpdvkgadvpyvDlysifqdldgiqnpsayvyGFettkaCCGyGgryN
                +-  +  +yvD+ ++
     NP_631558  235     ------EETGATYVDFSGVSDG---------------------------- 250 ynrvCGnaglcnvtakaC.npssyll.sflfwDgf...HpsekGykavAe
                          ++aC+ p +++ +  1f - - +  Hp-++ G -++Ae
     NP_631558  251     --------------HDACeAPGTRWIePLLFGHSLvpvHPNALGERRMAE 286 al<-*
                +
     NP_631558  287     HT  288

Alignment of pfam00657.6 consensus sequence with CAC42140
                *->ivafGDSlTdgeayygdsdgggwgagladrLtallrlrarprgvdvf
                   +va+GDS ++g         +g +  +++L     + + + ++   +
     CAC42140   42      YVALGDSYSAG---------SGVLPVDPANL----LCLRSTANYPHV  75 nrgisGrtsdGrlivD.a.l.vallFlaqslglpnLpPYLsgdflrGANF
                 +  ++G+-           D  +  + +
     CAC42140   76     IADTTGAR-----LTDvTcGaAQ--------------------------  93

AsagAtIlptsgpfliQvqFkdfksqvlelrqalgllqellrllpvldak
                                          +++      ++ +  -+ +++
     CAC42140   94     ----------------------------TADFTRAQYPGVAPQLDALGT 114 spdlvtimiGtNDl...............itsaffgpkstesdrnvsvp
                 + dlvt+ iG+ND ++   +   + ++ +     +- +  +k   -+ +  +-+
     CAC42140  115     GTDLVTLTIGGNDNstfinaitacgtagvlSGGKGSPCKDRHGTSFDDEI 164 efkdn..lrqlikrLrs.nngariivlitlvilnlg..........pLG
                e  -+- l+-++  +r+++ +ar+ +l  ++i-+-   ++-+    + +    G
     CAC42140  165     EANTYpaLKEALLGVRArAPHARVAALGYPWITPATadpscflklplAAG 214

ClPlklalalassknvdasgclerlneavadfnealrelaiskledqlrk
                P-                         l+ ++a  n a+l    a
     CAC42140  215     DVPY-------------------LRAIQAHLNDAVRRAA---------- 234 dglpdvkgadvpyvDlysifqdldgiqnpsayvyGFettkaCCGyGgryN
                +-  +  +yvD+ ++
     CAC42140  235     ------EETGATYVDFSGVSDG---------------------------- 250 ynrvCGnaglcnvtakaC.npssyll.sflfwDgf...HpsekGykavAe
                          ++aC+ p +++ +  1f - - +  Hp++ G +++Ae
     CAC42140  251     --------------HDACeAPGTRWIePLLFGHSLvpvHPNALGERRMAE 286
```

Figure 7C

```
al<-*
              +
   CAC42140  287 HT   288

Alignment of pfam00657.6 consensus sequence with P41734
              *->ivafGDSlTdg....eayygdsdgggwqaglaarLtallrlrarprg
                 +-fGDS+T+    +++ + +   d+    ga-l + +       +r+
   P41734     6  FLLFGDSITEFafntRPIEDGKDQYALGAALVNEY---------TRK  43 vdvfnrgisGrtsdGrlivDalvallFlaqslglpnLpPYLsgdflrGAN
              +d+  rg++G+t
   P41734    44 MDILQRGFKGYT--------------------------------------  55

FAsagAtIlptsgpfliQvqFkdfksqvlelrgalgllqellrllpvlda
                                                +r-al++l-e+l-      +
   P41734    56 ----------------------------SRWALKILPEILKH-----E  70 kspdlvtimiGtNDlitsaffgpkstesdrnvsvpefkdnlrqlikrLrs
              -  + ti+-G+ND+            ++ +++ v-+pef+dn-rq+++-+-s
   P41734    71 SNIVMATIFLGANDA---------CSAGPQSVPLPEFIDNIRQMVSLMKS 111 nngariivlitlvilnlgplGClPlklalalassknvdasgclerlneav
              -+-+ii-+-+lv  ++              +- k ++ +  - r+re +
   P41734   112 YHIRPIIIGPGLVDREKW-------------EKEKSEEIALGYFRTNENF 148 adfnealrelaisklkedqlrkdglpdvkgadvpyvDlysifqdldgiqnp
              a +  al +la                    ++  +vp+v l+-+fq- +g-+-+
   P41734   149 AIYSDALAKLA---------------NEEKVPFVALNKAFQQEGGDAWQ 182 sayvyGFettkaCCGyGgryNynrvCGnaglcnvtakaCnpssyllsflf
              +                                                 L+
   P41734   183 Q-----------------------------------------------LI 185 wDgfHpsekGykavAeal<-*
              Dg-H-s kGyk+++++l
   P41734   186 TDGLHFSGKGYKIFHDEL    203
```

Figure 8

```
A.sal   1   MKKWFVCLLGLIALTVQAADTRPAFSRIVMFGDSLSDTGKMYSKMRGYLPSSPPYYEGRF  60
                 +            +
A.hyd   1   MKKWFVCLLGLVALTVQAADSRPAFSRIVMFGDSLSDTGKMYSKMRGYLPSSPPYYEGRF  60

A. sal  61  SNGPVWLEQLTKQFPGLTIANEAEGGATAVAYNKISWNPKYQVINNLDYEVTQFLQKDSF 120
                       ++         +
A. hyd  61  SNGPVWLEQLTNEFPGLTIANEAEGGPTAVAYNKISWNPKYQVINNLDYEVTQFLQKDSF 120

A. sal 121  KPDDLVILWVGANDYLAYGWNTEQDAKRVRDAISDAANRMVLNGAKQILLFNLPDLGQNP 180
                                                               +
A. hyd 121  KPDDLVILWVGANDYLAYGWNTEQDAKRVRDAISDAANRMVLNGAKEILLFNLPDLGQNP 180

A. sal 181  SARSQKVVEAVSHVSAYHNKLLLNLARQLAPTGMVKLFEIDKQFAEMLRDPQNFGLSDVE 240
                       +        +                                       ++
A.hyd  181  SARSQKVVEAASHVSAYHNQLLLNLARQLAPTGMVKLFEIDKQFAEMLRDPQNFGLSDQR 240

A. sal 241  NPCYDGGYVWKPFATRSVSTDRQLSAFSPQERLAIAGNPLLAQAVASPMARRSASPLNCE 300
              + ++ +       + +     +          +                +     +
A. hyd 241  NACYGGSYVWKPFASRSASTDSQLSAFNPQERLAIAGNPLLAQAVASPMAARSASTLNCE 300

A. sal 301  GKMFWDQVHPTTVVHAALSERAATFIETQYEFLAH 335
                        +           +
A. hyd 301  GKMFWDQVHPTTVVHAALSEPAATFIESQYEFLAH 335
```

Figure 9

```
  1 ATGAAAAAAT GGTTTGTGTG TTTATTGGGA TTGGTCGCGC TGACAGTTCA GGCAGCCGAC
 61 AGCCGTCCCG CCTTCTCCCG GATCGTGATG TTTGGCGACA GCCTCTCCGA TACCGGCAAG
121 ATGTACAGCA AGATGCGCGG TTACCTCCCC TCCAGCCCCC CCTACTATGA GGGCCGCTTC
181 TCCAACGGGC CCGTCTGGCT GGAGCAGCTG ACCAACGAGT TCCCGGGCCT GACCATAGCC
241 AACGAGGCGG AAGGCGGACC GACCGCCGTG GCTTACAACA AGATCTCCTG GAATCCCAAG
301 TATCAGGTCA TCAACAACCT GGACTACGAG GTCACCCAGT TCCTGCAAAA AGACAGCTTC
361 AAGCCGGACG ATCTGGTGAT CCTCTGGGTC GGCGCCAACG ACTATCTGGC CTATGGCTGG
421 AACACAGAGC AGGATGCCAA GCGGGTGCGC GACGCCATCA GCGATGCGGC CAACCGCATG
481 GTGCTGAACG GCGCCAAGGA GATACTGCTG TTCAACCTGC CGGATCTGGG CCAGAACCCC
541 TCGGCCCGCA GCCAGAAGGT GGTCGAGGCG GCCAGCCATG TCTCCGCCTA CCACAACCAG
601 CTGCTGCTGA ACCTGGCACG CCAGCTGGCT CCCACCGGCA TGGTGAAGCT GTTCGAGATC
661 GACAAGCAGT TTGCCGAGAT GCTGCGTGAT CCGCAGAACT TCGGCCTGAG CGACCAGAGG
721 AACGCCTGCT ACGGTGGCAG CTATGTATGG AAGCCGTTTG CCTCCCGCAG CGCCAGCACC
781 GACAGCCAGC TCTCCGCCTT CAACCCGCAG GAGCGCCTCG CCATCGCCGG CAACCCGCTG
841 CTGGCCCAGG CCGTCGCCAG CCCCATGGCT GCCCGCAGCG CCAGCACCCT CAACTGTGAG
901 GGCAAGATGT TCTGGGATCA GGTCCACCCC ACCACTGTCG TGCACGCCGC CCTGAGCGAG
961 CCCGCCGCCA CCTTCATCGA GAGCCAGTAC GAGTTCCTCG CCCAC
```

Figure 10

```
  1 ATGAAAAAAT GGTTTGTTTG TTTATTGGGG TTGATCGCGC TGACAGTTCA GGCAGCCGAC
 61 ACTCGCCCCG CCTTCTCCCG GATCGTGATG TTCGGCGACA GCCTCTCCGA TACCGGCAAA
121 ATGTACAGCA AGATGCGCGG TTACCTCCCC TCCAGCCCGC CCTACTATGA GGGCCGTTTC
181 TCCAACGGAC CCGTCTGGCT GGAGCAGCTG ACCAAGCAGT TCCCGGGTCT GACCATCGCC
241 AACGAAGCGG AAGGCGGTGC CACTGCCGTG GCTTACAACA AGATCTCCTG GAATCCCAAG
301 TATCAGGTCT ACAACAACCT GGACTACGAG GTCACCCAGT TCTTGCAGAA AGACAGCTTC
361 AAGCCGGACG ATCTGGTGAT CCTCTGGGTC GGTGCCAATG ACTATCTGGC ATATGGCTGG
421 AATACGGAGC AGGATGCCAA GCGAGTTCGC GATGCCATCA GCGATGCGGC CAACCGCATG
481 GTACTGAACG GTGCCAAGCA GATACTGCTG TTCAACCTGC CGGATCTGGG CCAGAACCCG
541 TCAGCCCGCA GTCAGAAGGT GGTCGAGGCG GTCAGCCATG TCTCCGCCTA TCACAACAAG
601 CTGCTGCTGA ACCTGGCACG CCAGCTGGCC CCCACCGGCA TGGTAAAGCT GTTCGAGATC
661 GACAAGCAAT TTGCCGAGAT GCTGCGTGAT CCGCAGAACT TCGGCCTGAG CGACGTCGAG
721 AACCCCTGCT ACGACGGCGG CTATGTGTGG AAGCCGTTTG CCACCCGCAG CGTCAGCACC
781 GACCGCCAGC TCTCCGCCTT CAGTCCGCAG GAACGCCTCG CCATCGCCGG CAACCCGCTG
841 CTGGCACAGG CCGTTGCCAG TCCTATGGCC CGCCGCAGCG CCAGCCCCCT CAACTGTGAG
901 GGCAAGATGT TCTGGGATCA GGTACACCCG ACCACTGTCG TGCACGCAGC CCTGAGCGAG
961 CGCGCCGCCA CCTTCATCGA GACCCAGTAC GAGTTCCTCG CCCACGGATG A
```

Figure 11

```
  1  ATGCCGAAGC CTGCCCTTCG CCGTGTCATG ACCGCGACAG TCGCCGCCGT CGGCACGCTC
 61  GCCCTCGGCC TCACCGACGC CACCGCCCAC GCCGCGCCCG CCCAGGCCAC TCCGACCCTG
121  GACTACGTCG CCCTCGGCGA CAGCTACAGC GCCGGCTCCG GCGTCCTGCC CGTCGACCCC
181  GCCAACCTGC TCTGTCTGCG CTCGACGGCC AACTACCCCC ACGTCATCGC GGACACGACG
241  GGCGCCCGCC TCACGGACGT CACCTGCGGC GCCGCGCAGA CCGCCGACTT CACGCGGGCC
301  CAGTACCCGG GCGTCGCACC CCAGTTGGAC GCGCTCGGCA CCGGCACGGA CCTGGTCACG
361  CTCACCATCG GCGGCAACGA CAACAGCACC TTCATCAACG CCATCACGGC CTGCGGCACG
421  GCGGGTGTCC TCAGCGGCGG CAAGGGCAGC CCCTGCAAGG ACAGGCACGG CACCTCCTTC
481  GACGACGAGA TCGAGGCCAA CACGTACCCC GCGCTCAAGG AGGCGCTGCT CGGCGTCCGC
541  GCCAGGGCTC CCCACGCCAG GGTGGCGGCT CTCGGCTACC CGTGGATCAC CCCGGCCACC
601  GCCGACCCGT CCTGCTTCCT GAAGCTCCCC CTCGCCGCCG GTGACGTGCC CTACCTGCGG
661  GCCATCCAGG CACACCTCAA CGACGCGGTC CGGCGGGCCG CCGAGGAGAC CGGAGCCACC
721  TACGTGGACT TCTCCGGGGT GTCCGACGGC CACGACGCCT GCGAGGCCCC CGGCACCCGC
781  TGGATCGAAC GCTGCTCTT CGGGCACAGC CTCGTTCCCG TCCACCCCAA CGCCCTGGGC
841  GAGCGGCGCA TGGCCGAGCA CACGATGGAC GTCCTCGGCC TGGACTGA
```

Figure 12

```
  1  TCAGTCCAGG CCGAGGACGT CCATCGTGTG CTCGGCCATG CGCCGCTCGC CCAGGGCGTT
 61  GGGGTGGACG GGAACGAGGC TGTGCCCGAA GAGCAGCGGT TCGATCCAGC GGGTGCCGGG
121  GGCCTCGCAG GCGTCGTGGC CGTCGGACAC CCCGGAGAAG TCCACGTAGG TGGCTCCGGT
181  CTCCTCGGCG GCCCGCCGGA CCGCGTCGTT GAGGTGTGCC TGGATGGCCC GCAGGTAGGG
241  CACGTCACCG GCGGCGAGGG GGAGCTTCAG GAAGCAGGAC GGGTCGGCGG TGGCCGGGGT
301  GATCCACGGG TAGCCGAGAG CCGCCACCCT GGCGTGGGGA GCCCTGGCGC GGACGCCGAG
361  CAGCGCCTCC TTGAGCGCGG GGTACGTGTT GGCCTCGATC TCGTCGTCGA AGGAGGTGCC
421  GTGCCTGTCC TTGCAGGGGC TGCCCTTGCC GCCGCTGAGG ACACCCGCCG TGCCGCAGGC
481  CGTGATGGCG TTGATGAAGG TGCTGTTGTC GTTGCCGCCG ATGGTGAGCG TGACCAGGTC
541  CGTGCCGGTG CCGAGCGCGT CCAACTGGGG TGCGACGCCC GGGTACTGGG CCCGCGTGAA
601  GTCGGCGGTC TGCGCGGCGC CGCAGGTGAC GTCCGTGAGG CGGGCGCCCG TCGTGTCCGC
661  GATGACGTGG GGGTAGTTGG CCGTCGAGCG CAGACAGAGC AGGTTGGCGG GGTCGACGGG
721  CAGGACGCCG GAGCCGGCGC TGTAGCTGTC GCCGAGGGCG ACGTAGTCCA GGGTCGGAGT
781  GGCCTGGGCG GGCGCGGCGT GGGCGGTGGC GTCGGTGAGG CCGAGGGCGA GCGTGCCGAC
841  GGCGGCGACT GTCGCGGTCA TGACACGGCG AAGGGCAGGC TTCGGCAT
```

Figure 13

```
  1  ATGGATTACG AGAAGTTTCT GTTATTTGGG GATTCCATTA CTGAATTTGC TTTTAATACT
 61  AGGCCCATTG AAGATGGCAA AGATCAGTAT GCTCTTGGAG CCGCATTAGT CAACGAATAT
121  ACGAGAAAAA TGGATATTCT TCAAAGAGGG TTCAAAGGGT ACACTTCTAG ATGGGCGTTG
181  AAAATACTTC CTGAGATTTT AAAGCATGAA TCCAATATTG TCATGGCCAC AATATTTTTG
241  GGTGCCAACG ATGCATGCTC AGCAGGTCCC CAAAGTGTCC CCCTCCCCGA ATTTATCGAT
301  AATATTCGTC AAATGGTATC TTTGATGAAG TCTTACCATA TCCGTCCTAT TATAATAGGA
361  CCGGGGCTAG TAGATAGAGA GAAGTGGGAA AAAGAAAAAT CTGAAGAAAT AGCTCTCGGA
421  TACTTCCGTA CCAACGAGAA CTTTGCCATT TATTCCGATG CCTTAGCAAA ACTAGCCAAT
481  GAGGAAAAAG TTCCCTTCGT GGCTTTGAAT AAGGCGTTTC AACAGGAAGG TGGTGATGCT
541  TGGCAACAAC TGCTAACAGA TGGACTGCAC TTTTCCGGAA AAGGGTACAA AATTTTTCAT
601  GACGAATTAT TGAAGGTCAT TGAGACATTC TACCCCCAAT ATCATCCCAA AAACATGCAG
661  TACAAACTGA AGATTGGAG AGATGTGCTA GATGATGGAT CTAACATAAT GTCTTGA
```

Figure 14

(SEQ ID No. 12)

```
          10         20         30         40         50         60
          |          |          |          |          |          |
MNLRQWMGAA TAALALGLAA CGGGGTDQSG NPNVAKVQRM VVFGDSLSDI GTYTPVAQAV 70         80         90        100        110        120
          |          |          |          |          |          |
GGGKFTTNPG PIWAETVAAQ LGVTLTPAVM GYATSVQNCP KAGCFDYAQG GSRVTDPNGI 130        140        150        160        170        180
          |          |          |          |          |          |
GHNGGAGALT YPVQQQLANF YAASNNTFNG NNDVVFVLAG SNDIFFWTTA AATSGSGVTP 190        200        210        220        230        240
          |          |          |          |          |          |
AIATAQVQQA ATDLVGYVKD MIAKGATQVY VFNLPDSSLT PDGVASGTTG QALLHALVGT 250        260        270        280        290        300
          |          |          |          |          |          |
FNTTLQSGLA GTSARIIDFN AQLTAAIQNG ASFGFANTSA RACDATKINA LVPSAGGSSL 310        320        330        340
          |          |          |          |
FCSANTLVAS GADQSYLFAD GVHPTTAGHR LIASNVLARL LADNVAH
```

Figure 15

(SEQ ID No. 13)

```
atgaacctgc gtcaatggat gggcgccgcc acggctgccc ttgccttggg cttggccgcg      60
tgcggggcg gtgggaccga ccagagcggc aatcccaatg tcgccaaggt gcagcgcatg      120
gtggtgttcg gcgacagcct gagcgatatc ggcacctaca ccccgtcgc gcaggcggtg      180
ggcggcggca agttcaccac caacccgggc ccgatctggg ccgagaccgt ggccgcgcaa      240
ctgggcgtga cgctcacgcc ggcggtgatg ggctacgcca cctccgtgca gaattgcccc     300
aaggccggct gcttcgacta tgcgcagggc ggctcgcgcg tgaccgatcc gaacggcatc     360
ggccacaacg gcggcgcggg ggcgctgacc tacccggttc agcagcagct cgccaacttc     420
tacgcggcca gcaacaacac attcaacggc aataacgatg tcgtcttcgt gctggccggc     480
agcaacgaca ttttcttctg gaccactgcg gcggccacca gcggctccgg cgtgacgcc      540
gccattgcca cggcccaggt gcagcaggcc gcgacggacc tggtcggcta tgtcaaggac     600
atgatcgcca agggtgcgac gcaggtctac gtgttcaacc tgcccgacag cagcctgacg     660
ccggacggcg tggcaagcgg cacgaccggc caggcgctgc tgcacgcgct ggtgggcacg     720
ttcaacacga cgctgcaaag cgggctggcc ggcacctcgg cgcgcatcat cgacttcaac     780
gcacaactga ccgcggcgat ccagaatggc gcctcgttcg gcttcgccaa caccagcgcc     840
cgggcctgcg acgccaccaa gatcaatgcc ctggtgccga gcgccggcgg cagctcgctg     900
ttctgctcgg ccaacacgct ggtggcttcc ggtgcggacc agagctacct gttcgccgac     960
ggcgtgcacc cgaccacggc cggccatcgc ctgatcgcca gcaacgtgct ggcgcgcctg    1020
ctggcggata acgtcgcgca ctga                                           1044
```

Figure 16 (SEQ ID No. 20)

```
  1 migsyvavgd sftegvgdpg pdgafvgwad rlavlladrr pegdftytnl avrgrlldqi
 61 vaeqvprvvg lapdlvsfaa ggndiirpgt dpdevaerfe lavaaltaaa gtvlvttgfd
121 trgvpvlkhl rgkiatyngh vraiadrygc pvldlwslrs vqdrrawdad rlhlspeght
181 rvalragqal glrvpadpdq pwpplpprgt ldvrrddvhw areylvpwig rrlrgessgd
241 hvtakgtlsp daiktriaav a
```

Figure 17 (SEQ ID No. 21)

```
  1 gtgatcgggt cgtacgtggc ggtgggggac agcttcaccg agggcgtcgg cgacccggc
 61 cccgacgggg cgttcgtcgg ctgggccgac cggctcgccg tactgctcgc ggaccggcgc
121 ccgagggcg acttcacgta cacgaacctc gccgtgcgcg gcaggctcct cgaccagatc
181 gtggcggaac aggtcccgcg ggtcgtcgga ctcgcgcccg acctcgtctc gttcgcggcg
241 ggcggcaacg acatcatccg gcccggcacc gatcccgacg aggtcgccga gcggttcgag
301 ctggcggtgg ccgcgctgac cgccgcggcc ggaaccgtcc tggtgaccac cgggttcgac
361 acccgggggg tgcccgtcct caagcacctg cgcggcaaga tcgccacgta caacgggcac
421 gtccgcgcca tcgccgaccg ctacggctgc ccggtgctcg acctgtggtc gctgcggagc
481 gtccaggacc gcagggcgtg ggacgccgac cggctgcacc tgtcgccgga ggggcacacc
541 cgggtgacgc tgcgcgcggg gcaggccctg ggcctgcgcg tcccggccga ccctgaccag
601 ccctggccgc ccctgccgcc gcgcggcacg ctcgacgtcc ggcgcgacga cgtgcactgg
661 gcgcgcgagt acctggtgcc gtggatcggg cgccggctgc ggggcgagtc gtcgggcgac
721 cacgtgacgg ccaaggggac gctgtcgccg gacgccatca agacgcggat cgccgcggtg
781 gcctga
```

Figure 18
(SEQ ID No. 22)

```
  1 mqtnpaytsl vavgdsfteg msdllpdgsy rgwadllatr maarspgfry anlavrgkli
 61 gqivdeqvdv aaamgadvit lvgglndtlr pkcdmarvrd lltqaverla phceqlvlmr
121 spgrqgpvle rfrprmealf aviddlagrh gavvvdlyga qsladprmwd vdrlhltaeg
181 hrrvaeavwq slghepedpe whapipatpp pgwvtrrtad vrfarqhllp wigrrltgrs
241 sgdglpakrp dllpyedpar
```

Figure 19 (SEQ ID No. 23)

```
  1 atgcagacga accccgcgta caccagtctc gtcgccgtcg gcgactcctt caccgagggc
 61 atgtcggacc tgctgcccga cggctcctac cgtggctggg ccgacctcct cgccacccgg
121 atggcggccc gctccccgg cttccggtac gccaacctgg cggtgcgcgg gaagctgatc
181 ggacagatcg tcgacgagca ggtggacgtg gccgccgcca tgggagccga cgtgatcacg
241 ctggtcggcg ggctcaacga cacgctgcgg cccaagtgcg acatggcccg ggtgcgggac
301 ctgctgaccc aggccgtgga acggctcgcc cgcactgcg agcagctggt gctgatgcgc
361 agtccggtc gccagggtcc ggtgctggag cgcttccggc ccgcatgga ggccctgttc
421 gccgtgatcg acgacctggc cgggcggcac ggcgccgtgg tcgtcgacct gtacggggcc
481 cagtcgctgg ccgacccctc gatgtgggac gtggaccggc tgcacctgac cgccgagggc
541 caccgccggg tcgcggaggc ggtgtggcag tcgctcggcc acgagcccga ggaccccgag
601 tggcacgcgc cgatcccggc gaccgccgcg ccggggtggg tgacgcgcag gaccgcggac
661 gtccggttcg cccggcagca cctgctgccc tggataggcc gcaggctgac cgggcgctcg
721 tccggggacg gcctgccggc caagcgcccg gacctgctgc cctacgagga ccccgcacgg
781 tga
```

Figure 20 (SEQ ID No. 24)

```
  1 mtrgrdggag apptkhrall aaivtlivai saaiyagasa ddgsrdhalq aggrlprgda
 61 apastgawvg awatapaaae pgtettglag rsvrnvvhts vggtgaritl snlygqsplt
121 vthasialaa gpdtaaaiad tmrrltfggs arviipaggq vmsdtarlai pyganvlvtt
181 yspipsgpvt yhpqarqtsy ladgdrtadv tavayttptp ywryltaldv lsheadgtvv
241 afgdsitdga rsqsdanhrw tdvlaarlhe aagdgrdtpr ysvvnegisg nrlltsrpgr
301 padnpsglsr fqrdvlertn vkavvvvlgv ndvlnspela drdailtglr tlvdraharg
361 lrvvgatitp fggyggytea retmrqevne eirsgrvfdt vvdfdkalrd pydprrmrsd
421 ydsgdhlhpg dkgyarmgav idlaalkgaa pvka
```

Figure 21 (SEQ ID No. 25)

```
   1 atgacccggg gtcgtgacgg gggtgcgggg gcgcccccca ccaagcaccg tgccctgctc
  61 gcggcgatcg tcaccctgat agtggcgatc tccgcggcca tatacgccgg agcgtccgcg
 121 gacgacggca gcagggacca cgcgctgcag gccggaggcc gtctcccacg aggagacgcc
 181 gccccgcgt ccaccggtgc ctgggtgggc gcctgggcca ccgcaccggc cgcggccgag
 241 ccggcaccg agacgaccgg cctggcgggc cgctccgtgc gcaacgtcgt gcacacctcg
 301 gtcggcggca ccggcgcgcg gatcaccctc tgaacctgt acgggcagtc gccgctgacc
 361 gtcacacacg cctcgatcgc cctggccgcc gggcccgaca ccgccgccgc gatcgccgac
 421 accatgcgcc ggctcacctt cggcggcagc gcccgggtga tcatcccggc gggcggccag
 481 gtgatgagcg acaccgcccg cctcgccatc ccctacgggg cgaacgtcct ggtcaccacg
 541 tactccccca tcccgtccgg gccggtgacc taccatccgc aggcccggca gaccagctac
 601 ctggccgacg gcgaccgcac ggcggacgtc accgccgtcg cgtacaccac ccccacgccc
 661 tactgcgcgct acctgaccgc cctcgacgtg ctgagccacg aggccgacgg cacggtcgtg
 721 gcgttcggcg actccatcac cgacgcgcgc cgctcgcaga gcgacgccaa ccaccgctgg
 781 accgacgtcc tcgccgcacg cctgcacgag gcggcgggcg acggccggga cacgccccgc
 841 tacagcgtcg tcaacgaggg catcagcggc aaccggctcc tgaccagcag gccggggcgg
 901 ccggccgaca cccgagcgg actgagccgg ttccagcggg acgtgctgga acgcaccaac
 961 gtcaaggccg tcgtcgtcgt cctcggcgtc aacgacgtcc tgaacagccc ggaactcgcc
1021 gaccgcgacg ccatcctgac cggcctgcgc accctcgtcg accgggcgca cgcccgggga
1081 ctgcgggtcg tcggcgccac gatcacgccg ttcggcggct acggcggcta caccgaggcc
1141 cgcgagacga tgcggcagga ggtcaacgag gagatccgct ccggccgggt cttcgacacg
1201 gtcgtcgact tcgacaaggc cctgcgcgac ccgtacgacc cgcgccggat gcgctccgac
1261 tacgacagcg gcgaccacct gcacccggc gacaagggt acgcgcgcat gggcgcggtc
1321 atcgacctgg ccgcgctgaa gggcgcggcg ccggtcaagg cgtag
```

Figure 22 (SEQ ID No. 26)

```
  1 mtsmsrarva rriaagaayg gggiglagaa avglvvaevq larrrvgvgt ptrvpnaqgl
 61 yggtlptagd pplrlmmlgd staagqgvhr agqtpgalla sglaavaerp vrlgsvaqpg
121 acsddldrqv alvlaepdrv pdicvimvga ndvthrmpat rsvrhlssav rrlrtagaev
181 vvgtcpdlgt iervrqplrw larrasrqla aaqtigaveq ggrtvslgdl lgpefaqnpr
241 elfgpdnyhp saegyataam avlpsvcaal glwpadeehp dalrregflp varaaaeaas
301 eagtevaaam ptgprgpwal lkrrrrrrvs eaepsspsgv
```

Figure 23 (SEQ ID No. 27)

```
   1 atgacgagca tgtcgagggc gagggtggcg cggcggatcg cggccggcgc ggcgtacggc
  61 ggcggcggca tcggcctggc gggagcggcg gcggtcggtc tggtggtggc cgaggtgcag
 121 ctggccagac gcagggtggg ggtgggcacg ccgacccggg tgccgaacgc gcagggactg
 181 tacggcggca ccctgcccac ggccggcgac ccgccgctgc ggctgatgat gctgggcgac
 241 tccacggccg ccgggcaggg cgtgcaccgg gccgggcaga cgccgggcgc gctgctggcg
 301 tccgggctcg cggcggtggc ggagcggccg gtgcggctgg gtcggtcgc ccagccgggg
 361 gcgtgctcgg acgacctgga ccggcaggtg gcgctggtgc tcgccgagcc ggacgggtg
 421 cccgacatct gcgtgatcat ggtcggcgcc aacgacgtca cccaccggat gccggcgacc
 481 cgctcggtgc ggcacctgtc ctcggcggta cggcggctgc gcacggccgg tgcggaggtg
 541 gtggtcggca cctgtccgga cctgggcacg atcgagcggg tgcggcagcc gctgcgctgg
 601 ctggcccggc gggcctcacg gcagctcgcg gcggcacaga ccatcggcgc cgtcgagcag
 661 ggcgggcgca cggtgtcgct gggcgacctg ctgggtccgg agttcgcgca gaaccgcgg
 721 gagctcttcg gccccgacaa ctaccacccc tccgccgagg gtacgccac ggccgcgatg
 781 gcggtactgc cctcggtgtg cgccgcgctc ggcctgtggc cggccgacga ggagcacccg
 841 gacgcgctgc gccgcgaggg cttcctgccg gtggcgcgcg cggcggcgga ggcggcgtcc
 901 gaggcgggta cggaggtcgc cgccgccatg cctacggggc ctcgggggcc ctggcgctg
 961 ctgaagcgcc ggagacggcg tcgggtgtcg gaggcggaac cgtccagccc gtccggcgtt
1021 tga
```

Figure 24 (SEQ ID No. 28)

```
  1 mgrgtdqrtr ygrrrarval aaltaavlgv gvagcdsvgg dspapsgsps krtrtapawd
 61 tspasvaavg dsitrgfdac avlsdcpevs watgssakvd slavrllgka daaehswnya
121 vtgarmadlt aqvtraaqre pelvavmaga ndacrsttsa mtpvadfraq feeamatlrk
181 klpkaqvyvs sipdlkrlws qgrtnplgkq vwklglcpsm lgdadsldsa atlrrntvrd
241 rvadynevlr evcakdrrcr sddgavhefr fgtdqlshwd wfhpsvdgqa rlaeiayrav
301 taknp
```

Figure 25 (SEQ ID No. 29)

```
  1 atgggtcgag ggacggacca gcggacgcgg tacggccgtc gccgggcgcg tgtcgcgctc
 61 gccgccctga ccgccgccgt cctgggcgtg ggcgtggcgg gctgcgactc cgtgggcggc
121 gactcacccg ctccttccgg cagcccgtcg aagcggacga ggacggcgcc cgcctgggac
181 accagcccgg cgtccgtcgc cgccgtgggc gactccatca cgcgcggctt cgacgcctgt
241 gcggtgctgt cggactgccc ggaggtgtcg tgggcgaccg gcagcagcgc gaaggtcgac
301 tcgctggccg tacggctgct ggggaaggcg gacgcggccg agcacagctg gaactacgcg
361 gtcaccgggg cccggatggc ggacctgacc gctcaggtga cgcgggcggc gcagcgcgag
421 ccggagctgg tggcggtgat ggccggggcg aacgacgcgt gccggtccac gacctcggcg
481 atgacgccgg tggcggactt ccgggcgcag ttcgaggagg cgatggccac cctgcgcaag
541 aagctcccca aggcgcaggt gtacgtgtcg agcatcccgg acctcaagcg gctctggtcc
601 cagggccgca ccaacccgct gggcaagcag gtgtggaagc tcggcctgtg cccgtcgatg
661 ctgggcgacg cggactccct ggactcggcg gcgaccctgc ggcgcaacac ggtgcgcgac
721 cgggtggcgg actacaacga ggtgctgcgg gaggtctgcg cgaaggaccg gcggtgccgc
781 agcgacgacg gcgcggtgca cgagttccgg ttcggcacgg accagttgag ccactgggac
841 tggttccacc cgagtgtgga cggccaggcc cggctggcgg agatcgccta ccgcgcggtc
901 accgcgaaga tccctga
```

Figure 26 (SEQ ID No. 30)

```
  1 mrlsrraata sallltpala lfgasaavsa priqatdyva lgdsyssgvg agsydsssgs
 61 ckrstksypa lwaashtgtr fnftacsgar tgdvlakqlt pvnsgtdlvs itiggndagf
121 adtmttcnlq gesaclaria karayiqqtl paqldqvyda idsrapaaqv vvlgyprfyk
181 lggscavgls eksraainaa addinavtak raadhgfafg dvnttfaghe lcsgapwlhs
241 vtlpvensyh ptangqskgy lpvlnsat
```

Figure 27 (SEQ ID No. 31)

```
   1 ttcatcacaa cgatgtcaca acaccggcca tccgggtcat ccctgatcgt gggaatgggt
  61 gacaagcctt cccgtgacga aagggtcctg ctacatcaga aatgacagaa atcctgctca
 121 gggaggttcc atgagactgt cccgacgcgc ggccacggcg tccgcgctcc tcctcacccc
 181 ggcgctcgcg ctcttcggcg cgagcgccgc cgtgtccgcg ccgcgaatcc aggccaccga
 241 ctacgtggcc ctcggcgact cctactcctc ggggtcggc gcgggcagct acgacagcag
 301 cagtggctcc tgtaagcgca gcaccaagtc ctacccggcc ctgtgggccg cctcgcacac
 361 cggtacgcgg ttcaacttca ccgcctgttc gggcgcccgc acaggagacg tgctggccaa
 421 gcagctgacc ccggtcaact ccggcaccga cctggtcagc attaccatcg gcggcaacga
 481 cgcgggcttc gccgacacca tgaccacctg caacctccag ggcgagagcg cgtgcctggc
 541 gcggatcgcc aaggcgcgcg cctacatcca gcagacgctg cccgccagc tggaccaggt
 601 ctacgacgcc atcgacagcc gggccccgc agcccaggtc gtcgtcctgg gctaccgcg
 661 cttctacaag ctgggcggca gctgcgccgt cggtctctcg gagaagtccc gcgcggccat
 721 caacgccgcc gccgacgaca tcaacgccgt caccgccaag cgcgccgccg accacggctt
 781 cgccttcggg gacgtcaaca cgaccttcgc cgggcacgag ctgtgctccg gcgcccctg
 841 gctgcacagc gtcacccttc ccgtggagaa ctcctaccac cccacggcca acggacagtc
 901 caagggctac ctgcccgtcc tgaactccgc cacctgatct cgcggctact ccgcccctga
 961 cgaagtcccg ccccggggcg gggcttcgcc gtaggtgcgc gtaccgccgt cgcccgtcgc
1021 gccggtggcc ccgccgtacg tgccgccgcc cccggacgcg gtcggttc
```

Figure 28 (SEQ ID No. 32)

```
  1  MKKWFVCLLG  LVALTVQAAD  SRPAFSRIVM  FGDSLSDTGK  MYSKMRGYLP
 51  SSPPYYEGRF  SNGPVWLEQL  TKQFPGLTIA  NEAEGGATAV  AYNKISWNPK
101  YQVINNLDYE  VTQFLQKDSF  KPDDLVILWV  GANDYLAYGW  NTEQDAKRVR
151  DAISDAANRM  VLNGAKQILL  FNLPDLGQNP  SARSQKVVEA  VSHVSAYHNQ
201  LLLNLARQLA  PTGMVKLFEI  DKQFAEMLRD  PQNFGLSDVE  NPCYDGGYVW
251  KPFATRSVST  DRQLSAFSPQ  ERLAIAGNPL  LAQAVASPMA  RRSASPLNCE
301  GKMFWDQVHP  TTVVHAALSE  RAATFIANQY  EFLAH*
```

Figure 29 (SEQ ID No. 33)

```
  1  ATGAAAAAAT GGTTTGTGTG TTTATTGGGA TTGGTCGCGC TGACAGTTCA
     TACTTTTTTA CCAAACACAC AAATAACCCT AACCAGCGCG ACTGTCAAGT

51  GGCAGCCGAC AGTCGCCCCG CCTTTTCCCG GATCGTGATG TTCGGCGACA
     CCGTCGGCTG TCAGCGGGGC GGAAAAGGGC CTAGCACTAC AAGCCGCTGT

101  GCCTCTCCGA TACCGGCAAA ATGTACAGCA AGATGCGCGG TTACCTCCCC
     CGGAGAGGCT ATGGCCGTTT TACATGTCGT TCTACGCGCC AATGGAGGGG

151  TCCAGCCCGC CCTACTATGA GGGCCGTTTC TCCAACGGAC CCGTCTGGCT
     AGGTCGGGCG GGATGATACT CCCGGCAAAG AGGTTGCCTG GGCAGACCGA

201  GGAGCAGCTG ACCAAACAGT TCCCGGGTCT GACCATCGCC AACGAAGCGG
     CCTCGTCGAC TGGTTTGTCA AGGGCCCAGA CTGGTAGCGG TTGCTTCGCC

251  AAGGCGGTGC CACTGCCGTG GCTTACAACA AGATCTCCTG GAATCCCAAG
     TTCCGCCACG GTGACGGCAC CGAATGTTGT TCTAGAGGAC CTTAGGGTTC

301  TATCAGGTCA TCAACAACCT GGACTACGAG GTCACCCAGT TCTTGCAGAA
     ATAGTCCAGT AGTTGTTGGA CCTGATGCTC CAGTGGGTCA AGAACGTCTT

351  AGACAGCTTC AAGCCGGACG ATCTGGTGAT CCTCTGGGTC GGTGCCAATG
     TCTGTCGAAG TTCGGCCTGC TAGACCACTA GGAGACCCAG CCACGGTTAC

401  ACTATCTGGC CTATGGCTGG AACACGGAGC AGGATGCCAA GCGGGTTCGC
     TGATAGACCG GATACCGACC TTGTGCCTCG TCCTACGGTT CGCCCAAGCG

451  GATGCCATCA GCGATGCGGC CAACCGCATG GTACTGAACG GTGCCAAGCA
     CTACGGTAGT CGCTACGCCG GTTGGCGTAC CATGACTTGC CACGGTTCGT

501  GATACTGCTG TTCAACCTGC CGGATCTGGG CCAGAACCCG TCAGCTCGCA
     CTATGACGAC AAGTTGGACG GCCTAGACCC GGTCTTGGGC AGTCGAGCGT

551  GTCAGAAGGT GGTCGAGGCG GTCAGCCATG TCTCCGCCTA TCACAACCAG
     CAGTCTTCCA CCAGCTCCGC CAGTCGGTAC AGAGGCGGAT AGTGTTGGTC

601  CTGCTGCTGA ACCTGGCACG CCAGCTGGCC CCCACCGGCA TGGTAAAGCT
     GACGACGACT TGGACCGTGC GGTCGACCGG GGGTGGCCGT ACCATTTCGA

651  GTTCGAGATC GACAAGCAAT TTGCCGAGAT GCTGCGTGAT CCGCAGAACT
     CAAGCTCTAG CTGTTCGTTA AACGGCTCTA CGACGCACTA GGCGTCTTGA

701  TCGGCCTGAG CGACGTCGAG AACCCCTGCT ACGACGGCGC CTATGTGTGG
     AGCCGGACTC GCTGCAGCTC TTGGGGACGA TGCTGCCGCC GATACACACC

751  AAGCCGTTTG CCACCCGCAG CGTCAGCACC GACCGCCAGC TCTCCGCCTT
     TTCGGCAAAC GGTGGGCGTC GCAGTCGTGG CTGGCGGTCG AGAGGCGGAA

801  CAGTCCGCAG GAACGCCTCG CCATCGCCGG CAACCCGCTG CTGGCACAGG
     GTCAGGCGTC CTTGCGGAGC GGTAGCGGCC GTTGGGCGAC GACCGTGTCC

851  CCGTTGCCAG TCCTATGGCC CGCCGCAGCG CCAGCCCCCT CAACTGTGAG
     GGCAACGGTC AGGATACCGG GCGGCGTCGC GGTCGGGGA GTTGACACTC

901  GGCAAGATGT TCTGGGATCA GGTACACCCG ACCACTGTCG TGCACGCAGC
     CCGTTCTACA AGACCCTAGT CCATGTGGGC TGGTGACAGC ACGTGCGTCG

951  CCTGAGCGAG CGCGCCGCCA CCTTCATCGC GAACCAGTAC GAGTTCCTCG
     GGACTCGCTC GCGCGGCGGT GGAAGTAGCG CTTGGTCATG CTCAAGGAGC

1001 CCCAC TGA
     GGGTG ACT
```

Figure 30 (SEQ ID No. 34)

```
  1  MKKWFVCLLG  LIALTVQAAD  TRPAFSRIVM  FGDSLSDTGK  MYSKMRGYLP
 51  SSPPYYEGRF  SNGPVWLEQL  TKQFPGLTIA  NEAEGGATAV  AYNKISWNPK
101  YQVINNLDYE  VTQFLQKDSF  KPDDLVILWV  GANDYLAYGW  NTEQDAKRVR
151  DAISDAANRM  VLNGAKQILL  FNLPDLGQNP  SARSQKVVEA  VSHVSAYHNK
201  LLLNLARQLA  PTGMVKLFEI  DKQFAEMLRD  PQNFGLSDVE  NPCYDGGYVW
251  KPFATRSVST  DRQLSAFSPQ  ERLAIAGNPL  LAQAVASPMA  RRSASPLNCE
301  GKMFWDQVHP  TTVVHAALSE  RAATFIETQY  EFLAHG*
```

Figure 31 (SEQ ID No. 35)

```
   1 ATGAAAAAAT GGTTTGTTTG TTTATTGGGG TTGATCGCGC TGACAGTTCA
     TACTTTTTTA CCAAACAAAC AAATAACCCC AACTAGCGCG ACTGTCAAGT

51 GGCAGCCGAC ACTCGCCCCG CCTTCTCCCG GATCGTGATG TTCGGCGACA
     CCGTCGGCTG TGAGCGGGGC GGAAGAGGGC CTAGCACTAC AAGCCGCTGT

101 GCCTCTCCGA TACCGGCAAA ATGTACAGCA AGATGCGCGG TTACCTCCCC
     CGGAGAGGCT ATGGCCGTTT TACATGTCGT TCTACGCGCC AATGGAGGGG

151 TCCAGCCCGC CCTACTATGA GGGCCGTTTC TCCAACGGAC CCGTCTGGCT
     AGGTCGGGCG GGATGATACT CCCGGCAAAG AGGTTGCCTG GGCAGACCGA

201 GGAGCAGCTG ACCAAGCAGT TCCCGGGTCT GACCATCGCC AACGAAGCGG
     CCTCGTCGAC TGGTTCGTCA AGGGCCCAGA CTGGTAGCGG TTGCTTCGCC

251 AAGGCGGTGC CACTGCCGTG GCTTACAACA AGATCTCCTG GAATCCCAAG
     TTCCGCCACG GTGACGGCAC CGAATGTTGT TCTAGAGGAC CTTAGGGTTC

301 TATCAGGTCA TCAACAACCT GGACTACGAG GTCACCCAGT TCTTGCAGAA
     ATAGTCCAGT AGTTGTTGGA CCTGATGCTC CAGTGGGTCA AGAACGTCTT

351 AGACAGCTTC AAGCCGGACG ATCTGGTGAT CCTCTGGGTC GGTGCCAATG
     TCTGTCGAAG TTCGGCCTGC TAGACCACTA GGAGACCCAG CCACGGTTAC

401 ACTATCTGGC ATATGGCTGG AATACGGAGC AGGATGCCAA GCGAGTTCGC
     TGATAGACCG TATACCGACC TTATGCCTCG TCCTACGGTT CGCTCAAGCG

451 GATGCCATCA GCGATGCGGC CAACCGCATG GTACTGAACG GTGCCAAGCA
     CTACGGTAGT CGCTACGCCG GTTGGCGTAC CATGACTTGC CACGGTTCGT

501 GATACTGCTG TTCAACCTGC CGGATCTGGG CCAGAACCCG TCAGCCCGCA
     CTATGACGAC AAGTTGGACG GCCTAGACCC GGTCTTGGGC AGTCGGGCGT

551 GTCAGAAGGT GGTCGAGGCC GTCAGCCATG TCTCCGCCTA TCACAACAAG
     CAGTCTTCCA CCAGCTCCGC CAGTCGGTAC AGAGGCGGAT AGTGTTGTTC

601 CTGCTGCTGA ACCTGGCACG CCAGCTGGCC CCCACCGGCA TGGTAAAGCT
     GACGACGACT TGGACCGTGC GGTCGACCGG GGGTGGCCGT ACCATTTCGA

651 GTTCGAGATC GACAAGCAAT TGCCGAGAT GCTGCGTGAT CCGCAGAACT
     CAAGCTCTAG CTGTTCGTTA ACGGCTCTA CGACGCACTA GGCGTCTTGA

701 TCGGCCTGAG CGACGTCGAG AACCCCTGCT ACGACGGCGG CTATGTGTGG
     AGCCGGACTC GCTGCAGCTC TTGGGACGA TGCTGCCGCC GATACACACC

751 AAGCCGTTTG CCACCCGCAG CGTCAGCACC GACCGCCAGC TCTCCGCCTT
     TTCGGCAAAC GGTGGGCGTC GCAGTCGTGG CTGGCGGTCG AGAGGCGGAA

801 CAGTCCGCAG GAACGCCTCG CCATCGCCGG CAACCCGCTG CTGGCACAGG
     GTCAGGCGTC CTTGCGGAGC GGTAGCGGCC GTTGGGCGAC GACCGTGTCC

851 CCGTTGCCAG TCCTATGGCC CGCCGCAGCG CCAGCCCCCT CAACTGTGAG
     GGCAACGGTC AGGATACCGG GCGGCGTCGC GGTCGGGGA GTTGACACTC

901 GGCAAGATGT TCTGGGATCA GGTACACCCG ACCACTGTCG TGCACGCAGC
     CCGTTCTACA AGACCCTAGT CCATGTGGGC TGGTGACAGC ACGTGCGTCG

951 CCTGAGCGAG CGCGCCGCCA CCTTCATCGA GACCCAGTAC GAGTTCCTCG
     GGACTCGCTC GCGCGGCGGT GGAAGTAGCT CTGGGTCATG CTCAAGGAGC

1001 CCCACGGATG A
     GGGTGCCTAC T
```

Figure 32

```
                   1         10        20        30        40        50
                   |---------+---------+---------+---------+---------|
          satA     ADTRPAFSRIVMFGDSLSDTGKMYSKMRGYLPSSPPYYEGRFSN--G
          R.sol    QSGNPNVAKYQRMVVFGDSLSDIGT--------YTPVAQAYGGGKFTTNPG
          Consensus ...adnraafqRiVmFGDSLSDiGk.......YlPsaqaygeGrFsn..G 51        60        70        80        90        100
                   |---------+---------+---------+---------+---------|
          satA     PVHLEQLTKQFPGLTIANEAEGGATAVAYNKISHNPKYQVINNLDYEVTQ
          R.sol    PIHAETVAAQL-GVTLTPAVMGYATSVQNCPKAGCFDYAQGGSRVTDPNG
          Consensus P!HaEqlaaQl.GlTianaaeGgATaVannkiagnfdYaqgnnrdt#pnq 101       110       120       130       140       150
                   |---------+---------+---------+---------+---------|
          satA     FLQKDSFKPDDLVILMVGANDYLAYG--HMTEQDAKRVRDAISDAANRMV
          R.sol    IGHNGGAGALTYPVQQQLAMFYAASNNTFNGMNDVYFVLAGSNDIFFHTT
          Consensus igqndgagaddlp!qqqgAMdYaAsn..fNg##DakrVraainDaanrnt 151       160       170       180       190       200
                   |---------+---------+---------+---------+---------|
          satA     LNGAKQILLFNLPDLGQNPSARSQKVVEAVSHVSAYHNKL-LLNLARQLA
          R.sol    AAATSGSGVTPAIATAQVQQAATDLVGYYKDHIAKGATQVYYFNLPDSSL
          Consensus aaaakqiglfnaialaQnqqAas#lVgeakdh!aaganql.llNLarqla 201       210       220       230       240       250
                   |---------+---------+---------+---------+---------|
          satA     PTGMVKLFEIDKQFAEHLRDPQNFGLSDVENPCYDGGYVHKPFATRSVST
          R.sol    TPDGVASGTTGQALLHALVGTFNTTLQSGLAGTSARIIDFNAQLTAAIQN
          Consensus ppdgValgeidqalaeaLrdpqNfgLqdgeagcsargidfnaqaTaa!qn 251       260       270       280       290       300
                   |---------+---------+---------+---------+---------|
          satA     DRQLSAFSPQERLAIAG--NPLLAQAVASPM---ARRSASPLNCEGKMFH
          R.sol    GASFGFANTSARACDATKIMALVPSAGGSSLFCSANTLVASGADQSYLFA
          Consensus daqlgaanpqaRaadAg..NaLlaqAgaSp$...Arrlaapgad#gk$Fa 301       310       320       330
                   |---------+---------+---------|
          satA     DQVHPTTVVHAALSERAATFIETQYEFLAH
          R.sol    DGVHPTTAGHRLIASNVLARLLA--DNVAH
          Consensus DqVHPTTagHaaiaeraaariea..#nlAH
```

Figure 33A

```
Pfam          *->ivafGDSltdggg..............ayygdsdgggwgagladrltsla..rlrargrgvdv
Sriml    38   YVALGDSYSSGVG............agSYDSSSGSCKRSTKSYPALWAAS..------HTGTRF  81
Scoe1     5   YVAVGDSFTEG--............---VGDPGPDGAFVGWADRLAVLL..ADRRPEGDFTY  47
Scoe2    10   LVAVGDSFTEG--............--MSDLLPDGSYRGWADLLATRM..--AARSPGFRY  50
Scoe3   239   VVAFGDSITDG--............ARSQSDANHRWTDVLAARLHEAA..GDGRDTPRYSV 283
Scoe4    75   LMMLGDSTAAG--............------QGVHRAGQTPGALLASG..LAAVAERPVRL 113
Scoe5    66   VAAVGDSITRGFD............acAVLSDCPEVSWATGSSAKVDSLAvrLLGKADAAEHS 116
Ahyd1    28   IVMFGDSLSDTGKmyskmrgylpssppyYEGRFSNGPVWLEQLTNEFPGLTiaNEAEGGPTAVA  91
Asal1    28   IVMFGDSLSDTGKmyskmrgylpssppyYEGRFSNGPVWLEQLTKQF----..------PGLTI  79
Ahyd2    40   IVMFGDSLSDTGKmyskmrgylpssppyYEGRFSNGPVWLEQLTKQFPGLTiaNEAEGGATAVA 103

Pfam          fnrgisGrtsdGrlvvDarlvatllFlaqflGlnlpPYLsgdflrGANFAsagAtllgtslipflni
Sriml    82   NFTACSGAR------------------------------------------------------  90
Scoe1    48   TNLAVRGRL------------------------------------------------------  56
Scoe2    51   ANLAVRGKL------------------------------------------------------  59
Scoe3   284   VNEGISGNR------------------------------------------------------ 292
Scoe4   114   GSVAQPGAC------------------------------------------------------ 122
Scoe5   117   WNYAVTGAR------------------------------------------------------ 125
Ahyd1    92   YNKISWNPK------------------------------------------------------ 100
Asal1    80   ANEAEGGAT------------------------------------------------------  88
Ahyd2   104   YNKISWNPK------------------------------------------------------ 112

Pfam          QvqFkdtkskvlelrqa......lgllqellrlvpvldakspdlvtimiGtNDI...itvakfgpks
Sriml    91   -----------------......---TGDVLAKQLTPVNSGTDLVSITIGGNDAgfaDTMTTCNLQG 131
Scoe1    57   -----------------......--LDQIVAEQVPRVVGLAPDLVSFAAGGNDI...--------I----  86
Scoe2    60   -----------------......--IGQIVDEQVDVAAAMGADVITLVGGINDT...-----------  88
Scoe3   293   -------LLTSRPGRPA......DNPSGLSRFQRDVLERTNVKAVVVVLGVNDV...---------- 333
Scoe4   123   -----------------......SDDLDRQVALVLAEPDRVPDICVIMVGANDV...---------- 153
Scoe5   126   -----------------......---MADLTAQVTRAAQREPELVAVMAGANDA..........---CR 155
Ahyd1   101   -------------YQVI......NNLDYEVTQFLQKDSFKPDDLVILWVGANDY...---------LA 137
Asal1    89   -------AVAYNKISWNpkyqvyNNLDYEVTQFLQKDSFKPDDLVILWVGANDY...---------LA 137
Ahyd2   113   -------------YQVI......NNLDYEVTQFLQKDSFKPDDLVILWVGANDY...---------LA 149

Pfam          .......tksdrnvsvpcfrdnlrklikrLrsangariiilitlvllnlpl..........plGCl
Sriml   132   esaclarIAKARAYIQQTLPAQLDQVYDAIDSRAPAA-----QVVVLGYP-..............----- 176
Scoe1    87   .......---RPGTDPDEVAERFELAVAALT-AAAGTVLVTTGFDTRGVP-..............----- 125
Scoe2    89   .......---LRPKCDMARVRDLLTQAVERLAPHCEQLVLMRSP-.................----- 122
Scoe3   334   .......LNSPELADRDAILTGLRTLVDRAHARGLRVVGATITPFGGYGG-.............----- 376
Scoe4   154   .......---THRMPATRSVRHLSSAVRRLR-TAGAEVVVGTCPDLGTIE-.............----- 192
Scoe5   156   .......STTSAMTPVADFRAQFEEAMATLR-KKLPKAQVYVSSIPDLKRLwsqgrtr.plgkQVWKL 214
Ahyd1   138   .......YGWNTEQDAKRVRDAISDAANRMV-LNGAK-----EILLFNLP-.............----- 174
Asal1   138   .......YGWNTEQDAKRVRDAISDAANRMV-LNGAK-----QILLFNLP-.............----- 174
Ahyd2   150   .......YGWNTEQDAKRVRDAISDAANRMV-LNGAK-----QILLFNLP-.............----- 186

Pfam          pq.klalalassknvdatgclerlneavadyneαlrelaei.ek.l.q.aqlrkdglpdlkeanvpy
Sriml   177   --.RFYKLGGSCAVGLSEKSRAAINAAADDINAVTAKRA--.--.-.-.-----------ADHGFAF 219
Scoe1   126   --.-----------VLKHLRGKIATYNGHVRAIA--.--.-.-.-----------DRYGCPV 152
Scoe2   123   --.-----------GRQGPVLERFRPRMEALFAVIDDLA--.--.-.-.-----------GRHGAVV 154
Scoe3   377   --.YTEARETMRQEVNEEIRSGRVFDTVVDFDKALRDPY--.--.-.-.------------------ 412
Scoe4   193   --.-----------------RVRQPLRWLaRRaSrQlAAAQTIGAVEQGGRTVSL 227
Scoe5   215   GLcPSMLGDADSLDSAATLRRNTVRDRVADYNEVLREVC--.--.-.-.AkDRRCRSDDGAVHEFRFGT 273
Ahyd1   175   --.-----DLGQNPSARSQKVVEAASHVSAYHNQLLLNLA--.--.-.-.RQLAPTGMVKLFEIDKQF 224
Asal1   175   --.-----DLGQNPSARSQKVVEAVSHVSAYHNKLLLNLA--.--.-.-.RQLAPTGMVKLFEIDKQF 224
Ahyd2   187   --.-----DLGQNPSARSQKVVEAVSHVSAYHNQLLLNLA--.--.-.-.RQLAPTGMVKLFEIDKQF 236

Pfam          VDlysifqdldgiqnpsayv.y....GFeet.kaCCGyGgr.yNyn..rv.CGnag.l.ck.vtakaC
Sriml   220   GDVNT----------------.-...------.----------.-TFAgHELCSGAPWL.HS.VT---- 242
Scoe1   153   LDLWSLRSVQDRRA------.-...------.----------.----.--.------.-.--.------ 166
Scoe2   155   VDLYGAQSLADPRM------.-...------.----------.----.--.------.-.--.------ 168
Scoe3   413   ------------------.-...------.----------.----.--.------.-.--.------ 413
Scoe4   228   GDLLGPEFAQNPREL------.-...------.----------.----.--.------.-.--.------ 242
Scoe5   274   DQL----------------.-...------.----------.----.--.------.-.--.------ 276
Ahyd1   225   AEMLRDPQNFGLSDQRNACYgGsyvwKPFASrSASTDSQLSaFNPQeRLaIAGNPLLaQAVASPMAA 291
Asal1   225   AEMLRDPQNFGLSDVENPCYdGgyvwKPFATrSVSTDRQLSaFSPQeRLaIAGNPLLaQAVASPMAR 291
Ahyd2   237   AEMLRDPQNFGLSDVENPCYdGgyvwKPFATrSVSTDRQLSaFSPQeRLaIAGNPLLaQAVASPMAR 303
```

Figure 33B

```
                            ▼
Pfam         .dassyll.atlfwDgf.HpsekGykavAeal<-*
Sriml  243 .--------.--LPVENSyHPTANGQSKGYLPV    263
Scoe1  167 .--------.--WDADRL.HLSPEGHTRVALRA    186
Scoe2  169 .--------.--WDVDRL.HLTAEGHRRVAEAV    188
Scoe3  413 .-DPRRMRsDYDSGDHL.HPGDKGYARMGAVI    441
Scoe4  243 .--------.--FGPDNY.HPSAEGYATAAMAV    262
Scoe5  277 .--------.--SHWDWF.HPSVDGQARLAEIA    296
Ahyd1  292 rSASTLNCeGKMFWDQV.HPTTVVHAALSEPA    322
Asal1  292 rSASPLNCeGKMFWDQV.HPTTVVHAALSERA    322
Ahyd2  304 rSASPLNCeGKMFWDQV.HPTTVVHAALSERA    334
```

Figure 34

```
Pfam         *->ivafGDSltdggg...............ayygdsdgggwgagladrltsla..rlrargrgvdv
Sriml   38   YVALGDSYSSGVG.............agSYDSSSGSCKRSTKSYPALWAAS..-----HTGTRF  81
Scoe1    5   YVAVGDSFTEG--.............--VGDPGPDGAFVGWADRLAVLL..ADRRPEGDFTY     47
Scoe2   10   LVAVGDSFTEG--.............--MSDLLPDGSYRGWADLLATRM..--AARSPGFRY     50
Ahyd1   28   IVMFGDSLSDTGKmyskmrgylpssppyYEGRFSNGPVWLEQLTNEFPGLTiaNEAEGGPTAVA  91
Asal1   28   IVMFGDSLSDTGKmyskmrgylpssppyYEGRFSNGPVWLEQLTKQF----..-------PGLTI   79
Ahyd2   40   IVMFGDSLSDTGKmyskmrgylpssppyYEGRFSNGPVWLEQLTKQFPGLTiaNEAEGGATAVA 103

Pfam         fnrgisGrtsdGrlvvDarlvatllFlaqflGlnlpPYLsgdflrGANFAsagAtIlgtslipflni
Sriml   82   NFTACSGAR------------------------------------------------------  90
Scoe1   48   TNLAVRGRL------------------------------------------------------  56
Scoe2   51   ANLAVRGKL------------------------------------------------------  59
Ahyd1   92   YNKISWNPK------------------------------------------------------ 100
Asal1   80   ANEAEGGAT------------------------------------------------------  88
Ahyd2  104   YNKISWNPK------------------------------------------------------ 112

Pfam         QvqFkdfkskvlelrqa......lgllqellrlvpvldakspdlvtimiGtND1...itvakfgpks
Sriml   91   ------------------......---TGDVLAKQLTPVNSGTDLVSITIGGNDAgfaDTMTTCNLQG .131
Scoe1   57   ------------------......---LDQIVAEQVPRVVGLAPDLVSFAAGGNDI...-I----  86
Scoe2   60   ------------------......---IGQIVDEQVDVAAAMGADVITLVGGLNDT..--------  88
Ahyd1  101   --------------YQVI......NNLDYEVTQFLQKDSFKPDDLVILWVGANDY...--------LA 137
Asal1   89   -------AVAYNKISWNpkyqvyNNLDYEVTQFLQKDSFKPDDLVILWVGANDY...--------LA 137
Ahyd2  113   --------------YQVI......NNLDYEVTQFLQKDSFKPDDLVILWVGANDY...--------LA 149

Pfam         .......tksdrnvsvpefrdnlrklikrLrsangariiilitlvllnlplplGCl
Sriml  132   esaclarIAKARAYIQQTLPAQLDQVYDAIDSRAPAA-----QVVVLGYP------ 176
Scoe1   87   .......---RPGTDPDEVAERFELAVAALT-AAAGTVLVTTGFDTRGVP------ 125
Scoe2   89   .......---------LRPKCDMARVRDLLTQAVERLAPHCEQLVLMRSP------ 122
Ahyd1  138   .......YGWNTEQDAKRVRDAISDAANRMV-LNGAK-----EILLFNLP------ 174
Asal1  138   .......YGWNTEQDAKRVRDAISDAANRMV-LNGAK-----QILLFNLP------ 174
Ahyd2  150   .......YGWNTEQDAKRVRDAISDAANRMV-LNGAK-----QILLFNLP------ 186

Pfam         pqklalalasssknvdatgclerlneavadynealrelaeieklqaqlrkdglpdlkeanvpy
Sriml  177   --RFYKLGGSCAVGLSEKSRAAINAAADDINAVTAKRA------------------ADHGFAF 219
Scoe1  126   ---------------VLKHLRGKIATYNGHVRAIA------------------DRYGCPV 152
Scoe2  123   ---------------GRQGPVLERFRPRMEALFAVIDDLA------------------GRHGAVV 154
Ahyd1  175   ------DLGQNPSARSQKVVEAASHVSAYHNQLLLNLA------RQLAPTGMVKLFEIDKQF 224
Asal1  175   ------DLGQNPSARSQKVVEAVSHVSAYHNKLLLNLA------RQLAPTGMVKLFEIDKQF 224
Ahyd2  187   ------DLGQNPSARSQKVVEAVSHVSAYHNQLLLNLA------RQLAPTGMVKLFEIDKQF 236

Pfam         VDlysifqdldgiqnpsayv.y....GFeet.kaCCGyGgr.yNyn.rv.CGnag.l.ck.vtakaC
Sriml  220   GDVNT------------------.-...-----.----------.-TFAgHElCSGAPwL.HS.VT---- 242
Scoe1  153   LDLWSLRSVQDRRA------.-...-----.----------.----.--.-----.-.--.------- 166
Scoe2  155   VDLYGAQSLADPRM------.-...-----.----------.----.--.-----.-.--.------- 168
Ahyd1  225   AEMLRDPQNFGLSDQRNACYgGsyvwKPFASrSASTDSQLSaFNPQeRLaIAGNPllAQAvASPMAA 291
Asal1  225   AEMLRDPQNFGLSDVENPCYdGgyvwKPFATrSVSTDRQLSaFSPQeRLaIAGNPllAQAvASPMAR 291
Ahyd2  237   AEMLRDPQNFGLSDVENPCYdGgyvwKPFATrSVSTDRQLSaFSPQeRLaIAGNPllAQAvASPMAR 303

Pfam         .dassyll.atlfwDgf.HpsekGykavAeal<-*
Sriml  243   .-------.--LPVENSyHPTANGQSKGYLPV      263
Scoe1  167   .-------.--WDADRL.HLSPEGHTRVALRA      186
Scoe2  169   .-------.--WDVDRL.HLTAEGHRRVAEAV      188
Ahyd1  292   rSASTLNCeGKMFWDQV.HPTTVVHAALSEPA      322
Asal1  292   rSASPLNCeGKMFWDQV.HPTTVVHAALSERA      322
Ahyd2  304   rSASPLNCeGKMFWDQV.HPTTVVHAALSERA      334
```

Controls
Pos  Neg        SE  His  SE  His  SE  His  SE  His

A. hydrophila enzyme         A. salmonicida
                                enzyme

Figure 47

(SEQ ID No. 36)

```
  1  MFKFKKNFLV GLSAALMSIS LFSATASAAS ADSRPAFSRI VMFGDSLSDT
 51  GKMYSKMRGY LPSSPPYYEG RFSNGPVWLE QLTKQFPGLT IANEAEGGAT
101  AVAYNKISWN PKYQVINNLD YEVTQFLQKD SFKPDDLVIL WVGANDYLAY
151  GWNTEQDAKR VRDAISDAAN RMVLNGAKQI LLFNLPDLGQ NPSARSQKVV
201  EAVSHVSAYH NQLLLNLARQ LAPTGMVKLF EIDKQFAEML RDPQNFGLSD
251  VENPCYDGGY VWKPFATRSV STDRQLSAFS PQERLAIAGN PLLAQAVASP
301  MARRSASPLN CEGKMFWDQV HPTTVVHAAL SERAATFIAN QYEFLAH**
```

Figure 48 (SEQ ID No. 54)

```
   1 ATGTTTAAGT TTAAAAAGAA TTTCTTAGTT GGATTATCGG CAGCTTTAAT
     TACAAATTCA AATTTTTCTT AAAGAATCAA CCTAATAGCC GTCGAAATTA

51 GAGTATTAGC TTGTTTTCGG CAACCGCCTC TGCAGCTAGC GCCGACAGCC
     CTCATAATCG AACAAAAGCC GTTGGCGGAG ACGTCGATCG CGGCTGTCGG

101 GTCCCGCCTT TTCCCGGATC GTGATGTTCG GCGACAGCCT CTCCGATACC
     CAGGGCGGAA AAGGGCCTAG CACTACAAGC CGCTGTCGGA GAGGCTATGG

151 GGCAAAATGT ACAGCAAGAT GCGCGGTTAC CTCCCCTCCA GCCCGCCCTA
     CCGTTTTACA TGTCGTTCTA CGCGCCAATG GAGGGGAGGT CGGGCGGGAT

201 CTATGAGGGC CGTTTCTCCA ACGGACCCGT CTGGCTGGAG CAGCTGACCA
     GATACTCCCG GCAAAGAGGT TGCCTGGGCA GACCGACCTC GTCGACTGGT

251 AACAGTTCCC GGGTCTGACC ATCGCCAACG AAGCGGAAGG CGGTGCCACT
     TTGTCAAGGG CCCAGACTGG TAGCGGTTGC TTCGCCTTCC GCCACGGTGA

301 GCCGTGGCTT ACAACAAGAT CTCCTGGAAT CCCAAGTATC AGGTCATCAA
     CGGCACCGAA TGTTGTTCTA GAGGACCTTA GGGTTCATAG TCCAGTAGTT

351 CAACCTGGAC TACGAGGTCA CCCAGTTCTT GCAGAAAGAC AGCTTCAAGC
     GTTGGACCTG ATGCTCCAGT GGGTCAAGAA CGTCTTTCTG TCGAAGTTCG

401 CGGACGATCT GGTGATCCTC TGGGTCGGTG CCAATGACTA TCTGGCCTAT
     GCCTGCTAGA CCACTAGGAG ACCCAGCCAC GGTTACTGAT AGACCGGATA

451 GGCTGGAACA CGGAGCAGGA TGCCAAGCGG GTTCGCGATG CCATCAGCGA
     CCGACCTTGT GCCTCGTCCT ACGGTTCGCC CAAGCGCTAC GGTAGTCGCT

501 TGCGGCCAAC CGCATGGTAC TGAACGGTGC CAAGCAGATA CTGCTGTTCA
     ACGCCGGTTG GCGTACCATG ACTTGCCACG GTTCGTCTAT GACGACAAGT

551 ACCTGCCGGA TCTGGGCCAG AACCCGTCAG CTCGCAGTCA GAAGGTGGTC
     TGGACGGCCT AGACCCGGTC TTGGGCAGTC GAGCGTCAGT CTTCCACCAG

601 GAGGCGGTCA GCCATGTCTC CGCCTATCAC AACCAGCTGC TGCTGAACCT
     CTCCGCCAGT CGGTACAGAG GCGGATAGTG TTGGTCGACG ACGACTTGGA

651 GGCACGCCAG CTGGCCCCCA CCGGCATGGT AAAGCTGTTC GAGATCGACA
     CCGTGCGGTC GACCGGGGGT GGCCGTACCA TTTCGACAAG CTCTAGCTGT

701 AGCAATTTGC CGAGATGCTG CGTGATCCGC AGAACTTCGG CCTGAGCGAC
     TCGTTAAACG GCTCTACGAC GCACTAGGCG TCTTGAAGCC GGACTCGCTG

751 GTCGAGAACC CCTGCTACGA CGGCGGCTAT GTGTGGAAGC CGTTTGCCAC
     CAGCTCTTGG GGACGATGCT GCCGCCGATA CACACCTTCG GCAAACGGTG

801 CCGCAGCGTC AGCACCGACC GCCAGCTCTC CGCCTTCAGT CCGCAGGAAC
     GGCGTCGCAG TCGTGGCTGG CGGTCGAGAG GCGGAAGTCA GGCGTCCTTG

851 GCCTCGCCAT CGCCGGCAAC CCGCTGCTGG CACAGGCCGT TGCCAGTCCT
     CGGAGCGGTA GCGGCCGTTG GCGACGACC GTGTCCGGCA ACGGTCAGGA

901 ATGGCCCGCC GCAGCGCCAG CCCCCTCAAC TGTGAGGGCA AGATGTTCTG
     TACCGGGCGG CGTCGCGGTC GGGGGAGTTG ACACTCCCGT TCTACAAGAC

951 GGATCAGGTA CACCCGACCA CTGTCGTGCA CGCAGCCCTG AGCGAGCGCG
     CCTAGTCCAT GTGGGCTGGT GACAGCACGT GCGTCGGGAC TCGCTCGCGC

1001 CCGCCACCTT CATCGCGAAC CAGTACGAGT TCCTCGCCCA CTGATGA
     GGCGGTGGAA GTAGCGCTTG GTCATGCTCA AGGAGCGGGT GACTACT
```

METHOD OF USING LIPID ACYLTRANSFERASE

REFERENCE TO RELATED APPLICATIONS

This application is a divisional of U.S. application Ser. No. 11/182,480, filed Jul. 15, 2005 now U.S. Pat. No. 7,638,293 which is a continuation-in-part of International Patent Application PCT/IB2004/000575 filed Jan. 15, 2004 and published as WO 2004/064987 on Aug. 5, 2004 which claims priority to Great Britain Application Numbers 0301117.8, 0301118.6, 0301119.4, 0301120.2, 0301121.0, 0301122.8, all of which were filed Jan. 17, 2003, U.S. Patent Application No. 60/489,441 filed Jul. 23, 2003, and Great Britain Application Number 0330016.7 filed Dec. 24, 2003. Each of the above referenced applications, and each document cited in this text ("application cited documents") and each document cited or referenced in each of the application cited documents, and any manufacturer's specifications or instructions for any products mentioned in this text and in any document incorporated into this text, are hereby incorporated herein by reference; and, technology in each of the documents incorporated herein by reference can be used in the practice of this invention.

FIELD OF INVENTION

The present invention relates to a method for the bioconversion of lipids to produce a carbohydrate ester and/or a protein ester and/or a protein subunit ester and/or a hydroxy acid ester by use of a lipid acyltransferase.

The present invention further relates to the use of a lipid acyltransferase to bioconvert a lipid into one or more of the following: a carbohydrate ester and/or a protein and/or a protein subunit ester and/or and/or a hydroxy acid ester.

The present invention further relates to the use of an immobilised lipid acyltransferase as defined herein, which, immobilised lipid acyltransferase may be used in bioconversion of a lipid in a high water environment to produce one or more of a carbohydrate ester and/or a protein ester and/or a protein subunit ester and/or a hydroxy acid ester.

The present invention yet further relates to an immobilised lipid acyltransferase.

TECHNICAL BACKGROUND

Lipases have been extensively used in bioconversion of lipids to make high value products, for example sugar esters, for use in a wide range of industries, including the food and/or feed industries, the cosmetics and/or skin care industries, the oleochemical industry and the pharmaceutical industry.

When bioconversion processes require hydrolysis of lipid substrates, lipolytic enzymes can be used in high water environments. However, when bioconversion processes require interesterification or transesterification reactions such as by alcoholysis the use of lipases in high water environments can be detrimental due to unwanted hydrolysis reactions, which result in unwanted bioproducts and/or lower yields of the bioconversion product.

Typically, bioconversion processes requiring interesterification and/or transesterification have utilised lipases in non-water environments such as in oil systems and/or in organic solvent systems such as in butanol, methanol or hexane. Such systems provide an environment in which both the polar acceptor molecule and the lipid donor molecule can be at least partially solubilised, and the lipase has sufficient enzyme activity. Although a small amount of water is required for any enzymatic activity, the amount of water is strictly maintained at a low level to avoid hydrolytic activity of the enzyme.

Conventionally sugar esters, protein esters or hydroxyacid esters have been produced by chemical synthesis using inorganic catalysts. Convention bioconversion processes for the production of sugar esters or hydroxyacid esters utilise lipases in organic solvent environments or supercritical fluids where there is only a low amount of (if any) water present.

Lecointe et al Biotechnology Letters, Vol 18., No. 8 (August), pp 869-874 disclose a study of a number of lipase enzymes and their activity in an aqueous media on the production of methyl ester or butyl ester from methanol and butanol, respectively, Lecointe et al teach a lipase/acyltransferase from *Candida parapsilosis* which as methanol or butanol concentrations increased showed a reduced hydrolysis activity and an enhanced capability of the enzyme to produce methyl ester and butyl ester. The use of a lipase/acyltransferase from *C. parapsilosis* in the production of fatty hydroxamic acid is taught in Vaysse et al J. of Biotechnology 53 (1997) 41-46.

Lipase:cholesterol acyltransferases have been known for some time (see for example Buckley—Biochemistry 1983, 22, 5490-5493). In particular, glycerophospholipid:cholesterol acyl transferases (often referred to as GCATs) have been found, which like the plant and/or mammalian lecithin:cholesterol acyltransferases (LCATs), will catalyse fatty acid transfer between phosphatidylcholine and cholesterol.

Upton and Buckley (TIBS 20, May 1995 p 178-179) and Brumlik and Buckley (J. of Bacteriology Apr. 1996 p 2060-2064) teach a lipase/acyltransferase from *Aeromonas hydrophila* which has the ability to carry out acyl transfer to alcohol acceptors in an aqueous media.

SUMMARY ASPECTS OF THE PRESENT INVENTION

According to a first aspect of the present invention there is provided a method of producing one or more of a carbohydrate ester, a protein ester, a protein subunit ester or a hydroxy acid ester, which method comprises admixing an acyl donor, an acyl acceptor and water to produce a high water environment comprising 5-98% water, wherein said acyl donor is a lipid substrate selected from one or more of the group consisting of a phospholipid, a lysophospholipid, a triacylglyceride, a diglyceride, a glycolipid or a lysoglycolipid and said acyl acceptor is selected from one or more of the group consisting of a carbohydrate, a protein, a protein subunit or a hydroxy acid; and contacting the admixture with a lipid acyltransferase, such that said lipid acyltransferase catalyses one or both of the following reactions: alcoholysis or transesterification.

In a further aspect the present invention provides use of a lipid acyltransferase to produce one or more of a carbohydrate ester, a protein ester, a protein subunit ester or a hydroxy acid ester by catalysis of one or both of alcoholysis or transesterification in an admixture of an acyl donor, an acyl acceptor and water, which admixture comprises 5-98% water, wherein said acyl donor is a lipid substrate selected from one or more of the group consisting of a phospholipid, a lysophospholipid, a triacylglyceride, a diglyceride, a glycolipid or a lysoglycolipid and said acyl acceptor is selected from one or more of the group consisting of a carbohydrate, a protein, a protein subunit or a hydroxy acid.

In accordance with another aspect of the present invention, there is provided a carbohydrate ester, a protein ester, a protein subunit ester or a hydroxy acid ester produced by a method according to the present invention.

In accordance with a further aspect of the present invention, there is provided a pharmaceutical, a cosmetic, a foodstuff, a feedstuff, a paint comprising a carbohydrate ester, a protein ester, a protein subunit ester or a hydroxy acid ester produced by a method according to the present invention.

In accordance with a further aspect, the present invention provides an immobilised lipid acyltransferase enzyme as defined herein.

DETAILED ASPECTS OF THE PRESENT INVENTION

The term "lipid acyltransferase" as used herein means an enzyme which as well as having lipase activity (generally classified as E.C. 3.1.1.x in accordance with the Enzyme Nomenclature Recommendations (1992) of the Nomenclature Committee of the International Union of Biochemistry and Molecular Biology) also has acyltransferase activity (generally classified as E.C. 2.3.1.x), whereby the enzyme is capable of transferring an acyl group from a lipid to one or more of the following acceptor substrates: a carbohydrate; a protein; a protein subunit or a hydroxy acid.

Preferably, the "acyl acceptor" according to the present invention is not water.

In one aspect, preferably the enzyme is capable of transferring an acyl group from a lipid substrate to a carbohydrate.

The carbohydrate acyl acceptor may be one or more of the following: a monosaccharide, a disaccharide, an oligosaccharide or a polysaccharide. Preferably, the carbohydrate is one or more of the following: glucose, fructose, anhydrofructose, maltose, lactose, sucrose, galactose, xylose, xylooligosaccharides, arabinose, maltooligosaccharides, tagatose, microthecin, ascopyrone P, ascopyrone T or cortalcerone.

Carbohydrate esters can function as valuable emulsifiers for example in foodstuffs.

In one aspect, preferably the enzyme is capable of transferring an acyl group from a lipid substrate to a protein and/or a protein subunit.

Preferably the protein sub-unit is one or more of the following: an amino acid, a protein hydrolysate, a peptide, a dipeptide, an oligopeptide, a polypeptide.

Suitable proteins may be one or more of the following: proteins found in a food product, for example in a dairy product and/or a meat product. By way of example only, suitable proteins may be those found in curd or whey, such as lactoglobulin. Other suitable proteins include ovalbumin (from egg), gliadin, glutenin, puroindoline, wheat protein, lipid transfer proteins from grains, myosin from meat, or the following milk proteins: caseins, lactalbumins and lactoferrins.

Suitably in the protein or protein subunit the acyl acceptor may be one or more of the following constituents of the protein or protein subunit: a serine, a threonine, a tyrosine or a cysteine.

When the protein subunit is an amino acid, suitably the amino acid may be any amino acid. Preferably the amino acid is one or more of a serine, a threonine, a tyrosine or a cysteine for example.

In one aspect, preferably the enzyme is capable of transferring an acyl group from a lipid substrate to a hydroxy acid.

Suitably the hydroxy acid may be one or more of the following acids: citric acid, tartaric acid, lactic acid, ascorbic acid, glycolic acid, malic acid, alpha-hydroxyethanoic acid, alpha-hydroxyoctanoic acid, alpha-hydroxycaprylic acid, hydroxycaprylic acid, gluconic acid, lactobionic acid or maltobionic acid.

Suitably the hydroxy acid may be a fruit acid, for example one or more of malic acid, lactic acid, tartaric acid, citric acid or glycolic acid.

In one embodiment, preferably the hydroxy acid is one or more of the following acids: citric acid, lactic acid, tartaric acid or malic acid.

The term "hydroxy acid" as used herein means a carboxylic acid in which one or more hydrogen atom of the alkyl group has been replaced by a hydroxyl group.

In one aspect, the lipid acyltransferase may, as well as being able to transfer an acyl group from a lipid substrate to one or more of a carbohydrate, a protein, a protein subunit or a hydroxy acid, the lipid acyltransferase is additionally able to transfer the acyl group from a lipid to one or more of the following: a sterol and/or a stanol, in particular a phytosterol and/or a phytostanol.

Suitably, when the lipid substrate is a phospholipid it may be a lecithin, e.g. phosphatidylcholine. The term lecithin as used herein encompasses phosphatidylcholine, phosphatidylethanolamine, phosphatidylinositol, phosphatidylserine and phosphatidylglycerol.

Suitably, when the lipid substrate is a lysophospholipid it may be a lysolecithin, e.g. lysophosphatidylcholine. The term lysophosphatidylcholine as used herein is synonymous with the term lysolecithin and these terms may be used herein interchangeably.

Suitably, when the lipid substrate is a glycolipid it may be digalactosyldiglyceride (DGDG) for example.

The lipid substrate may be referred to herein as the "lipid acyl donor" or "acyl donor". These terms are used interchangeably herein.

For some aspects, preferably the lipid substrate upon which the lipid acyltransferase acts is a phospholipid, such as lecithin, for example phosphatidylcholine.

For some aspects, preferably the lipid substrate is a glycolipid, such as DGDG for example.

For some aspects the lipid substrate may be a food lipid, that is to say a lipid component of a foodstuff.

For some aspects, the lipid acyltransferase according to the present invention may be incapable, or substantially incapable, of acting on a triglyceride and/or a 1-monoglyceride and/or 2-monoglyceride.

Suitably, the lipid substrate or lipid acyl donor may be one or more lipids present in one or more of the following substrates: fats, including lard, tallow and butter fat; oils including oils extracted from or derived from palm oil, sunflower oil, soya bean oil, safflower oil, cotton seed oil, ground nut oil, corn oil, olive oil, peanut oil, coconut oil, and rape seed oil. Lecithin from soya, rape seed or egg yolk is also a suitable lipid substrate. The lipid substrate may be an oat lipid or other plant based material containing galactolipids.

For some aspects of the present invention, the lipid may be selected from lipids having a fatty acid chain length of from 8 to 22 carbons.

For some aspects of the present invention, the lipid may be selected from lipids having a fatty acid chain length of from 16 to 22 carbons, more preferably of from 16 to 20 carbons.

For some aspects of the present invention, the lipid may be selected from lipids having a fatty acid chain length of no greater than 14 carbons, suitably from lipids having a fatty acid chain length of from 4 to 14 carbons, suitably 4 to 10 carbons, suitably 4 to 8 carbons.

Preferably the acyl donor is not a free fatty acid.

Preferably, the acyl donor is not a carbohydrate (sugar) ester.

Suitably, the lipid acyltransferase according to the present invention may exhibit one or more of the following lipase activities: glycolipase activity (E.C. 3.1.1.26), triacylglycerol lipase activity (E.C. 3.1.1.3), phospholipase A2 activity (E.C. 3.1.1.4) or phospholipase A1 activity (E.C. 3.1.1.32). The term "glycolipase activity" as used herein encompasses "galactolipase activity".

Suitably, the lipid acyltransferase according to the present invention may have at least one or more of the following activities: glycolipase activity (E.C. 3.1.1.26) and/or phospholipase A1 activity (E.C. 3.1.1.32) and/or phospholipase A2 activity (E.C. 3.1.1.4).

For some aspects, the lipid acyltransferase according to the present invention may have at least glycolipase activity (E.C. 3.1.1.26).

Suitably, for some aspects the lipid acyltransferase according to the present invention may be capable of transferring an acyl group from a glycolipid and/or a phospholipid to one or more of the following acceptor substrates: a carbohydrate, a protein, a protein subunit, a hydroxy acid.

For some aspects, preferably the lipid acyltransferase according to the present invention is capable of transferring an acyl group from a glycolipid and/or a phospholipid to a carbohydrate to form at least a carbohydrate ester.

For some aspects, preferably the lipid acyltransferase according to the present invention is capable of transferring an acyl group from a glycolipid and/or a phospholipid to a protein or a protein subunit to form at least a protein ester (or a protein fatty acid condensate) or a protein subunit ester.

The term "protein subunit ester" as used herein means the ester formed from any protein subunit, such as a dipeptide ester, an oligopeptide ester, a polypeptide ester or a protein hydrolysate ester for example.

For some aspects, preferably the lipid acyltransferase according to the present invention does not exhibit triacylglycerol lipase activity (E.C. 3.1.1.3).

Preferably, the lipid acyltransferase enzyme according to the present invention may be characterised using the following criteria:

(i) the enzyme possesses acyl transferase activity which may be defined as ester transfer activity whereby the acyl part of an original ester bond of a lipid acyl donor is transferred to one or more of a carbohydrate, protein, protein subunit or hydroxy acid acyl acceptor to form a new ester, i.e. a carbohydrate ester and/or a protein ester and/or a protein subunit ester and/or a hydroxy acid ester; and (ii) the enzyme comprises the amino acid sequence motif GDSX, wherein X is one or more of the following amino acid residues L, A, V, I, F, Y, H, Q, T, N, M or S.

Preferably, X of the GDSX motif is L. Thus, preferably the enzyme according to the present invention comprises the amino acid sequence motif GSDL (SEQ ID NO: 16).

To determine if a protein has the GDSX motif according to the present invention, the sequence is preferably compared with the hidden markov model profiles (HMM profiles) of the pfam database.

Pfam is a database of protein domain families. Pfam contains curated multiple sequence alignments for each family as well as profile hidden Markov models (profile HMMs) for identifying these domains in new sequences. An introduction to Pfam can be found in Bateman A et al. (2002) Nucleic Acids Res. 30; 276-280. Hidden Markov models are used in a number of databases that aim at classifying proteins, for review see Bateman A and Haft D H (2002) Brief Bioinform 3; 236-245.

http://www.ncbi.nlm.nih.gov/entrez/query.fcgi?cmd=Retrieve&db=PubMed&list_uids=12230032&dopt=Abstract http://www.ncbi.nlm.nih.gov/entrez/query.fcgi?cmd=Retrieve&db=PubMed&list_uids=11752314&dopt=Abstract A multiple alignment, including *Aeromonas salmonicida* or *Aeromonas hydrophila* can be obtained by:

a) manual
  obtain an alignment of the protein of interest with the Pfam00657 consensus sequence and obtain an alignment of P10480 with the Pfam00657 consensus sequence following the procedure described above;
Or
b) through the database
  After identification of the Pfam00657 consensus sequence the database offers the option to show an alignment of the query sequence to the seed alignment of the Pfam00657 consensus sequence. P10480 is part of this seed alignment and is indicated by GCAT_AERHY. Both the query sequence and P10480 will be displayed in the same window.

The *Aeromonas hydrophila* reference sequence:

The residues of *Aeromonas hydrophila* GDSX lipase are numbered in the NCBI file P10480, the numbers in this text refer to the numbers given in that file which in the present invention is used to determine specific amino acids residues which, in a preferred embodiment are present in the lipid acyltransferase enzymes of the invention.

The Pfam alignment was performed (FIGS. 33 and 34):

The following conserved residues can be recognised and in a preferable embodiment may be present in the enzymes for use in the compositions and methods of the invention;

```
Block 1 - GDSX block
hid hid hid hid Gly Asp Ser hid
 28  29  30  31  32  33  34  35

Block 2 - GANDY block
hid Gly hid Asn Asp hid
130 131 132 133 134 135

Block 3 - HPT block
His
309
```

Where 'hid' means a hydrophobic residue selected from Met, Ile, Leu, Val, Ala, Gly, Cys, His, Lys, Trp, Tyr, Phe.

Preferably the lipid acyltransferase enzyme for use in the compositions/methods of the invention can be aligned using the Pfam00657 consensus sequence.

Preferably, a positive match with the hidden markov model profile (HMM profile) of the pfam00657 domain family indicates the presence of the GDSL (SEQ ID NO: 16) or GDSX domain according to the present invention.

Preferably when aligned with the Pfam00657 consensus sequence the lipid acyltransferase for use in the compositions/methods of the invention have at least one, preferably more than one, preferably more than two, of the following, a GDSx block, a GANDY block, a HPT block. Suitably, the lipid acyltransferase may have a GDSx block and a GANDY block. Alternatively, the enzyme may have a GDSx block and a HPT block. Preferably the enzyme comprises at least a GDSx block.

Preferably, when aligned with the Pfam00657 consensus sequence the enzyme for use in the compositions/methods of the invention have at least one, preferably more than one, preferably more than two, preferably more than three, preferably more than four, preferably more than five, preferably more than six, preferably more than seven, preferably more than eight, preferably more than nine, preferably more than ten, preferably more than eleven, preferably more than twelve, preferably more than thirteen, preferably more than fourteen, of the following amino acid residues when compared to the reference *A. hydrophilia* polypeptide sequence, namely SEQ ID No. 32: 28hid, 29hid, 30hid, 31hid, 32gly, 33Asp, 34Ser, 35hid, 130hid, 131Gly, 132Hid, 133Asn, 134Asp, 135hid, 309His The pfam00657 GDSX domain is a unique identifier which distinguishes proteins possessing this domain from other enzymes.

The pfam00657 consensus sequence is presented in FIG. 1 as SEQ ID No. 1. This is derived from the identification of the pfam family 00657, database version 6, which may also be referred to as pfam00657.6 herein.

The consensus sequence may be updated by using further releases of the pfam database.

For example, FIGS. 33 and 34 show the pfam alignment of family 00657, from database version 11, which may also be referred to as pfam00657.11 herein.

The presence of the GDSx, GANDY and HPT blocks are found in the pfam family 00657 from both releases of the database. Future releases of the pfam database can be used to identify the pfam family 00657.

Preferably, the lipid acyltransferase enzyme according to the present invention may be characterised using the following criteria:
(i) the enzyme possesses acyl transferase activity which may be defined as ester transfer activity whereby the acyl part of an original ester bond of a lipid acyl donor is transferred to one or more of a carbohydrate, protein, protein subunit or hydroxy acid acyl acceptor to form a new ester, i.e. a carbohydrate ester and/or a protein ester and/or a protein subunit ester and/or a hydroxy acid ester;
(ii) the enzyme comprises the amino acid sequence motif GDSX, wherein X is one or more of the following amino acid residues L, A, V, I, F, Y, H, Q, T, N, M or S;
(iii) the enzyme comprises His-309 or comprises a histidine residue at a position corresponding to His-309 in the *Aeromonas hydrophila* lipolytic enzyme shown in FIG. 2 (SEQ ID No. 2 or SEQ ID No. 32).

Preferably, the amino acid residue of the GDSX motif is L.

In SEQ ID No. 2 or SEQ ID No. 32 the first 18 amino acid residues form a signal sequence. His-309 of the full length sequence, that is the protein including the signal sequence, equates to His-291 of the mature part of the protein, i.e. the sequence without the signal sequence.

Preferably, the lipid acyltransferase enzyme according to the present invention comprises the following catalytic triad: Ser-34, Asp-134 and His-309 or comprises a serine residue, an aspartic acid residue and a histidine residue, respectively, at positions corresponding to Ser-34, Asp-134 and His-309 in the *Aeromonas hydrophila* lipolytic enzyme shown in FIG. 2 (SEQ ID No. 2) or FIG. 28 (SEQ ID No. 32). As stated above, in the sequence shown in SEQ ID No. 2 or SEQ ID No. 32 the first 18 amino acid residues form a signal sequence. Ser-34, Asp-134 and His-309 of the full length sequence, that is the protein including the signal sequence, equate to Ser-16, Asp-116 and His-291 of the mature part of the protein, i.e. the sequence without the signal sequence. In the pfam00657 consensus sequence, as given in FIG. 1 (SEQ ID No. 1) the active site residues correspond to Ser-7, Asp-157 and His-348.

Preferably, the lipid acyltransferase enzyme according to the present invention may be characterised using the following criteria:
(i) the enzyme possesses acyl transferase activity which may be defined as ester transfer activity whereby the acyl part of an original ester bond of a first lipid acyl donor is transferred to one or more of a carbohydrate, protein, protein subunit or hydroxy acid acyl acceptor to form a new ester, i.e. a carbohydrate ester and/or a protein ester and/or a protein subunit ester and/or a hydroxy acid ester; and
(ii) the enzyme comprises at least Gly-32, Asp-33, Ser-34, Asp-134 and His-309 or comprises glycine, aspartic acid, serine, aspartic acid and histidine residues at positions corresponding to Gly-32, Asp-33, Ser-34, Asp-134 and His-309, respectively, in the *Aeromonas hydrophila* lipolytic enzyme shown in FIG. 2 (SEQ ID No. 2) or FIG. 28 (SEQ ID No. 32).

Suitably, the lipid acyltransferase enzyme according to the present invention may be obtainable, preferably obtained, from organisms from one or more of the following genera: *Aeromonas, Streptomyces, Saccharomyces, Lactococcus, Mycobacterium, Streptococcus, Lactobacillus, Desulfitobacterium, Bacillus, Campylobacter, Vibrionaceae, Xylella, Sulfolobus, Aspergillus, Schizosaccharomyces, Listeria, Neisseria, Mesorhizobium, Ralstonia, Xanthomonas* and *Candida*.

Suitably, the lipid acyltransferase enzyme according to the present invention may be obtainable, preferably obtained, from one or more of the following organisms: *Aeromonas hydrophila, Aeromonas salmonicida, Streptomyces coelicolor, Streptomyces rimosus, Mycobacterium, Streptococcus pyogenes, Lactococcus lactis, Streptococcus pyogenes, Streptococcus thermophilus, Lactobacillus helveticus, Desulfitobacterium dehalogenans, Bacillus* sp, *Campylobacter jejuni, Vibrionaceae, Xylella fastidiosa, Sulfolobus solfataricus, Saccharomyces cerevisiae, Aspergillus terreus, Schizosaccharomyces pombe, Listeria innocua, Listeria monocytogenes, Neisseria meningitidis, Mesorhizobium loti, Ralstonia solanacearum, Xanthomonas campestris, Xanthomonas axonopodis* and *Candida parapsilosis*.

In one aspect, preferably the lipid acyltransferase enzyme according to the present invention is obtainable, preferably obtained, from one or more of *Aeromonas hydrophila* or *Aeromonas salmonicida*.

Suitably, the lipid acyltransferase enzyme according to the present invention comprises one or more of the following amino acid sequences:
(i) the amino acid sequence shown as SEQ ID No. 2 (see FIG. 2)
(ii) the amino acid sequence shown as SEQ ID No. 3 (see FIG. 3)
(iii) the amino acid sequence shown as SEQ ID No. 4 (see FIG. 4)
(iv) the amino acid sequence shown as SEQ ID No. 5 (see FIG. 5)
(v) the amino acid sequence shown as SEQ ID No. 6 (see FIG. 6)
(vi) the amino acid sequence shown as SEQ ID No. 12 (see FIG. 14)
(vii) the amino acid sequence shown as SEQ ID No. 20 (FIG. 16)
(viii) the amino acid sequence shown as SEQ ID No. 22 (FIG. 18)
(ix) the amino acid sequence shown as SEQ ID No. 24 (FIG. 20)
(x) the amino acid sequence shown as SEQ ID No. 26 (FIG. 22)
(xi) the amino acid sequence shown as SEQ ID No. 28 (FIG. 24)
(xii) the amino acid sequence shown as SEQ ID No. 30 (FIG. 26)

(xiii) the amino acid sequence shown as SEQ ID No. 32 (FIG. 28)
(xiv) the amino acid sequence shown as SEQ ID No. 34 (FIG. 30) or
an amino acid sequence which has 75% or more identity with any one of the sequences shown as SEQ ID No. 2, SEQ ID No. 3, SEQ ID No. 4, SEQ ID No. 5, SEQ ID No. 6, SEQ ID No. 12, SEQ ID No. 20, SEQ ID No. 22, SEQ ID No. 24, SEQ ID No. 26, SEQ ID No. 28, SEQ ID No. 30, SEQ ID No. 32, or SEQ ID No. 34.

Suitably, the lipid acyltransferase enzyme according to the present invention comprises either the amino acid sequence shown as SEQ ID No. 2 or as SEQ ID No. 3 or SEQ ID No. 32 or SEQ ID No. 34 or comprises an amino acid sequence which has 75% or more, preferably 80% or more, preferably 85% or more, preferably 90% or more, preferably 95% or more, identity with the amino acid sequence shown as SEQ ID No. 2 or the amino acid sequence shown as SEQ ID No. 3 or the amino acid sequence shown as SEQ ID No. 32 or the amino acid sequence shown as SEQ ID No. 34.

For the purposes of the present invention, the degree of identity is based on the number of sequence elements which are the same. The degree of identity in accordance with the present invention may be suitably determined by means of computer programs known in the art, such as GAP provided in the GCG program package (Program Manual for the Wisconsin Package, Version 8, August 1994, Genetics Computer Group, 575 Science Drive, Madison, Wis., US 53711) (Needleman & Wunsch (1970), J. of Molecular Biology 48, 443-45) using the following settings for polypeptide sequence comparison: GAP creation penalty of 3.0 and GAP extension penalty of 0.1.

Suitably the lipid acyltransferase enzyme according to the present invention comprises an amino acid sequence which has 80% or more, preferably 85% or more, more preferably 90% or more and even more preferably 95% or more identity with any one of the sequences shown as SEQ ID No. 2, SEQ ID No. 3, SEQ ID No. 4, SEQ ID No. 5, SEQ ID No. 6, SEQ ID No. 12, SEQ ID No. 20, SEQ ID No. 22, SEQ ID No. 24, SEQ ID No. 26, SEQ ID No. 28, SEQ ID No. 30, SEQ ID No. 32, or SEQ ID No. 34.

Suitably, the lipid acyltransferase enzyme according to the present invention comprises one or more of the following amino acid sequences:
(a) an amino acid sequence shown as amino acid residues 1-100 of SEQ ID No. 2 or SEQ ID No. 32;
(b) an amino acid sequence shown as amino acids residues 101-200 of SEQ ID No. 2 or SEQ ID No. 32;
(c) an amino acid sequence shown as amino acid residues 201-300 of SEQ ID No. 2 or SEQ ID No. 32; or
(d) an amino acid sequence which has 75% or more, preferably 85% or more, more preferably 90% or more, even more preferably 95% or more identity to any one of the amino acid sequences defined in (a)-(c) above.

Suitably, the lipid acyltransferase enzyme according to the present invention comprises one or more of the following amino acid sequences:
(a) an amino acid sequence shown as amino acid residues 28-39 of SEQ ID No. 2 or SEQ ID No. 32;
(b) an amino acid sequence shown as amino acids residues 77-88 of SEQ ID No. 2 or SEQ ID No. 32;
(c) an amino acid sequence shown as amino acid residues 126-136 of SEQ ID No. 2 or SEQ ID No. 32;
(d) an amino acid sequence shown as amino acid residues 163-175 of SEQ ID No. 2 or SEQ ID No. 32;
(e) an amino acid sequence shown as amino acid residues 304-311 of SEQ ID No. 2 or SEQ ID No. 32; or
(f) an amino acid sequence which has 75% or more, preferably 85% or more, more preferably 90% or more, even more preferably 95% or more identity to any one of the amino acid sequences defined in (a)-(e) above.

Suitably, the lipid acyltransferase enzyme according to the present invention may comprise an amino acid sequence produced by the expression or one or more of the following nucleotide sequences:
(a) the nucleotide sequence shown as SEQ ID No. 7 (see FIG. 9);
(b) the nucleotide sequence shown as SEQ ID No. 8 (see FIG. 10);
(c) the nucleotide sequence shown as SEQ ID No. 9 (see FIG. 11);
(d) the nucleotide sequence shown as SEQ ID No. 10 (see FIG. 12);
(e) the nucleotide sequence shown as SEQ ID No. 11 (see FIG. 13);
(f) the nucleotide sequence shown as SEQ ID No. 13 (see FIG. 15);
(g) the nucleotide sequence shown as SEQ ID No. 21 (see FIG. 17);
(h) the nucleotide sequence shown as SEQ ID No. 23 (see FIG. 19);
(i) the nucleotide sequence shown as SEQ ID No. 25 (see FIG. 21);
(j) the nucleotide sequence shown as SEQ ID No. 27 (see FIG. 23);
(k) the nucleotide sequence shown as SEQ ID No. 29 (see FIG. 25);
(l) the nucleotide sequence shown as SEQ ID No. 31 (see FIG. 27);
(m) the nucleotide sequence shown as SEQ ID No. 33 (see FIG. 29);
(n) the nucleotide sequence shown as SEQ ID No. 35 (see FIG. 31);
(o) or
a nucleotide sequence which has 75% or more identity with any one of the sequences shown as SEQ ID No. 7, SEQ ID No. 8, SEQ ID No. 9, SEQ ID No. 10, SEQ ID No. 11, SEQ ID No. 13, SEQ ID No. 21, SEQ ID No. 23, SEQ ID No. 25, SEQ ID No. 27, SEQ ID No. 29, SEQ ID No. 31, SEQ ID No. 33 or SEQ ID No. 35.

Suitably the nucleotide sequence may have 80% or more, preferably 85% or more, more preferably 90% or more and even more preferably 95% or more identity with any one of the sequences shown as SEQ ID No. 7, SEQ ID No. 8, SEQ ID No. 9, SEQ ID No. 10, SEQ ID No. 11, SEQ ID No. 13, SEQ ID No. 21, SEQ ID No. 23, SEQ ID No. 25, SEQ ID No. 27, SEQ ID No. 29, SEQ ID No. 31, SEQ ID No. 33 or SEQ ID No. 35.

In one aspect, the lipid acyltransferase according to the present invention may be a lecithin:cholesterol acyltransferases (LCAT) or variant thereof (for example a variant made by molecular evolution)

Suitable LCATs are known in the art and may be obtainable from one or more of the following organisms for example: mammals, rat, mice, chickens, *Drosophila melanogaster*, plants, including *Arabidopsis* and *Oryza sativa*, nematodes, fungi and yeast.

In one embodiment the lipid acyltransferase enzyme according to the present invention may be the lipid acyltransferase obtainable, preferably obtained, from the *E. coli* strains TOP 10 harbouring pPet12aAhydro and pPet12aASalmo deposited by Danisco A/S of Langebrogade 1, DK-1001 Copenhagen K, Denmark under the Budapest Treaty on the International Recognition of the Deposit of Microorganisms for the purposes of Patent Procedure at the National Collection of Industrial, Marine and Food Bacteria (NCIMB) 23 St. Machar Street, Aberdeen Scotland, GB on 22 Dec. 2003 under accession numbers NICMB 41204 and NCIMB 41205, respectively.

The term "transferase" as used herein is interchangeable with the term "lipid acyltransferase".

Suitably, the lipid acyltransferase as defined herein catalyses one or both of the following reactions: transesterification, alcoholysis.

Thus in accordance with the present invention, one or more of the following advantageous properties can be achieved: the bioconversion of lipids to form one or more of a carbohydrate ester, a protein ester, a protein subunit ester or a hydroxy acid ester can take place in a high water environment which comprises no organic solvent or a reduced amount of organic solvent compared with conventional bioconversion processes.

The term "bioconversion" as used herein means the modification of one organic compound to produce another organic compound and/or synthesis of organic compounds from other organic compounds by enzyme catalysis.

The term "transesterification" as used herein means the enzymatic catalysed transfer of an acyl group from a lipid donor (other than a free fatty acid) to an acyl acceptor (other than water). For the avoidance of doubt, the use of the term "transesterification" as used herein includes transfer of an acyl group from a lipid donor to an acyl acceptor (other than water) where the acyl acceptor comprises a suitable chemical group, which may for example be either an —OH or —SH group.

As used herein, the term "alcoholysis" refers to the enzymatic cleavage of a covalent bond of an acid derivative by reaction with an alcohol group ROH so that one of the products combines with the H of the alcohol group and the other product combines with the OR group of the alcohol group.

As used herein, the term "hydrolysis" refers to the enzymatic catalysed transfer of an acyl group from a lipid to the OH group of a water molecule. Acyl transfer which results from hydrolysis requires the separation of the water molecule.

The term "interesterification" refers to the enzymatic catalysed transfer of acyl groups between a lipid donor and lipid acceptor, wherein the lipid donor is not a free acyl group. In other words "interesterification" refers to the interchange of a fatty acid between two lipid molecules.

In one aspect, the lipid acyl transferase as defined herein catalyses interesterification.

Suitably, the method or use according to the present invention may further comprise one or more of the following steps: dissolving the acyl acceptor in water; adding a lipid acyl donor to a dissolved acyl acceptor to form a two-phase system or an emulsion; stirring or sonicating the reaction mixture; heating the reaction mixture, for example to denature the enzyme; separating the water phase from the fat/emulsifier phase by standard separation techniques, such as solvent extraction or water evaporation for example; fractionating the fat phase by hydrophobic interaction chromatography, crystallisation or high vacuum distillation. Suitably, one or more of the heating, separating or fractionating steps may be carried out after the reaction has reached equilibrium.

In one embodiment the lipase acyl transferase for use in the methods of the present invention may be immobilised. When it is the case that the enzyme is immobilised the admixture comprising an acyl donor, an acyl acceptor and water passed through a column for example comprising the immobilised enzyme. By immobilising the enzyme it is possible to easily reuse it.

Suitably the immobilised enzyme may be used in a flow reactor or in a batch reactor containing a reaction mixture which comprises an acyl acceptor dissolved in water and a lipid acyl donor as a two-phase system or as an emulsion. The reaction mixture may be optionally stirred or sonicated. Once the reaction has reached equilibrium for example, the reaction mixture and the immobilised enzyme may be separated. Suitably, the reaction product may be fractionated for example by hydrophobic interaction chromatography, crystallisation or high vacuum distillation.

Immobilised lipid acyl transferase can be prepared using immobilisation techniques known in the art. There are numerous methods of preparing immobilised enzymes, which will be apparent to a person skilled in the art (for example the techniques referred to in EP 0 746 608; or Balcao V. M., Paiva A. L., Malcata F. X., Enzyme Microb Technol. 1996 May 1; 18(6):392-416; or Retz M. T., Jaeger K. E. Chem Phys Lipids. 1998 June; 93(1-2):3-14; Bornscheuer U. T., Bessler C, Srinivas R, Krishna S. H. Trends Biotechnol. 2002 October; 20(10):433-7; Plou et al, J. Biotechnology 92 (2002) 55-66; Warmth et al., 1992. Bio Forum 9, 282-283; Ferrer et al., 2000. J. Chem. Technol. Biotechnol. 75, 1-8; or Christensen et al., 1998. Nachwachsende Rohstoff 10, 98-105; Petersen and Christenen, 2000, Applied Biocatalysis. Harwood Academic Publishers, Amsterdam. (each of which is incorporated herein by reference). Techniques which may be used herein include covalent coupling to Eupergit C, adsorption on polypropylene and silica-granulation for example.

The term "high water environment" as used herein preferably means an environment which is low in or absent an organic solvent, preferably low in or absent a polar organic solvent. The term organic solvent as used herein preferably does not encompass food oils when used as lipid substrate, and preferably does not encompass food oils that are high in non-polar lipids for example. Suitably, the high water environment according to the present invention may comprise less than 50% by volume organic solvents, less than 30% by volume organic solvents, more preferably less than 15% by volume organic solvents, more preferably less than 5%, more preferably less than 1%, more preferably less than 0.5% by volume organic solvent, more preferably 0% by volume organic solvents.

When it is the case that a carbohydrate ester is produced in accordance with the present invention, the carbohydrate ester is preferably an oligosaccharide ester, a monosaccharide ester or a disaccharide ester.

Suitably, the carbohydrate ester when produced in accordance with the present invention may be one or more of the following: glucose ester, fructose ester, anhydrofructose ester, maltose ester, lactose ester, galactose ester, xylose ester, xylooligosaccharide ester, arabinose ester, maltooligosaccharide ester, tagatose ester, sucrose ester, microthecin ester, ascopyrone P ester, ascopyrone T ester or cortalcerone ester.

Preferably, the carbohydrate ester when produced in accordance with the present invention is one or more of the following: a carbohydrate mono-ester, a sugar mono-ester, an oligosaccharide mono-ester, a trisaccharide mono-ester, a disaccharide mono-ester, a monosaccharide mono-ester, a glucose mono-ester, a fructose mono-ester, anhydrofructose mono-ester, maltose mono-ester, lactose mono-ester, galactose mono-ester, xylose mono-ester, xylooligosaccharide mono-ester, arabinose mono-ester, maltooligosaccharide mono-ester, tagatose mono-ester, sucrose mono-ester, microthecin ester, ascopyrone P ester, ascopyrone T ester or cortalcerone ester.

In one embodiment, the microthecin ester, ascopyrone P ester, ascopyrone T ester and/or cortalcerone ester may function as an antimicrobial agent. Alternatively or in addition thereto, the microthecin ester, ascopyrone P ester, ascopyrone T ester and/or cortalcerone ester may function as one or both of an antioxidant and/or emulsifier.

Preferably, the formation of the carbohydrate ester (if any) in accordance with the present invention is independent of UDP-glucose.

Preferably, the foodstuff according to the present invention does not comprise UDP-glucose, or only comprises UDP-glucose in insignificant amounts.

The lipid acyl transferases used in the compositions and methods of the invention have been found to have unique properties when compared to lipolytic enzymes in that they have a marked preference for transfer of acyl groups from lipids to acceptors other than water, even in the presence of significant water. In a comparison with prior art enzymes, the lipid acyl transferase used in the invention were found to have a high relative transferase activity in the presence of 6% water, 54% water, 73% water, 89% water and approximately 95%. Lipolytic enzymes tested had virtually no significant relative transferase activity at these water concentrations.

The % transferase activity (i.e. the transferase activity as a percentage of the total enzymatic activity) may be determined by the following protocol:

Protocol for the Determination of % Acyltransferase Activity:

A substrate to which a lipid acyltransferase according to the present invention has been added may be extracted following the enzymatic reaction with $CHCl_3:CH_3OH$ 2:1 and the organic phase containing the lipid material is isolated and analysed by GLC and HPLC according to the procedure detailed hereinbelow. From the GLC and HPLC analyses the amount of free fatty acids and one or more of carbohydrate esters, protein esters; protein subunit esters; hydroxy acid esters are determined. A control substrate to which no enzyme according to the present invention has been added, is analysed in the same way.

Calculation:

From the results of the GLC and HPLC analyses the increase in free fatty acids and carbohydrate esters and/or protein esters and/or protein subunit esters and/or hydroxy acid can be calculated:

Δ % fatty acid=% Fatty acid(enzyme)−% fatty acid (control); Mv fatty acid=average molecular weight of the fatty acids;

$A$=Δ % protein ester/Mv protein ester (where Δ % protein ester=% protein ester(enzyme)−% protein ester(control) and Mv protein ester=average molecular weight of the protein esters)—applicable where the acyl acceptor is a protein;

$B$=Δ % carbohydrate ester/Mv carbohydrate ester (where Δ % carbohydrate ester=carbohydrate ester(enzyme)−% carbohydrate ester(control) and Mv carbohydrate ester=average molecular weight of the carbohydrate ester)—applicable where the acyl acceptor is a carbohydrate;

$C$=Δ % protein subunit ester/Mv protein subunit ester (where Δ % protein subunit ester=% protein subunit ester(enzyme)−% protein subunit ester(control) and Mv protein subunit ester=average molecular weight of the protein subunit ester)—applicable where the acyl acceptor is a protein subunit; and $D$=Δ % hydroxy acid ester/Mv hydroxy acid ester (where Δ % hydroxy acid ester=% hydroxy acid ester(enzyme)−% hydroxy acid ester(control) and Mv hydroxy acid ester=average molecular weight of the hydroxy acid ester)—applicable where the acyl acceptor is a hydroxy acid.

The transferase activity is calculated as a percentage of the total enzymatic activity:

$$\% \text{ transferase activity} = \frac{A^* + B^* + C^* + D^* \times 100}{A^* + B^* + C^* + D^* + \Delta \% \text{ fatty acid}/(Mv \text{ fatty acid})}.$$

*delete as appropriate.

The lipase and acyltransferase activity of an enzyme may be evaluated using the following assays. In this way, a lipid acyltransferase having the enzyme characteristics defined herein may be obtained/identified.

Transferase Assay in Buffered Substrate (see Example 6)

Enzymes which function as lipid acyltransferases for use in the compositions and methods of the invention can be routinely identified using the assay taught herein in Example 6. This assay will be hereinafter referred to as the 'Transferase Assay in Buffered Substrate'. In Example 6 the lipid acyltransferase enzyme from *Aeromonas salmonicida* in accordance with the present invention was analysed and compared with a range of lipolytic enzymes not encompassed by the present invention. As can be seen, of the lipolytic enzymes only LIPOPAN® F (Novozymes, Denmark) was found to have any transferase activity and then only a very low level (1.3%).

Enzymes suitable for use in the compositions and methods of the invention can be routinely identified using the Transferase Assay in Buffered Substrate. Using this assay, in which there is a very high water content—approximately 95%, lipid acyltransferases in accordance with the present invention are those which have at least 2% acyltransferase activity (relative transferase activity), preferably at least 5% relative transferase activity, preferably at least 10% relative transferase activity, preferably at least 15%, 20%, 25% 26%, 28%, 30%, 40% 50%, 60% or 75% relative transferase activity. Suitably, the lipid acyltransferase in accordance with the present invention may have less than 28%, less than 30%, preferably less than 40%, 50%, 60%, 70%, 80%, 90% or 100% acyltransferase activity.

Transferase Assay in a Low Water Environment

As an alternative to (or in addition to) using the "Transferase Assay in Buffered Substrate", lipid acyltransferases for use in accordance with the present invention may be identified using the "Transferase Assay in a Low Water Environment".

In order to determine if an enzyme is a lipid acyltransferase according to the present invention, one may carry out a "Transferase Assay in a Low Water Environment", namely in an oily environment with 6% water as taught in Example 9. This example illustrates that in an oily environment with 6% water content the lipid acyltransferase of the invention has a high relative transferase activity, where the prior art lipolytic enzymes have hydrolytic activity.

In one embodiment, the lipid acyltransferase suitable for use in the methods and/or uses according to the present invention is one which when tested using the "Transferase Assay in a Low Water Environment", measured after a time period selected from 30, 20 or 120 minutes, has a relative transferase activity of at least 1%, preferably at least 2%, preferably at least 5%, preferably at least 10%, preferably at least 20%, preferably at least 30%, preferably at least 40%; preferably at least 50%, preferably at least 60%, preferably at least 70%, preferably at least 75%. Suitably, the lipid acyl transferase in accordance with the present invention may have less than 30%, 40%, 50%, 60%, 70%, or 80% activity when measured after a time period of 10, 20, 30 or 120 minutes using the "Transferase Assay in a Low Water Environment".

As described above, the lipase acyltransferase of the invention can be identified using either the "Transferase Assay in Buffered Substrate" or in the "Transferase Assay in Low Water Environment" using cholesterol as the acyl acceptor. Of course, the skilled person would be readily aware that, with obvious amendments to the analytical methods the 'Transferase Assay in Buffered Substrate' or the 'Transferase Assay in Low Water Environment may be used to determine the lipid acyltransferase activity for any lipid acyl donor or any acyl acceptor combination. The skilled person would, if necessary, simply replace the acyl donor substrate (e.g. phospholipid) with an alternative acyl donor substrate (e.g. glycolipid, triacylglyceride) and/or replace the acyl acceptor (e.g. cholesterol) with an alternative acyl acceptor substrate (e.g. a carbohydrate, a protein, a protein subunit or a hydroxy acid) (for example see Examples 10-13).

The term "high water environment" as used herein means any environment comprising 5-98% water. Preferably the environment comprises more than 6% water content, preferably more than 7%, 8%, 9%, 10%, 20%, 30%, 40%, 50%, 60%, 70%, 80% or 90%. Suitably, the high water environment may be comprised of 20-98%, suitably 50-98%, suitably of 70-98%, suitably 75-98% water.

In one embodiment, in the admixture the ratio of the amount of lipid acyltransferase added compared with water is at least 1:700, preferably 1:10,000, as measured on a by weight basis.

The term "low water" as used herein means any substrate or foodstuff with less than 5% water content, preferably less than 4%, 3%, 2%, 1% or 0.5%.

Preferably the method and/or use according to the present invention may be carried out at a temperature of 15-60° C., preferably at a temperature of 20-60° C., preferably 20-50° C., preferably 20-45° C., preferably 20-40° C.

Suitably, the method or use according to the present invention comprises a further step of purifying and/or isolating the reaction product, namely one or more of a carbohydrate ester a protein ester, a protein subunit ester, or a hydroxy acid ester. Thus, preferably the reaction product is in a purified and/or isolated form.

Numerous methods for purification of esters are known to the skilled person. By way of example only the esters produced by the methods/uses taught herein may be purified using chromatography, such as hydrophobic interaction, filtration, centrifugation, solvent extraction/distillation or crystallisation. Suitable methodologies are taught in Ulmann's Encyclopedia of Industrial Chemistry (2002) by Wiley-VCH Verlag GmbH & Co. KgaA.

The lipid acyl-transferase of the invention may be expressed in any suitable expression host. For example the lipid acyltransferase of the invention may be expressed in *Bacillus subtilis* and may be purified by ultrafiltration and/or by precipitation in ethanol and/or centrifugation, and may be subsequently spray dried using starch (maltodextrin) as carrier for the enzyme. The spray-dried enzyme may be standardized to specified PLU activity by adding further carrier in powder forms. The techniques involved are well established and routine in the art.

In one embodiment, the method according to the present invention is an in vitro process. The method may suitably be a continuous or batch process.

The enzyme according to the present invention may be used in combination with one or more other further enzymes. Thus, it is within the scope of the present invention that, in addition to the enzyme of the invention, the admixture is contacted with at least one further enzyme. Such further enzymes include starch degrading enzymes such as endo- or exoamylases, pullulanases, debranching enzymes, hemicellulases including xylanases, cellulases, oxidoreductases, e.g. glucose oxidase or a carbohydrate oxidase such as one which oxidises maltose, for example hexose oxidase (HOX), lipases, phospholipases and hexose oxidase, and proteases. The admixture may be contacted with the enzyme of the invention and the at least one further enzyme at the same time or sequentially.

In one embodiment for example the lipid acyltransferase may be used in combination with a lipase having one or more of the following lipase activities: glycolipase activity (E.C. 3.1.1.26, triacylglycerol lipase activity (E.C. 3.1.1.3), phospholipase A2 activity (E.C. 3.1.1.4) or phospholipase A1 activity (E.C. 3.1.1.32). Suitable lipase enzymes are well know within the art and include by way of example the following lipases: LIPOPAN® F and/or LECITASE® ULTRA (Novozymes A/S, Denmark), phospholipase A2 (e.g. phospholipase A2 from LIPOMOD™ 22L from Biocatalysts, LIPOMAX™ from Genecor), LIPOLASE® (Novozymes A/S, Denmark), the lipases taught in WO03/97835, EP 0 977 869 or EP 1 193 314.

Uses

Thus, the methods according to the present invention produce one or more of a carbohydrate ester, a protein ester, a protein subunit ester, a hydroxyacid ester. Many of these esters are useful emulsifiers. By way of example only amino acid esters, peptide esters, protein esters, carbohydrate esters and hydroxy acid esters (such as tartaric acid esters) for example are functionally important emulsifiers. Emulsifiers are useful in a wide range of industries, such as the food industry, the feed industry, the cosmetics industry (for example in cosmetic bases), the pharmaceutical industry (in both pharmaceutical synthesis and formulation for example) and the paint industry for example. Emulsifiers can function as wetting agents, food ingredients and active ingredients.

In addition protein fatty acid condensates owing to their excellent physiological properties, are suited for use in cosmetics and personal hygiene products for example. For example, protein esters may be used in shower and bath preparations as well as in shampoos and body cleansers. The protein fatty acid condensates may also be useful in pharmaceutical compositions, for example as a base.

Protein fatty acid condensates are well known for their application in the cosmetic industry. Conventionally, these products are produced by reacting protein hydrolysate with fatty acid chloride under Schotten-Baumann conditions, using water as solvent.

In the development of the protein-fatty acid condensates it is possible to combine the renewable resources fatty acids (from vegetable oil) and protein, which can be obtained from both animal waste (leather) as well as from many plants, to construct a surfactant structure with a hydrophobic (fatty acid) and a hydrophilic (protein) part. In this process the fatty acid chloride reacts with the amine group of the amino acid and forms the protein fatty acid condensate (See FIG. 49). Products are obtained which have an excellent skin compatibility and additionally have a good cleaning effect.

The fact that even small additions of the acylated protein hydrolysate have a synergistic effect on the skin compatibility of other surfactants is highly important from a technical formulation point of view. An explanation for this protective effect could lie in the amphoteric behaviour of the product. There is an interaction between the protein-fatty acid condensate and skin collagen. This leads to the formation of a protective layer, which reduces the excessive attack of surfactants on the upper layers of the skin, their strong degreasing effect and the direct interaction of anionic surfactants with the skin.

In the cosmetic branch, protein-based surfactants are mainly used in mild shower and bath products, mild shampoos, surfactant-based face cleansers, cold-wave preparations and fixatives or surfactant preparations for babies.

Protein hydrolysate fatty acid condensates are also useful as bases for pharmaceutical preparations, for example for creams and ointments which contain active ingredients for topical application to the skin.

The present invention provides a new way to produce protein fatty acid condensate without using fatty acid chloride. The reaction according to the present invention is depicted in FIG. 50. This reaction can be conducted in water or buffer system at low temperature without formation of waste products.

The term "protein fatty acid condensate" as used herein encompasses all of the following protein esters, polypeptide esters, dipeptide esters, oligopeptide esters, peptide esters, and amino acid esters.

As a skilled person would be readily aware, carbohydrate esters (particularly sugar esters) have a broad application in the food industry. Other fields of application include cosmetics, oral-care products and medical supplies. In addition, these compounds can be used as antibiotics, antitumorals, fungicides and insecticides. The lipid acyltransferase according to the present invention is able to catalyse the formation of glucose ester in a high water environment (FIG. 51).

The esters produced in accordance with the present invention find application in the following fields:

Cosmetics: including essential oil emulsions (o/w, HLB 16-18) Paraffin oil emulsions, o/w, HLB 10-14; Stearic acid emulsions; Wax emulsions, o/w, HLB 14-16; Lanolin emulsions, o/w, HLB 12-14; Silicone emulsions; Toothpastes, o/w; Foam baths, o/w, HLB 14-18; Hair Lotion.

Pharmaceutical Preparations: including in drug emulsions; ointment bases; suppository compound, w/o; encapsulation; injection preparation.

Agriculture: including in soil improvement; as a fertilizer additive; as all-purpose cleaners; cleaners for fruit and vegetables; cleaners for milk churns.

Crop Protection: including in naturally occurring insecticides; chlorinated hydrocarbons, and 140; phosphoric acid esters o/w, HLB 10-14; fungicides, o/w; herbicides, o/w.

Food Industry: including in bread and cakes; margarine; chocolate; fat bloom prevention, w/o, HLB 5-10; sugar frosting, o/w, HLB 14-16; softeners for caramels and chewing gum, w/o, HLB. 2-4; prevention of sticking, w/o, HLB 2-4; ice cream additives w/o, HLB 4-6; wetting of milk and baking powders, w/o, HLB 9-11; custard powder, w/o, HLB 2-4; in the drinks industry; in fruit and vegetables; in flavourings, w/o and o/w, HLB 10-12; in meat, salad, or other flavouring sauces, o/w; in food dyes, w/o, HLB 2-4; o/w, HLB 8-18; in foam inhibitors.

The benefit of using protein fatty acid esters, hydroxy acid esters and carbohydrate esters produced in accordance with the present invention as emulsifiers in food applications is that these are harmless food compatible components which are more easily biodegradable compared to other conventionally used emulsifier like ethoxylated fatty acid esters for example. These emulsifiers are thus more environmentally friendly to use in both the food industry and the non-food industry.

In one embodiment, the microthecin ester, ascopyrone P ester, ascopyrone T ester and/or cortalcerone ester may function as an antimicrobial agent. Alternatively or in addition thereto, the microthecin ester, ascopyrone P ester, ascopyrone T ester and/or cortalcerone ester may function as one or both of an antioxidant and/or emulsifier In one embodiment, the methods or uses of the present invention can be used to produce emulsifiers for use in drug formulations, particularly in the production of controlled release formulations of active ingredients, wherein the active ingredient is acylated using the lipid acyl-transferase. Such slow release formulations are particularly useful for pharmaceutical compositions administered orally, where the gradual hydrolysis of the ester in the digestive tract provides gradual delivery of the active ingredient. Such acylated compositions could further be used for a subcutaneous or an intravenous formulation.

In another embodiment, the methods or uses of the present invention can be used to produce phase transfer catalysts for transfer of salts into a solution of organic solvents for instance in an organic reaction. For example, the transfer of an acyl group to an appropriate cationic acceptor, such as a hydroxy acid (citric acid), or alternatively with an anionic acceptor group, such as hydroxy-amines can produce phase transfer catalysts for transfer of salts into a solution of organic solvents.

In another embodiment, the methods of the present invention may be used to produce ester prodrugs of pharmaceutical compounds with low biological availability and/or low solubility, for instance antiviral agents like aciclovir and gangaciclovir. The method could further be used for other medicinal compounds with a free hydroxy-group, for instance a primary, secondary or tertiary hydroxy-group.

Preferably, the ester produced in accordance with the present invention is used in a pharmaceutical formulation.

Preferably, the ester produced in accordance with the present invention is used in a cosmetic and/or a personal hygiene product.

Preferably, the ester produced in accordance with the present invention is used in a foodstuff and/or a feedstuff.

The method in accordance with the present invention may be one step in the manufacturing process of one or more of a pharmaceutical, a cosmetic, a personal hygiene product a foodstuff or a feedstuff.

Advantages

One advantage of the method according to the present invention is that it results in the manufacture of one or more of a carbohydrate ester, a protein ester, a protein subunit ester or a hydroxy acid ester without the need to use organic solvents. Thus, the present invention allows the use of the organic solvents to be reduced or eliminated. This has many advantages, for example in reduced production costs, reduced human and/or environmental exposure to organic solvents, simplification of the production process.

In the production of esters for food applications it is particularly advantageous to use lipids rather than fatty acids because it is not necessary to remove surplus lipids because these can from part of the food item where the reaction product is used. On the other hand, surplus free fatty acids would have to be removed because these are deleterious for most food products.

Isolated

In one aspect, preferably the polypeptide or protein for use in the present invention is in an isolated form. The term "isolated" means that the sequence is at least substantially free from at least one other component with which the sequence is naturally associated in nature and as found in nature.

In one aspect, preferably the bioconversion product according to the present invention for example the carbohydrate ester and/or the protein ester and/or the protein subunit ester and/or the hydroxy acid ester is isolated from the reaction mixture. The term "isolated" means that the bioconversion product is at least substantially free from at least one other component with which the bioconversion product is associated during the bioconversion reaction.

Purified

In one aspect, preferably the polypeptide or protein for use in the present invention is in a purified form. The term "purified" means that the sequence is in a relatively pure state—e.g. at least about 51% pure, or at least about 75%, or at least about 80%, or at least about 90% pure, or at least about 95% pure or at least about 98% pure.

In one aspect, preferably the bioconversion product produced in accordance with the present invention, for example the carbohydrate ester and/or the protein ester and/or the protein subunit ester and/or the hydroxy acid ester is purified from the reaction mixture and is therefore in a purified form. The term "purified" means that the bioconversion product is in a relatively pure state—e.g. at least about 51% pure, or at least about 75%, or at least about 80%, or at least about 90% pure, or at least about 95% pure or at least about 98% pure.

Pharmaceutical Compositions

The present invention also provides a pharmaceutical composition comprising the product of the present invention and a pharmaceutically acceptable carrier, diluent or excipient (including combinations thereof).

The pharmaceutical compositions may be for human or animal usage in human and veterinary medicine and will typically comprise any one or more of a pharmaceutically acceptable diluent, carrier, or excipient. Acceptable carriers or diluents for therapeutic use are well known in the pharmaceutical art, and are described, for example, in Remington's Pharmaceutical Sciences, Mack Publishing Co. (A. R. Gennaro edit. 1985). The choice of pharmaceutical carrier, excipient or diluent can be selected with regard to the intended route of administration and standard pharmaceutical practice. The pharmaceutical compositions may comprise as—or in addition to—the carrier, excipient or diluent any suitable binder(s), lubricant(s), suspending agent(s), coating agent(s), solubilising agent(s).

Preservatives, stabilizers, dyes and even flavoring agents may be provided in the pharmaceutical composition. Examples of preservatives include sodium benzoate, sorbic acid and esters of p-hydroxybenzoic acid. Antioxidants and suspending agents may be also used.

There may be different composition/formulation requirements dependent on the different delivery systems. By way of example, the pharmaceutical composition of the present invention may be formulated to be administered using a mini-pump or by a mucosal route, for example, as a nasal spray or aerosol for inhalation or ingestable solution, or parenterally in which the composition is formulated by an injectable form, for delivery, by, for example, an intravenous, intramuscular or subcutaneous route. Alternatively, the formulation may be designed to be administered by a number of routes.

Where the agent is to be administered mucosally through the gastrointestinal mucosa, it should be able to remain stable during transit though the gastrointestinal tract; for example, it should be resistant to proteolytic degradation, stable at acid pH and resistant to the detergent effects of bile.

Where appropriate, the pharmaceutical compositions can be administered by inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavouring or colouring agents, or they can be injected parenterally, for example intravenously, intramuscularly or subcutaneously. For parenteral administration, the compositions may be best used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner.

Cloning a Nucleotide Sequence Encoding a Polypeptide According to the Present Invention A nucleotide sequence encoding either a polypeptide which has the specific properties as defined herein or a polypeptide which is suitable for modification may be isolated from any cell or organism producing said polypeptide. Various methods are well known within the art for the isolation of nucleotide sequences.

For example, a genomic DNA and/or cDNA library may be constructed using chromosomal DNA or messenger RNA from the organism producing the polypeptide. If the amino acid sequence of the polypeptide is known, labelled oligonucleotide probes may be synthesised and used to identify polypeptide-encoding clones from the genomic library prepared from the organism. Alternatively, a labelled oligonucleotide probe containing sequences homologous to another known polypeptide gene could be used to identify polypeptide-encoding clones. In the latter case, hybridisation and washing conditions of lower stringency are used.

Alternatively, polypeptide-encoding clones could be identified by inserting fragments of genomic DNA into an expression vector, such as a plasmid, transforming enzyme-negative bacteria with the resulting genomic DNA library, and then plating the transformed bacteria onto agar containing an enzyme inhibited by the polypeptide, thereby allowing clones expressing the polypeptide to be identified.

In a yet further alternative, the nucleotide sequence encoding the polypeptide may be prepared synthetically by established standard methods, e.g. the phosphoroamidite method described by Beucage S. L. et al (1981) Tetrahedron Letters 22, p 1859-1869, or the method described by Matthes et al (1984) EMBO J. 3, p 801-805. In the phosphoroamidite method, oligonucleotides are synthesised, e.g. in an automatic. DNA synthesiser, purified, annealed, ligated and cloned in appropriate vectors.

The nucleotide sequence may be of mixed genomic and synthetic origin, mixed synthetic and cDNA origin, or mixed genomic and cDNA origin, prepared by ligating fragments of synthetic, genomic or cDNA origin (as appropriate) in accordance with standard techniques. Each ligated fragment corresponds to various parts of the entire nucleotide sequence. The DNA sequence may also be prepared by polymerase chain reaction (PCR) using specific primers, for instance as described in U.S. Pat. No. 4,683,202 or in Sand R K et al (Science (1988) 239, pp 487-491).

Nucleotide Sequences

The present invention also encompasses nucleotide sequences encoding polypeptides having the specific properties as defined herein. The term "nucleotide sequence" as used herein refers to an oligonucleotide sequence or polynucleotide sequence, and variant, homologues, fragments and derivatives thereof (such as portions thereof). The nucleotide sequence may be of genomic or synthetic or recombinant origin, which may be double-stranded or single-stranded whether representing the sense or antisense strand.

The term "nucleotide sequence" in relation to the present invention includes genomic DNA, cDNA, synthetic DNA, and RNA. Preferably it means DNA, more preferably cDNA for the coding sequence.

In a preferred embodiment, the nucleotide sequence per se encoding a polypeptide having the specific properties as defined herein does not cover the native nucleotide sequence in its natural environment when it is linked to its naturally associated sequence(s) that is/are also in its/their natural environment. For ease of reference, we shall call this preferred embodiment the "non-native nucleotide sequence". In this regard, the term "native nucleotide sequence" means an entire nucleotide sequence that is in its native environment and when operatively linked to an entire promoter with which it is naturally associated, which promoter is also in its native environment. Thus, the polypeptide of the present invention can be expressed by a nucleotide sequence in its native organism but wherein the nucleotide sequence is not under the control of the promoter with which it is naturally associated within that organism.

Preferably the polypeptide is not a native polypeptide. In this regard, the term "native polypeptide" means an entire polypeptide that is in its native environment and when it has been expressed by its native nucleotide sequence.

Typically, the nucleotide sequence encoding polypeptides having the specific properties as defined herein is prepared using recombinant DNA techniques (i.e. recombinant DNA). However, in an alternative embodiment of the invention, the nucleotide sequence could be synthesised, in whole or in part, using chemical methods well known in the art (see Caruthers M H et al (1980) Nuc Acids Res Symp Ser 215-23 and Horn T et al (1980) Nuc Acids Res Symp Ser 225-232).

Molecular Evolution

Once an enzyme-encoding nucleotide sequence has been isolated, or a putative enzyme-encoding nucleotide sequence has been identified, it may be desirable to modify the selected nucleotide sequence, for example it may be desirable to mutate the sequence in order to prepare an enzyme in accordance with the present invention.

Mutations may be introduced using synthetic oligonucleotides. These oligonucleotides contain nucleotide sequences flanking the desired mutation sites.

A suitable method is disclosed in Morinaga et al (Biotechnology (1984) 2, p 646-649). Another method of introducing mutations into enzyme-encoding nucleotide sequences is described in Nelson and Long (Analytical Biochemistry (1989), 180, p 147-151).

Instead of site directed mutagenesis, such as described above, one can introduce mutations randomly for instance using a commercial kit such as the GeneMorph PCR mutagenesis kit from Stratagene, or the Diversify PCR random mutagenesis kit from Clontech. EP 0 583 265 refers to methods of optimising PCR based mutagenesis, which can also be combined with the use of mutagenic DNA analogues such as those described in EP 0 866 796. Error prone PCR technologies are suitable for the production of variants of lipid acyl transferases with preferred characteristics. WO0206457 refers to molecular evolution of lipases.

A third method to obtain novel sequences is to fragment non-identical nucleotide sequences, either by using any number of restriction enzymes or an enzyme such as Dnase I, and reassembling full nucleotide sequences coding for functional proteins. Alternatively one can use one or multiple non-identical nucleotide sequences and introduce mutations during the reassembly of the full nucleotide sequence. DNA shuffling and family shuffling technologies are suitable for the production of variants of lipid acyl transferases with preferred characteristics. Suitable methods for performing 'shuffling' can be found in EP0 752 008, EP1 138 763, EP1 103 606. Shuffling can also be combined with other forms of DNA mutagenesis as described in U.S. Pat. No. 6,180,406 and WO 01/34835.

Thus, it is possible to produce numerous site directed or random mutations into a nucleotide sequence, either in vivo or in vitro, and to subsequently screen for improved functionality of the encoded polypeptide by various means. Using in silico and exo mediated recombination methods (see WO 00/58517, U.S. Pat. No. 6,344,328, U.S. Pat. No. 6,361,974), for example, molecular evolution can be performed where the variant produced retains very low homology to known enzymes or proteins. Such variants thereby obtained may have significant structural analogy to known transferase enzymes, but have very low amino acid sequence homology.

As a non-limiting example, In addition, mutations or natural variants of a polynucleotide sequence can be recombined with either the wild type or other mutations or natural variants to produce new variants. Such new variants can also be screened for improved functionality of the encoded polypeptide.

The application of the above-mentioned and similar molecular evolution methods allows the identification and selection of variants of the enzymes of the present invention which have preferred characteristics without any prior knowledge of protein structure or function, and allows the production of non-predictable but beneficial mutations or variants. There are numerous examples of the application of molecular evolution in the art for the optimisation or alteration of enzyme activity, such examples include, but are not limited to one or more of the following: optimised expression and/or activity in a host cell or in vitro, increased enzymatic activity, altered substrate and/or product specificity, increased or decreased enzymatic or structural stability, altered enzymatic activity/specificity in preferred environmental conditions, e.g. temperature, pH, substrate As will be apparent to a person skilled in the art, using molecular evolution tools an enzyme may be altered to improve the functionality of the enzyme.

Suitably, the lipid acyltransferase used in the invention may be a variant, i.e. may contain at least one amino acid substitution, deletion or addition, when compared to a parental enzyme. Variant enzymes retain at least 1%, 2%, 3%, 5%, 10%, 15%, 20%, 30%, 40%, 50%, 60%, 70%, 80%; 90%, 95%, 97%, 99% homology with the parent enzyme. Suitable parent enzymes may include any enzyme with esterase or lipase activity. Preferably, the parent enzyme aligns to the pfam00657 consensus sequence.

In a preferable embodiment a variant lipid acyltransferase enzyme retains or incorporates at least one or more of the pfam00657 consensus sequence amino acid residues found in the GDSx, GANDY and HPT blocks.

Enzymes, such as lipases with no or low lipid acyltransferase activity in an aqueous environment may be mutated using molecular evolution tools to introduce or enhance the transferase activity, thereby producing a lipid acyltransferase enzyme with significant transferase activity suitable for use in the compositions and methods of the present invention.

Suitably, the lipid acyltransferase for use in the invention may be a variant with enhanced enzyme activity on polar lipids, preferably phospholipids and/or glycolipids when compared to the parent enzyme. Preferably, such variants also have low or no activity on lyso polar lipids. The enhanced activity on polar lipids, phospholipids and/or glycolipids may be the result of hydrolysis and/or transferase activity or a combination of both.

Variant lipid acyltransferases for use in the invention may have decreased activity on triglycerides, and/or monoglycerides and/or diglycerides compared with the parent enzyme.

Suitably the variant enzyme may have no activity on triglycerides and/or monoglycerides and/or diglycerides.

Alternatively, the variant enzyme for use in the invention may have increased activity on triglycerides, and/or may also have increased activity on one or more of the following, polar lipids, phospholipids, lecithin, phosphatidylcholine, glycolipids, digalactosyl monoglyceride, monogalactosyl monoglyceride.

Variants of lipid acyltransferases are known, one or more of such variants may be suitable for use in the methods and uses of the invention. For example, variants of lipid acyl transferases are described in the following references:

Hilton S, Buckley J T. Studies on the reaction mechanism of a microbial lipase/acyltransferase using chemical modification and site-directed mutagenesis. J Biol Chem. 1991 Jan. 15; 266(2):997-1000.

Robertson D L, Hilton S, Wong K R, Koepke A, Buckley J T. Influence of active site and tyrosine modification on the secretion and activity of the *Aeromonas hydrophila* lipase/acyltransferase. J Biol Chem. 1994 Jan. 21; 269(3):2146-50.

Brumlik M J, Buckley J T. Identification of the catalytic triad of the lipase/acyltransferase from *Aeromonas hydrophila*. J Bacteriol. 1996 April; 178(7):2060-4.

Peelman F, Vinaimont N, Verhee A, Vanloo B, Verschelde J L, Labeur C, Seguret-Mace S, Duverger N, Hutchinson G, Vandekerckhove J, Tavernier J, Rosseneu M. A proposed architecture for lecithin cholesterol acyl transferase (LCAT): identification of the catalytic triad and molecular modeling. Protein Sci. 1998 March; 7(3):587-99.

Amino Acid Sequences

The present invention also encompasses amino acid sequences of polypeptides having the specific properties as defined herein.

As used herein, the term "amino acid sequence" is synonymous with the term "polypeptide" and/or the term "protein". In some instances, the term "amino acid sequence" is synonymous with the term "peptide".

The amino acid sequence may be prepared/isolated from a suitable source, or it may be made synthetically or it may be prepared by use of recombinant DNA techniques.

Suitably, the amino acid sequences may be obtained from the isolated polypeptides taught herein by standard techniques.

One suitable method for determining amino acid sequences from isolated polypeptides is as follows:

Purified polypeptide may be freeze-dried and 100 µg of the freeze-dried material may be dissolved in 50 µl of a mixture of 8 M urea and 0.4 M ammonium hydrogen carbonate, pH 8.4. The dissolved protein may be denatured and reduced for 15 minutes at 50° C. following overlay with nitrogen and addition of 5 µl of 45 mM dithiothreitol. After cooling to room temperature, 5 µl of 100 mM iodoacetamide may be added for the cysteine residues to be derivatized for 15 minutes at room temperature in the dark under nitrogen.

135 µl of water and 5 µg of endoproteinase Lys-C in 5 µl of water may be added to the above reaction mixture and the digestion may be carried out at 37° C. under nitrogen fox 24 hours.

The resulting peptides may be separated by reverse phase HPLC on a VYDAC C18 column (0.46×15 cm; 10 µm; The Separation Group, California, USA) using solvent A: 0.1% TFA in water and solvent B: 0.1% TFA in acetonitrile. Selected peptides may be re-chromatographed on a Develosil C18 column using the same solvent system, prior to N-terminal sequencing. Sequencing may be done using an Applied Biosystems 476A sequencer using pulsed liquid fast cycles according to the manufacturer's instructions (Applied Biosystems, California, USA).

Sequence Identity or Sequence Homology

The present invention also encompasses the use of sequences having a degree of sequence identity or sequence homology with amino acid sequence(s) of a polypeptide having the specific properties defined herein or of any nucleotide sequence encoding such a polypeptide (hereinafter referred to as a "homologous sequence(s)"). Here, the term "homologue" means an entity having a certain homology with the subject amino acid sequences and the subject nucleotide sequences. Here, the term "homology" can be equated with "identity".

The homologous amino acid sequence and/or nucleotide sequence should provide and/or encode a polypeptide which retains the functional activity and/or enhances the activity of the enzyme.

In the present context, a homologous sequence is taken to include an amino acid sequence which may be at least 75, 85 or 90% identical, preferably at least 95 or 98% identical to the subject sequence. Typically, the homologues will comprise the same active sites etc. as the subject amino acid sequence. Although homology can also be considered in terms of similarity (i.e. amino acid residues having similar chemical properties/functions), in the context of the present invention it is preferred to express homology in terms of sequence identity.

In the present context, a homologous sequence is taken to include a nucleotide sequence which may be at least 75, 85 or 90% identical, preferably at least 95 or 98% identical to a nucleotide sequence encoding a polypeptide of the present invention (the subject sequence). Typically, the homologues will comprise the same sequences that code for the active sites etc. as the subject sequence. Although homology can also be considered in terms of similarity (i.e. amino acid residues having similar chemical properties/functions), in the context of the present invention it is preferred to express homology in terms of sequence identity.

Homology comparisons can be conducted by eye, or more usually, with the aid of readily available sequence comparison programs. These commercially available computer programs can calculate % homology between two or more sequences.

% homology may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the moss commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package the default gap penalty for amino acid sequences is –12 for a gap and –4 for each extension.

Calculation of maximum % homology therefore firstly requires the production of an optimal alignment, taking into consideration gap penalties. A suitable compute program for carrying out such an alignment is the GCG Wisconsin Bestfit package (Devereux et al 1984 Nuc. Acids Research 12 p 387). Examples of other software that can perform sequence comparisons include, but are not limited to, the BLAST package (see Ausubel et al 1999 Short Protocols in Molecular Biology, 4$^{th}$ Ed—Chapter 18), FASTA (Altschul et al 1990 J. Mol. Biol. 403-410) and the GENEWORKS suite of comparison tools. Both BLAST and FASTA are available for offline and online searching (see Ausubel et al 1999, pages 7-58 to 7-60). However, for some applications, it is preferred to use the GCG Bestfit program. A new tool, called BLAST 2 Sequences is also available for comparing protein and nucleotide sequence (see FEMS Microbiol Lett 1999 174(2): 247-50; FEMS Microbiol Lett 1999 177(1): 187-8 and tatiana@ncbi.nlm.nih.gov).

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). For some applications, it is preferred to use the public default values for the GCG package, or in the case of other software, the default matrix, such as BLOSUM62.

Alternatively, percentage homologies may be calculated using the multiple alignment feature in DNASIS™ (Hitachi Software), based on an algorithm, analogous to CLUSTAL (Higgins D G & Sharp P M (1988), Gene 73(1), 237-244).

Once the software has produced an optimal alignment, it is possible to calculate % homology, preferably % sequence identity. The software typically does this as part of the sequence comparison and generates a numerical result.

The sequences may also have deletions, insertions or substitutions of amino acid residues which produce a silent change and result in a functionally equivalent substance. Deliberate amino acid substitutions may be made on the basis of similarity in polarity, charge, solubility, hydrophobicity, hydrophilicity, and/or the amphipathic nature of the residues as long as the secondary binding activity of the substance is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Conservative substitutions may be made, for example according to the Table below. Amino acids in the same block in the second column and preferably in the same line in the third column may be substituted for each other:

| ALIPHATIC | Non-polar | G A P |
| | | I L V |
| | Polar - uncharged | C S T M |
| | | N Q |
| | Polar - charged | D E |
| | | K R |
| AROMATIC | | H F W Y |

The present invention also encompasses homologous substitution (substitution and replacement are both used herein to mean the interchange of an existing amino acid residue, with an alternative residue) that may occur i.e. like-for-like substitution such as basic for basic, acidic for acidic, polar for polar etc. Non-homologous substitution may also occur i.e. from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyriylalanine, thienylalanine, naphthylalanine and phenylglycine.

Replacements may also be made by unnatural amino acids.

Variant amino acid sequences may include suitable spacer groups that may be inserted between any two amino acid residues of the sequence including alkyl groups such as methyl, ethyl or propyl groups in addition to amino acid spacers such as glycine or β-alanine residues. A further form of variation, involves the presence of one or more amino acid residues in peptoid form, will be well understood by those skilled in the art. For the avoidance of doubt, "the peptoid form" is used to refer to variant amino acid residues wherein the α-carbon substituent group is on the residue's nitrogen atom rather than the α-carbon. Processes for preparing peptides in the peptoid form are known in the art, for example Simon R J et al., PNAS (1992) 89(20), 9367-9371 and Horwell D C, Trends Biotechnol. (1995) 13(4), 132-134.

Nucleotide sequences for use in the present invention or encoding a polypeptide having the specific properties defined herein may include within them synthetic or modified nucleotides. A number of different types of modification to oligonucleotides are known in the art. These include methylphosphonate and phosphorothioate backbones and/or the addition of acridine or polylysine chains at the 3' and/or 5' ends of the molecule. For the purposes of the present invention, it is to be understood that the nucleotide sequences described herein may be modified by any method available in the art. Such modifications may be carried out in order to enhance the in vivo activity or life span of nucleotide sequences.

The present invention also encompasses the use of nucleotide sequences that are complementary to the sequences discussed herein, or any derivative, fragment or derivative thereof. If the sequence is complementary to a fragment thereof then that sequence can be used as a probe to identify similar coding sequences in other organisms etc.

Polynucleotides which are not 100% homologous to the sequences of the present invention but fall within the scope of the invention can be obtained in a number of ways. Other variants of the sequences described herein may be obtained for example by probing DNA libraries made from a range of individuals, for example individuals from different populations. In addition, other viral/bacterial, or cellular homologues particularly cellular homologues found in mammalian cells (e.g. rat, mouse, bovine and primate cells), may be obtained and such homologues and fragments thereof in general will be capable of selectively hybridising to the sequences shown in the sequence listing herein. Such sequences may be obtained by probing cDNA libraries made from or genomic DNA libraries from other animal species, and probing such libraries with probes comprising all or part of any one of the sequences in the attached sequence listings under conditions of medium to high stringency. Similar considerations apply to obtaining species homologues and allelic variants of the polypeptide or nucleotide sequences of the invention.

Variants and strain/species homologues may also be obtained using degenerate PCR which will use primers designed to target sequences within the variants and homologues encoding conserved amino acid sequences within the sequences of the present invention. Conserved sequences can be predicted, for example, by aligning the amino acid sequences from several variants/homologues. Sequence alignments can be performed using computer software known in the art. For example the GCG Wisconsin PileUp program is widely used.

The primers used in degenerate PCR will contain one or more degenerate positions and will be used at stringency conditions lower than those used for cloning sequences with single sequence primers against known sequences.

Alternatively, such polynucleotides may be obtained by site directed mutagenesis of characterised sequences. This may be useful where for example silent codon sequence changes are required to optimise codon preferences for a particular host cell in which the polynucleotide sequences are being expressed. Other sequence changes may be desired in order to introduce restriction polypeptide recognition sites, or to alter the property or function of the polypeptides encoded by the polynucleotides.

Polynucleotides (nucleotide sequences) of the invention may be used to produce a primer, e.g. a PCR primer, a primer for an alternative amplification reaction, a probe e.g. labelled with a revealing label by conventional means using radioactive or non-radioactive labels, or the polynucleotides may be cloned into vectors. Such primers, probes and other fragments will be at least 15, preferably at least 20, for example at least 25, 30 or 40 nucleotides in length, and are also encompassed by the term polynucleotides of the invention as used herein.

Polynucleotides such as DNA polynucleotides and probes according to the invention may be produced recombinantly, synthetically, or by any means available to those of skill in the art. They may also be cloned by standard techniques.

In general, primers will be produced by synthetic means, involving a stepwise manufacture of the desired nucleic acid sequence one nucleotide at a time. Techniques for accomplishing this using automated techniques are readily available in the art.

Longer polynucleotides will generally be produced using recombinant means, for example using a PCR (polymerase chain reaction) cloning techniques. This will involve making a pair of primers (e.g. of about 15 to 30 nucleotides) flanking a region of the lipid targeting sequence which it is desired to clone, bringing the primers into contact with mRNA or cDNA obtained from an animal or human cell, performing a polymerase chain reaction under conditions which bring about amplification of the desired region, isolating the amplified fragment (e.g. by purifying the reaction mixture on an agarose gel) and recovering the amplified DNA. The primers may be designed to contain suitable restriction enzyme recognition sites so that the amplified DNA can be cloned into a suitable cloning vector.

Hybridisation

The present invention also encompasses sequences that are complementary to the sequences of the present invention or sequences that are capable of hybridising either to the sequences of the present invention or to sequences that are complementary thereto.

The term "hybridisation" as used herein shall include "the process by which a strand of nucleic acid joins with a complementary strand through base pairing" as well as the process of amplification as carried out in polymerase chain reaction (PCR) technologies.

The present invention also encompasses the use of nucleotide sequences that are capable of hybridising to the sequences that are complementary to the subject sequences discussed herein, or any derivative, fragment or derivative thereof.

The present invention also encompasses sequences that are complementary to sequences that are capable of hybridising to the nucleotide sequences discussed herein.

Hybridisation conditions are based on the melting temperature (Tm) of the nucleotide binding complex, as taught in Berger and Kimmel (1987, Guide to Molecular Cloning Techniques, Methods in Enzymology, Vol. 152, Academic Press, San Diego Calif.), and confer a defined "stringency" as explained below.

Maximum stringency typically occurs at about Tm−5° C. (5° C. below the Tm of the probe); high stringency at about 5° C. to 10° C. below Tm; intermediate stringency at about 10° C. to 20° C. below Tm; and low stringency at about 20° C. to 25° C. below Tm. As will be understood by those of skill in the art, a maximum stringency hybridisation can be used to identify or detect identical nucleotide sequences while an intermediate (or low) stringency hybridisation can be used to identify or detect similar or related polynucleotide sequences.

Preferably, the present invention encompasses sequences that are complementary to sequences that are capable of hybridising under high stringency conditions or intermediate stringency conditions to nucleotide sequences encoding polypeptides having the specific properties as defined herein.

More preferably, the present invention encompasses sequences that are complementary to sequences that are capable of hybridising under high stringent conditions (e.g. 65° C. and 0.1×SSC {1×SSC=0.15 M NaCl, 0.015 M Na-citrate pH 7.0}) to nucleotide sequences encoding polypeptides having the specific properties as defined herein.

The present invention also relates to nucleotide sequences that can hybridise to the nucleotide sequences discussed herein (including complementary sequences of those discussed herein).

The present invention also relates to nucleotide sequences that are complementary to sequences that can hybridise to the nucleotide sequences discussed herein (including complementary sequences of those discussed herein).

Also included within the scope of the present invention are polynucleotide sequences that are capable of hybridising to the nucleotide sequences discussed herein under conditions of intermediate to maximal stringency.

In a preferred aspect, the present invention covers nucleotide sequences that can hybridise to the nucleotide sequences discussed herein, or the complement thereof, under stringent conditions (e.g. 50° C. and 0.2×SSC).

In a more preferred aspect, the present invention covers nucleotide sequences that can hybridise to the nucleotide sequences discussed herein, or the complement thereof, under high stringent conditions (e.g. 65° C. and 0.1×SSC).

Expression of Polypeptides

A nucleotide sequence for use in the present invention or for encoding a polypeptide having the specific properties as defined herein can be incorporated into a recombinant replicable vector. The vector may be used to replicate and express the nucleotide sequence, in polypeptide form, in and/or from a compatible host cell. Expression may be controlled using control sequences which include promoters/enhancers and other expression regulation signals. Prokaryotic promoters and promoters functional in eukaryotic cells may be used. Tissue specific or stimuli specific promoters may be used. Chimeric promoters may also be used comprising sequence elements from two or more different promoters described above.

The polypeptide produced by a host recombinant cell by expression of the nucleotide sequence may be secreted or may be contained intracellularly depending on the sequence and/or the vector used. The coding sequences can be designed with signal sequences which direct secretion of the substance coding sequences through a particular prokaryotic or eukaryotic cell membrane.

Expression Vector

The term "expression vector" means a construct capable of in vivo or in vitro expression.

Preferably, the expression vector is incorporated in the genome of the organism. The term "incorporated" preferably covers stable incorporation into the genome.

The nucleotide sequence of the present invention or coding for a polypeptide having the specific properties as defined herein may be present in a vector, in which the nucleotide sequence is operably linked to regulatory sequences such that the regulatory sequences are capable of providing the expression of the nucleotide sequence by a suitable host organism, i.e. the vector is an expression vector.

The vectors of the present invention may be transformed into a suitable host cell as described below to provide for expression of a polypeptide having the specific properties as defined herein.

The choice of vector, e.g. plasmid, cosmid, virus or phage vector, will often depend on the host cell into which it is to be introduced.

The vectors may contain one or more selectable marker genes—such as a gene which confers antibiotic resistance e.g. ampicillin, kanamycin, chloramphenicol or tetracyclin resistance. Alternatively, the selection may be accomplished by co-transformation (as described in WO91/17243).

Vectors may be used in vitro, for example for the production of RNA or used to transfect or transform a host cell.

Thus, in a further embodiment, the invention provides a method of making nucleotide sequences of the present invention or nucleotide sequences encoding polypeptides having the specific properties as defined herein by introducing a nucleotide sequence into a replicable vector, introducing the vector into a compatible host cell, and growing the host cell under conditions which bring about replication of the vector.

The vector may further comprise a nucleotide sequence enabling the vector to replicate in the host cell in question. Examples of such sequences are the origins of replication of plasmids pUC19, pACYC177, pUB110, pE194, pAMB1 and pIJ702.

Regulatory Sequences

In some applications, a nucleotide sequence for use in the present invention or a nucleotide sequence encoding a polypeptide having the specific properties as defined herein may be operably linked to a regulatory sequence which is capable of providing for the expression of the nucleotide sequence, such as by the chosen host cell. By way of example, the present invention covers a vector comprising the nucleotide sequence of the present invention operably linked to such a regulatory sequence, i.e. the vector is an expression vector.

The term "operably linked" refers to a juxtaposition wherein the components described are in a relationship permitting them to function in their intended manner. A regulatory sequence "operably linked" to a coding sequence is ligated in such a way that expression of the coding sequence is achieved under conditions compatible with the control sequences.

The term "regulatory sequences" includes promoters and enhancers and other expression regulation signals.

The term "promoter" is used in the normal sense of the art, e.g. an RNA polymerase binding site.

Enhanced expression of the nucleotide sequence encoding the enzyme having the specific properties as defined herein may also be achieved by the selection of heterologous regulatory regions, e.g. promoter, secretion leader and terminator regions.

Preferably, the nucleotide sequence of the present invention may be operably linked to at least a promoter.

Examples of suitable promoters for directing the transcription of the nucleotide sequence in a bacterial, fungal or yeast host are well known in the art.

Constructs

The term "construct"—which is synonymous with terms such as "conjugate", "cassette" and "hybrid"—includes a nucleotide sequence encoding a polypeptide having the specific properties as defined herein for use according to the present invention directly or indirectly attached to a promoter. An example of an indirect attachment is the provision of a suitable spacer group such as an, intron sequence, such as the Sh1-intron or the ADH intron, intermediate the promoter and the nucleotide sequence of the present invention. The same is true for the term "fused" in relation to the present invention which includes direct or indirect attachment. In some cases, the terms do not cover the natural combination of the nucleotide sequence coding for the protein ordinarily associated with the wild type gene promoter and when they are both in their natural environment.

The construct may even contain or express a marker which allows for the selection of the genetic construct.

For some applications, preferably the construct comprises at least a nucleotide sequence of the present invention or a nucleotide sequence encoding a polypeptide having the specific properties as defined herein operably linked to a promoter.

Host Cells

The term "host cell"—in relation to the present invention includes any cell that comprises either a nucleotide sequence encoding a polypeptide having the specific properties as defined herein or an expression vector as described above and which is used in the recombinant production of a polypeptide having the specific properties as defined herein.

Thus, a further embodiment of the present invention provides host cells transformed or transfected with a nucleotide sequence of the present invention or a nucleotide sequence that expresses a polypeptide having the specific properties as defined herein. The cells will be chosen to be compatible with the said vector and may for example be prokaryotic (for example bacterial), fungal, yeast or plant cells. Preferably, the host cells are not human cells.

Examples of suitable bacterial host organisms are gram negative bacterium or gram positive bacteria.

Depending on the nature of the nucleotide sequence encoding a polypeptide having the specific properties as defined herein, and/or the desirability for further processing of the expressed protein, eukaryotic hosts such as yeasts or other fungi may be preferred. In general, yeast cells are preferred over fungal cells because they are easier to manipulate. However, some proteins are either poorly secreted from the yeast cell, or in some cases are not processed properly (e.g. hyperglycosylation in yeast). In these instances, a different fungal host organism should be selected.

The use of suitable host cells, such as yeast, fungal and plant host cells—may provide for post-translational modifications (e.g. myristoylation, glycosylation, truncation, lapidation and tyrosine, serine or threonine phosphorylation) as may be needed to confer optimal biological activity on recombinant expression products of the present invention.

The host cell may be a protease deficient or protease minus strain.

Organism

The term "organism" in relation to the present invention includes any organism that could comprise a nucleotide sequence according to the present invention or a nucleotide sequence encoding for a polypeptide having the specific properties as defined herein and/or products obtained therefrom.

Suitable organisms may include a prokaryote, fungus, yeast or a plant.

The term "transgenic organism" in relation to the present invention includes any organism that comprises a nucleotide sequence coding for a polypeptide having the specific properties as defined herein and/or the products obtained therefrom, and/or wherein a promoter can allow expression of the nucleotide sequence coding for a polypeptide having the specific properties as defined herein within the organism. Preferably the nucleotide sequence is incorporated in the genome of the organism.

The term "transgenic organism" does not cover native nucleotide coding sequences in their natural environment when they are under the control of their native promoter which is also in its natural environment.

Therefore, the transgenic organism of the present invention includes an organism comprising any one of, or combinations of, a nucleotide sequence coding for a polypeptide having the specific properties as defined herein, constructs as defined herein, vectors as defined herein, plasmids as defined herein, cells as defined herein, or the products thereof. For example the transgenic organism can also comprise a nucleotide sequence coding for a polypeptide having the specific properties as defined herein under the control of a heterologous promoter.

Transformation of Host Cells/Organism

As indicated earlier, the host organism can be a prokaryotic or a eukaryotic organism. Examples of suitable prokaryotic hosts include *E. coli* and *Bacillus subtilis*.

Teachings on the transformation of prokaryotic hosts is well documented in the art, for example see Sambrook et al (Molecular Cloning: A Laboratory Manual, 2nd edition, 1989, Cold Spring Harbor Laboratory Press). If a prokaryotic host is used then the nucleotide sequence may need to be suitably modified before transformation—such as by removal of introns.

In another embodiment the transgenic organism can be a yeast.

Filamentous fungi cells may be transformed using various methods known in the art—such as a process involving protoplast formation and transformation of the protoplasts followed by regeneration of the cell wall in a manner known. The use of *Aspergillus* as a host microorganism is described in EP 0 238 023.

Another host organism can be a plant. A review of the general techniques used for transforming plants may be found in articles by Potrykus (*Annu Rev Plant Physiol Plant Mol Biol* [1991] 42:205-225) and Christou (Agro-Food-Industry Hi-Tech March/April 1994 17-27). Further teachings on plant transformation may be found in EP-A-0449375.

General teachings on the transformation of fungi, yeasts and plants are presented in following sections.

Transformed Fungus

A host organism may be a fungus—such as a filamentous fungus. Examples of suitable such hosts include any member belonging to the genera *Thermomyces, Acremonium, Aspergillus, Penicillium, Mucor, Neurospora, Trichoderma* and the like.

Teachings on transforming filamentous fungi are reviewed in U.S. Pat. No. 5,741,665 which states that standard techniques for transformation of filamentous fungi and culturing the fungi are well known in the art. An extensive review of techniques as applied to *N. crassa* is found, for example in Davis and de Serres, *Methods Enzymol* (1971) 17A: 79-143.

Further teachings on transforming filamentous fungi are reviewed in U.S. Pat. No. 5,674,707.

In one aspect, the host organism can be of the genus *Aspergillus*, such as *Aspergillus niger*.

A transgenic *Aspergillus* according to the present invention can also be prepared by following, for example, the teachings of Turner G. 1994 (Vectors for genetic manipulation. In: Martinelli S. D., Kinghorn J. R. (Editors) *Aspergillus*: 50 years on. Progress in industrial microbiology vol 29. Elsevier Amsterdam 1994. pp. 641-666).

Gene expression in filamentous fungi has been reviewed in Punt et al. (2002) Trends Biotechnol 2002 May; 20(5):200-6, Archer & Peberdy Crit Rev Biotechnol (1997) 17(4):273-306.

Transformed Yeast

In another embodiment, the transgenic organism can be a yeast.

A review of the principles of heterologous gene expression in yeast are provided in, for example, *Methods Mol Biol* (1995), 49:341-54, and *Curr Opin Biotechnol* (1997) October; 8(5):554-60

In this regard, yeast—such as the species *Saccharomyces cerevisi* or *Pichia pastoris* (see FEMS Microbiol Rev (2000 24(1):45-66), may be used as a vehicle for heterologous gene expression.

A review of the principles of heterologous gene expression in *Saccharomyces cerevisiae* and secretion of gene products is given by E Hinchcliffe E Kenny (1993, "Yeast as a vehicle for the expression of heterologous genes", *Yeasts*, Vol 5, Anthony H Rose and J Stuart Harrison, eds, 2nd edition, Academic Press Ltd.).

For the transformation of yeast, several transformation protocols have been developed. For example, a transgenic *Saccharomyces* according to the present invention can be prepared by following the teachings of Hinnen et al., (1978, *Proceedings of the National Academy of Sciences of the USA*

75, 1929); Beggs, J D (1978, *Nature*, London, 275, 104); and Ito, H et al (1983, J Bacteriology 153, 163-168).

A suitable yeast host organism can be selected from the biotechnologically relevant yeasts species such as but not limited to yeast species such as *Pichia* sp., *Hansenula* sp or *Kluyveromyces, Yarrowinia* species or a species of *Saccharomyces* including *Saccharomyces cerevisiae* or a species belonging to *Schizosaccharomyce* such as, for example, *S. pombe* species.

A strain of the methylotrophic yeast species *Pichia pastoris* can be used used as the host organism.

In one embodiment the host organism is a *Hansenula* species, such as *Hansenula polymorpha* (as described in WO01/38544).

The transformed yeast cells may be selected using various selective markers—such as auxotrophic markers dominant antibiotic resistance markers.

Transformed Plants/Plant Cells

A host organism suitable for the present invention may be a plant. A review of the general techniques may be found in articles by Potrykus (*Annu Rev Plant Physiol Plant Mol Biol* [1991] 42:205-225) and Christou (Agro-Food-Industry Hi-Tech March/April 1994 17-27), or in WO01/16308. The transgenic plant may produce enhanced levels of phytosterol esters and phytostanol esters, for example.

Therefore the present invention also relates to a method for the production of a transgenic plant with enhanced levels of phytosterol esters and phytostanol esters, comprising the steps of transforming a plant cell with a lipid acyltransferase as defined herein (in particular with an expression vector or construct comprising a lipid acyltransferase as defined herein), and growing a plant from the transformed plant cell.

Secretion

Often, it is desirable for the polypeptide to be secreted from the expression host into the culture medium from where the enzyme may be more easily recovered. According to the present invention, the secretion leader sequence may be selected on the basis of the desired expression host. Hybrid signal sequences may also be used with the context of the present invention.

Typical examples of heterologous secretion leader sequences are those originating from the fungal amyloglucosidase (AG) gene (glaA—both 18 and 24 amino acid versions e.g. from *Aspergillus*), the a-factor gene (yeasts e.g. *Saccharomyces, Kluyveromyces* and *Hansenula*) or the α-amylase gene (*Bacillus*).

Detection

A variety of protocols for detecting and measuring the expression of the amino acid sequence are known in the art. Examples include enzyme-linked immunosorbent assay (ELISA), radioimmunoassay (RIA) and fluorescent activated cell sorting (FACS).

A wide variety of labels and conjugation techniques are known by those skilled in the art and can be used in various nucleic and amino acid assays.

A number of companies such as Pharmacia Biotech (Piscataway, N.J.), Promega (Madison, Wis.), and US Biochemical Corp (Cleveland, Ohio) supply commercial kits and protocols for these procedures.

Suitable reporter molecules or labels include those radionuclides; enzymes, fluorescent, chemiluminescent, or chromogenic agents as well as substrates, cofactors, inhibitors, magnetic particles and the like. Patents teaching the use of such labels include U.S. Pat. No. 3,817,837; U.S. Pat. No. 3,850,752; U.S. Pat. No. 3,939,350; U.S. Pat. No. 3,996,345; U.S. Pat. No. 4,277,437; U.S. Pat. No. 4,275,149 and U.S. Pat. No. 4,366,241.

Also, recombinant immunoglobulins may be produced as shown in U.S. Pat. No. 4,816,567.

Fusion Proteins

A polypeptide having the specific properties as defined herein may be produced as a fusion protein, for example to aid in extraction and purification thereof. Examples of fusion protein partners include glutathione-S-transferase (GST), 6xHis (SEQ ID NO: 17), GAL4 (DNA binding and/or transcriptional activation domains) and β-galactosidase. It may also be convenient to include a proteolytic cleavage site between the fusion protein partner and the protein sequence of interest to allow removal of fusion protein sequences. Preferably the fusion protein will not hinder the activity of the protein sequence.

Gene fusion expression systems in *E. coli* have been reviewed in Curr. Opin. Biotechnol. (1995) 6(5):501-6.

In another embodiment of the invention, the amino acid sequence of a polypeptide having the specific properties as defined herein may be ligated to a heterologous sequence to encode a fusion protein. For example, for screening of peptide libraries for agents capable of affecting the substance activity, it may be useful to encode a chimeric substance expressing a heterologous epitope that is recognised by a commercially available antibody.

The invention will now be described, by way of example only, with reference to the following Figures and Examples.

FIG. 1 shows a pfam00657 consensus sequence from database version 6 (SEQ ID No. 1);

FIG. 2 shows an amino acid sequence (SEQ ID No. 2) obtained from the organism *Aeromonas hydrophila* (P10480; GI:121051);

FIG. 3 shows an amino acid sequence (SEQ ID No. 3) obtained from the organism *Aeromonas salmonicida* (AAG098404; GI:9964017);

FIG. 4 shows an amino acid sequence (SEQ ID No. 4) obtained from the organism *Streptomyces coelicolor* A3(2) (Genbank accession number NP_631558);

FIG. 5 shows an amino acid sequence (SEQ ID No. 5) obtained from the organism *Streptomyces coelicolor* A3(2) (Genbank accession number: CAC42140);

FIG. 6 shows an amino acid sequence (SEQ ID No. 6) obtained from the organism *Saccharomyces cerevisiae* (Genbank accession number P41734);

FIGS. 7A, 7B and 7C show an alignment of selected sequences (SEQ ID NOS: 55-59) respectively, in order of appearance) to pfam00657 consensus sequence (SEQ ID NO:1);

Figure 35:
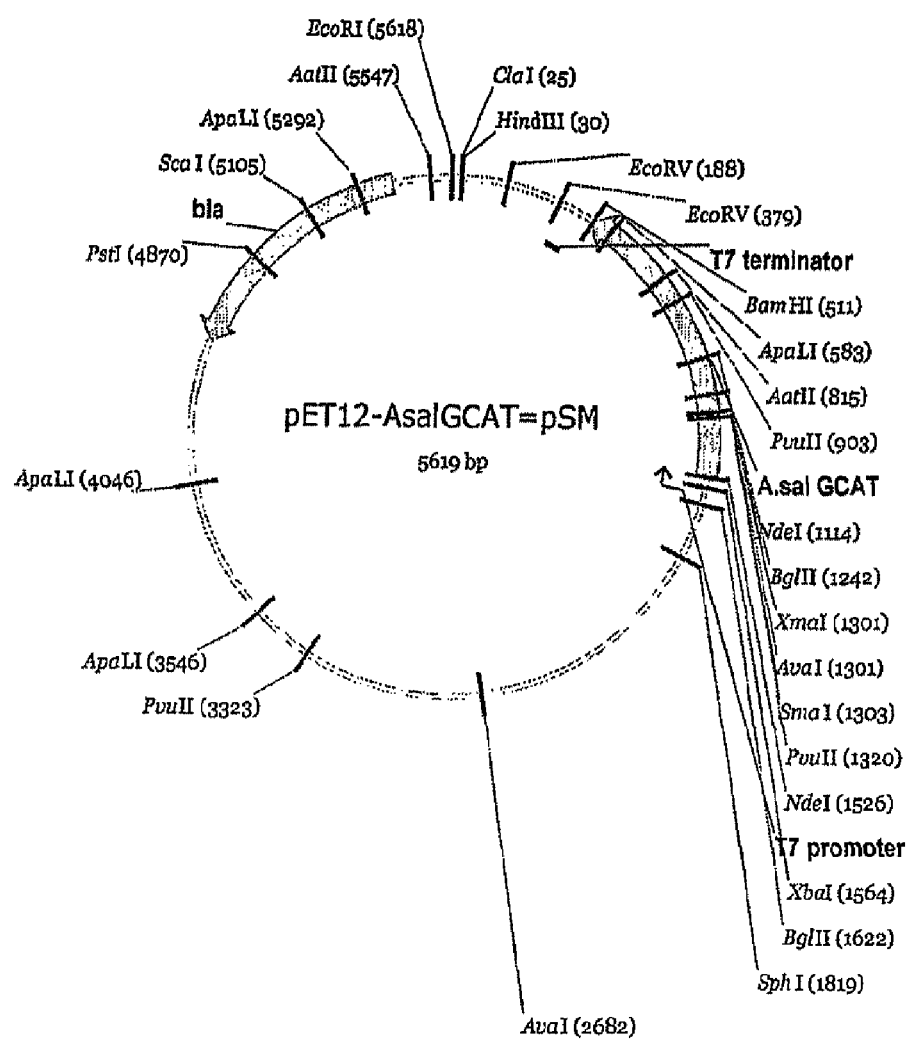

FIG. 8 shows a pairwise alignment of residues 1-335 of SEQ ID NO: 3 with SEQ ID NO: 2 showing 93% amino acid sequence identity. The signal sequence is underlined. + denotes differences. The GnSX motif containing the active site serine 16, and the active sites aspartic acid 116 and histidine 291 are highlighted (see shaded regions). Numbers after the amino acid is minus the signal sequence.

FIG. 9 shows a nucleotide sequence (SEQ ID No. 7) encoding a lipid acyl transferase according to the present invention obtained from the organism *Aeromonas hydrophila*;

FIG. 10 shows a nucleotide sequence (SEQ ID No. 8) encoding a lipid acyl transferase according to the present invention obtained from the organism *Aeromonas salmonicida*;

FIG. 11 shows a nucleotide sequence (SEQ ID No. 9) encoding a lipid acyl transferase according to the present invention obtained from the organism *Streptomyces coelicolor* A3(2) (Genbank accession number NC_003888.1: 8327480.8328367);

FIG. 12 shows a nucleotide sequence (SEQ ID No. 10) encoding a lipid acyl transferase according to the present invention obtained from the organism *Streptomyces coelicolor* A3(2) (Genbank accession number AL939131.1: 265480.266367);

FIG. 13 shows a nucleotide sequence (SEQ ID No. 11) encoding a lipid acyl transferase according to the present invention obtained from the organism *Saccharomyces cerevisiae* (Genbank accession number Z75034);

FIG. 14 shows an amino acid sequence (SEQ ID No. 12) obtained from the organism *Ralstonia* (Genbank accession number: AL646052);

FIG. 15 shows a nucleotide sequence (SEQ ID No. 13) encoding a lipid acyl transferase according to the present invention obtained from the organism *Ralstonia*;

FIG. 16 shows SEQ ID No. 20. Scoe1 NCBI protein accession code CAB39707.1 GI:4539178 conserved hypothetical protein [*Streptomyces coelicolor* A3(2)];

FIG. 17 shows a nucleotide sequence shown as SEQ ID No. 21 encoding NCBI protein accession code CAB39707.1 GI:4539178 conserved hypothetical protein [*Streptomyces coelicolor* A3(2)];

FIG. 18 shows an amino acid shown as SEQ ID No. 22. Scoe2 NCBI protein accession code CAC01477.1 GI:9716139 conserved hypothetical protein [*Streptomyces coelicolor* A3(2)];

FIG. 19 shows a nucleotide sequence shown as SEQ ID No. 23 encoding Scoe2 NCBI protein accession code CAC01477.1 GI:9716139 conserved hypothetical protein [*Streptomyces coelicolor* A3(2)];

FIG. 20 shows an amino acid sequence (SEQ ID No. 24) Scoe3 NCBI protein accession code CAB88833.1 GI:7635996 putative secreted protein. [*Streptomyces coelicolor* A3(2)];

FIG. 21 shows a nucleotide sequence shown as SEQ ID No. 25 encoding Scoe3 NCBI protein accession code CAB88833.1 GI:7635996 putative secreted protein. [*Streptomyces coelicolor* A3(2)];

FIG. 22 shows an amino acid sequence (SEQ ID No. 26) Scoe4 NCBI protein accession code CAB89450.1 GI:7672261 putative secreted protein. [*Streptomyces coelicolor* A3(2)];

FIG. 23 shows an nucleotide sequence shown as SEQ ID No. 27 encoding Scoe4 NCBI protein accession code CAB89450.1 GI:7672261 putative secreted protein. [*Streptomyces coelicolor* A3(2)];

FIG. 24 shows an amino acid sequence (SEQ ID No. 28) Scoe5 NCBI protein accession code CAB62724.1 GI:6562793 putative lipoprotein [*Streptomyces coelicolor* A3(2)];

FIG. 25 shows a nucleotide sequence shown as SEQ ID No. 29, encoding Scoe5 NCBI protein accession code CAB62724.1 GI:6562793 putative lipoprotein [*Streptomyces coelicolor* A3(2)];

FIG. 26 shows an amino acid sequence (SEQ ID No. 30) Srim1 NCBI protein accession code AAK84028.1 GI:15082088 GDSL-lipase [*Streptomyces rimosus*];

FIG. 27 shows a nucleotide sequence shown as SEQ ID No. 31 encoding Srim1 NCBI protein accession code AAK84028.1 GI:15082088 GDSL-lipase [*Streptomyces rimosus*];

FIG. 28 shows an amino acid sequence (SEQ ID No. 32) A lipid acyl transferase from *Aeromonas hydrophila* (ATCC #7965);

FIG. 29 shows a nucleotide sequence (SEQ ID No. 33) encoding a lipid acyltransferase from *Aeromonas hydrophila* (ATCC #7965);

FIG. 30 shows an amino acid sequence (SEQ ID No. 34) of a lipid acyltransferase from *Aeromonas salmonicida* subsp. *Salmonicida* (ATCC#14174);

FIG. 31 shows a nucleotide sequence (SEQ ID No 35) encoding a lipid acyltransferase from *Aeromonas salmonicida* subsp. *Salmonicida* (ATCC#14174);

FIG. 32 shows that homologues of the *Aeromonas* genes can be identified using the basic local alignment search tool service at the National Center for Biotechnology Information, NIH, MD, USA and the completed genome databases. The GLDSX motif was used in the database search and a number of sequences/genes potentially encoding enzymes with lipolytic activity were identified. Genes were identified from the genus *Streptomyces, Xanthomonas* and *Ralstonia*. As an example below, the *Ralstonia solanacearum* was aligned to the *Aeromonas salmonicida* (satA) gene. Pairwise alignment showed 23% identity. The active site serine is present at the amino terminus and the catalytic residues histidine and aspartic acid can be identified (SEQ ID NOS: 60-61);

FIGS. 33A and 33B show the Pfam00657.11 [family 00657, database version 11] consensus sequence (SEQ ID NO: 70) (hereafter called Pfam consensus) and the alignment of various sequences (SEQ ID NOS: 62-68, AND 14-15 respectively, in order of appearance) to the Pfam consensus sequence. The arrows indicate the active site residues, the underlined boxes indicate three of the homology boxes indicated by [Upton C and Buckley JT (1995) Trends Biochem Sci 20; 179-179]. Capital letters in the Pfam consensus indicate conserved residues in many family members. The – symbol indicates a position where the hidden Markov model of the Pfam consensus expected to find a residue but did not, so a gap is inserted. The . symbol indicates a residue without a corresponding residue in the Pfam consensus. The sequences are the fragments of amino acid sequences listed in FIGS. 16, 18, 20, 22, 24, 26, 28 and 30.

FIG. 34 shows the Pfam00657.11 [family 00657, database version 11] consensus sequence (SEQ ID NO: 70) (hereafter called Pfam consensus) and the alignment of various sequences (SEQ ID NOS: 62-64, 68, and 14-15 respectively, in order of appearance) to the Pfam consensus sequence. The arrows indicate the active site residues, the underlined boxes indicate three of the homology boxes indicated by [Upton C and Buckley J T (1995) Trends Biochem Sci 20; 179-179]. Capital letters in the Pfam consensus indicate conserved residues in many family members. The – symbol indicates a position where the hidden Markov model of the Pfam consensus expected to find a residue but did not, so a gap is inserted. The . symbol indicates a residue without a corresponding residue in the Pfam consensus. The sequences are the fragments of amino acid sequences listed in FIGS. 2, 16, 18, 20, 26, 28, and 30. All these proteins were found to be active against lipid substrates.

Figure 36:
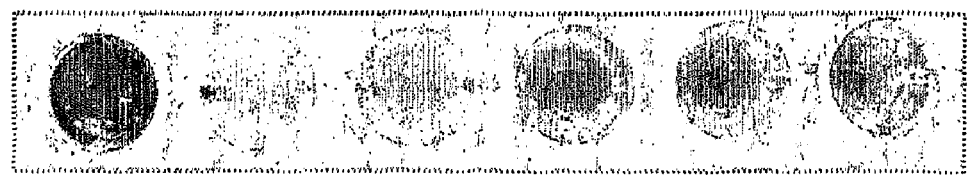
Figure 37:
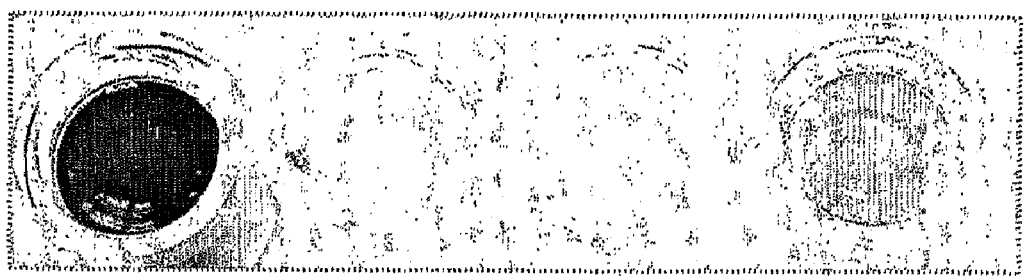
Figure 38:
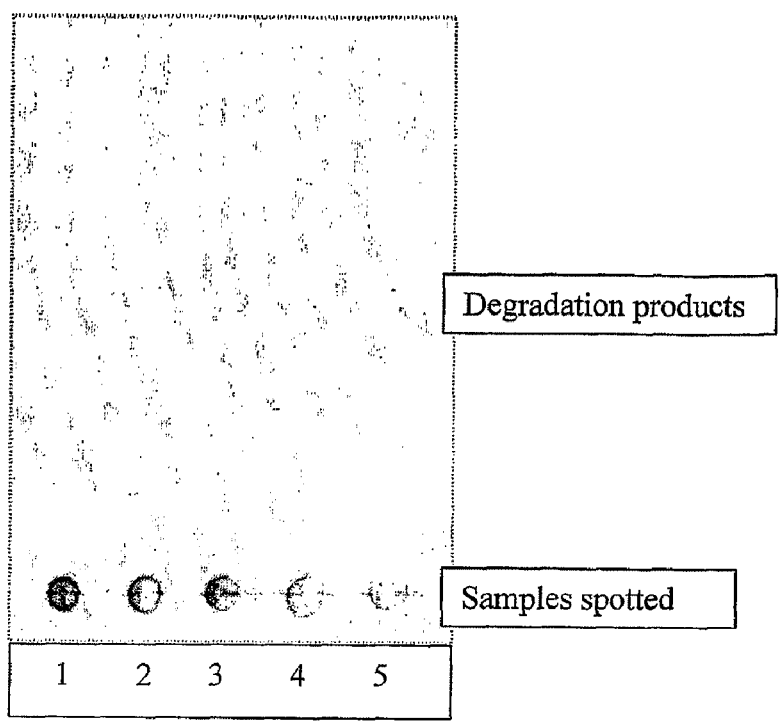
Figure 39:
Figure 40:
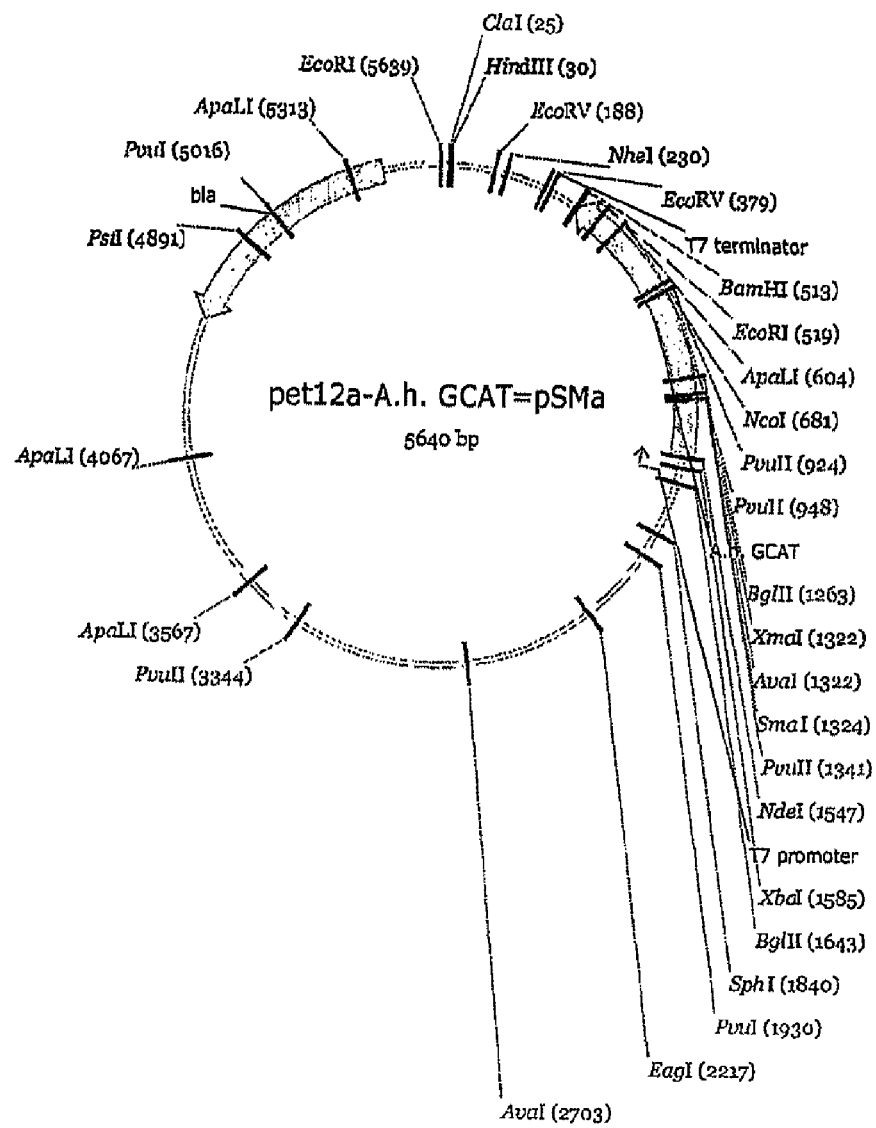
Figure 41:
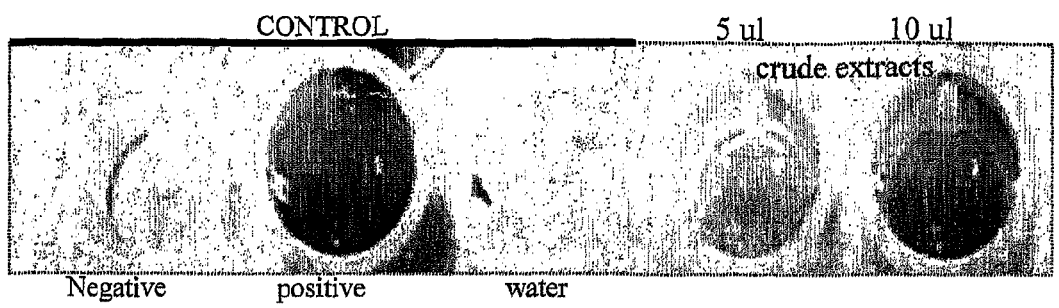
Figure 42:
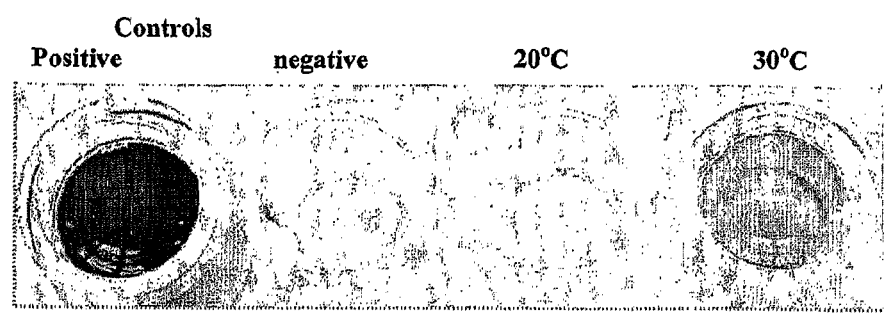
Figure 43:
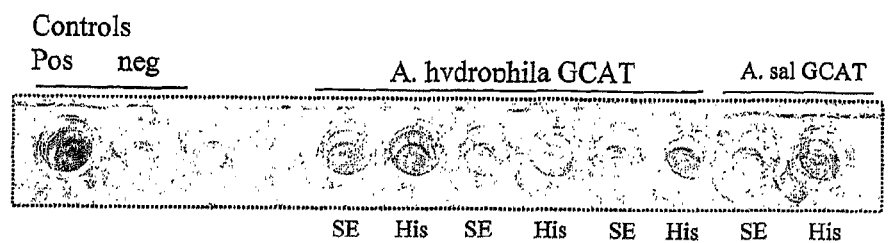
Figure 44:
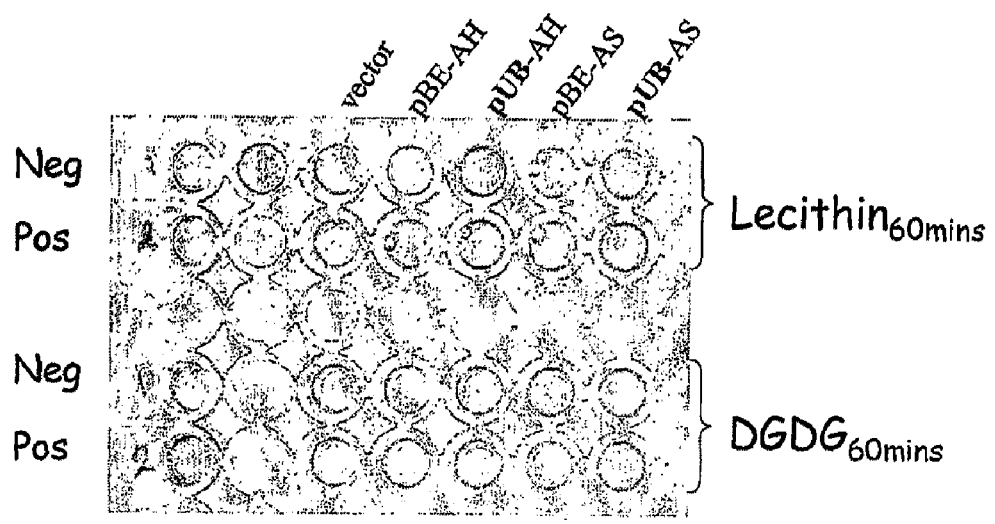

FIG. 35 shows a expression vector pet12-AsalGCAT=pSM containing the C-terminal His-tagged *Aeromonas salmonicida* lipid acyltransferase gene;

FIG. 36 shows the results of testing cell extracts in a NEFA Kit Assay, which depicts the activity of a recombinant, *A. salmonicida* lipid acyltransferase, towards lecithin. The wells from left to right indicate: a positive control, a negative control (i.e. extracts from empty plasmid) and samples collected after 0, 1, 2 and 3 hours cultivation after IPTG induction;

FIG. 37 shows growth optimisation of BL21(DE3)pLysS harboring the expression vector pet12-AsalGCAT=pSM showing cultivation at 30° C. resulted in the production of enzyme with high activity towards lecithin. Cell extracts were tested for phospholipase activity using the NEFA kit assay. Wells from left to right: positive control; negative control; 20° C.; 30° C.;

FIG. 38 shows crude cell extracts from BL21(DE3)pLysS expressing active lipid acyltransferase incubated with the substrate lecithin and reaction mixture was analyzed using thin layer chromatography showing the presence of degradation products. Lanes: 1. No enzyme; 2. +A.sal–10 ul 37° C.; 3. +A.sal–20 ul 37° C.; 4. +A.sal–10 ul 24° C.; 5. +A.sal–20 u 24° C.;

FIG. 39 shows partial purification of the *Aeromonas salmonicida* Acyl Transferase showing the phospholipase activity associated with purified His-tag protein. SE=Sonicated extracts, His=Purified with Ni-NTA spin-kit from Qiagen;

FIG. 40 shows the expression vector pet12-A.h. GCAT=pSMa containing the C-terminal His-tagged *Aeromonas hydrophila* Glycerolipid Acyl Transferase (GCAT) gene was used to transform *E. coli* strain BL21(DE3)pLysS;

FIG. 41 shows the activity of the crude extracts (5 & 10 ul) containing the recombinant *Aeromonas hydrophila* GCAT enzyme was tested towards lecithin using Non-Esterified Fatty Acid (NEFA) kit (Roche, Switzerland), showing the presence of active enzyme towards the phospholipid, lecithin;

FIG. 42 shows growth optimisation of BL21(DE3)pLysS harboring the expression vector pet12-AsalGCAT=pSM showing cultivation at 30° C. resulted in the production of enzyme with high activity towards lecithin. Cell extracts were tested for phospholipase activity using the NEFA kit assay;

FIG. 43 shows the partial purification of the *Aeromonas hydrophila* & *A. salmonicida* Acyl Transferases showing the phospholipase activity associated with purified His-tag protein. SE=Sonicated extracts, His=Purified with Ni-NTA spin-kit from Qiagen);

FIG. 44 shows the expression of the *Aeromonas* genes in *Bacillus subtilis* 163 showing the production of secreted enzyme with activity towards both lecithin and DGDG. pUB-AH=construct containing the *A. hydrophila* gene and pUB-AS, construct with the *A. salmonicida* gene, Culture filtrate was incubated with the substrates for 60 minutes.

Figure 45:
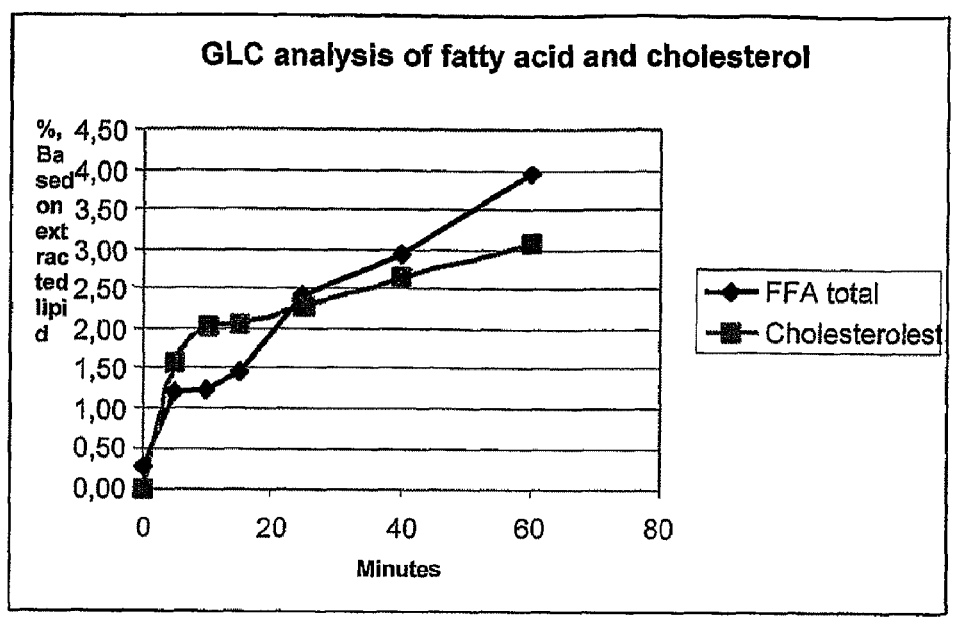
Figure 46:
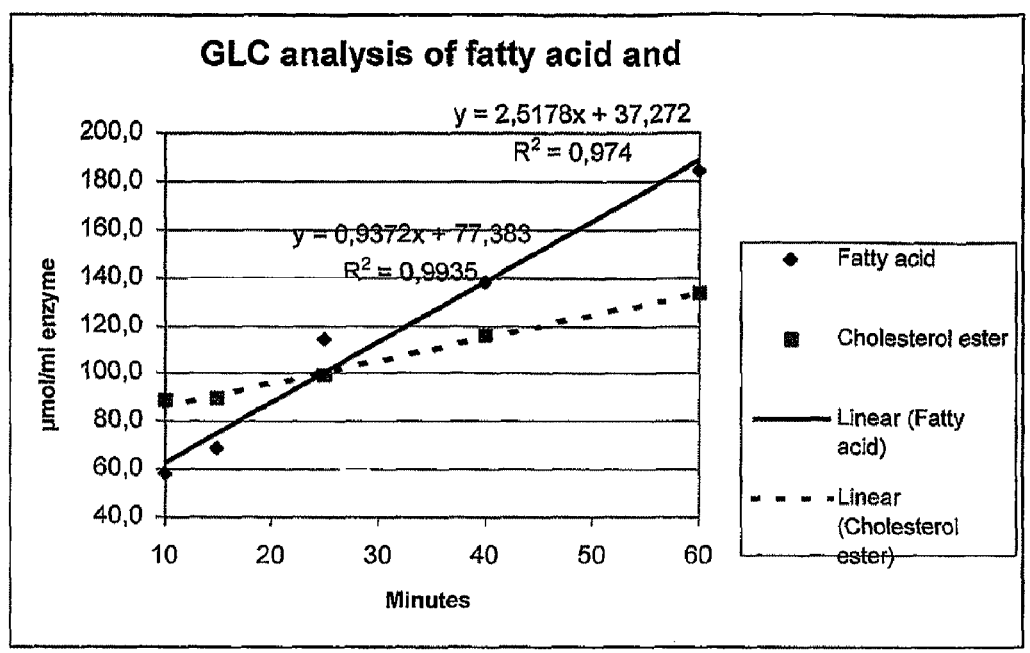
Figure 49:
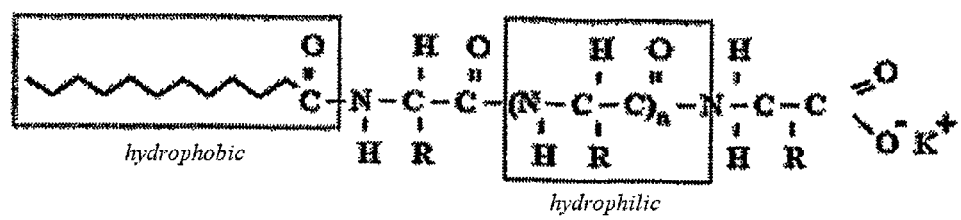
Figure 50:
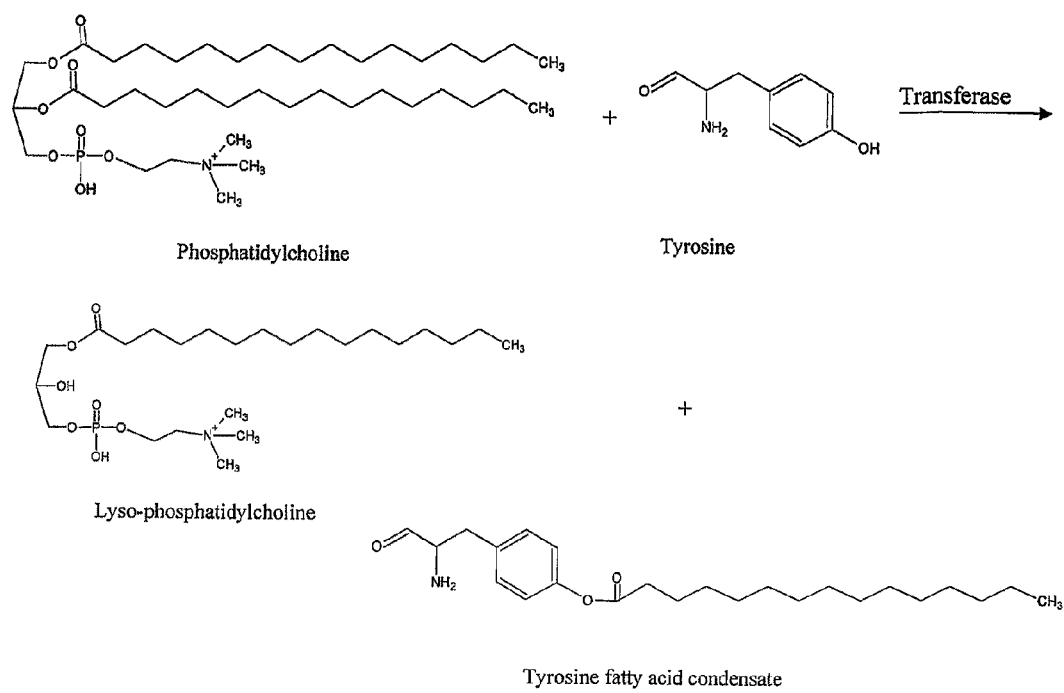
Figure 51:
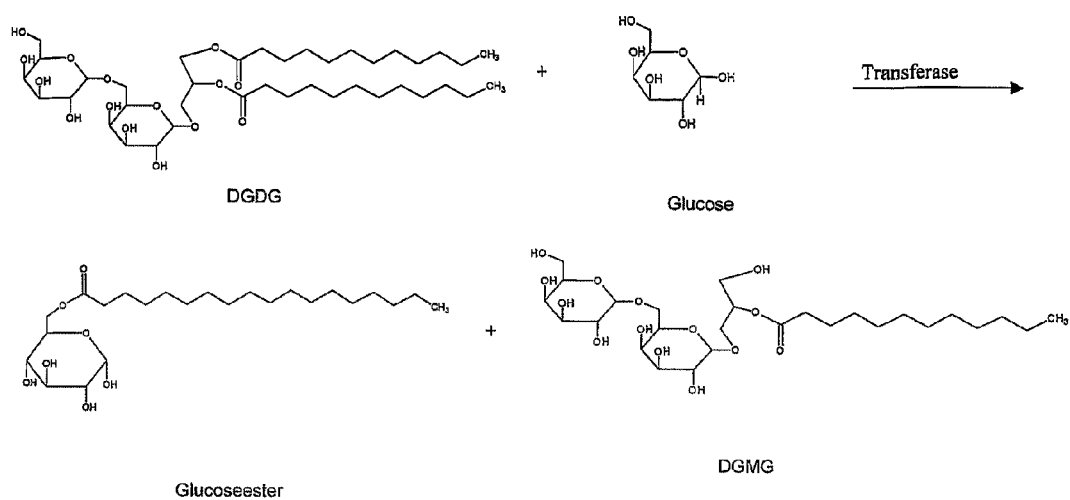

FIG. 45 and FIG. 46 show graphs depicting fatty acid and cholesterol ester as a function of time. The graphs depict results obtained for GLC analysis in the assay for measurement of acyltransferase activity in a foodstuff using lecithin and cholesterol in buffer as substrate;

FIG. 47 shows an amino acid sequence (SEQ ID No. 36) of the fusion construct used for mutagenesis of the *Aeromonas hydrophila* lipid acyltransferase gene in Example 17. The underlined amino acids is a xylanase signal peptide;

FIG. 48 shows a nucleotide sequence (SEQ ID No. 54) encoding an enzyme from *Aeromonas hydrophila* including a xylanase signal peptide;

FIG. 49 shows the structure of protein-fatty acid condensates of amino acids;

FIG. 50 shows a schematic representing the reaction between a fatty acid from phosphatidylcholine when transferred to the free hydroxyl group of amino acids having a free hydroxyl group available for esterification, e.g. tyrosine or serine; and FIG. 51 shows a schematic of the reaction between DGDG and glucose when catalysed by a lipid acyltransferase.

EXAMPLES

Example 1

The Cloning, Sequencing and Heterologous Expression of a Transferase from *Aeromonas salmonicida* Subsp. *Salmonicida*

Strains Used:

*Aeromonas salmonicida* subsp. *Salmonicida* (ATCC 14174) was obtained from ATCC and grown overnight at 30° C. in Luria-Bertani medium (LB). The cells were centrifuged and genomic DNA was isolated using the procedures for genomic DNA isolation from Qiagen Ltd. Genomic DNA buffer set (cat.19060), protease K (cat. 19131) and RNAse A (cat. 19101) were all obtained from Qiagen Ltd. (Boundary court Gatwick Court, West Sussex, RH10 2AX).

Host bacterial strain BL21(DE3)pLysS (Novagen) was used for production of the recombinant *Aeromonas* enzymes. Competent cells of BL21(DE3)pLysS were used as host for transformation with the expression vector pet12-AsalGCAT=pSM. Transformants containing the appropriate plasmid were grown at 37° C. in LB agar medium containing 100-ug ampicillin/ml.

Construction of Expression Vector pet12-AsalGCAT-pSM:

For all DNA amplifications of the transferase genes from *Aeromonas*, genomic DNA (0.2-1 ul) was used as template and pfu DNA polymerase (2.5 units) was used with 10 ul of 10× pfu buffer, 1 ul each primer (50 pmol/ul), 200 uMdNTP in a total reaction volume of 100 ul. PCR reactions were performed in a programmable thermal cycler using the following conditions: 95° C. for 30 seconds, 30 cycles of 95° C. for 30 seconds, 60° C. for 1 minute and 68° C. for 2 minutes. An additional extension of 5 minutes at 72° C. was applied.

The PCR amplification of the transferase gene from *A. salmonicida* was carried in 2 separate PCR reactions. PCR reaction 1 was performed using primer pairs, as1USNEW (5'AGCATATGAAAA AATGGTTTGT TTGTTTATTG GGG 3' [SEQ ID NO: 69]) and as1s950new (5' GTG ATG GTG GGC GAG GAA CTC GTA CTG3' [SEQ ID NO: 37]). A second PCR reaction was performed to incorporate a C-terminal Histidine tag using the PCR product from the first reaction and the primers: as1USNEW (5'AGCATATGAAAA AATGGTTTGT TTGTTTATTG GGG 3' [SEQ ID NO: 38]) and AHLS1001 (5'TTGGATCC GAATTCAT CAATG GTG ATG GTG ATG GTG GGC3' [SEQ ID NO: 39]). The PCR product from the second reaction was purified and digested with restriction enzymes Nde1 and BamHI. 2 ug of pET 12a vector DNA was also digested with restriction enzymes Nde1 and BamHI and treated with phosphatase. The restriction enzyme-treated pet12a and PCR product from reaction 2 were purified and ligated using the Rapid Ligation Kit (Roche, Switzerland). The ligation mix was used to transform *E. coli* TOP10 cells. Transformants were plated on LB agar medium containing 100 ug/ml ampicillin.

The T7 promoter primer (5'TAATACGACTCACTATAG3' [SEQ ID No. 40]) and the T7 terminator primer (5'CTAGT-TATTGCTCAGCGG3' [SEQ ID No. 41]) were used to verify the sequences and the orientation of the cloned transferase genes in pET12a vector. DNA sequencing was performed using ABI Prism® BigDye™ Terminators Cycle sequencing kit with 500 ng plasmid DNA as template and 3.2 pmol T7 promoter and terminator primers.

The construct shown in FIG. 35 was used to transform competent bacterial host strain BL21(DE3)pLysS (Novagen) and ampicillin resistant transformants were picked and used for expression analysis.

Expression of the Recombinant *Aeromonas salmonicida* Lipid Acyltransferase

Quantification of enzyme activity towards lecithin was determined on cell extracts using Non-Esterified Fatty Acid (NEFA) kit (Roche, Switzerland).

In FIG. 36, BL21(DE3)pLysS harboring the expression vector pet12-AsalGCAT=pSM was grown in LB medium+100 ug/ml ampicillin and incubated with shaking at 37° C. until $OD_{600}$=0.6 to 1.0 is reached. The cultures are then induced using IPTG (0.4 mM) and incubation was continued for the next 3 hours. Samples where taken at 0 hour, 1, 2, and 3 hours after IPTG induction. Enzyme Activity was tested using the NEFA kit and lecithin as substrate.

Growth Optimisation for the Production of More Active Enzymes

BL21(DE3)pLysS harboring the expression vector pet12-AsalGCAT=pSM was grown in LB medium+100 ug/ml ampicillin and incubated with shaking at different growth temperatures (37° C., 30° C., & 20° C.). The optimal condition for the production of active lipid acyltransferase enzyme was when cultures are grown at 30° C. as shown in FIG. 37.

Partial Purification of Recombinant *Aeromonas salmonicida* Transferase

Strain BL21(DE3)pLysS harboring the expression vector pet12-AsalGCAT=pSM was grown at 37° C. & crude cell extracts were prepared by sonication. The recombinant enzyme was further purified from the sonicated crude cell extracts using the Ni-NTA spin kit from Qiagen. Phospholipase activity using the NEFA kit & Lecithin as substrate. Crude cell extracts from BL21(DE3)pLysS expressing active transferase incubated with the substrate lecithin and reaction mixture was analysed using thin layer chromatography showing the presence of degradation products (see FIG. 38).

Partial Purification of recombinant *Aeromonas salmonicidae* transferase. Strain BL21(DE3)pLysS harbouring the expression vector pet12-AsalGCAT=pSM was grown at 37° C. and crude cell extracts were prepared by sonication. The recombinant enzyme ware further purified from the sonicated crude cell extract using the Ni-NTA spin kit from Qiagen. Phospholipase activity using the NEFA kit and lecithin as substrate was tested (see FIG. 39).

Example 2

Cloning and Expression of *Aeromonas hydrophila* Transferase in *E. coli*

*Aeromonas hydrophila* (ATCC #7965) was obtained from ATCC and grown overnight at 30° C. in Luria-Bertani medium (LB). The cells were centrifuged and genomic DNA was isolated using the procedures for genomic DNA isolation from Qiagen Ltd. Genomic DNA buffer set (cat.19060), protease K (cat. 19131) and RNAse A (cat. 19101) were all obtained from Qiagen Ltd. (Boundary court Gatwick Court, West Sussex, RH10 2AX).

Host bacterial strain BL21(DE3)pLysS (Novagen) was used for production of the recombinant *Aeromonas* enzymes. Competent cells of BL21(DE3)pLysS were used as host for transformation with the expression vector pet12a-A.h.GCAT=pSMa. Transformants containing the appropriate plasmid were grown at 37° C. in LB agar medium containing 100-ug ampicillin/ml.

Construction of Expression Vector pet12a-A.h.GCAT-pSMa:

For all DNA amplifications of the transferase gene from *Aeromonas*, genomic DNA (0.2-1 ul) was used as template and pfu DNA polymerase (2.5 units) was used with 10 ul of 10× pfu buffer, 1 ul each primer (50 pmol/ul), 200 uMdNTP in a total reaction volume of 100 ul. PCR reactions were performed in a programmable thermal cycler using the following conditions: 95° C. for 30 seconds, 30 cycles of 95° C. for 30 seconds, 60° C. for 1 minute and 68° C. for 2 minutes. An additional extension of 5 minutes at 72° C. was applied.

The PCR amplification of the transferase gene from *A. hydrophila* (ATCC #7965) was carried out in 2 separate PCR reactions.

PCR reaction 1 was performed using primer pairs, AHUS1 (5'GTCATATGAAAAAATGGTTTGTGTGTTTATTGGG ATTGGTC3', SEQ ID No. 42) and ahls950 (5'ATGGT GATGGTGGGCGAGGAACTCGTACTG3', SEQ ID No. 43).

A second PCR reaction was performed to incorporate a C-terminal Histidine tag using the PCR product from the first reaction and the primer pairs:

AHUS1

SEQ ID No. 44
(5'GTCATATGAAAAAATGGTTTGTGTGTTTATTGGGATTGGTC3'),
and

AHLS1001

SEQ ID No. 45
(5'TTGGATCCGAATTCATCAATGGTGATGGTGATGGTGGGC3').

The PCR product from the second reaction was purified and digested with restriction enzymes Nde1 and BamHI. 2 ug of pET 12a vector DNA was also digested with restriction enzymes Nde1 and BamHI and treated with phosphatase. The restriction enzyme-treated pet12a and PCR product from reaction 2 were purified and ligated using the Rapid Ligation Kit (Roche, Switzerland). The ligation mix was used to transform *E. coli* TOP10 cells. Transformants were plated on LB agar medium containing 100 ug/ml ampicillin.

The T7 promoter primer (5'TAATACGACTCAC-TATAG3') (SEQ ID NO: 18) and the T7 terminator primer (5'CTAGTTATTGCTCAGCGG3') (SEQ ID NO: 19) were used to verify the sequences and the orientation of the cloned GCAT genes in pET12a vector. DNA sequencing was performed using ABI Prism® BigDye™ Terminators Cycle sequencing kit with 500 ng plasmid DNA as template and 3.2 pmol T7 promoter and terminator primers.

The construct shown in FIG. 40 was used to transform competent bacterial host strain BL21 (DE3)pLysS (Novagen) and ampicillin resistant transformants were picked and used for expression analysis.

Expression of the *Aeromonas hydrophila* Transferase in BL21(DE3)pLysS

The *E. coli* strain BL21(DE3)pLysS harboring the expression vector pet12a-A.h.GCAT=pSMa was grown in LB medium+100 ug/ml ampicillin and incubated with shaking at 37° C. until $OD_{600}$=0.6 to 1.0 is reached. The cultures are then induced using IPTG (0.4 mM) and incubation was continued for the next 3 hours. Samples where taken at 0 hour, 1, 2, and 3 hours after IPTG induction. Enzyme Activity was tested using the NEFA kit and lecithin as substrate (FIG. 41).

Growth Optimisation for the Production of More Active Enzymes

BL21(DE3)pLysS harboring the expression vector pet12a-A.h.GCAT=pSMa was grown in LB medium+100 ug/ml ampicillin and incubated with shaking at different growth temperatures (37° C., 30° C., & 20° C.). The optimal condition for the production of active GCAT enzyme was when cultures are grown at 30° C. as shown in FIG. 42.

Partial Purification of Recombinant *A. hydrophila* Transferase (GCAT)

Strain BL21(DE3)pLysS harboring the expression vector pet12a-A.h.GCAT=pSMa was grown at 37° C. & crude cell extracts were prepared by sonication. The recombinant enzyme was further purified from the sonicated crude cell extracts using the Ni-NTA spin kit from Qiagen. Phospholipase activity assay using the NEFA kit & Lecithin as substrate. (FIG. 43).

Example 3

Expression of *Aeromonas* Transferases in *Bacillus subtilis* 163

Plasmid Construction

Two different *Bacillus subtilis* expression vectors (pUB 110 & pBE5) were used for the heterologous expression of the *Aeromonas* genes in *Bacillus subtilis*. The pUB110 vector contains the alpha amylase promoter while the pBE vector has the P32 promoter as the regulatory region for the expression of the fused *Aeromonas* genes. In pUB110, the first amino acid of the mature GCAT genes of *Aeromonas* were fused in frame with the last amino acid of the xylanase signal peptide sequence from *Bacillus subtilis* via the restriction site Nhe1, creating an additional 2 amino acids in front of the mature proteins. pBE5 contains the cgtase signal sequence fusion at the Nco1 site for secretion of the recombinant proteins into the culture filtrate.

PCR reactions were carried out to obtain the *Aeromonas* genes fuse in frame to the signal sequences of the pUB 110 and the pBE5 vectors. PCRs were performed using the following primer pairs for *A. hydrophila* gene:

```
PCR reaction 1:
usAHncol
(5'ATGCCATGGCCGACAGCCGTCCCGCC3'),    SEQ ID No. 46
and 1sAH
(5'TTGGATCCGAATTCATCAATGGTGATG3'),   SEQ ID No. 47

PCR reaction 2:
US-AhnheI
(5'TTGCTAGCGCCGACAGCCGTCCCGCC3'),.   SEQ ID No. 48
and 1sAH
(5'TTGGATCCGAATTCATCAATGGTGATG3),    SEQ ID No. 49
```

PCRs were performed using the following primer pairs for *A. salmonicida* gene:

```
PCR reaction 3:
US-Asncol
(5'TTGCCATGGCCGACACTCGCCCCGCC3'),    SEQ ID No. 50
and 1sAH
(5'TTGGATCCGAATTCATCAATGGTGATG3'),   SEQ ID No. 51

PCR reaction 4:
US-ASnhe1
(5'TTGCTAGCGCCGACACTCGCCCCGCC3'),    SEQ ID No. 52
and 1sAH
(5'TTGGATCCGAATTCATCAATGGTGATG3'),   SEQ ID No. 53
```

All the PCR products were cloned into PCR blunt II (TOPO vector) and sequenced with reverse & forward sequencing primers.

Clones from PCR reactions 1 & 3 were cut with Nco1 & Bam HI and used as inserts for ligation to the pBE5 vector cut with Nco1/BamH1/phosphatase. Clones from PCR reactions 2 & 4 were cut with Nhe1 & Bam H1 and used as inserts for ligation to the pUB vector that was cut with Nhe1/BamH1/phosphatase.

Expression of the *Aeromonas* Transferase Genes in *Bacillus subtilis* and Characterization of the Enzyme Activity.

The acyl transferases from the two *Aeromonas* species have been successfully expressed in *E. coli* (results above). The *Bacillus* pUB110 & pBE5 gene fusion constructs were used to transform *Bacillus subtilis* and transformants were selected by plating on kanamycin plates. The kanamycin resistant transformants isolated and grown in 2x YT are capable of heterologous expression of the *Aeromonas* genes in *Bacillus*. The culture filtrates have digalactosyldiacylglycerol (DGDG) galactolipase activity, in addition to having both acyl transferase and phospholipase activities. The activity towards digalactosyldiacylglycerol (DGDG) was measured after 60 minutes of incubation of culture supernatant with the substrate, DGDG from wheat flour (obtainable form Sigma) as well as the activity towards lecithin as shown in FIG. 44. *Bacillus* produced the enzyme after overnight (20-24 hours) to 48 hours of cultivation in the culture medium as a secreted protein. In some instances, the expression of the *Aeromonas* genes has been shown to interfere with cell viability and growth in *Bacillus* & *E. coli*, it is therefore necessary to carefully select expression strains and optimise the growth conditions to ensure expression. For example, several *Bacillus* host strains (B.s 163, DB104 and OS 21) were transformed with the expression vectors for, growth comparison. B.s163 is transformable with the 2 *Aeromonas* genes and is capable of expressing active protein. DB 104 is transformable with all the constructs but is only able to express *A. salmonicida* transferase.

Example 4

Fermentation and Purification of *Aeromonas* Lipid Acyltransferases Produced in *E. coli*

*E. coli* Fermentations:
Microorganisms

Two strains of *Eschericia coli*, one containing an *Aeromonas hydrophila* (Example 2) lipid acyltransferase and two containing *Aeromonas salmonicida* lipid acyltransferases, (Example 1) were used in this study.

The *E. coli* strain containing the *A. hydrophila* gene was named DIDK0124, and the *E. coli* strain containing the *A. salmonicida* gene was named DIDK0125. The fermentation with DIDK0124 was named HYDRO0303 and the fermentation with DIDK0125 was named SAL0302. The purified protein from HYDRO025 was named REF#138. The purified protein from HYDRO0303 was named REF#135.
Growth Media and Culture Conditions
LB-Agar The LB agar plates used for maintaining the strains contained: 10 g/L tryptone, 5 g/L yeast extract, 5 g/L NaCl, 15 g/L agar, 100 mg/L ampicillin and 35 mg/L chloramphenicol. The agar plates were incubated at 30° C.
LB Shake Flask The LB medium (50 mL pr shake flask) used for production of inoculum material for the bioreactor cultivations contained: 10 g/L tryptone, 5 g/L yeast extract, 5 g/L NaCl, 100 mg/L ampicillin and 35 mg/L chloramphenicol. The shake flasks were inoculated from the LB agar plates, and incubated at 30° C. and 200 rpm.
Bioreactor Cultivation The bioreactor cultivations were carried out in 6 L in-house built bioreactors filled with 4 L medium containing: 10 g/L tryptone, 5 g/L yeast extract, 5 g/L NaCl, 8 g/L $KH_2PO_4$, 0.9 g/L $MgSO_4$, $7H_2O$, 40 g/L glucose monohydrate, 0.4 mL/ADD APT® Foamstop Sin 260 (ADD APT Chemicals AG, Helmond, The Netherlands), 10 mg/L $(NH_4)_2Fe(SO_4)_2 \cdot 6H_2O$, 0.7 mg/L $CuSO_4.5H_2O$, 3 mg/L $ZnSO_4.7H_2O$, 3 mg/L $MnSO_4.H_2O$, 10 mg/L EDTA, 0.1 mg/L $NiSO_4.6H_2O$, 0.1 mg/L $CoCl_2$, 0.1 mg/L $H_3BO_4$, 0.1 mg/L KI, 0.1 mg/L $Na_2MoO_4.2H_2O$, 1 g/L ampicillin and 35 mg/L chloramphenicol.

The bioreactors were inoculated with an amount of LB culture ensuring end of growth after approximately 20 hours of cultivation (calculated from the maximum specific growth rate of 0.6 $h^{-1}$, the $OD_{600}$ of the LB shake flask and the final $OD_{600}$ in the bioreactor of approximately 20).

SAL0302 was inoculated with 10 mL of LB culture, and HYDRO0303 was inoculated with 4 mL of LB culture.

The bioreactors were operated at the following conditions: temperature 30° C., stirring 800-1000 rpm (depending on experiment), aeration 5 L/min, pH 6.9, pH control 8.75% (w/v) $NH_3$-water and 2 M $H_2SO_4$. Induction was achieved by addition of isopropyl β-D-thiogalactoside to a final concentration of 0.6 mM, when 0.4 moles (HYDRO0303) and 0.7 moles $CO_2$ was produced respectively.

Harvest

The following procedure was used for harvest and homogenisation of the biomass:
1) The fermentation broth from the fermentations was centrifuged at 5000×g and 4° C. for 10 minutes, and the supernatant was discharged. The biomass was stored at −20° C. until use. The biomass was thawed and resuspended in 500 mL of 20 mM $NaH_2PO_4$, pH 7.4, 500 mM NaCl, 10 mM Imidazole and Complete (EDTA-free) protease inhibitor (Roche, Germany).
2) The suspended biomass was homogenized at 2 kbar and 4° C. in a cell disrupter from Constant Systems Ltd (Warwick, UK).
3) The cell debris was removed by centrifugation at 10,000×g and 4° C. for 30 minutes followed by collection of the supernatant.
4) The supernatant was clarified further by centrifugation at 13,700×g and 4° C. for 60 minutes, followed by collection of the supernatant.
5) The supernatant was filtered through 0.2 μm Vacu Cap filters (Pall Life Sciences, UK) and the filtrate was collected for immediate chromatographic purification.

Chromatographic Purification of the Transferases

A column (2.5×10 cm) was packed with 50 ml of Chelating Sepharose ff. gel and charged with Ni-sulphate (according to the method described by manufacturer, Amersham Biosciences). The column was equilibrated with 200 ml of 20 mM $NaH_2PO_4$, pH 7.4, 500 mM NaCl, 10 mM Imidazole. 400 ml of crude was applied to the column at a flow rate of 5 ml/min. The column was then washed with 20 mM $NaH_2PO_4$, pH 7.4, 500 mM NaCl, 10 mM Imidazole until the $UV_{280}$ reached the base line. The GCAT was then eluted with 40 ml of 20 mM $NaH_2PO_4$, pH 7.4, 500 mM NaCl and 500 mM Imidazole.

Example 5

Fermentation and Purification of *Aeromonas* Lipid Acyltransferases Produced in *Bacillus subtilis*

Fermentations

BAC0318-19, BAC0323-24

Microorganism

The microorganisms used in this study originate from transformation of a *Bacillus subtilis* host strain, #163 with a plasmid containing the gene encoding the *Aeromonas salmonicida* transferase inserted in the vector pUB110OIS. The expression of the gene is controlled by an alpha-amylase promoter, and the secretion of the transferase is mediated by the *B. subtilis* xylanase signal sequence (Example 3). The strains were named DIDK0138 (fermentation BAC0318-19) and DIDK0153 (fermentation BAC0323-24).

Growth Media and Culture Conditions

Pre Culture Medium

A shake flask (500 mL total volume, with baffles) was added 100 mL of a medium containing:

| | |
|---|---|
| NaCl | 5 g/L |
| $K_2HPO_4$ | 10 g/L |
| Soy flour | 20 g/L |
| Yeast extract, BioSpringer 106 | 20 g/L |
| Antifoam, SIN260 | 5 mL/L | pH was adjusted to 7.0 before autoclaving

After autoclaving 6 mL 50% (w/w) Nutriose were added pr flask. Kanamycin was added at a concentration of 50 mg/L after autoclaving.

Inoculation

A pre culture shake flask was inoculated with frozen culture directly from a 25% (w/v) glycerol stock. The shake flask was incubated at 33° C. and 175 rpm for approximately 16 hours, whereupon 50 mL was used to inoculate the fermenter.

Fermentations

The fermentations were carried out in 6 L in house built fermentors.

The batch medium (3 L) contained:

| | |
|---|---|
| Corn steep liquor (50% dw) | 40 g/L |
| Yeast extract BioSpringer 153 (50% dw) | 10 g/L |
| NaCl | 5 g/L |
| $CaCl_2$, $2H_2O$ | 0.25 g/L |
| $Mn(NO_3)_2$, $H_2O$ | 0.2 g/L |
| Antifoam SIN260 | 1 mL/L |
| Kanamycin (filter sterilised to the fermentor after autoclaving | 50 mg/L |

The feed contained:

| | |
|---|---|
| Glucose monohydrate | 540 g/kg |
| $MgSO_4$, $7H_2O$ | 4.8 g/kg |
| Antofoam SIN260 | 4 mL/kg |
| Yeast extract, BioSpringer 153 (50% dw) (autoclaved separately) | 150 g/kg |

The feed in fermentation BAC0318 and BAC0323 was started based on the accumulated $CO_2$, according to the equations below:

Feed–flow[g/h]=0, $AcCO_2$<0.15

Feed–flow[g/h]=2.85+t·1.54, $AcCO_2 \geq 0.15$ and t<12

Feed–flow[g/h]=21.3, t>12 t: time (hours) from the point when the accumulated $CO_2$ ($AcCO_2$) reached 0.15 moles.

The feed in fermentation BAC0319 and BAC0324 was started based on the accumulated $CO_2$, according to the equations below:

Feed–flow[g/h]=0, $AcCO_2$<0.15

Feed–flow[g/h]=2.0+t·1.08, $AcCO_2 \geq 0.15$ and t<12

Feed–flow[g/h]=15, t>12 t: time (hours) from, the point when the accumulated $CO_2$ ($AcCO_2$) reached 0.15 moles.

The pH was controlled at 7.0 by adding 12.5%. (w/v) $NH_3$-water or 2M phosphoric acid.

The aeration was 3 L/min corresponding to 1 vvm.

The temperature was 33° C.

The fermentor was equipped with two 8 cm Ø Rushton impellers placed with a distance of 10 cm.

Harvest

The biomass was removed by centrifugation at 16,000×g for 10 minutes at room temperature. The supernatant was filter sterilized, and the filtrate was used for purification and application tests.

Example 6

The "Transferase Assay in Buffered Substrate" for Measurement of Acyltransferase Activity of an Enzyme The lipid acyltransferase was isolated from *Aeromonas salmonicida* and expressed in *Bacillus subtilis*. This enzyme is very efficient in transferring fatty acid from lecithin to cholesterol during formation of cholesterol esters. It has also been shown that the enzyme has some hydrolytic activity, which is observed by the formation of free fatty acid. Traditional phospholipases (EC3.1.1.4 and EC3.1.1.32) have the ability to hydrolyse lecithin during formation of free fatty acids and lysolecithin, and no transferase reactions has been reported for these enzymes.

We detail herein an assay that is able to measure both transferase and hydrolytic activity of enzymes and thus to identify lipid acyltransferases in accordance with the present invention, the assay uses a substrate which contains lecithin and cholesterol. In this work a substrate based on phosphatidylcholine and cholesterol dispersed in a buffer was used. Quantification of reaction products was made by extraction of lipids from the substrate followed by GLC analysis of the lipid components.

Procedure
Materials
L-alpha-Phosphatidylcholine 95% (Plant) Avanti no. 441601
Cholesterol: Sigma cat. C 8503
Cholesteryl Palmitate, Sigma C 6072
Cholesteryl Stearate, Sigma C 3549
HEPES buffer Sigma cat. No. H 3375
Chloroform, Analytical grade.
Enzymes
Purified GCAT from *A. salmonicida* #178-9
TLC Analysis.
TLC-plate was activated in a heat cupboard (110° C.) for ½ h.
100 ml running buffer was poured into a chromatography chamber with lid. The walls of the chamber were covered with filter paper (Whatman 2) in order to saturate the chamber with the solvent vapour.

The TLC-plate was placed in a frame and the sample was applied onto the TLC plate 2 cm from the bottom. The TLC plate was then placed in the TLC chamber with the running buffer. When the running buffer reached 14 cm from the bottom of the plate, the TLC plate was taken out and dried in fume board, and then placed in the heat cupboard at 110° C. for 10 minutes.

The TLC-plate was then immersed in the developing reagent, and dried in the heat cupboard at 110° C. for 15 minutes Running-Buffer:
Nr. IV:Chloroform:Methanol:$H_2O$ (65:25:4)
Nr. I:P-ether:MTBE:Acetic acid (60:40:1)
Developing Buffer (Vanadate-Buffer):
32 g $Na_2CO_3$ ad 300 ml $H_2O$ (1M)
18.2 g vanadate pentoxide ($V_2O_5$) is added and dissolved during gentle heating.
The solution is cooled to ambient.
Carefully 460 ml 2.5 M $H_2SO_4$. (460 ml $H_2O$+61 ml $H_2SO_4$) is added
Water is added to 1000 ml.
GLC Analysis
Perkin Elmer Autosystem 9000 Capillary Gas Chromatograph equipped with WCOT fused silica column 12.5 m×0.25 mm ID×0.1µ film thickness 5% phenyl-methyl-silicone (CP Sil 8 CB from Chrompack).
Carrier gas: Helium.
Injector. PSSI cold split injection (initial temp 50° C. heated to 385° C.), volume 1.0 µl Detector FID: 395° C.

| Oven program: | 1 | 2 | 3 |
|---|---|---|---|
| Oven temperature, ° C. | 90 | 280 | 350 |
| Isothermal, time, min. | 1 | 0 | 10 |
| Temperature rate, ° C./min. | 15 | 4 | |

Sample preparation: 30 mg of sample was dissolved in 9 ml Heptane:Pyridin, 2:1 containing internal standard heptadecane, 0.5 mg/ml. 300 µl sample solution was transferred to a crimp vial, 300 µl MSTFA (N-Methyl-N-trimethylsilyl-trifluoraceamid) was added and reacted for 20 minutes at 60° C.

Calculation: Response factors for mono-di-triglycerides and free fatty acid are determined from Standard 2 (mono-di-triglyceride). The response factors for Cholesterol, Cholesteryl Palmitate and Cholesteryl Stearate were determined from pure reference materials.

Results: Transferase assay based on phosphatidylcholine and cholesterol as substrate.

In the following the transferase activity of the transferase was tested in a substrate based on phosphatidylcholine and cholesterol according to the following procedure.

450 mg phosphatidylcholine (>95% PC Avanti item no. 441601) and 50 mg cholesterol was dissolved in chloroform and evaporated to dryness under vacuum. 300 mg cholesterol/phosphatidylcholine mixture was transferred to a Wheaton glass and 15 ml 50 mM HEPES buffer pH 7 was added. The lipid was dispersed in the buffer during agitation.

The substrate was heated to 35° C. during mixing with a magnetic stirrer and 0.25 ml enzyme solution was added. This is a very high water environment of approximately 95% water.

Samples of 2 ml were taken out after 0, 5, 10, 15, 25, 40 and 60 minutes reaction time. Immediately 25 µM HCl was added to acidify the free fatty acid and stop the enzyme reaction. 3.00 ml chloroform was added, and the sample was shaken vigorously on a Whirley for 30 seconds. The sample was centrifuged and 2 ml of the chloroform phase was isolated and filtered through 0.45-µm filters into a 10 ml tared Dram glass. The chloroform was evaporated under a stream of nitrogen at 60° C., and the samples were scaled again. The extracted lipid was analysed by GLC.

The results from the GLC analysis are shown in Table 1. The results are expressed in % calculated on extracted lipid. The amount of fatty acid and cholesterol ester formed as a function of time is illustrated in FIG. 45. It can be concluded from FIG. 45 that the enzyme reaction is not linear as a function of time, because an initially strong both hydrolytic and transferase activity is observed. After approximately 10 minutes and until approximately 60 minutes the reaction shows an almost linear response of fatty acid and cholesterol ester formation as a function of time. It was therefore decided to look at the enzymatic reaction in this time interval.

TABLE 1

| | Minutes | | | | | | |
|---|---|---|---|---|---|---|---|
| | 0 | 5 | 10 | 15 | 25 | 40 | 60 |
| Cholesterol, % | 10.064 | 8.943 | 8.577 | 8.656 | 8.102 | 7.856 | 7.809 |
| Cholesterol ester, % | 0.000 | 1.571 | 2.030 | 2.058 | 2.282 | 2.659 | 3.081 |
| FFA total, % | 0.260 | 1.197 | 1.239 | 1.466 | 2.445 | 2.943 | 3.940 |

From the knowledge about the amount of lipid in the reaction mixture and the amount of enzyme added it was possible to calculate the formation of fatty acid and cholesterol ester expressed in μmol/ml enzyme (Table 2 and FIG. 46).

TABLE 2

| | Minutes | | | | |
|---|---|---|---|---|---|
| | 10 μmol/ml | 15 μmol/ml | 25 μmol/ml | 40 μmol/ml | 60 μmol/ml |
| FFA total | 58.1 | 68.7 | 114.6 | 138.0 | 184.7 |
| Cholesterol ester | 88.8 | 90.0 | 99.3 | 115.6 | 133.8 |

From the results in Table 2 and the slope of the curves in FIG. 46 it was possible to calculate the amount of fatty acid and cholesterol ester as a function of time expressed in μmol/min per ml enzyme.

The calculation of the hydrolytic activity and the transferase activity is shown in Table 3. The relative transferase activity was determined using the protocol for the determination of % acyltransferase activity as described hereinbefore.

TABLE 3

| | | |
|---|---|---|
| Hydrolytic activity (fatty acid) | 2.52 | μmol/min per ml enzyme |
| Transferase activity (cholesterol ester) | 0.94 | μmol/min per ml enzyme |
| Total activity | 3.45 | μmol/min per ml enzyme |
| Relative Transferase activity | 27.1 | % |
| Relative hydrolytic activity | 72.9 | % |

Screening of Other Enzymes for Transferase Activity.

The method mentioned above was used to screen different lipolytic enzymes for transferase and hydrolytic activity. The enzymes were tested as shown in Table 4.

TABLE 4

| | | 1 | 2 | 3 | 4 | 5 |
|---|---|---|---|---|---|---|
| Substrate | ml | 15 | 15 | 15 | 15 | 15 |
| #178-9Transferase | ml | 0.25 | | | | |
| *A. salmonicida* 32 PLU-7/ml | | | | | | |
| 5% #3016, LIPOPAN ® F (*F. oxysporum*) | ml | | 0.25 | | | |
| 5%, *Thermomyces lanuginosus* | ml | | | 0.25 | | |
| 5% *Candida rugosa* #2983 | ml | | | | 0.25 | |
| 5% *Candida cylindracea* #3076 | ml | | | | | 0.25 |

The substrate containing 300 mg phosphatidylcholine/cholesterol dispersed in 50 mM HEPES buffer pH 7.0 was heated to 35° C. with agitation. Enzyme solution was added and the sample was kept at 35° C. with agitation. Samples were taken out with regular interval and extracted with Chloroform. The isolated lipids were analysed by GLC with results shown in Table 5.

TABLE 5

| Sample | | | | | | | | |
|---|---|---|---|---|---|---|---|---|
| 1 | Transferase 178-9 | | | | | | | |
| | Minutes | 0 | 5 | 10 | 15 | 25 | 40 | 60 |
| | FFA | 1.216 | 2.516 | 2.983 | 2.62 | 2.894 | 3.448 | 3.911 |
| | Cholesterol | 7.547 | 6.438 | 6.365 | 6.15 | 6.136 | 5.936 | 5.662 |
| | Chl. Ester | 0 | 1.835 | 2.177 | 2.44 | 2.58 | 2.851 | 3.331 |
| 2 | *Fusarium oxysporum* (LIPOPAN ® F) | 0 | 5 | 10 | 15 | 25 | 40 | 60 |
| | FFA | 1.216 | 1.345 | 1.796 | 1.95 | 2.487 | 2.424 | 2.977 |
| | Cholesterol | 7.547 | 7.309 | 7.366 | 7.33 | 7.429 | 7.341 | 7.326 |
| | Chl. Ester | 0 | 0.26 | 0.386 | 0.35 | 0.267 | 0.36 | 0.394 |
| 3 | *Thermomyces lanuginosus* | 0 | 5 | 10 | 15 | 25 | 40 | 60 |
| | FFA | 1.216 | 0.853 | 0.875 | 1 | 0.896 | 1.105 | 1.009 |
| | Cholesterol | 7.547 | 7.384 | 7.639 | 7.63 | 7.675 | 7.603 | 7.529 |
| | Chl. Ester | 0 | 0 | 0 | 0 | 0 | 0 | 0 |
| 4 | *Candida rugosa* (#2938) | 0 | 5 | 10 | 15 | 25 | 40 | 60 |
| | FFA | 1.216 | 0.982 | 0.987 | 1.02 | 1.135 | 1.131 | 1.15 |
| | Cholesterol | 7.547 | 7.438 | 7.656 | 7.66 | 7.638 | 7.575 | 7.585 |
| | Chl. Ester | 0 | 0 | 0 | 0 | 0 | 0 | 0 |
| 5 | *Candida cylandracea* (#3076) | 0 | 5 | 10 | 15 | 25 | 40 | 60 |
| | FFA | 1.216 | 1.032 | 1.097 | 1.07 | 1.203 | 1.131 | 1.43 |
| | Cholesterol | 7.547 | 7.502 | 7.425 | 7.65 | 7.619 | 7.502 | 7.411 |
| | Chl. Ester | 0 | 0 | 0 | 0 | 0 | 0 | 0 |

From the GLC analysis it was observed that only the lipid acyltransferase (178-9) produced significant amount of cholesterol ester and fatty acids. Phospholipase from *Fusarium oxysporum* also gave a steady increase in free fatty acid but only an initial small amount formation of cholesterol ester was formed but no increase in cholesterol ester as a function of time was observed.

Based on the knowledge about the amount of lipid substrate and the GLC analyses it was possible to calculate the relative transferase activity and the relative hydrolytic activity based on the results from 10 to 60 minutes reaction time. The results from Transferase 178-9 and *Fusarium oxysporum* lipase are shown in Table 6. The other enzymes tested showed no activity.

TABLE 6

|  | Transferase 178-9 | *Fusarium oxysporum* |
|---|---|---|
| Hydrolytic activity, micromole/min per ml enzyme | 1.03 | 0.96 |
| Transferase activity, micromole/min per ml enzyme | 0.40 | 0.01 |
| Total activity, micromole/min per ml enzyme | 1.43 | 0.98 |
| Relative hydrolytic activity | 71.8 | 98.7 |
| Relative transferase activity | 28.2 | 1.3 |

The result shown in Table 6 confirm a significant transferase activity from the lipid acyltransferase (sample 178-9). It is also observed that the relative transferase activity is in good agreement with the experiment mentioned in Table 3.

A very low transferase activity form Fusarium oxysporum phospholipase is however observed. This transferase level is so low that it falls within the uncertainty of the analysis. As expected *Fusarium oxysporum* phospholipase has a significant hydrolytic activity.

Conclusion.

An artificial substrate based on purified phosphatidylcholine and cholesterol was used as a substrate to measure the activity of transferase from *Aeromonas salmonicida*. Between 10 minutes and 60 minutes reaction time the assay gave an almost linear formation of free fatty acids and cholesterol ester as a function of time. Based on the activity between 10 and 60 minutes reaction time the hydrolytic activity and the transferase activity was calculated.

Based on the results from the assay of the lipid acyltransferase (in this instance a GCAT) from *Aeromonas salmonicida* in a artificial substrate of phosphatidylcholine/cholesterol in buffer it is concluded that this enzyme has very good transferase activity also in a system with a very high water content.

The phosphatidylcholine/cholesterol in buffer assay, can be used to measure the transferase and hydrolytic activity of an enzyme. The phosphatidylcholine/cholesterol in buffer is only linear within a certain time limit.

Example 7

Immobilisation of a Lipid Acyltransferase from *Aeromonas salmonicida*

A lipid acyltransferase (in this instance a GCAT) from *A. salmonicida* was immobilised on Celite 535 535 (from Fluka) by acetone precipitation. 10 ml enzyme solution in 20 mM TEA buffer pH 7 was agitated slowly with 0.1 gram Celite 535 535 (from Fluka) for 2 hours at room temperature.

50 ml cool acetone was added during continued agitation.

The precipitate was isolated by centrifugation 5000 g for 1 minute.

The precipitate was washed 2 times with 20 ml cold acetone.

The Celite was tried at ambient temperature for about 1 hour

The enzyme has also been shown to have a high activity in environments with high water content (6-89%) water environments, the use of the transferase, and other transferases for use in the invention can therefore also be used in immobilised enzyme applications with a significant water content. This allows the replacement of the solvents used by the current immobilised lipases in the bioconversion of lipids using transferases.

Example 8

Variants of a Lipid Acyltransferase from *Aeromonas hydrophila* (Ahyd2) (SEQ ID No. 36 (see FIG. 47))

Mutations were introduced using the QuikChange® Multi-Site Directed Mutagenesis kit from Stratagene, La Jolla, Calif. 92037, USA following the instructions provided by Stratagene.

Variants at Tyr256 showed an increased activity towards phospholipids.

Variants at Tyr256 and Tyr260 showed an increased activity towards galactolipids.

Variants at Tyr265 show an increased transferase activity with galactolipids as the acyl donor.

The numbers indicate positions on the following sequence: An enzyme from *Aeromonas hydrophila* the amino acid sequence of which is shown as SEQ ID No. 36 in FIG. 47 (the underlined amino acids show a xylanase signal peptide). The nucleotide sequence is as shown as SEQ ID No. 54 in FIG. 48.

Example 9

Assay in Low Water Environment

Transferase reactions of lipolytic enzymes in low water environment.

Procedure

Materials.

Cholesterol Sigma cat. C 8503
L-alpha-Phosphatidylcholine 95% (Plant) Avanti #441601
Soybean oil, Aarhus United, DK.
Chloroform, Analytical grade
Enzymes.
179, GCAT from *A. salmonicida*
2427, Phospholipase A1 from *Fusarium oxysporum*. LIPOPAN® F from Novozymes, Denmark
1991, Phospholipase A2 from Pancreas, LIPOMOD 22L from Biocatalysts, UK
2373, *Candida Antarctica* lipase, Novozyme 525 L from Novozymes Denmark.
Enzyme Assay 13.1% Lecithin and 6.6% cholesterol was dissolved in soybean oil by heating to 60° C. during agitation The substrate was scaled in a 20 ml Wheaton glass and heated to 46° C.

Water and enzyme solution was added and a stopwatch is started.

At regular intervals 50 mg samples ware transferred to a 10 ml Dram glass and frozen.

The isolated lipids were analysed by GLC

GLC Analysis

For GLC analysis protocols—see example 6

Results

The experiment was set up as shown in Table 8.

The substrate based on soybean oil containing 13.1% lecithin and 6.6% cholesterol was heated to 46° C. The enzyme solution was added and a stopwatch started. After 30, 60 and 120 minutes reaction time samples were taken out for GLC analysis.

TABLE 8

|  |  | 1 | 2 | 3 | 4 | 5 |
|---|---|---|---|---|---|---|
| Substrate | Gram | 5 | 5 | 5 | 5 | 5 |
| Transferase #179-C72, 56 PLU-7/ml | Ml |  | 0.3 |  |  |  |
| #2427, 200 PLU-7/ml | Ml |  |  | 0.3 |  |  |
| Pancreas PLA 2 #1991 6300 PLU/ml | Ml |  |  |  | 0.3 |  |
| Novozyme 525 L, #2373, 200 LIPU/ml | Ml |  |  |  |  | 0.3 |
| Water | Ml | 0.3 |  |  |  |  |
| % water |  | 6 | 6 | 6 | 6 | 6 |

The results from the GLC analysis is shown in Table 9. The results are expressed in percent based total sample composition. Based on the GLC results it was possible to calculate the amount of fatty acid and cholesterol ester produced by enzymatic reaction relative to the control sample without enzyme added. Under these experimental conditions the total enzymatic activity was estimated as the hydrolytic activity measured as free fatty acid formation and the transferase activity estimated as cholesterol ester formation. From these results and the information about molecular weight of fatty acid and cholesterol ester it was possible to calculate to relative molar hydrolytic activity and the relative molar transferase activity as shown in Table 10.

TABLE 9

| Enzyme | Reaction time minutes | Fatty acid % | Cholesterol % | Cholesterol ester % |
|---|---|---|---|---|
| Control | 120 | 0.533 | 7.094 | 0.000 |
| #179 | 30 | 0.770 | 5.761 | 2.229 |
| #179 | 60 | 0.852 | 5.369 | 2.883 |
| #179 | 120 | 0.876 | 4.900 | 3.667 |
| #2427 | 30 | 3.269 | 7.094 | 0.000 |
| #2427 | 60 | 3.420 | 7.094 | 0.000 |
| #2427 | 120 | 3.710 | 7.094 | 0.000 |
| #1991 | 30 | 2.871 | 7.094 | 0.000 |
| #1991 | 60 | 3.578 | 7.094 | 0.000 |
| #1991 | 120 | 3.928 | 7.094 | 0.000 |
| #2373 | 30 | 1.418 | 7.094 | 0.000 |
| #2373 | 60 | 1.421 | 7.094 | 0.000 |
| #2373 | 120 | 1.915 | 7.094 | 0.000 |

TABLE 10

| Enzyme | Reaction time minutes | Fatty acid produced | Cholesterol Used | Cholesterol ester produced | Hydrolytic activity % | Transferase Activity % |
|---|---|---|---|---|---|---|
| #179 | 30 | 0.238 | 1.334 | 2.229 | 20 | 80 |
| #179 | 60 | 0.319 | 1.725 | 2.883 | 21 | 79 |
| #179 | 120 | 0.343 | 2.195 | 3.667 | 18 | 82 |
| #2427 | 30 | 2.737 | 0.000 | 0.000 | 100 | 0 |
| #2427 | 60 | 2.887 | 0.000 | 0.000 | 100 | 0 |
| #2427 | 120 | 3.177 | 0.000 | 0.000 | 100 | 0 |
| #1991 | 30 | 2.338 | 0.000 | 0.000 | 100 | 0 |
| #1991 | 60 | 3.046 | 0.000 | 0.000 | 100 | 0 |
| #1991 | 120 | 3.395 | 0.000 | 0.000 | 100 | 0 |
| #2373 | 30 | 0.885 | 0.000 | 0.000 | 100 | 0 |
| #2373 | 60 | 0.888 | 0.000 | 0.000 | 100 | 0 |
| #2373 | 120 | 1.383 | 0.000 | 0.000 | 100 | 0 |

Conclusion

In these experiments it was observed that all the tested enzymes showed hydrolytic activity because the amount of fatty acid increased. However the only enzyme which showed transferase activity was GCAT from *A. salmonicida*. It is therefore concluded that in an oily system with lecithin and cholesterol containing 6% water phospholipase A1 from *Fusarium oxysporum*, phospholipase A2 from pancreas and a lipase from *Candida antarctica* only showed hydrolytic activity.

Example 10

Carbohydrate Ester Production with Immobilised Lipid Acytransferase According to the Present Invention Carbohydrate esters of fatty acids like sucrose esters and glucose esters are traditionally produced by the reaction of a fatty acid or a fatty acid soap and the carbohydrate at high temperature (Journal of the Americal Oil Chemists' Society (1978) 55; 4; 398-401) This procedure however has the disadvantage of forming side reactions and coloured by-products.

In the present invention carbohydrate esters of fatty acids are produced by a transferase reaction using lecithin as fatty acid donor and a carbohydrate like glucose as acceptor molecule.

The reaction is conducted in a flow reactor with a lipid acyl transferase immobilised on a solid support.

Procedure.

100 gram glucose is dissolved in 1000 ml water during agitation then 200 gram phosphatidylcholine is dispersed in the water phase during agitation and heated to 40° C.

pH is adjusted to pH 6.5.

A flow reactor is packed with 100 g of a lipid acyltransferase from *A. salmonicida* immobilised on a solid support.

The flow reactor is placed in a heating cabinet at 40° C.

The reaction mixture is pumped into the column with 2 ml/min.

The reaction product is collected.

The water in the reaction product is removed by thin film vacuum evaporation and the lipids isolated.

The glucose ester is separated from the other lipids by solvent fractionation.

Carbohydrate esters can be used for many applications, such as efficient emulsifiers within the food and non-food industry

Example 11

Protein Ester Production with a Lipid Acytransferase According to the Present Invention In the present invention fatty-acid condensates of amino acids, peptides or proteins are produced by a transferase reaction. In this reaction phosphatidylcholine is used as donor for the transfer of fatty acid to the free hydroxyl group of amino acids (such as tyrosine, serine or threonine) having a free hydroxyl group available for esterification.

Procedure 1.

50 gram 1-tyrosine (or serine or threonine) is dissolved in 1000 ml water during agitation then 200 gram phosphatidylcholine is dispersed in the water phase during agitation and heating to 40° C.

pH is adjusted to pH 7 and kept at this pH with NaOH or HCl.

50 ml of the lipid acyltransferase enzyme from *A. salmonicida* is added and the reaction is continued at 40° C. with agitation.

Samples are taken out at regular intervals and analysed by TLC and HPLC.

After 20 h reaction time the reaction has reached equilibrium and the reaction is stopped.

Tyrosine fatty acid condensate, lecithin and lysolecithin are isolated from the reaction media by centrifugation according to standard methods (see "Centrifuges, Filtering" in Ullmann's Encyclopedia of Industrial Chemistry for example (2002) by Wiley-VCH Verlag GmbH & Co. KgaA).

Tyrosine fatty acid condensate is further purified by hydrophobic interaction column chromatography and the fraction containing tyrosine fatty acid condensate is isolated and the solvent removed by evaporation. (see 'Basic Principles of Chromatography' in Ullmann's Encyclopedia of Industrial Chemistry (2002) by Wiley-VCH Verlag GmbH & Co. KGaA.)

Procedure 2.

In the following the transferase activity of a lipid acyltransferse is tested in a substrate based on phosphatidylcholin and 1-tyrosine according to the following procedure.

450 mg phophatidylcholine (>95% PC Avanti item no. 441601) and 50 mg 1-tyrosine is scaled in a Wheaton glass and 15 ml 50 mM HEPES buffer pH 7 is added. The lipid is dispersed in the buffer during agitation.

The substrate is heated to 35° C. whilst mixing with a magnetic stirrer and 0.25 ml Transferase 10 PLU/ml is added.

Samples of 2 ml are taken out after 0, 5, 10, 15, 25, 40 and 60 minutes reaction time.

Immediately 25 µl 4M HCl is added to acidify the free fatty acid and stop the enzyme reaction. 3.00 ml chloroform is added, and the sample is shaken vigorously on a Whirley for 30 seconds. The sample is centrifuged and 2 ml of the chloroform phase is isolated and filtered through 0.45-µm filters into a 10 ml tared Dram glass.

The chloroform is evaporated under a steam of nitrogen at 60° C., and the sample is scaled again. The extracted lipid is analysed by TLC.

Example 12

Hydroxy Acid Ester (in Particular Lactic Acid Ester) Production with a Lipid Acytransferase According to the Present Invention Hydroxy esters of fatty acids are traditionally produced by the reaction between a fatty acid and a hydroxy acid at high temperature using an inorganic salts or metal ions as catalysts (see for example Bailey's Industrial Oil and Fat Products, Fifth edition, Volume 3. Edible Oil and Fat Products: Products and Application Technology, page 502-511.) This procedure however has the disadvantage of forming side reactions and coloured by-products.

In the present invention hydroxy acid esters of fatty acids are produced by a transferase reaction using lecithin as fatty acid donor and a hydroxy acid (in particular lactic acid) as acceptor molecule.

Procedure.

50 gram lactic is dissolved in 1000 ml water whilst agitating, then 200 gram phosphatidylcholine is dispersed in the water phase during agitation and heated to 40° C.

pH is adjusted to pH 6.5 and kept at this pH with NaOH or HCl.

50 ml of lipid acyltransferase enzyme from *A. salmonicida* is added and the reaction is continued at 40° C. whilst agitating.

Samples are taken out at regular intervals and analysed by TLC and GLC.

After 20 h reaction time the reaction has reached equilibrium and the reaction is stopped.

Lactic acid ester, lecithin and lysolecithin are isolated from the reaction media by centrifugation according to standard methods (see "Centrifuges, Filtering" in Ullmann's Encyclopedia of Industrial Chemistry for example (2002) by Wiley-VCH Verlag GmbH & Co. KgaA).

Lactic acid ester is further purified by molecular distillation and a lactic acid ester of fatty acid with high purity is obtained.

Example 13

Citric Acid Ester Production with a Lipid Acytransferase According to the Present Invention Transferase Assay Based on Phosphatidylcholin and Citric Acid as Substrate.

In the following the transferase activity of lipid acyl transferase from *A. salmonicida* is tested in a substrate based on phosphatidylcholin and citric acid according to the following procedure.

450 mg phophatidylcholine (>95% PC Avanti item no. 441601) and 50 mg citric acid is scaled in a Wheaton glass and 15 ml 50 mM HEPES buffer pH 7 is added. The lipid is dispersed in the buffer during agitation.

The substrate is heated to 35° C. during mixing with a magnetic stirrer and 0.25 ml lipid acyltransferase from *A. salmonicida* 10 PLU/ml is added.

Samples of 2 ml are taken out after 0, 5, 10, 15, 25, 40 and 60 minutes reaction time.

Immediately 25 µl 4M HCl is added to acidify the free fatty acid and stop the enzyme reaction. 3.00 ml chloroform is added, and the sample is shaken vigorously on a Whirley for 30 seconds. The sample is centrifuged and 2 ml of the chloroform phase is isolated and filtered through 0.45-µm filters into a 10 ml tared Dram glass.

The chloroform is evaporated under a steam of nitrogen at 60° C., and the sample is scaled again. The extracted lipid is analysed by TLC.

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the following claims.

The invention will now be further described by the following numbered paragraphs:

1. A method of producing one or more of a carbohydrate ester, a protein ester, a protein subunit ester, a hydroxy acid ester, which method comprises admixing an acyl donor, an acyl acceptor and water to produce a high water environment comprising 5-98% water, wherein said acyl donor is a lipid substrate selected from one or more of the group consisting of a phospholipid, a lysophospholipid, a triacylglyceride, a diglyceride, a glycolipid or a lysoglycolipid and said acyl acceptor is selected from one or more of the group consisting of a carbohydrate, a protein, a protein subunit, or a hydroxy acid; and contacting the admixture with a lipid acyltransferase, such that said lipid acyltransferase catalyses one or both of the following reactions: alcoholysis or transesterification, wherein the lipid acyltransferase is characterised as an enzyme which possesses acyl transferase activity and which comprises the amino acid sequence motif GDSX, wherein X is one or more of the following amino acid residues L, A, V, I, F, Y, H, Q, T, N, M or S.

2. A method according to paragraph 1 wherein the lipid acyltransferase is immobilised.

3. A method according to paragraph 1 wherein the method comprises purifying the carbohydrate ester, protein ester, protein subunit ester, hydroxy acid ester.

4. A method according to any one of the preceding paragraphs wherein the lipid acyltransferase enzyme comprises H-309 or comprises a histidine residue at a position corresponding to His-309 in the amino acid sequence of the *Aeromonas hydrophila* lipolytic enzyme shown as SEQ ID No. 2 or SEQ ID No. 32.

5. A method according to paragraph 1 wherein the lipid acyltransferase is obtainable from an organism from one or more of the following genera: *Aeromonas, Streptomyces, Saccharomyces, Lactococcus, Mycobacterium, Streptococcus, Lactobacillus, Desulfitobacterium, Bacillus, Campylobacter, Vibrionaceae, Xylella, Sulfolobus, Aspergillus, Schizosaccharomyces, Listeria, Neisseria, Mesorhizobium, Ralstonia, Xanthomonas* and *Candida*.

6. A method according to paragraph 1 wherein the lipid acyltransferase comprises one or more of the following amino acid sequences: (i) the amino acid sequence shown as SEQ ID No. 2; (ii) the amino acid sequence shown as SEQ ID No. 3; (iii) the amino acid sequence shown as SEQ ID No. 4; (iv) the amino acid sequence shown as SED ID No. 5; (v) the amino acid sequence shown as SEQ ID No. 6; (vi) the amino acid sequence shown as SEQ ID No. 12, (vii) the amino acid sequence shown as SEQ ID No. 20, (viii) the amino acid sequence shown as SEQ ID No. 22, (ix) the amino acid sequence shown as SEQ ID No. 24, (x) the amino acid sequence shown as SEQ ID No. 26, (xi) the amino acid sequence shown as SEQ ID No. 28, (xii) the amino acid sequence shown as SEQ ID No. 30, (xiii) the amino acid sequence shown as SEQ ID No. 32, (xiv) the amino acid sequence shown as SEQ ID No. 34, or an amino acid sequence which has 75% or more identity with any one of the sequences shown as SEQ ID No. 2, SEQ ID No. 3, SEQ ID No. 4, SEQ ID No. 5, SEQ ID No. 6, SEQ ID No. 12, SEQ ID No. 20, SEQ ID No. 22, SEQ ID No. 24, SEQ ID No. 26, SEQ ID No. 28, SEQ ID No. 30, SEQ ID No. 32 or SEQ ID No. 34.

7. Use of a lipid acyltransferase to produce one or more of a carbohydrate ester, a protein ester, a protein subunit ester, or a hydroxy acid ester by catalysis of one or both of alcoholysis or transesterification in an admixture of an acyl donor, an acyl acceptor and water, which admixture comprises 5-98% water, wherein said acyl donor is a lipid substrate selected from one or more of the group consisting of a phospholipid, a lysophospholipid, a triacylglyceride, a diglyceride, a glycolipid or a lysoglycolipid and said acyl acceptor is selected from one or more of the group consisting of a carbohydrate, a protein, a protein subunit, or a hydroxy acid, wherein the lipid acyltransferase is characterised as an enzyme which possesses acyl transferase activity and which comprises the amino acid sequence motif GDSX, wherein X is one or more of the following amino acid residues L, A, V, I, F, Y, H, Q, T, N, M or S.

8. Use according to paragraph 7 wherein the lipid acyltransferase is immobilised.

9. Use according to paragraph 7 wherein the carbohydrate ester, protein ester, protein subunit ester or a hydroxy acid ester is purified.

10. Use according to paragraph 7 wherein the lipid acyltransferase enzyme comprises H-309 or comprises a histidine residue at a position corresponding to His-309 in the amino acid sequence of the *Aeromonas hydrophila* lipolytic enzyme shown as SEQ ID No. 2 or SEQ ID No. 32.

11. Use according to paragraph 7 wherein the lipid acyltransferase is obtainable from an organism from one or more of the following genera: *Aeromonas, Streptomyces, Saccharomyces, Lactococcus, Mycobacterium, Streptococcus, Lactobacillus, Desulfitobacterium, Bacillus, Campylobacter, Vibrionaceae, Xylella, Sulfolobus, Aspergillus, Schizosaccharomyces, Listeria, Neisseria, Mesorhizobium, Ralstonia, Xanthomonas* and *Candida*.

12. Use according to paragraph 7 wherein the lipid acyltransferase comprises one or more of the following amino acid sequences: (i) the amino acid sequence shown as SEQ ID No. 2; (ii) the amino acid sequence shown as SEQ ID No. 3; (iii) the amino acid sequence shown as SEQ ID No. 4; (iv) the amino acid sequence shown as SEQ ID No. 5; (v) the amino acid sequence shown as SEQ ID No. 6; (vi) the amino acid sequence shown as SEQ ID No. 12, (vii) the amino acid sequence shown as SEQ ID No. 20, (viii) the amino acid sequence shown as SEQ ID No. 22, (ix) the amino acid sequence shown as SEQ ID No. 24, (x) the amino acid sequence shown as SEQ ID No. 26, (xi) the amino acid sequence shown as SEQ ID No. 28, (xii) the amino acid sequence shown as SEQ ID No. 30, (xiii) the amino acid sequence shown as SEQ ID No. 32, (xiv) the amino acid sequence shown as SEQ ID No. 34, or an amino acid sequence which has 75% or more identity with any one of the sequences shown as SEQ ID No. 2, SEQ ID No. 3, SEQ ID No. 4, SEQ ID No. 5, SEQ ID No. 6, SEQ ID No. 12, SEQ ID No. 20, SEQ ID No. 22, SEQ ID No. 24, SEQ ID No. 26, SEQ ID No. 28, SEQ ID No. 30, SEQ ID No. 32 or SEQ ID No. 34.

13. A carbohydrate ester produced by a method according to paragraph 1.

14. A protein ester produced by a method according to paragraph 1.

15. A protein subunit ester produced by a method according to paragraph 1.

16. A hydroxy acid ester produced by a method according to paragraph 1.

17. An immobilised lipid acyltransferase enzyme, wherein the lipid acyltransferase is characterised as an enzyme which possesses acyl transferase activity and which comprises the amino acid sequence motif GDSX, wherein X is one or more of the following amino acid residues L, A, V, I, F, Y, H, Q, T, N, M or S.

18. An immobilised lipid acyltransferase according to paragraph 17 wherein the lipid acyltransferase enzyme comprises H-309 or comprises a histidine residue at a position corresponding to His-309 in the amino acid sequence of the *Aeromonas hydrophila* lipolytic enzyme shown as SEQ ID No. 2 or SEQ ID No. 32.

19. An immobilised lipid acyltransferase according to paragraph 17 wherein the lipid acyltransferase is obtainable from an organism from one or more of the following genera: *Aeromonas, Streptomyces, Saccharomyces, Lactococcus, Mycobacterium, Streptococcus, Lactobacillus, Desulfitobacterium, Bacillus, Campylobacter, Vibrionaceae, Xylella, Sulfolobus, Aspergillus, Schizosaccharomyces, Listeria, Neisseria, Mesorhizobium, Ralstonia, Xanthomonas* and *Candida*.

20. An immobilised lipid acyltransferase according to paragraph 17 wherein the lipid acyltransferase comprises one or more of the following amino acid sequences: (i) the amino acid sequence shown as SEQ ID No. 2; (ii) the amino acid sequence shown as SEQ ID No. 3; (iii) the amino acid sequence shown as SEQ ID No. 4; (iv) the amino acid sequence shown as SEQ ID No. 5; (v) the amino acid sequence shown as SEQ ID No. 6; (vi) the amino acid sequence shown as SEQ ID No. 12, (vii) the amino acid sequence shown as SEQ ID No. 20, (viii) the amino acid sequence shown as SEQ ID No. 22, (ix) the amino acid sequence shown as SEQ ID No. 24, (x) the amino acid sequence shown as SEQ ID No. 26, (xi) the amino acid sequence shown as SEQ ID No. 28, (xii) the amino acid sequence shown as SEQ ID No. 30, (xiii) the amino acid sequence shown as SEQ ID No. 32, (xiv) the amino acid sequence shown as SEQ ID No. 34, or an amino acid sequence which has 75% or more identity with any one of the sequences shown as SEQ ID No. 2, SEQ ID No. 3, SEQ ID No. 4, SEQ ID No. 5, SEQ ID No. 6, SEQ ID No. 12, SEQ ID No. 20, SEQ ID No. 22, SEQ ID No. 24, SEQ ID No. 26, SEQ ID No. 28, SEQ ID No. 30, SEQ ID No. 32 or SEQ ID No. 34.

The invention claimed is:

1. A method of producing a carbohydrate ester, a protein ester, a protein subunit ester or a hydroxy acid ester, wherein the method comprises contacting an acyl donor, an acyl acceptor and 5-98% water with a lipid acyltransferase enzyme capable of transferring an acyl group from a lipid to one or more of the following acyl acceptors: a sterol, a stanol, a carbohydrate, a protein or a sub-unit thereof, and glycerol, whereby the carbohydrate ester, the protein ester, the protein subunit ester or the hydroxy acid ester is produced; and wherein the lipid acyltransferase when tested using the Transferase Assay in Buffered Substrate has at least 5% acyltransferase activity (relative acyltransferase activity) wherein the Transferase Assay in Buffered Substrate comprises: (a) heating to 35° C. a substrate solution comprising phosphatidylcholine, cholesterol, water and HEPES buffer, wherein the substrate solution comprises approximately 95% water and has pH 7.0; (b) adding an enzyme to the substrate solution; and (c) determining acyltransferase activity of the enzyme based upon cholesterol ester and fatty acids formed.

2. The method of claim 1, wherein the acyl donor is selected from a phospholipid, a lysophospholipid, a triacylglyceride, a diglyceride, a glycolipid or a lysoglycolipid.

3. The method of claim 1, wherein the acyl acceptor is selected from a carbohydrate, a protein, a protein subunit, or a hydroxy acid.

4. The method according to claim 1, wherein the lipid acyltransferase is capable of transferring an acyl group from a glycolipid and/or phospholipid to one of the following acceptor substrates: a carbohydrate, a protein, a protein subunit, or a hydroxy acid.

5. The method of claim 1, wherein the acyl acceptor is a carbohydrate.

6. The method of claim 1, wherein the acyl acceptor is a hydroxy acid.

7. A method according to claim 1 wherein the method further comprises purifying the carbohydrate ester, protein ester, protein subunit ester or hydroxy acid ester.

8. The method of claim 1, wherein the enzyme is immobilized.

9. The method of claim 1, wherein the enzyme additionally has glycolipase activity.

10. The method of claim 1 wherein the lipid acyltransferase is from an organism from one or more of the following genera: *Aeromonas, Streptomyces, Saccharomyces, Lactococcus, Mycobacterium, Streptococcus, Lactobacillus, Desulfitobacterium, Bacillus, Campylobacter, Vibrionaceae, Xylella, Sulfolobus, Aspergillus, Schizosaccharomyces, Listeria, Neisseria, Mesorhizobium, Ralstonia, Xanthomonas* and *Candida*.

11. The method of claim 1 wherein the lipid acyltransferase comprises amino acid sequence motif GDSX, wherein X is one or more of the following amino acid residues L, A, V, I, F, Y, H, Q, T, N, M or S.

12. A method of producing a protein ester, a protein subunit ester or a hydroxy acid ester comprising:
admixing an acyl donor, an acyl acceptor and water to form an admixture wherein the acyl donor and acyl acceptor are in an environment comprising 5-98% water, and contacting the admixture with a lipid acyltransferase, wherein: the acyl donor is a lipid substrate selected from one or more of the group consisting of a phospholipid, a lysophospholipid, a triacylglyceride, a diglyceride, a glycolipid or a lysoglycolipid; the acyl acceptor is a protein, a protein subunit or a hydroxy acid; the lipid acyltransferase possesses acyl transferase activity and catalyses one or both of the following reactions: alcoholysis or transesterification; and the lipid acyltransferase has an amino acid sequence containing a GDSX motif, wherein X is one or more of the following amino acid residues L, A, V, I, F, Y, H, Q, T, N, M or S, and the lipid acyltransferase amino acid sequence is expressed by a nucleic acid molecule having at least 90% sequence identity with SEQ ID NO: 8.

* * * * *

```
                        SEQUENCE LISTING

<160> NUMBER OF SEQ ID NOS: 70

<210> SEQ ID NO 1
<211> LENGTH: 361
<212> TYPE: PRT
<213> ORGANISM: Artificial Sequence
<220> FEATURE:
<223> OTHER INFORMATION: Description of Artificial Sequence: Synthetic
      pfam00657 consensus sequence

<400> SEQUENCE: 1

Ile Val Ala Phe Gly Asp Ser Leu Thr Asp Gly Glu Ala Tyr Tyr Gly
  1               5                  10                  15

Asp Ser Asp Gly Gly Gly Trp Gly Ala Gly Leu Ala Asp Arg Leu Thr
             20                  25                  30

Ala Leu Leu Arg Leu Arg Ala Arg Pro Arg Gly Val Asp Val Phe Asn
         35                  40                  45

Arg Gly Ile Ser Gly Arg Thr Ser Asp Gly Arg Leu Ile Val Asp Ala
     50                  55                  60

Leu Val Ala Leu Leu Phe Leu Ala Gln Ser Leu Gly Leu Pro Asn Leu
 65                  70                  75                  80

Pro Pro Tyr Leu Ser Gly Asp Phe Leu Arg Gly Ala Asn Phe Ala Ser
                 85                  90                  95

Ala Gly Ala Thr Ile Leu Pro Thr Ser Gly Pro Phe Leu Ile Gln Val
                100                 105                 110

Gln Phe Lys Asp Phe Lys Ser Gln Val Leu Glu Leu Arg Gln Ala Leu
            115                 120                 125

Gly Leu Leu Gln Glu Leu Leu Arg Leu Leu Pro Val Leu Asp Ala Lys
        130                 135                 140

Ser Pro Asp Leu Val Thr Ile Met Ile Gly Thr Asn Asp Leu Ile Thr
145                 150                 155                 160

Ser Ala Phe Phe Gly Pro Lys Ser Thr Glu Ser Asp Arg Asn Val Ser
                165                 170                 175

Val Pro Glu Phe Lys Asp Asn Leu Arg Gln Leu Ile Lys Arg Leu Arg
            180                 185                 190

Ser Asn Asn Gly Ala Arg Ile Ile Val Leu Ile Thr Leu Val Ile Leu
        195                 200                 205

Asn Leu Gly Pro Leu Gly Cys Leu Pro Leu Lys Leu Ala Leu Ala Leu
    210                 215                 220

Ala Ser Ser Lys Asn Val Asp Ala Ser Gly Cys Leu Glu Arg Leu Asn
```

```
                225                 230                 235                 240
Glu Ala Val Ala Asp Phe Asn Glu Ala Leu Arg Glu Leu Ala Ile Ser
                245                 250                 255

Lys Leu Glu Asp Gln Leu Arg Lys Asp Gly Leu Pro Asp Val Lys Gly
                260                 265                 270

Ala Asp Val Pro Tyr Val Asp Leu Tyr Ser Ile Phe Gln Asp Leu Asp
                275                 280                 285

Gly Ile Gln Asn Pro Ser Ala Tyr Val Tyr Gly Phe Glu Thr Thr Lys
                290                 295                 300

Ala Cys Cys Gly Tyr Gly Gly Arg Tyr Asn Tyr Asn Arg Val Cys Gly
305                 310                 315                 320

Asn Ala Gly Leu Cys Asn Val Thr Ala Lys Ala Cys Asn Pro Ser Ser
                325                 330                 335

Tyr Leu Leu Ser Phe Leu Phe Trp Asp Gly Phe His Pro Ser Glu Lys
                340                 345                 350

Gly Tyr Lys Ala Val Ala Glu Ala Leu
                355                 360

<210> SEQ ID NO 2
<211> LENGTH: 335
<212> TYPE: PRT
<213> ORGANISM: Aeromonas hydrophila

<400> SEQUENCE: 2

Met Lys Lys Trp Phe Val Cys Leu Leu Gly Leu Val Ala Leu Thr Val
1               5                   10                  15

Gln Ala Ala Asp Ser Arg Pro Ala Phe Ser Arg Ile Val Met Phe Gly
                20                  25                  30

Asp Ser Leu Ser Asp Thr Gly Lys Met Tyr Ser Lys Met Arg Gly Tyr
                35                  40                  45

Leu Pro Ser Ser Pro Pro Tyr Tyr Glu Gly Arg Phe Ser Asn Gly Pro
            50                  55                  60

Val Trp Leu Glu Gln Leu Thr Asn Glu Phe Pro Gly Leu Thr Ile Ala
65                  70                  75                  80

Asn Glu Ala Glu Gly Gly Pro Thr Ala Val Ala Tyr Asn Lys Ile Ser
                85                  90                  95

Trp Asn Pro Lys Tyr Gln Val Ile Asn Asn Leu Asp Tyr Glu Val Thr
                100                 105                 110

Gln Phe Leu Gln Lys Asp Ser Phe Lys Pro Asp Asp Leu Val Ile Leu
                115                 120                 125

Trp Val Gly Ala Asn Asp Tyr Leu Ala Tyr Gly Trp Asn Thr Glu Gln
                130                 135                 140

Asp Ala Lys Arg Val Arg Asp Ala Ile Ser Asp Ala Ala Asn Arg Met
145                 150                 155                 160

Val Leu Asn Gly Ala Lys Glu Ile Leu Leu Phe Asn Leu Pro Asp Leu
                165                 170                 175

Gly Gln Asn Pro Ser Ala Arg Ser Gln Lys Val Val Glu Ala Ala Ser
                180                 185                 190

His Val Ser Ala Tyr His Asn Gln Leu Leu Leu Asn Leu Ala Arg Gln
                195                 200                 205

Leu Ala Pro Thr Gly Met Val Lys Leu Phe Glu Ile Asp Lys Gln Phe
                210                 215                 220

Ala Glu Met Leu Arg Asp Pro Gln Asn Phe Gly Leu Ser Asp Gln Arg
225                 230                 235                 240

Asn Ala Cys Tyr Gly Gly Ser Tyr Val Trp Lys Pro Phe Ala Ser Arg
```

```
                    245                 250                 255
Ser Ala Ser Thr Asp Ser Gln Leu Ser Ala Phe Asn Pro Gln Glu Arg
                260                 265                 270

Leu Ala Ile Ala Gly Asn Pro Leu Ala Gln Ala Val Ala Ser Pro
            275                 280                 285

Met Ala Ala Arg Ser Ala Ser Thr Leu Asn Cys Glu Gly Lys Met Phe
            290                 295                 300

Trp Asp Gln Val His Pro Thr Thr Val Val His Ala Ala Leu Ser Glu
305                 310                 315                 320

Pro Ala Ala Thr Phe Ile Glu Ser Gln Tyr Glu Phe Leu Ala His
                325                 330                 335

<210> SEQ ID NO 3
<211> LENGTH: 336
<212> TYPE: PRT
<213> ORGANISM: Aeromonas salmonicida

<400> SEQUENCE: 3

Met Lys Lys Trp Phe Val Cys Leu Leu Gly Leu Ile Ala Leu Thr Val
1               5                   10                  15

Gln Ala Ala Asp Thr Arg Pro Ala Phe Ser Arg Ile Val Met Phe Gly
            20                  25                  30

Asp Ser Leu Ser Asp Thr Gly Lys Met Tyr Ser Lys Met Arg Gly Tyr
        35                  40                  45

Leu Pro Ser Ser Pro Tyr Tyr Glu Gly Arg Phe Ser Asn Gly Pro
    50                  55                  60

Val Trp Leu Glu Gln Leu Thr Lys Gln Phe Pro Gly Leu Thr Ile Ala
65                  70                  75                  80

Asn Glu Ala Glu Gly Gly Ala Thr Ala Val Ala Tyr Asn Lys Ile Ser
                85                  90                  95

Trp Asn Pro Lys Tyr Gln Val Tyr Asn Asn Leu Asp Tyr Glu Val Thr
            100                 105                 110

Gln Phe Leu Gln Lys Asp Ser Phe Lys Pro Asp Asp Leu Val Ile Leu
        115                 120                 125

Trp Val Gly Ala Asn Asp Tyr Leu Ala Tyr Gly Trp Asn Thr Glu Gln
    130                 135                 140

Asp Ala Lys Arg Val Arg Asp Ala Ile Ser Asp Ala Ala Asn Arg Met
145                 150                 155                 160

Val Leu Asn Gly Ala Lys Gln Ile Leu Leu Phe Asn Leu Pro Asp Leu
                165                 170                 175

Gly Gln Asn Pro Ser Ala Arg Ser Gln Lys Val Val Glu Ala Val Ser
            180                 185                 190

His Val Ser Ala Tyr His Asn Lys Leu Leu Asn Leu Ala Arg Gln
        195                 200                 205

Leu Ala Pro Thr Gly Met Val Lys Leu Phe Glu Ile Asp Lys Gln Phe
    210                 215                 220

Ala Glu Met Leu Arg Asp Pro Gln Asn Phe Gly Leu Ser Asp Val Glu
225                 230                 235                 240

Asn Pro Cys Tyr Asp Gly Gly Tyr Val Trp Lys Pro Phe Ala Thr Arg
                245                 250                 255

Ser Val Ser Thr Asp Arg Gln Leu Ser Ala Phe Ser Pro Gln Glu Arg
            260                 265                 270

Leu Ala Ile Ala Gly Asn Pro Leu Ala Gln Ala Val Ala Ser Pro
    275                 280                 285

Met Ala Arg Arg Ser Ala Ser Pro Leu Asn Cys Glu Gly Lys Met Phe
```

```
            290                 295                 300
Trp Asp Gln Val His Pro Thr Thr Val Val His Ala Ala Leu Ser Glu
305                 310                 315                 320

Arg Ala Ala Thr Phe Ile Glu Thr Gln Tyr Glu Phe Leu Ala His Gly
                325                 330                 335

<210> SEQ ID NO 4
<211> LENGTH: 295
<212> TYPE: PRT
<213> ORGANISM: Streptomyces coelicolor

<400> SEQUENCE: 4

Met Pro Lys Pro Ala Leu Arg Arg Val Met Thr Ala Thr Val Ala Ala
1               5                   10                  15

Val Gly Thr Leu Ala Leu Gly Leu Thr Asp Ala Thr Ala His Ala Ala
                20                  25                  30

Pro Ala Gln Ala Thr Pro Thr Leu Asp Tyr Val Ala Leu Gly Asp Ser
            35                  40                  45

Tyr Ser Ala Gly Ser Gly Val Leu Pro Val Asp Pro Ala Asn Leu Leu
    50                  55                  60

Cys Leu Arg Ser Thr Ala Asn Tyr Pro His Val Ile Ala Asp Thr Thr
65                  70                  75                  80

Gly Ala Arg Leu Thr Asp Val Thr Cys Gly Ala Ala Gln Thr Ala Asp
                85                  90                  95

Phe Thr Arg Ala Gln Tyr Pro Gly Val Ala Pro Gln Leu Asp Ala Leu
            100                 105                 110

Gly Thr Gly Thr Asp Leu Val Thr Leu Thr Ile Gly Gly Asn Asp Asn
        115                 120                 125

Ser Thr Phe Ile Asn Ala Ile Thr Ala Cys Gly Thr Ala Gly Val Leu
    130                 135                 140

Ser Gly Gly Lys Gly Ser Pro Cys Lys Asp Arg His Gly Thr Ser Phe
145                 150                 155                 160

Asp Asp Glu Ile Glu Ala Asn Thr Tyr Pro Ala Leu Lys Glu Ala Leu
                165                 170                 175

Leu Gly Val Arg Ala Arg Ala Pro His Ala Arg Val Ala Ala Leu Gly
            180                 185                 190

Tyr Pro Trp Ile Thr Pro Ala Thr Ala Asp Pro Ser Cys Phe Leu Lys
        195                 200                 205

Leu Pro Leu Ala Ala Gly Asp Val Pro Tyr Leu Arg Ala Ile Gln Ala
    210                 215                 220

His Leu Asn Asp Ala Val Arg Arg Ala Ala Glu Thr Gly Ala Thr
225                 230                 235                 240

Tyr Val Asp Phe Ser Gly Val Ser Asp Gly His Asp Ala Cys Glu Ala
                245                 250                 255

Pro Gly Thr Arg Trp Ile Glu Pro Leu Leu Phe Gly His Ser Leu Val
            260                 265                 270

Pro Val His Pro Asn Ala Leu Gly Glu Arg Arg Met Ala Glu His Thr
        275                 280                 285

Met Asp Val Leu Gly Leu Asp
    290                 295

<210> SEQ ID NO 5
<211> LENGTH: 295
<212> TYPE: PRT
<213> ORGANISM: Streptomyces coelicolor

<400> SEQUENCE: 5
```

Met Pro Lys Pro Ala Leu Arg Arg Val Met Thr Ala Thr Val Ala Ala
 1               5                  10                  15

Val Gly Thr Leu Ala Leu Gly Leu Thr Asp Ala Thr Ala His Ala Ala
             20                  25                  30

Pro Ala Gln Ala Thr Pro Thr Leu Asp Tyr Val Ala Leu Gly Asp Ser
         35                  40                  45

Tyr Ser Ala Gly Ser Gly Val Leu Pro Val Asp Pro Ala Asn Leu Leu
 50                  55                  60

Cys Leu Arg Ser Thr Ala Asn Tyr Pro His Val Ile Ala Asp Thr Thr
 65                  70                  75                  80

Gly Ala Arg Leu Thr Asp Val Thr Cys Gly Ala Ala Gln Thr Ala Asp
                 85                  90                  95

Phe Thr Arg Ala Gln Tyr Pro Gly Val Ala Pro Gln Leu Asp Ala Leu
             100                 105                 110

Gly Thr Gly Thr Asp Leu Val Thr Leu Thr Ile Gly Gly Asn Asp Asn
         115                 120                 125

Ser Thr Phe Ile Asn Ala Ile Thr Ala Cys Gly Thr Ala Gly Val Leu
 130                 135                 140

Ser Gly Gly Lys Gly Ser Pro Cys Lys Asp Arg His Gly Thr Ser Phe
145                 150                 155                 160

Asp Asp Glu Ile Glu Ala Asn Thr Tyr Pro Ala Leu Lys Glu Ala Leu
                 165                 170                 175

Leu Gly Val Arg Ala Arg Ala Pro His Ala Arg Val Ala Ala Leu Gly
             180                 185                 190

Tyr Pro Trp Ile Thr Pro Ala Thr Ala Asp Pro Ser Cys Phe Leu Lys
         195                 200                 205

Leu Pro Leu Ala Ala Gly Asp Val Pro Tyr Leu Arg Ala Ile Gln Ala
 210                 215                 220

His Leu Asn Asp Ala Val Arg Arg Ala Ala Glu Glu Thr Gly Ala Thr
225                 230                 235                 240

Tyr Val Asp Phe Ser Gly Val Ser Asp Gly His Asp Ala Cys Glu Ala
                 245                 250                 255

Pro Gly Thr Arg Trp Ile Glu Pro Leu Leu Phe Gly His Ser Leu Val
             260                 265                 270

Pro Val His Pro Asn Ala Leu Gly Glu Arg Arg Met Ala Glu His Thr
         275                 280                 285

Met Asp Val Leu Gly Leu Asp
     290                 295

<210> SEQ ID NO 6
<211> LENGTH: 238
<212> TYPE: PRT
<213> ORGANISM: Saccharomyces cerevisiae

<400> SEQUENCE: 6

Met Asp Tyr Glu Lys Phe Leu Leu Phe Gly Asp Ser Ile Thr Glu Phe
 1               5                  10                  15

Ala Phe Asn Thr Arg Pro Ile Glu Asp Gly Lys Asp Gln Tyr Ala Leu
             20                  25                  30

Gly Ala Ala Leu Val Asn Glu Tyr Thr Arg Lys Met Asp Ile Leu Gln
         35                  40                  45

Arg Gly Phe Lys Gly Tyr Thr Ser Arg Trp Ala Leu Lys Ile Leu Pro
 50                  55                  60

Glu Ile Leu Lys His Glu Ser Asn Ile Val Met Ala Thr Ile Phe Leu
 65                  70                  75                  80

```
Gly Ala Asn Asp Ala Cys Ser Ala Gly Pro Gln Ser Val Pro Leu Pro
                85                  90                  95

Glu Phe Ile Asp Asn Ile Arg Gln Met Val Ser Leu Met Lys Ser Tyr
            100                 105                 110

His Ile Arg Pro Ile Ile Gly Pro Gly Leu Val Asp Arg Glu Lys
            115                 120                 125

Trp Glu Lys Glu Lys Ser Glu Glu Ile Ala Leu Gly Tyr Phe Arg Thr
130                 135                 140

Asn Glu Asn Phe Ala Ile Tyr Ser Asp Ala Leu Ala Lys Leu Ala Asn
145                 150                 155                 160

Glu Glu Lys Val Pro Phe Val Ala Leu Asn Lys Ala Phe Gln Gln Glu
                165                 170                 175

Gly Gly Asp Ala Trp Gln Gln Leu Leu Thr Asp Gly Leu His Phe Ser
            180                 185                 190

Gly Lys Gly Tyr Lys Ile Phe His Asp Glu Leu Leu Lys Val Ile Glu
        195                 200                 205

Thr Phe Tyr Pro Gln Tyr His Pro Lys Asn Met Gln Tyr Lys Leu Lys
    210                 215                 220

Asp Trp Arg Asp Val Leu Asp Asp Gly Ser Asn Ile Met Ser
225                 230                 235
```

<210> SEQ ID NO 7
<211> LENGTH: 1005
<212> TYPE: DNA
<213> ORGANISM: Aeromonas hydrophila

<400> SEQUENCE: 7

```
atgaaaaaat ggtttgtgtg tttattggga ttggtcgcgc tgacagttca ggcagccgac      60
agccgtcccg ccttctcccg gatcgtgatg tttggcgaca gcctctccga taccggcaag     120
atgtacagca gatgcgcgg ttacctcccc tccagccccc cctactatga gggccgcttc     180
tccaacgggc ccgtctggct ggagcagctg accaacgagt tcccgggcct gaccatagcc     240
aacgaggcgg aaggcggacc gaccgccgtg gcttacaaca gatctcctg gaatcccaag     300
tatcaggtca tcaacaacct ggactacgag gtcacccagt cctgcaaaa agacagcttc     360
aagccggacg atctggtgat cctctgggtc ggcgccaacg actatctggc ctatggctgg     420
aacacagagc aggatgccaa gcgggtgcgc gacgccatca gcgatgcggc caaccgcatg     480
gtgctgaacg cgccaagga gatactgctg ttcaacctgc cggatctggg ccagaacccc     540
tcggcccgca gccagaaggt ggtcgaggcg ccagccatg tctccgccta ccacaaccag     600
ctgctgctga acctggcacg ccagctggct cccaccggca tggtgaagct gttcgagatc     660
gacaagcagt tgccgagat gctgcgtgat ccgcagaact tcggcctgag cgaccagagg     720
aacgcctgct acggtggcag ctatgtatgg aagccgtttg cctcccgcag cgccagcacc     780
gacagccagc tctccgcctt caacccgcag gagcgcctcg ccatcgccgg caacccgctg     840
ctggcccagg ccgtcgccag ccccatggct gcccgcagcg ccagcaccct caactgtgag     900
ggcaagatgt tctgggatca ggtccacccc accactgtcg tgcacgccgc cctgagcgag     960
cccgccgcca ccttcatcga gagccagtac gagttcctcg cccac                    1005
```

<210> SEQ ID NO 8
<211> LENGTH: 1011
<212> TYPE: DNA
<213> ORGANISM: Aeromonas salmonicida

<400> SEQUENCE: 8

```
atgaaaaaat ggtttgtttg tttattgggg ttgatcgcgc tgacagttca ggcagccgac      60
actcgccccg ccttctcccg gatcgtgatg ttcggcgaca gcctctccga taccggcaaa     120
atgtacagca agatgcgcgg ttacctcccc tccagcccgc cctactatga gggccgtttc     180
tccaacggac ccgtctggct ggagcagctg accaagcagt tcccgggtct gaccatcgcc     240
aacgaagcgg aaggcggtgc cactgccgtg gcttacaaca agatctcctg gaatcccaag     300
tatcaggtct acaacaacct ggactacgag gtcacccagt tcttgcagaa agacagcttc     360
aagccggacg atctggtgat cctctgggtc ggtgccaatg actatctggc atatggctgg     420
aatacggagc aggatgccaa gcgagttcgc gatgccatca gcgatgcggc caaccgcatg     480
gtactgaacg gtgccaagca gatactgctg ttcaacctgc cggatctggg ccagaacccg     540
tcagcccgca gtcagaaggt ggtcgaggcg gtcagccatg tctccgccta tcacaacaag     600
ctgctgctga acctggcacg ccagctggcc cccaccggca tggtaaagct gttcgagatc     660
gacaagcaat tgccgagat gctgcgtgat ccgcagaact tcggcctgag cgacgtcgag     720 aaccctgct acgacggcgg ctatgtgtgg aagccgtttg ccacccgcag cgtcagcacc     780
gaccgccagc tctccgcctt cagtccgcag gaacgcctcg ccatcgccgg caacccgctg     840
ctggcacagg ccgttgccag tcctatggcc cgccgcagcg ccagccccct caactgtgag     900
ggcaagatgt tctgggatca ggtacacccg accactgtcg tgcacgcagc cctgagcgag     960
cgcgccgcca ccttcatcga gacccagtac gagttcctcg cccacggatg a             1011
```

<210> SEQ ID NO 9
<211> LENGTH: 888
<212> TYPE: DNA
<213> ORGANISM: Streptomyces coelicolor

<400> SEQUENCE: 9

```
atgccgaagc ctgcccttcg ccgtgtcatg accgcgacag tcgccgccgt cggcacgctc      60
gccctcggcc tcaccgacgc caccgcccac gccgcgcccg cccaggccac tccgaccctg     120
gactacgtcg ccctcggcga cagctacagc gccggctccg gcgtcctgcc cgtcgacccc     180
gccaacctgc tctgtctgcg ctcgacggcc aactacccc acgtcatcgc ggacacgacg     240
ggcgcccgcc tcacggacgt cacctgcggc gccgcgcaga ccgccgactt cacgcgggcc     300
cagtacccgg gcgtcgcacc ccagttggac gcgctcggca ccggcacgga cctggtcacg     360
ctcaccatcg gcggcaacga caacagcacc ttcatcaacg ccatcacggc ctgcggcacg     420
gcgggtgtcc tcagcggcgg caagggcagc ccctgcaagg acaggcacgg cacctccttc     480
gacgacgaga tcgaggccaa cacgtacccc gcgctcaagg aggcgctgct cggcgtccgc     540
gccagggctc cccacgccag ggtggcggct ctcggctacc cgtggatcac cccggccacc     600
gccgacccgt cctgcttcct gaagctcccc ctcgccgccg gtgacgtgcc ctacctgcgg     660
gccatccagg cacacctcaa cgacgcgtc cggcgggccc ccgaggagac cggagccacc     720
tacgtggact tctccggggt gtccgacggc cacgacgcct gcgaggcccc cggcacccgc     780
tggatcgaac cgctgctctt cgggcacagc ctcgttcccg tccaccccaa cgccctgggc     840
gagcggcgca tggccgagca cacgatggac gtcctcggcc tggactga                  888
```

<210> SEQ ID NO 10
<211> LENGTH: 888
<212> TYPE: DNA
<213> ORGANISM: Streptomyces coelicolor

<400> SEQUENCE: 10

-continued

```
tcagtccagg ccgaggacgt ccatcgtgtg ctcggccatg cgccgctcgc ccagggcgtt      60
ggggtggacg ggaacgaggc tgtgcccgaa gagcagcggt tcgatccagc gggtgccggg     120
ggcctcgcag gcgtcgtggc cgtcggacac cccggagaag tccacgtagg tggctccggt     180
ctcctcggcg gcccgccgga ccgcgtcgtt gaggtgtgcc tggatggccc gcaggtaggg     240
cacgtcaccg gcggcgaggg ggagcttcag gaagcaggac gggtcggcgg tggccggggt     300
gatccacggg tagccgagag ccgccaccct ggcgtgggga gccctggcgc ggacgccgag     360
cagcgcctcc ttgagcgcgg ggtacgtgtt ggcctcgatc tcgtcgtcga aggaggtgcc     420
gtgcctgtcc ttgcaggggc tgcccttgcc gccgctgagg acacccgccg tgccgcaggc     480
cgtgatggcg ttgatgaagg tgctgttgtc gttgccgccg atggtgagcg tgaccaggtc     540
cgtgccggtg ccgagcgcgt ccaactgggg tgcgacgccc gggtactggg cccgcgtgaa     600
gtcggcggtc tgcgcggcgc cgcaggtgac gtccgtgagg cgggcgcccg tcgtgtccgc     660
gatgacgtgg gggtagttgg ccgtcgagcg cagacagagc aggttggcgg ggtcgacggg     720
caggacgccg gagccggcgc tgtagctgtc gccgagggcg acgtagtcca gggtcggagt     780
ggcctgggcg ggcgcggcgt gggcggtggc gtcggtgagg ccgagggcga gcgtgccgac     840
ggcggcgact gtcgcggtca tgacacggcg aagggcaggc ttcggcat                  888
```

```

<210> SEQ ID NO 11
<211> LENGTH: 717
<212> TYPE: DNA
<213> ORGANISM: Saccharomyces cerevisiae

<400> SEQUENCE: 11
atggattacg agaagtttct gttatttggg gattccatta ctgaatttgc ttttaatact      60
aggcccattg aagatggcaa agatcagtat gctcttggag ccgcattagt caacgaatat     120
acgagaaaaa tggatattct tcaaagaggg ttcaaagggt acacttctag atgggcgttg     180
aaaatacttc ctgagatttt aaagcatgaa tccaatattg tcatggccac aatatttttg     240
ggtgccaacg atgcatgctc agcaggtccc caaagtgtcc ccctccccga atttatcgat     300
aatattcgtc aaatggtatc tttgatgaag tcttaccata tccgtcctat tataatagga     360
ccggggctag tagatagaga gaagtgggaa aaagaaaaat ctgaagaaat agctctcgga     420
tacttccgta ccaacgagaa ctttgccatt tattccgatg ccttagcaaa actagccaat     480
gaggaaaaag ttcccttcgt ggctttgaat aaggcgtttc aacaggaagg tggtgatgct     540
tggcaacaac tgctaacaga tggactgcac ttttccggaa aagggtacaa aatttttcat     600
gacgaattat tgaaggtcat tgagacattc tacccccaat atcatcccaa aaacatgcag     660
tacaaactga aagattggag agatgtgcta gatgatggat ctaacataat gtcttga        717
```

```

<210> SEQ ID NO 12
<211> LENGTH: 347
<212> TYPE: PRT
<213> ORGANISM: Ralstonia solanacearum

<400> SEQUENCE: 12

Met Asn Leu Arg Gln Trp Met Gly Ala Ala Thr Ala Ala Leu Ala Leu
1               5                   10                  15

Gly Leu Ala Ala Cys Gly Gly Gly Gly Thr Asp Gln Ser Gly Asn Pro
            20                  25                  30

Asn Val Ala Lys Val Gln Arg Met Val Val Phe Gly Asp Ser Leu Ser
        35                  40                  45
```

```
Asp Ile Gly Thr Tyr Thr Pro Val Ala Gln Ala Val Gly Gly Gly Lys
     50                  55                  60

Phe Thr Thr Asn Pro Gly Pro Ile Trp Ala Glu Thr Val Ala Ala Gln
 65                  70                  75                  80

Leu Gly Val Thr Leu Thr Pro Ala Val Met Gly Tyr Ala Thr Ser Val
                 85                  90                  95

Gln Asn Cys Pro Lys Ala Gly Cys Phe Asp Tyr Ala Gln Gly Gly Ser
            100                 105                 110

Arg Val Thr Asp Pro Asn Gly Ile Gly His Asn Gly Gly Ala Gly Ala
        115                 120                 125

Leu Thr Tyr Pro Val Gln Gln Gln Leu Ala Asn Phe Tyr Ala Ala Ser
    130                 135                 140

Asn Asn Thr Phe Asn Gly Asn Asn Asp Val Val Phe Val Leu Ala Gly
145                 150                 155                 160

Ser Asn Asp Ile Phe Phe Trp Thr Thr Ala Ala Ala Thr Ser Gly Ser
                165                 170                 175

Gly Val Thr Pro Ala Ile Ala Thr Ala Gln Val Gln Gln Ala Ala Thr
            180                 185                 190

Asp Leu Val Gly Tyr Val Lys Asp Met Ile Ala Lys Gly Ala Thr Gln
        195                 200                 205

Val Tyr Val Phe Asn Leu Pro Asp Ser Ser Leu Thr Pro Asp Gly Val
    210                 215                 220

Ala Ser Gly Thr Thr Gly Gln Ala Leu Leu His Ala Leu Val Gly Thr
225                 230                 235                 240

Phe Asn Thr Thr Leu Gln Ser Gly Leu Ala Gly Thr Ser Ala Arg Ile
                245                 250                 255

Ile Asp Phe Asn Ala Gln Leu Thr Ala Ala Ile Gln Asn Gly Ala Ser
            260                 265                 270

Phe Gly Phe Ala Asn Thr Ser Ala Arg Ala Cys Asp Ala Thr Lys Ile
        275                 280                 285

Asn Ala Leu Val Pro Ser Ala Gly Gly Ser Ser Leu Phe Cys Ser Ala
    290                 295                 300

Asn Thr Leu Val Ala Ser Gly Ala Asp Gln Ser Tyr Leu Phe Ala Asp
305                 310                 315                 320

Gly Val His Pro Thr Thr Ala Gly His Arg Leu Ile Ala Ser Asn Val
                325                 330                 335

Leu Ala Arg Leu Leu Ala Asp Asn Val Ala His
            340                 345
```

<210> SEQ ID NO 13
<211> LENGTH: 1044
<212> TYPE: DNA
<213> ORGANISM: Ralstonia solanacearum

<400> SEQUENCE: 13

```
atgaacctgc gtcaatggat gggcgccgcc acggctgccc ttgccttggg cttggccgcg     60
tgcgggggcg gtgggaccga ccagagcggc aatcccaatg tcgccaaggt gcagcgcatg    120
gtggtgttcg gcgacagcct gagcgatatc ggcacctaca cccccgtcgc gcaggcggtg    180
ggcggcggca agttcaccac caacccgggc ccgatctggg ccgagaccgt ggccgcgcaa    240
ctgggcgtga cgctcacgcc ggcggtgatg ggctacgcca cctccgtgca gaattgcccc    300
aaggccggct gcttcgacta tgcgcagggc ggctcgcgcg tgaccgatcc gaacggcatc    360
ggccacaacg gcggcgcggg ggcgctgacc tacccggttc agcagcagct cgccaacttc    420
tacgcggcca gcaacaacac attcaacggc aataacgatg tcgtcttcgt gctggccggc    480
```

```
agcaacgaca tttcttctg gaccactgcg gcggccacca gcggctccgg cgtgacgccc    540
gccattgcca cggcccaggt gcagcaggcc gcgacggacc tggtcggcta tgtcaaggac    600
atgatcgcca aggtgcgac gcaggtctac gtgttcaacc tgcccgacag cagcctgacg     660
ccggacggcg tggcaagcgg cacgaccggc caggcgctgc tgcacgcgct ggtgggcacg    720
ttcaacacga cgctgcaaag cgggctggcc ggcacctcgg cgcgcatcat cgacttcaac    780
gcacaactga ccgcggcgat ccagaatggc gcctcgttcg gcttcgccaa caccagcgcc    840
cgggcctgcg acgccaccaa gatcaatgcc ctggtgccga gcgccggcgg cagctcgctg    900
ttctgctcgg ccaacacgct ggtggcttcc ggtgcggacc agagctacct gttcgccgac    960
ggcgtgcacc cgaccacggc cggccatcgc ctgatcgcca gcaacgtgct ggcgcgcctg    1020
ctggcggata acgtcgcgca ctga                                          1044
```

<210> SEQ ID NO 14
<211> LENGTH: 295
<212> TYPE: PRT
<213> ORGANISM: Aeromonas salmonicida

<400> SEQUENCE: 14

```
Ile Val Met Phe Gly Asp Ser Leu Ser Asp Thr Gly Lys Met Tyr Ser
  1               5                  10                  15

Lys Met Arg Gly Tyr Leu Pro Ser Ser Pro Tyr Tyr Glu Gly Arg
             20                  25                  30

Phe Ser Asn Gly Pro Val Trp Leu Glu Gln Leu Thr Lys Gln Phe Pro
         35                  40                  45

Gly Leu Thr Ile Ala Asn Glu Ala Glu Gly Gly Ala Thr Ala Val Ala
     50                  55                  60

Tyr Asn Lys Ile Ser Trp Asn Pro Lys Tyr Gln Val Tyr Asn Asn Leu
 65                  70                  75                  80

Asp Tyr Glu Val Thr Gln Phe Leu Gln Lys Asp Ser Phe Lys Pro Asp
             85                  90                  95

Asp Leu Val Ile Leu Trp Val Gly Ala Asn Asp Tyr Leu Ala Tyr Gly
            100                 105                 110

Trp Asn Thr Glu Gln Asp Ala Lys Arg Val Arg Asp Ala Ile Ser Asp
        115                 120                 125

Ala Ala Asn Arg Met Val Leu Asn Gly Ala Lys Gln Ile Leu Leu Phe
    130                 135                 140

Asn Leu Pro Asp Leu Gly Gln Asn Pro Ser Ala Arg Ser Gln Lys Val
145                 150                 155                 160

Val Glu Ala Val Ser His Val Ser Ala Tyr His Asn Lys Leu Leu Leu
            165                 170                 175

Asn Leu Ala Arg Gln Leu Ala Pro Thr Gly Met Val Lys Leu Phe Glu
        180                 185                 190

Ile Asp Lys Gln Phe Ala Glu Met Leu Arg Asp Pro Gln Asn Phe Gly
    195                 200                 205

Leu Ser Asp Val Glu Asn Pro Cys Tyr Asp Gly Gly Tyr Val Trp Lys
210                 215                 220

Pro Phe Ala Thr Arg Ser Val Ser Thr Asp Arg Gln Leu Ser Ala Phe
225                 230                 235                 240

Ser Pro Gln Glu Arg Leu Ala Ile Gly Asn Pro Leu Leu Ala Gln
            245                 250                 255

Ala Val Ala Ser Pro Met Ala Arg Arg Ser Ala Ser Pro Leu Asn Cys
        260                 265                 270
```

```
Glu Gly Lys Met Phe Trp Asp Gln Val His Pro Thr Val Val His
    275                 280                 285

Ala Ala Leu Ser Glu Arg Ala
    290                 295

<210> SEQ ID NO 15
<211> LENGTH: 295
<212> TYPE: PRT
<213> ORGANISM: Aeromonas hydrophila

<400> SEQUENCE: 15

Ile Val Met Phe Gly Asp Ser Leu Ser Asp Thr Gly Lys Met Tyr Ser
  1               5                  10                  15

Lys Met Arg Gly Tyr Leu Pro Ser Ser Pro Tyr Tyr Glu Gly Arg
             20                  25                  30

Phe Ser Asn Gly Pro Val Trp Leu Glu Gln Leu Thr Lys Gln Phe Pro
             35                  40                  45

Gly Leu Thr Ile Ala Asn Glu Ala Glu Gly Gly Ala Thr Ala Val Ala
     50                  55                  60

Tyr Asn Lys Ile Ser Trp Asn Pro Lys Tyr Gln Val Ile Asn Asn Leu
 65                  70                  75                  80

Asp Tyr Glu Val Thr Gln Phe Leu Gln Lys Asp Ser Phe Lys Pro Asp
                 85                  90                  95

Asp Leu Val Ile Leu Trp Val Gly Ala Asn Asp Tyr Leu Ala Tyr Gly
                100                 105                 110

Trp Asn Thr Glu Gln Asp Ala Lys Arg Val Arg Asp Ala Ile Ser Asp
            115                 120                 125

Ala Ala Asn Arg Met Val Leu Asn Gly Ala Lys Gln Ile Leu Leu Phe
    130                 135                 140

Asn Leu Pro Asp Leu Gly Gln Asn Pro Ser Ala Arg Ser Gln Lys Val
145                 150                 155                 160

Val Glu Ala Val Ser His Val Ser Ala Tyr His Asn Gln Leu Leu Leu
                165                 170                 175

Asn Leu Ala Arg Gln Leu Ala Pro Thr Gly Met Val Lys Leu Phe Glu
            180                 185                 190

Ile Asp Lys Gln Phe Ala Glu Met Leu Arg Asp Pro Gln Asn Phe Gly
        195                 200                 205

Leu Ser Asp Val Glu Asn Pro Cys Tyr Asp Gly Gly Tyr Val Trp Lys
    210                 215                 220

Pro Phe Ala Thr Arg Ser Val Ser Thr Asp Arg Gln Leu Ser Ala Phe
225                 230                 235                 240

Ser Pro Gln Glu Arg Leu Ala Ile Ala Gly Asn Pro Leu Leu Ala Gln
                245                 250                 255

Ala Val Ala Ser Pro Met Ala Arg Arg Ser Ala Ser Pro Leu Asn Cys
            260                 265                 270

Glu Gly Lys Met Phe Trp Asp Gln Val His Pro Thr Val Val His
    275                 280                 285

Ala Ala Leu Ser Glu Arg Ala
    290                 295

<210> SEQ ID NO 16
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide motif
```

```
<400> SEQUENCE: 16

Gly Ser Asp Leu
  1

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence: Synthetic
      6x His tag

<400> SEQUENCE: 17

His His His His His His
  1               5

<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
taatacgact cactatag                                                 18

<210> SEQ ID NO 19
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ctagttattg ctcagcgg                                                 18

<210> SEQ ID NO 20
<211> LENGTH: 261
<212> TYPE: PRT
<213> ORGANISM: Streptomyces coelicolor

<400> SEQUENCE: 20

Met Ile Gly Ser Tyr Val Ala Val Gly Asp Ser Phe Thr Glu Gly Val
  1               5                  10                  15

Gly Asp Pro Gly Pro Asp Gly Ala Phe Val Gly Trp Ala Asp Arg Leu
                 20                  25                  30

Ala Val Leu Leu Ala Asp Arg Arg Pro Glu Gly Asp Phe Thr Tyr Thr
             35                  40                  45

Asn Leu Ala Val Arg Gly Arg Leu Leu Asp Gln Ile Val Ala Glu Gln
         50                  55                  60

Val Pro Arg Val Val Gly Leu Ala Pro Asp Leu Val Ser Phe Ala Ala
  65                  70                  75                  80

Gly Gly Asn Asp Ile Ile Arg Pro Gly Thr Asp Pro Asp Glu Val Ala
                 85                  90                  95

Glu Arg Phe Glu Leu Ala Val Ala Ala Leu Thr Ala Ala Ala Gly Thr
                100                 105                 110

Val Leu Val Thr Thr Gly Phe Asp Thr Arg Gly Val Pro Val Leu Lys
            115                 120                 125

His Leu Arg Gly Lys Ile Ala Thr Tyr Asn Gly His Val Arg Ala Ile
        130                 135                 140
```

```
Ala Asp Arg Tyr Gly Cys Pro Val Leu Asp Leu Trp Ser Leu Arg Ser
145                 150                 155                 160

Val Gln Asp Arg Arg Ala Trp Asp Ala Asp Arg Leu His Leu Ser Pro
                165                 170                 175

Glu Gly His Thr Arg Val Ala Leu Arg Ala Gly Gln Ala Leu Gly Leu
            180                 185                 190

Arg Val Pro Ala Asp Pro Asp Gln Pro Trp Pro Pro Leu Pro Pro Arg
        195                 200                 205

Gly Thr Leu Asp Val Arg Arg Asp Asp Val His Trp Ala Arg Glu Tyr
        210                 215                 220

Leu Val Pro Trp Ile Gly Arg Arg Leu Arg Gly Glu Ser Ser Gly Asp
225                 230                 235                 240

His Val Thr Ala Lys Gly Thr Leu Ser Pro Asp Ala Ile Lys Thr Arg
                245                 250                 255

Ile Ala Ala Val Ala
            260

<210> SEQ ID NO 21
<211> LENGTH: 786
<212> TYPE: DNA
<213> ORGANISM: Streptomyces coelicolor

<400> SEQUENCE: 21
gtgatcgggt cgtacgtggc ggtgggggac agcttcaccg agggcgtcgg cgaccccggc      60
cccgacgggg cgttcgtcgg ctgggccgac cggctcgccg tactgctcgc ggaccggcgc     120
cccgagggcg acttcacgta cacgaacctc gccgtgcgcg gcaggctcct cgaccagatc     180
gtggcggaac aggtcccgcg ggtcgtcgga ctcgcgcccg acctcgtctc gttcgcggcg     240
ggcggcaacg acatcatccg gcccggcacc gatcccgacg aggtcgccga gcggttcgag     300
ctggcggtgg ccgcgctgac cgccgcggcc ggaaccgtcc tggtgaccac cgggttcgac     360
acccgggggg tgcccgtcct caagcacctg cgcggcaaga tcgccacgta caacgggcac     420
gtccgcgcca tcgccgaccg ctacggctgc ccggtgctcg acctgtggtc gctgcggagc     480
gtccaggacc gcagggcgtg ggacgccgac cggctgcacc tgtcgccgga ggggcacacc     540
cgggtggcgc tgcgcgcggg gcaggccctg gcctgcgcg tcccggccga ccctgaccag     600
ccctggccgc ccctgccgcc gcggcggacg ctcgacgtcc ggcgcgacga cgtgcactgg     660
gcgcgcgagt acctggtgcc gtggatcggg cgccggctgc ggggcgagtc gtcgggcgac     720
cacgtgacgg ccaagggga ctgtcgccg acgccatca agacgcggat cgccgcggtg     780
gcctga                                                                786

<210> SEQ ID NO 22
<211> LENGTH: 260
<212> TYPE: PRT
<213> ORGANISM: Streptomyces coelicolor

<400> SEQUENCE: 22

Met Gln Thr Asn Pro Ala Tyr Thr Ser Leu Val Ala Val Gly Asp Ser
  1               5                  10                  15

Phe Thr Glu Gly Met Ser Asp Leu Leu Pro Asp Gly Ser Tyr Arg Gly
                 20                  25                  30

Trp Ala Asp Leu Leu Ala Thr Arg Met Ala Ala Arg Ser Pro Gly Phe
             35                  40                  45

Arg Tyr Ala Asn Leu Ala Val Arg Gly Lys Leu Ile Gly Gln Ile Val
         50                  55                  60
```

```
Asp Glu Gln Val Asp Val Ala Ala Ala Met Gly Ala Asp Val Ile Thr
 65                  70                  75                  80
Leu Val Gly Gly Leu Asn Asp Thr Leu Arg Pro Lys Cys Asp Met Ala
                 85                  90                  95
Arg Val Arg Asp Leu Leu Thr Gln Ala Val Glu Arg Leu Ala Pro His
            100                 105                 110
Cys Glu Gln Leu Val Leu Met Arg Ser Pro Gly Arg Gln Gly Pro Val
        115                 120                 125
Leu Glu Arg Phe Arg Pro Arg Met Glu Ala Leu Phe Ala Val Ile Asp
    130                 135                 140
Asp Leu Ala Gly Arg His Gly Ala Val Val Asp Leu Tyr Gly Ala
145                 150                 155                 160
Gln Ser Leu Ala Asp Pro Arg Met Trp Asp Val Asp Arg Leu His Leu
                165                 170                 175
Thr Ala Glu Gly His Arg Arg Val Ala Glu Ala Val Trp Gln Ser Leu
            180                 185                 190
Gly His Glu Pro Glu Asp Pro Glu Trp His Ala Pro Ile Pro Ala Thr
        195                 200                 205
Pro Pro Pro Gly Trp Val Thr Arg Arg Thr Ala Asp Val Arg Phe Ala
    210                 215                 220
Arg Gln His Leu Leu Pro Trp Ile Gly Arg Arg Leu Thr Gly Arg Ser
225                 230                 235                 240
Ser Gly Asp Gly Leu Pro Ala Lys Arg Pro Asp Leu Leu Pro Tyr Glu
                245                 250                 255
Asp Pro Ala Arg
            260

<210> SEQ ID NO 23
<211> LENGTH: 783
<212> TYPE: DNA
<213> ORGANISM: Streptomyces coelicolor

<400> SEQUENCE: 23
atgcagacga accccgcgta caccagtctc gtcgccgtcg cgactcctt caccgagggc      60
atgtcggacc tgctgcccga cggctcctac cgtggctggg ccgacctcct cgccacccgg     120
atggcggccc gctcccccgg cttccggtac gccaacctgg cggtgcgcgg gaagctgatc     180
ggacagatcg tcgacgagca ggtggacgtg gccgccgcca tgggagccga cgtgatcacg     240
ctggtcggcg gctcaacga cacgctgcgg cccaagtgcg acatggcccg gtgcgggac      300
ctgctgaccc aggccgtgga acggctcgcc ccgcactgcg agcagctggt gctgatgcgc     360
agtcccggtc gccagggtcc ggtgctggag cgcttccggc cccgcatgga ggccctgttc     420
gccgtgatcg acgacctggc cgggcggcac ggcgccgtgg tcgtcgacct gtacggggcc     480
cagtcgctgg ccgaccctcg gatgtgggac gtggaccggc tgcacctgac cgccgagggc     540
caccgccggg tcgcggaggc ggtgtggcag tcgctcggcc acgagcccga ggaccccgag     600
tggcacgcgc cgatcccggc gacgccgccc cggggtggg tgacgcgcag gaccgcggac     660
gtccggttcg cccggcagca cctgctgccc tggataggcc gcaggctgac cgggcgctcg     720
tccggggacg gcctgccggc caagcgcccg gacctgctgc cctacgagga ccccgcacgg     780
tga                                                                    783

<210> SEQ ID NO 24
<211> LENGTH: 454
<212> TYPE: PRT
<213> ORGANISM: Streptomyces coelicolor
```

<400> SEQUENCE: 24

Met Thr Arg Gly Arg Asp Gly Gly Ala Gly Ala Pro Pro Thr Lys His
 1               5                  10                  15

Arg Ala Leu Leu Ala Ala Ile Val Thr Leu Ile Val Ala Ile Ser Ala
             20                  25                  30

Ala Ile Tyr Ala Gly Ala Ser Ala Asp Asp Gly Ser Arg Asp His Ala
         35                  40                  45

Leu Gln Ala Gly Gly Arg Leu Pro Arg Gly Asp Ala Ala Pro Ala Ser
     50                  55                  60

Thr Gly Ala Trp Val Gly Ala Trp Ala Thr Ala Pro Ala Ala Ala Glu
 65                  70                  75                  80

Pro Gly Thr Glu Thr Thr Gly Leu Ala Gly Arg Ser Val Arg Asn Val
             85                  90                  95

Val His Thr Ser Val Gly Gly Thr Gly Ala Arg Ile Thr Leu Ser Asn
             100                 105                 110

Leu Tyr Gly Gln Ser Pro Leu Thr Val Thr His Ala Ser Ile Ala Leu
         115                 120                 125

Ala Ala Gly Pro Asp Thr Ala Ala Ile Ala Asp Thr Met Arg Arg
    130                 135                 140

Leu Thr Phe Gly Gly Ser Ala Arg Val Ile Ile Pro Ala Gly Gly Gln
145                 150                 155                 160

Val Met Ser Asp Thr Ala Arg Leu Ala Ile Pro Tyr Gly Ala Asn Val
                165                 170                 175

Leu Val Thr Thr Tyr Ser Pro Ile Pro Ser Gly Pro Val Thr Tyr His
            180                 185                 190

Pro Gln Ala Arg Gln Thr Ser Tyr Leu Ala Asp Gly Asp Arg Thr Ala
        195                 200                 205

Asp Val Thr Ala Val Ala Tyr Thr Thr Pro Thr Pro Tyr Trp Arg Tyr
    210                 215                 220

Leu Thr Ala Leu Asp Val Leu Ser His Glu Ala Asp Gly Thr Val Val
225                 230                 235                 240

Ala Phe Gly Asp Ser Ile Thr Asp Gly Ala Arg Ser Gln Ser Asp Ala
                245                 250                 255

Asn His Arg Trp Thr Asp Val Leu Ala Ala Arg Leu His Glu Ala Ala
            260                 265                 270

Gly Asp Gly Arg Asp Thr Pro Arg Tyr Ser Val Val Asn Glu Gly Ile
        275                 280                 285

Ser Gly Asn Arg Leu Leu Thr Ser Arg Pro Gly Arg Pro Ala Asp Asn
    290                 295                 300

Pro Ser Gly Leu Ser Arg Phe Gln Arg Asp Val Leu Glu Arg Thr Asn
305                 310                 315                 320

Val Lys Ala Val Val Val Leu Gly Val Asn Asp Val Leu Asn Ser
                325                 330                 335

Pro Glu Leu Ala Asp Arg Asp Ala Ile Leu Thr Gly Leu Arg Thr Leu
            340                 345                 350

Val Asp Arg Ala His Ala Arg Gly Leu Arg Val Gly Ala Thr Ile
        355                 360                 365

Thr Pro Phe Gly Gly Tyr Gly Gly Tyr Thr Glu Ala Arg Glu Thr Met
    370                 375                 380

Arg Gln Glu Val Asn Glu Glu Ile Arg Ser Gly Arg Val Phe Asp Thr
385                 390                 395                 400

Val Val Asp Phe Asp Lys Ala Leu Arg Asp Pro Tyr Asp Pro Arg Arg
                405                 410                 415

Met Arg Ser Asp Tyr Asp Ser Gly Asp His Leu His Pro Gly Asp Lys
            420                 425                 430

Gly Tyr Ala Arg Met Gly Ala Val Ile Asp Leu Ala Ala Leu Lys Gly
        435                 440                 445

Ala Ala Pro Val Lys Ala
    450

<210> SEQ ID NO 25
<211> LENGTH: 1365
<212> TYPE: DNA
<213> ORGANISM: Streptomyces coelicolor

<400> SEQUENCE: 25

```
atgacccggg gtcgtgacgg gggtgcgggg gcgcccccca ccaagcaccg tgccctgctc     60
gcggcgatcg tcaccctgat agtggcgatc tccgcggcca tatacgccgg agcgtccgcg    120
gacgacggca gcagggacca cgcgctgcag gccggaggcc gtctcccacg aggagacgcc    180
gcccccgcgt ccaccggtgc ctgggtgggc gcctgggcca ccgcaccggc cgcggccgag    240
ccgggcaccg agacgaccgg cctggcgggc cgctccgtgc gcaacgtcgt gcacacctcg    300
gtcggcggca ccggcgcgcg gatcaccctc tcgaacctgt acgggcagtc gccgctgacc    360
gtcacacacg cctcgatcgc cctggccgcc gggcccgaca ccgccgccgc gatcgccgac    420
accatgcgcc ggctcacctt cggcggcagc gcccgggtga tcatcccggc gggcggccag    480
gtgatgagcg acaccgcccg cctcgccatc ccctacgggg cgaacgtcct ggtcaccacg    540
tactccccca tcccgtccgg gccggtgacc taccatccgc aggcccggca gaccagctac    600
ctggccgacg cgaccgcac ggcggacgtc accgccgtcg cgtacaccac ccccacgccc    660
tactggcgct acctgaccgc cctcgacgtg ctgagccacg aggccgacgg cacggtcgtg    720
gcgttcggcg actccatcac cgacggcgcc cgctcgcaga gcgacgccaa ccaccgctgg    780
accgacgtcc tcgccgcacg cctgcacgag gcggcgggcg acggcgggga cacgccccgc    840
tacagcgtcg tcaacgaggg catcagcggc aaccggctcc tgaccagcag gccggggcgg    900
ccggccgaca cccgagcgg actgagccgg ttccagcggg acgtgctgga acgcaccaac    960
gtcaaggccg tcgtcgtcgt cctcggcgtc aacgacgtcc tgaacagccc ggaactcgcc   1020
gaccgcgacg ccatcctgac cggcctgcgc accctcgtcg accgggcgca cgcccgggga   1080
ctgcgggtcg tcggcgccac gatcacgccg ttcggcggct acggcggcta caccgaggcc   1140
cgcgagacga tgcggcagga ggtcaacgag gagatccgct ccggccgggt cttcgacacg   1200
gtcgtcgact tcgacaaggc cctgcgcgac ccgtacgacc cgcgccggat cgctccgac   1260
tacgacagcg cgaccacct gcaccccggc gacaaggggt acgcgcgcat gggcgcggtc   1320
atcgacctgg ccgcgctgaa gggcgcggcg ccggtcaagg cgtag                  1365
```

<210> SEQ ID NO 26
<211> LENGTH: 340
<212> TYPE: PRT
<213> ORGANISM: Streptomyces coelicolor

<400> SEQUENCE: 26

Met Thr Ser Met Ser Arg Ala Arg Val Ala Arg Arg Ile Ala Ala Gly
  1               5                  10                  15

Ala Ala Tyr Gly Gly Gly Gly Ile Gly Leu Ala Gly Ala Ala Ala Val
             20                  25                  30

Gly Leu Val Val Ala Glu Val Gln Leu Ala Arg Arg Arg Val Gly Val
         35                  40                  45

```
Gly Thr Pro Thr Arg Val Pro Asn Ala Gln Gly Leu Tyr Gly Gly Thr
        50                  55                  60

Leu Pro Thr Ala Gly Asp Pro Pro Leu Arg Leu Met Met Leu Gly Asp
 65                  70                  75                  80

Ser Thr Ala Ala Gly Gln Gly Val His Arg Ala Gly Thr Pro Gly
                85                  90                  95

Ala Leu Leu Ala Ser Gly Leu Ala Ala Val Ala Glu Arg Pro Val Arg
            100                 105                 110

Leu Gly Ser Val Ala Gln Pro Gly Ala Cys Ser Asp Asp Leu Asp Arg
            115                 120                 125

Gln Val Ala Leu Val Leu Ala Glu Pro Asp Arg Val Pro Asp Ile Cys
        130                 135                 140

Val Ile Met Val Gly Ala Asn Asp Val Thr His Arg Met Pro Ala Thr
145                 150                 155                 160

Arg Ser Val Arg His Leu Ser Ser Ala Val Arg Arg Leu Arg Thr Ala
                165                 170                 175

Gly Ala Glu Val Val Val Gly Thr Cys Pro Asp Leu Gly Thr Ile Glu
            180                 185                 190

Arg Val Arg Gln Pro Leu Arg Trp Leu Ala Arg Arg Ala Ser Arg Gln
            195                 200                 205

Leu Ala Ala Ala Gln Thr Ile Gly Ala Val Glu Gln Gly Gly Arg Thr
        210                 215                 220

Val Ser Leu Gly Asp Leu Leu Gly Pro Glu Phe Ala Gln Asn Pro Arg
225                 230                 235                 240

Glu Leu Phe Gly Pro Asp Asn Tyr His Pro Ser Ala Glu Gly Tyr Ala
                245                 250                 255

Thr Ala Ala Met Ala Val Leu Pro Ser Val Cys Ala Ala Leu Gly Leu
            260                 265                 270

Trp Pro Ala Asp Glu Glu His Pro Asp Ala Leu Arg Arg Glu Gly Phe
        275                 280                 285

Leu Pro Val Ala Arg Ala Ala Glu Ala Ala Ser Glu Ala Gly Thr
290                 295                 300

Glu Val Ala Ala Ala Met Pro Thr Gly Pro Arg Gly Pro Trp Ala Leu
305                 310                 315                 320

Leu Lys Arg Arg Arg Arg Arg Val Ser Glu Ala Glu Pro Ser Ser
                325                 330                 335

Pro Ser Gly Val
            340

<210> SEQ ID NO 27
<211> LENGTH: 1023
<212> TYPE: DNA
<213> ORGANISM: Streptomyces coelicolor

<400> SEQUENCE: 27
atgacgagca tgtcgagggc gagggtggcg cggcggatcg cggccggcgc ggcgtacggc      60
ggcggcggca tcggcctggc gggagcggcg gcggtcggtc tggtggtggc cgaggtgcag     120
ctggccagac gcagggtggg ggtgggcacg ccgacccggg tgccgaacgc gcagggactg     180
tacggcggca ccctgcccac ggccggcgac ccgccgctgc ggctgatgat gctgggcgac     240
tccacggccg ccgggcaggg cgtgcaccgg gccgggcaga cgccgggcgc gctgctggcg     300
tccgggctcg cggcggtggc ggagcggccg gtgcggctgg gtcggtcgc ccagccgggg     360 gcgtgctcgg acgacctgga ccggcaggtg gcgctggtgc tcgccgagcc ggaccgggtg     420
```

-continued

```
cccgacatct gcgtgatcat ggtcggcgcc aacgacgtca cccaccggat gccggcgacc    480
cgctcggtgc ggcacctgtc ctcggcggta cggcggctgc gcacggccgg tgcggaggtg    540
gtggtcggca cctgtccgga cctgggcacg atcgagcggg tgcggcagcc gctgcgctgg    600
ctggcccggc gggcctcacg gcagctcgcg gcggcacaga ccatcggcgc cgtcgagcag    660
ggcgggcgca cggtgtcgct gggcgacctg ctgggtccgg agttcgcgca gaacccgcgg    720
gagctcttcg gccccgacaa ctaccacccc tccgccgagg ggtacgccac ggccgcgatg    780
gcggtactgc cctcggtgtg cgccgcgctc ggcctgtggc cggccgacga ggagcacccg    840
gacgcgctgc gccgcgaggg cttcctgccg gtggcgcgcg cggcggcgga gcggcgtcc     900 gaggcgggta cggaggtcgc cgccgccatg cctacggggc ctcgggggcc ctgggcgctg    960
ctgaagcgcc ggagacggcg tcgggtgtcg gaggcggaac cgtccagccc gtccggcgtt   1020
tga                                                                 1023
```

<210> SEQ ID NO 28
<211> LENGTH: 305
<212> TYPE: PRT
<213> ORGANISM: Streptomyces coelicolor

<400> SEQUENCE: 28

```
Met Gly Arg Gly Thr Asp Gln Arg Thr Arg Tyr Gly Arg Arg Ala
  1               5                  10                  15

Arg Val Ala Leu Ala Ala Leu Thr Ala Ala Val Leu Gly Val Gly Val
             20                  25                  30

Ala Gly Cys Asp Ser Val Gly Gly Asp Ser Pro Ala Pro Ser Gly Ser
         35                  40                  45

Pro Ser Lys Arg Thr Arg Thr Ala Pro Ala Trp Asp Thr Ser Pro Ala
     50                  55                  60

Ser Val Ala Ala Val Gly Asp Ser Ile Thr Arg Gly Phe Asp Ala Cys
 65                  70                  75                  80

Ala Val Leu Ser Asp Cys Pro Glu Val Ser Trp Ala Thr Gly Ser Ser
                 85                  90                  95

Ala Lys Val Asp Ser Leu Ala Val Arg Leu Leu Gly Lys Ala Asp Ala
            100                 105                 110

Ala Glu His Ser Trp Asn Tyr Ala Val Thr Gly Ala Arg Met Ala Asp
        115                 120                 125

Leu Thr Ala Gln Val Thr Arg Ala Ala Gln Arg Glu Pro Glu Leu Val
    130                 135                 140

Ala Val Met Ala Gly Ala Asn Asp Ala Cys Arg Ser Thr Thr Ser Ala
145                 150                 155                 160

Met Thr Pro Val Ala Asp Phe Arg Ala Gln Phe Glu Glu Ala Met Ala
                165                 170                 175

Thr Leu Arg Lys Lys Leu Pro Lys Ala Gln Val Tyr Val Ser Ser Ile
            180                 185                 190

Pro Asp Leu Lys Arg Leu Trp Ser Gln Gly Arg Thr Asn Pro Leu Gly
        195                 200                 205

Lys Gln Val Trp Lys Leu Gly Leu Cys Pro Ser Met Leu Gly Asp Ala
    210                 215                 220

Asp Ser Leu Asp Ser Ala Ala Thr Leu Arg Arg Asn Thr Val Arg Asp
225                 230                 235                 240

Arg Val Ala Asp Tyr Asn Glu Val Leu Arg Glu Val Cys Ala Lys Asp
                245                 250                 255

Arg Arg Cys Arg Ser Asp Asp Gly Ala Val His Glu Phe Arg Phe Gly
            260                 265                 270
```

Thr Asp Gln Leu Ser His Trp Asp Trp Phe His Pro Ser Val Asp Gly
        275                 280                 285

Gln Ala Arg Leu Ala Glu Ile Ala Tyr Arg Ala Val Thr Ala Lys Asn
        290                 295                 300

Pro
305

<210> SEQ ID NO 29
<211> LENGTH: 918
<212> TYPE: DNA
<213> ORGANISM: Streptomyces coelicolor

<400> SEQUENCE: 29
atgggtcgag ggacggacca gcggacgcgg tacggccgtc gccgggcgcg tgtcgcgctc      60
gccgccctga ccgccgccgt cctgggcgtg ggcgtggcgg gctgcgactc cgtgggcggc     120
gactcacccg ctccttccgg cagcccgtcg aagcggacga ggacggcgcc cgcctgggac     180
accagcccgg cgtccgtcgc cgccgtgggc gactccatca cgcgcggctt cgacgcctgt     240
gcggtgctgt cggactgccc ggaggtgtcg tgggcgaccg gcagcagcgc gaaggtcgac     300
tcgctggccg tacggctgct ggggaaggcg gacgcggccg agcacagctg gaactacgcg     360
gtcaccgggg cccggatggc ggacctgacc gctcaggtga cgcgggcggc gcagcgcgag     420
ccggagctgg tggcggtgat ggccggggcg aacgacgcgt gccggtccac gacctcggcg     480
atgacgccgg tggcggactt ccgggcgcag ttcgaggagg cgatggccac cctgcgcaag     540 aagctccccca aggcgcaggt gtacgtgtcg agcatcccgg acctcaagcg gctctggtcc     600
cagggccgca ccaacccgct gggcaagcag gtgtggaagc tcggcctgtg cccgtcgatg     660
ctgggcgacg cggactccct ggactcggcg gcgaccctgc ggcgcaacac ggtgcgcgac     720
cgggtggcgg actacaacga ggtgctgcgg gaggtctgcg cgaaggaccg gcggtgccgc     780
agcgacgacg cgcggtgca cgagttccgg ttcggcacgg accagttgag ccactgggac     840
tggttccacc cgagtgtgga cggccaggcc cggctggcgg agatcgccta ccgcgcggtc     900
accgcgaaga tccctga                                                    918

<210> SEQ ID NO 30
<211> LENGTH: 268
<212> TYPE: PRT
<213> ORGANISM: Streptomyces rimosus

<400> SEQUENCE: 30

Met Arg Leu Ser Arg Arg Ala Ala Thr Ala Ser Ala Leu Leu Leu Thr
  1               5                  10                  15

Pro Ala Leu Ala Leu Phe Gly Ala Ser Ala Ala Val Ser Ala Pro Arg
                 20                  25                  30

Ile Gln Ala Thr Asp Tyr Val Ala Leu Gly Asp Ser Tyr Ser Ser Gly
             35                  40                  45

Val Gly Ala Gly Ser Tyr Asp Ser Ser Gly Ser Cys Lys Arg Ser
         50                  55                  60

Thr Lys Ser Tyr Pro Ala Leu Trp Ala Ala Ser His Thr Gly Thr Arg
 65                  70                  75                  80

Phe Asn Phe Thr Ala Cys Ser Gly Ala Arg Thr Gly Asp Val Leu Ala
                 85                  90                  95

Lys Gln Leu Thr Pro Val Asn Ser Gly Thr Asp Leu Val Ser Ile Thr
                100                 105                 110

Ile Gly Gly Asn Asp Ala Gly Phe Ala Asp Thr Met Thr Thr Cys Asn

```
                 115                 120                 125
Leu Gln Gly Glu Ser Ala Cys Leu Ala Arg Ile Ala Lys Ala Arg Ala
    130                 135                 140

Tyr Ile Gln Gln Thr Leu Pro Ala Gln Leu Asp Gln Val Tyr Asp Ala
145                 150                 155                 160

Ile Asp Ser Arg Ala Pro Ala Ala Gln Val Val Leu Gly Tyr Pro
                165                 170                 175

Arg Phe Tyr Lys Leu Gly Gly Ser Cys Ala Val Gly Leu Ser Glu Lys
                180                 185                 190

Ser Arg Ala Ala Ile Asn Ala Ala Ala Asp Asp Ile Asn Ala Val Thr
                195                 200                 205

Ala Lys Arg Ala Ala Asp His Gly Phe Ala Phe Gly Asp Val Asn Thr
    210                 215                 220

Thr Phe Ala Gly His Glu Leu Cys Ser Gly Ala Pro Trp Leu His Ser
225                 230                 235                 240

Val Thr Leu Pro Val Glu Asn Ser Tyr His Pro Thr Ala Asn Gly Gln
                245                 250                 255

Ser Lys Gly Tyr Leu Pro Val Leu Asn Ser Ala Thr
                260                 265

<210> SEQ ID NO 31
<211> LENGTH: 1068
<212> TYPE: DNA
<213> ORGANISM: Streptomyces rimosus

<400> SEQUENCE: 31
ttcatcacaa cgatgtcaca acaccggcca tccgggtcat ccctgatcgt gggaatgggt    60
gacaagcctt cccgtgacga aagggtcctg ctacatcaga aatgacagaa atcctgctca   120
gggaggttcc atgagactgt cccgacgcgc ggccacggcg tccgcgctcc tcctcacccc   180
ggcgctcgcg ctcttcggcg cgagcgccgc cgtgtccgcg ccgcgaatcc aggccaccga   240
ctacgtggcc ctcggcgact cctactcctc gggggtcggc gcgggcagct acgacagcag   300
cagtggctcc tgtaagcgca gcaccaagtc ctacccggcc ctgtgggccg cctcgcacac   360
cggtacgcgg ttcaacttca ccgcctgttc gggcgcccgc acaggagacg tgctggccaa   420
gcagctgacc ccggtcaact ccggcaccga cctggtcagc attaccatcg cggcaacga   480 cgcgggcttc gccgacacca tgaccacctg caacctccag ggcgagagcg cgtgcctggc   540
gcggatcgcc aaggcgcgcg cctacatcca gcagacgctg cccgcccagc tggaccaggt   600
ctacgacgcc atcgacagcc gggcccccgc agcccaggtc gtcgtcctgg gctacccgcg   660
cttctacaag ctgggcggca gctgcgccgt cggtctctcg gagaagtccc gcgcggccat   720
caacgccgcc gccgacgaca tcaacgccgt caccgccaag cgcgccgccg accacggctt   780
cgccttcggg gacgtcaaca cgaccttcgc cgggcacgag ctgtgctccg gcgcccctg   840 gctgcacagc gtcacccttc ccgtggagaa ctcctaccac cccacggcca acggacagtc   900
caagggctac ctgccgtcc tgaactccgc cacctgatct cgcggctact ccgcccctga   960
cgaagtcccg ccccggggcg gggcttcgcc gtaggtgcgc gtaccgccgt cgcccgtcgc  1020
gccggtggcc ccgccgtacg tgccgccgcc cccggacgcg gtcggttc                1068

<210> SEQ ID NO 32
<211> LENGTH: 335
<212> TYPE: PRT
<213> ORGANISM: Aeromonas hydrophila

<400> SEQUENCE: 32
```

Met Lys Lys Trp Phe Val Cys Leu Leu Gly Leu Val Ala Leu Thr Val
 1               5                  10                  15

Gln Ala Ala Asp Ser Arg Pro Ala Phe Ser Arg Ile Val Met Phe Gly
                20                  25                  30

Asp Ser Leu Ser Asp Thr Gly Lys Met Tyr Ser Lys Met Arg Gly Tyr
            35                  40                  45

Leu Pro Ser Ser Pro Tyr Tyr Glu Gly Arg Phe Ser Asn Gly Pro
    50                  55                  60

Val Trp Leu Glu Gln Leu Thr Lys Gln Phe Pro Gly Leu Thr Ile Ala
65                  70                  75                  80

Asn Glu Ala Glu Gly Gly Ala Thr Ala Val Ala Tyr Asn Lys Ile Ser
                85                  90                  95

Trp Asn Pro Lys Tyr Gln Val Ile Asn Asn Leu Asp Tyr Glu Val Thr
                100                 105                 110

Gln Phe Leu Gln Lys Asp Ser Phe Lys Pro Asp Asp Leu Val Ile Leu
            115                 120                 125

Trp Val Gly Ala Asn Asp Tyr Leu Ala Tyr Gly Trp Asn Thr Glu Gln
    130                 135                 140

Asp Ala Lys Arg Val Arg Asp Ala Ile Ser Asp Ala Ala Asn Arg Met
145                 150                 155                 160

Val Leu Asn Gly Ala Lys Gln Ile Leu Leu Phe Asn Leu Pro Asp Leu
                165                 170                 175

Gly Gln Asn Pro Ser Ala Arg Ser Gln Lys Val Val Glu Ala Val Ser
                180                 185                 190

His Val Ser Ala Tyr His Asn Gln Leu Leu Leu Asn Leu Ala Arg Gln
            195                 200                 205

Leu Ala Pro Thr Gly Met Val Lys Leu Phe Glu Ile Asp Lys Gln Phe
    210                 215                 220

Ala Glu Met Leu Arg Asp Pro Gln Asn Phe Gly Leu Ser Asp Val Glu
225                 230                 235                 240

Asn Pro Cys Tyr Asp Gly Gly Tyr Val Trp Lys Pro Phe Ala Thr Arg
                245                 250                 255

Ser Val Ser Thr Asp Arg Gln Leu Ser Ala Phe Ser Pro Gln Glu Arg
                260                 265                 270

Leu Ala Ile Ala Gly Asn Pro Leu Leu Ala Gln Ala Val Ala Ser Pro
            275                 280                 285

Met Ala Arg Arg Ser Ala Ser Pro Leu Asn Cys Glu Gly Lys Met Phe
    290                 295                 300

Trp Asp Gln Val His Pro Thr Thr Val Val His Ala Ala Leu Ser Glu
305                 310                 315                 320

Arg Ala Ala Thr Phe Ile Ala Asn Gln Tyr Glu Phe Leu Ala His
                325                 330                 335

<210> SEQ ID NO 33
<211> LENGTH: 1008
<212> TYPE: DNA
<213> ORGANISM: Aeromonas hydrophila

<400> SEQUENCE: 33
atgaaaaaat ggtttgtgtg tttattggga ttggtcgcgc tgacagttca ggcagccgac    60
agtcgccccg ccttttcccg gatcgtgatg ttcggcgaca gcctctccga taccggcaaa   120
atgtacagca agatgcgcgg ttacctcccc tccagcccgc cctactatga gggccgtttc   180
tccaacggac ccgtctggct ggagcagctg accaaacagt tcccgggtct gaccatcgcc   240

```
aacgaagcgg aaggcggtgc cactgccgtg gcttacaaca agatctcctg gaatcccaag    300
tatcaggtca tcaacaacct ggactacgag gtcacccagt tcttgcagaa agacagcttc    360
aagccggacg atctggtgat cctctgggtc ggtgccaatg actatctggc ctatggctgg    420
aacacggagc aggatgccaa gcgggttcgc gatgccatca gcgatgcggc caaccgcatg    480
gtactgaacg gtgccaagca gatactgctg ttcaacctgc cggatctggg ccagaacccg    540
tcagctcgca gtcagaaggt ggtcgaggcg gtcagccatg tctccgccta tcacaaccag    600
ctgctgctga acctggcacg ccagctggcc cccaccggca tggtaaagct gttcgagatc    660
gacaagcaat tgccgagat gctgcgtgat ccgcagaact tcggcctgag cgacgtcgag    720
aaccctgct acgacggcgg ctatgtgtgg aagccgtttg ccacccgcag cgtcagcacc    780
gaccgccagc tctccgcctt cagtccgcag gaacgcctcg ccatcgccgg caacccgctg    840
ctggcacagg ccgttgccag tcctatggcc cgccgcagcg ccagccccct caactgtgag    900
ggcaagatgt tctgggatca ggtacacccg accactgtcg tgcacgcagc cctgagcgag    960
cgcgccgcca ccttcatcgc gaaccagtac gagttcctcg cccactga                1008
```

<210> SEQ ID NO 34
<211> LENGTH: 336
<212> TYPE: PRT
<213> ORGANISM: Aeromonas salmonicida

<400> SEQUENCE: 34

```
Met Lys Lys Trp Phe Val Cys Leu Leu Gly Leu Ile Ala Leu Thr Val
  1               5                  10                  15

Gln Ala Ala Asp Thr Arg Pro Ala Phe Ser Arg Ile Val Met Phe Gly
                 20                  25                  30

Asp Ser Leu Ser Asp Thr Gly Lys Met Tyr Ser Lys Met Arg Gly Tyr
             35                  40                  45

Leu Pro Ser Ser Pro Tyr Tyr Glu Gly Arg Phe Ser Asn Gly Pro
         50                  55                  60

Val Trp Leu Glu Gln Leu Thr Lys Gln Phe Pro Gly Leu Thr Ile Ala
 65                  70                  75                  80

Asn Glu Ala Glu Gly Gly Ala Thr Ala Val Ala Tyr Asn Lys Ile Ser
                 85                  90                  95

Trp Asn Pro Lys Tyr Gln Val Ile Asn Asn Leu Asp Tyr Glu Val Thr
                100                 105                 110

Gln Phe Leu Gln Lys Asp Ser Phe Lys Pro Asp Asp Leu Val Ile Leu
            115                 120                 125

Trp Val Gly Ala Asn Asp Tyr Leu Ala Tyr Gly Trp Asn Thr Glu Gln
        130                 135                 140

Asp Ala Lys Arg Val Arg Asp Ala Ile Ser Asp Ala Ala Asn Arg Met
145                 150                 155                 160

Val Leu Asn Gly Ala Lys Gln Ile Leu Leu Phe Asn Leu Pro Asp Leu
                165                 170                 175

Gly Gln Asn Pro Ser Ala Arg Ser Gln Lys Val Val Glu Ala Val Ser
            180                 185                 190

His Val Ser Ala Tyr His Asn Lys Leu Leu Leu Asn Leu Ala Arg Gln
        195                 200                 205

Leu Ala Pro Thr Gly Met Val Lys Leu Phe Glu Ile Asp Lys Gln Phe
    210                 215                 220

Ala Glu Met Leu Arg Asp Pro Gln Asn Phe Gly Leu Ser Asp Val Glu
225                 230                 235                 240

Asn Pro Cys Tyr Asp Gly Gly Tyr Val Trp Lys Pro Phe Ala Thr Arg
```

```
                      245                 250                 255
Ser Val Ser Thr Asp Arg Gln Leu Ser Ala Phe Ser Pro Gln Glu Arg
                260                 265                 270

Leu Ala Ile Ala Gly Asn Pro Leu Leu Ala Gln Ala Val Ala Ser Pro
            275                 280                 285

Met Ala Arg Arg Ser Ala Ser Pro Leu Asn Cys Glu Gly Lys Met Phe
        290                 295                 300

Trp Asp Gln Val His Pro Thr Thr Val Val His Ala Ala Leu Ser Glu
305                 310                 315                 320

Arg Ala Ala Thr Phe Ile Glu Thr Gln Tyr Glu Phe Leu Ala His Gly
                325                 330                 335

<210> SEQ ID NO 35
<211> LENGTH: 1011
<212> TYPE: DNA
<213> ORGANISM: Aeromonas salmonicida

<400> SEQUENCE: 35
atgaaaaaat ggtttgtttg tttattgggg ttgatcgcgc tgacagttca ggcagccgac     60
actcgccccg ccttctcccg gatcgtgatg ttcggcgaca gcctctccga taccggcaaa    120
atgtacagca agatgcgcgg ttacctcccc tccagcccgc cctactatga gggccgtttc    180
tccaacggac ccgtctggct ggagcagctg accaagcagt cccgggtctg accatcgcc    240
aacgaagcgg aaggcggtgc cactgccgtg gcttacaaca agatctcctg gaatcccaag    300
tatcaggtca tcaacaacct ggactacgag gtcaccagt tcttgcagaa agacagcttc    360
aagccggacg atctggtgat cctctgggtc ggtgccaatg actatctggc atatggctgg    420
aatacggagc aggatgccaa gcgagttcgc gatgccatca gcgatgcggc caaccgcatg    480
gtactgaacg gtgccaagca gatactgctg ttcaacctgc cggatctggg ccagaacccg    540
tcagcccgca gtcagaaggt ggtcgaggcg gtcagccatg tctccgccta tcacaacaag    600
ctgctgctga acctggcacg ccagctggcc cccaccggca tggtaaagct gttcgagatc    660
gacaagcaat tgccgagat gctgcgtgat ccgcagaact tcggcctgag cgacgtcgag    720
aaccctgct acgacggcgg ctatgtgtgg aagccgtttg ccacccgcag cgtcagcacc    780
gaccgccagc tctccgcctt cagtccgcag gaacgcctcg ccatcgcggg caacccgctg    840
ctggcacagg ccgttgccag tcctatggcc cgccgcagcg ccagcccct caactgtgag    900
ggcaagatgt tctgggatca ggtacacccg accactgtcg tgcacgcagc cctgagcgag    960
cgcgccgcca ccttcatcga gacccagtac gagttcctcg cccacggatg a           1011

<210> SEQ ID NO 36
<211> LENGTH: 347
<212> TYPE: PRT
<213> ORGANISM: Aeromonas hydrophila

<400> SEQUENCE: 36

Met Phe Lys Phe Lys Lys Asn Phe Leu Val Gly Leu Ser Ala Ala Leu
1               5                   10                  15

Met Ser Ile Ser Leu Phe Ser Ala Thr Ala Ser Ala Ala Ser Ala Asp
            20                  25                  30

Ser Arg Pro Ala Phe Ser Arg Ile Val Met Phe Gly Asp Ser Leu Ser
        35                  40                  45

Asp Thr Gly Lys Met Tyr Ser Lys Met Arg Gly Tyr Leu Pro Ser Ser
    50                  55                  60

Pro Pro Tyr Tyr Glu Gly Arg Phe Ser Asn Gly Pro Val Trp Leu Glu
```

```
                65                  70                  75                  80
Gln Leu Thr Lys Gln Phe Pro Gly Leu Thr Ile Ala Asn Glu Ala Glu
                    85                  90                  95

Gly Gly Ala Thr Ala Val Ala Tyr Asn Lys Ile Ser Trp Asn Pro Lys
                100                 105                 110

Tyr Gln Val Ile Asn Asn Leu Asp Tyr Glu Val Thr Gln Phe Leu Gln
                115                 120                 125

Lys Asp Ser Phe Lys Pro Asp Leu Val Ile Leu Trp Val Gly Ala
    130                 135                 140

Asn Asp Tyr Leu Ala Tyr Gly Trp Asn Thr Glu Gln Asp Ala Lys Arg
145                 150                 155                 160

Val Arg Asp Ala Ile Ser Asp Ala Ala Asn Arg Met Val Leu Asn Gly
                165                 170                 175

Ala Lys Gln Ile Leu Leu Phe Asn Leu Pro Asp Leu Gly Gln Asn Pro
            180                 185                 190

Ser Ala Arg Ser Gln Lys Val Val Glu Ala Val Ser His Val Ser Ala
        195                 200                 205

Tyr His Asn Gln Leu Leu Leu Asn Leu Ala Arg Gln Leu Ala Pro Thr
    210                 215                 220

Gly Met Val Lys Leu Phe Glu Ile Asp Lys Gln Phe Ala Glu Met Leu
225                 230                 235                 240

Arg Asp Pro Gln Asn Phe Gly Leu Ser Asp Val Glu Asn Pro Cys Tyr
                245                 250                 255

Asp Gly Gly Tyr Val Trp Lys Pro Phe Ala Thr Arg Ser Val Ser Thr
            260                 265                 270

Asp Arg Gln Leu Ser Ala Phe Ser Pro Gln Glu Arg Leu Ala Ile Ala
        275                 280                 285

Gly Asn Pro Leu Leu Ala Gln Ala Val Ala Ser Pro Met Ala Arg Arg
    290                 295                 300

Ser Ala Ser Pro Leu Asn Cys Glu Gly Lys Met Phe Trp Asp Gln Val
305                 310                 315                 320

His Pro Thr Thr Val Val His Ala Ala Leu Ser Glu Arg Ala Ala Thr
                325                 330                 335

Phe Ile Ala Asn Gln Tyr Glu Phe Leu Ala His
                340                 345

<210> SEQ ID NO 37
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
gtgatggtgg gcgaggaact cgtactg                                            27

<210> SEQ ID NO 38
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
agcatatgaa aaatggtttt gtttgtttat tgggg                                   35
```

```
<210> SEQ ID NO 39
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
ttggatccga attcatcaat ggtgatggtg atggtgggc                              39

<210> SEQ ID NO 40
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
taatacgact cactatag                                                     18

<210> SEQ ID NO 41
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
ctagttattg ctcagcgg                                                     18

<210> SEQ ID NO 42
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
gtcatatgaa aaatggttt gtgtgtttat tgggattggt c                            41

<210> SEQ ID NO 43
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
atggtgatgg tgggcgagga actcgtactg                                        30

<210> SEQ ID NO 44
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
gtcatatgaa aaatggttt gtgtgtttat tgggattggt c                            41

<210> SEQ ID NO 45
<211> LENGTH: 39
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
ttggatccga attcatcaat ggtgatggtg atggtgggc                              39

<210> SEQ ID NO 46
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
atgccatggc cgacagccgt cccgcc                                            26

<210> SEQ ID NO 47
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
ttggatccga attcatcaat ggtgatg                                           27

<210> SEQ ID NO 48
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
ttgctagcgc cgacagccgt cccgcc                                            26

<210> SEQ ID NO 49
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
ttggatccga attcatcaat ggtgatg                                           27

<210> SEQ ID NO 50
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
ttgccatggc cgacactcgc cccgcc                                            26

<210> SEQ ID NO 51
<211> LENGTH: 27
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 51
ttggatccga attcatcaat ggtgatg                                          27

<210> SEQ ID NO 52
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
ttgctagcgc cgacactcgc cccgcc                                           26

<210> SEQ ID NO 53
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
ttggatccga attcatcaat ggtgatg                                          27

<210> SEQ ID NO 54
<211> LENGTH: 1047
<212> TYPE: DNA
<213> ORGANISM: Aeromonas hydrophila

<400> SEQUENCE: 54
atgtttaagt ttaaaaagaa tttcttagtt ggattatcgg cagctttaat gagtattagc      60
ttgttttcgg caaccgcctc tgcagctagc gccgacagcc gtcccgcctt ttcccggatc     120
gtgatgttcg cgacagcct ctccgatacc ggcaaaatgt acagcaagat gcgcggttac      180
ctcccctcca gcccgcccta tatgagggc cgtttctcca acggacccgt ctggctggag      240
cagctgacca aacagttccc gggtctgacc atcgccaacg aagcggaagg cggtgccact     300
gccgtggctt acaacaagat ctcctggaat cccaagtatc aggtcatcaa caacctggac     360
tacgaggtca cccagttctt gcagaaagac agcttcaagc cggacgatct ggtgatcctc     420
tgggtcggtg ccaatgacta tctggcctat ggctggaaca cggagcagga tgccaagcgg     480
gttcgcgatg ccatcagcga tgcggccaac cgcatggtac tgaacggtgc caagcagata     540
ctgctgttca acctgccgga tctgggccag aacccgtcag ctcgcagtca gaaggtggtc     600
gaggcggtca gccatgtctc cgcctatcac aaccagctgc tgctgaacct ggcacgccag     660
ctggccccca ccggcatggt aaagctgttc gagatcgaca gcaatttgc cgagatgctg      720 cgtgatccgc agaacttcgg cctgagcgac gtcgagaacc cctgctacga cggcggctat     780
gtgtggaagc cgtttgccac ccgcagcgtc agcaccgacc gccagctctc cgccttcagt     840
ccgcaggaac gcctcgccat cgccggcaac ccgctgctgg cacaggccgt tgccagtcct     900
atggcccgcc gcagcgccag ccccctcaac tgtgagggca agatgttctg ggatcaggta     960
cacccgacca ctgtcgtgca cgcagccctg agcgagcgcg ccgccacctt catcgcgaac    1020
cagtacgagt cctcgcccca ctgatga                                       1047

<210> SEQ ID NO 55
```

```
<211> LENGTH: 295
<212> TYPE: PRT
<213> ORGANISM: Aeromonas hydrophila

<400> SEQUENCE: 55

Ile Val Met Phe Gly Asp Ser Leu Ser Asp Thr Gly Lys Met Tyr Ser
 1               5                  10                  15

Lys Met Arg Gly Tyr Leu Pro Ser Ser Pro Tyr Tyr Glu Gly Arg
            20                  25                  30

Phe Ser Asn Gly Pro Val Trp Leu Glu Gln Leu Thr Asn Glu Phe Pro
        35                  40                  45

Gly Leu Thr Ile Ala Asn Glu Ala Glu Gly Pro Thr Ala Val Ala
    50                  55                  60

Tyr Asn Lys Ile Ser Trp Asn Pro Lys Tyr Gln Val Ile Asn Asn Leu
65                  70                  75                  80

Asp Tyr Glu Val Thr Gln Phe Leu Gln Lys Asp Ser Phe Lys Pro Asp
                85                  90                  95

Asp Leu Val Ile Leu Trp Val Gly Ala Asn Asp Tyr Leu Ala Tyr Gly
            100                 105                 110

Trp Asn Thr Glu Gln Asp Ala Lys Arg Val Arg Asp Ala Ile Ser Asp
        115                 120                 125

Ala Ala Asn Arg Met Val Leu Asn Gly Ala Lys Glu Ile Leu Leu Phe
    130                 135                 140

Asn Leu Pro Asp Leu Gly Gln Asn Pro Ser Ala Arg Ser Gln Lys Val
145                 150                 155                 160

Val Glu Ala Ala Ser His Val Ser Ala Tyr His Asn Gln Leu Leu Leu
                165                 170                 175

Asn Leu Ala Arg Gln Leu Ala Pro Thr Gly Met Val Lys Leu Phe Glu
            180                 185                 190

Ile Asp Lys Gln Phe Ala Glu Met Leu Arg Asp Pro Gln Asn Phe Gly
        195                 200                 205

Leu Ser Asp Gln Arg Asn Ala Cys Tyr Gly Gly Ser Tyr Val Trp Lys
    210                 215                 220

Pro Phe Ala Ser Arg Ser Ala Ser Thr Asp Ser Gln Leu Ser Ala Phe
225                 230                 235                 240

Asn Pro Gln Glu Arg Leu Ala Ile Ala Gly Asn Pro Leu Leu Ala Gln
                245                 250                 255

Ala Val Ala Ser Pro Met Ala Ala Arg Ser Ala Ser Thr Leu Asn Cys
            260                 265                 270

Glu Gly Lys Met Phe Trp Asp Gln Val His Pro Thr Thr Val Val His
        275                 280                 285

Ala Ala Leu Ser Glu Pro Ala
    290                 295

<210> SEQ ID NO 56
<211> LENGTH: 295
<212> TYPE: PRT
<213> ORGANISM: Aeromonas salmonicida

<400> SEQUENCE: 56

Ile Val Met Phe Gly Asp Ser Leu Ser Asp Thr Gly Lys Met Tyr Ser
 1               5                  10                  15

Lys Met Arg Gly Tyr Leu Pro Ser Ser Pro Tyr Tyr Glu Gly Arg
            20                  25                  30

Phe Ser Asn Gly Pro Val Trp Leu Glu Gln Leu Thr Lys Gln Phe Pro
        35                  40                  45
```

```
Gly Leu Thr Ile Ala Asn Glu Ala Glu Gly Ala Thr Ala Val Ala
     50                  55                  60

Tyr Asn Lys Ile Ser Trp Asn Pro Lys Tyr Gln Val Tyr Asn Asn Leu
 65                  70                  75                  80

Asp Tyr Glu Val Thr Gln Phe Leu Gln Lys Asp Ser Phe Lys Pro Asp
                 85                  90                  95

Asp Leu Val Ile Leu Trp Val Gly Ala Asn Asp Tyr Leu Ala Tyr Gly
                100                 105                 110

Trp Asn Thr Glu Gln Asp Ala Lys Arg Val Arg Asp Ala Ile Ser Asp
            115                 120                 125

Ala Ala Asn Arg Met Val Leu Asn Gly Ala Lys Gln Ile Leu Leu Phe
        130                 135                 140

Asn Leu Pro Asp Leu Gly Gln Asn Pro Ser Ala Arg Ser Gln Lys Val
145                 150                 155                 160

Val Glu Ala Val Ser His Val Ser Ala Tyr His Asn Lys Leu Leu Leu
                165                 170                 175

Asn Leu Ala Arg Gln Leu Ala Pro Thr Gly Met Val Lys Leu Phe Glu
            180                 185                 190

Ile Asp Lys Gln Phe Ala Glu Met Leu Arg Asp Pro Gln Asn Phe Gly
        195                 200                 205

Leu Ser Asp Val Glu Asn Pro Cys Tyr Asp Gly Gly Tyr Val Trp Lys
    210                 215                 220

Pro Phe Ala Thr Arg Ser Val Ser Thr Asp Arg Gln Leu Ser Ala Phe
225                 230                 235                 240

Ser Pro Gln Glu Arg Leu Ala Ile Ala Gly Asn Pro Leu Leu Ala Gln
                245                 250                 255

Ala Val Ala Ser Pro Met Ala Arg Arg Ser Ala Ser Pro Leu Asn Cys
                260                 265                 270

Glu Gly Lys Met Phe Trp Asp Gln Val His Pro Thr Val Val His
                275                 280                 285

Ala Ala Leu Ser Glu Arg Ala
        290                 295

<210> SEQ ID NO 57
<211> LENGTH: 247
<212> TYPE: PRT
<213> ORGANISM: Streptomyces coelicolor

<400> SEQUENCE: 57

Tyr Val Ala Leu Gly Asp Ser Tyr Ser Ala Gly Ser Gly Val Leu Pro
 1               5                  10                  15

Val Asp Pro Ala Asn Leu Leu Cys Leu Arg Ser Thr Ala Asn Tyr Pro
                 20                  25                  30

His Val Ile Ala Asp Thr Thr Gly Ala Arg Leu Thr Asp Val Thr Cys
             35                  40                  45

Gly Ala Ala Gln Thr Ala Asp Phe Thr Arg Ala Gln Tyr Pro Gly Val
         50                  55                  60

Ala Pro Gln Leu Asp Ala Leu Gly Thr Gly Thr Asp Leu Val Thr Leu
 65                  70                  75                  80

Thr Ile Gly Gly Asn Asp Asn Ser Thr Phe Ile Asn Ala Ile Thr Ala
                 85                  90                  95

Cys Gly Thr Ala Gly Val Leu Ser Gly Gly Lys Gly Ser Pro Cys Lys
             100                 105                 110

Asp Arg His Gly Thr Ser Phe Asp Asp Glu Ile Glu Ala Asn Thr Tyr
        115                 120                 125
```

```
Pro Ala Leu Lys Glu Ala Leu Leu Gly Val Arg Ala Arg Ala Pro His
            130                 135                 140

Ala Arg Val Ala Ala Leu Gly Tyr Pro Trp Ile Thr Pro Ala Thr Ala
145                 150                 155                 160

Asp Pro Ser Cys Phe Leu Lys Leu Pro Leu Ala Ala Gly Asp Val Pro
                165                 170                 175

Tyr Leu Arg Ala Ile Gln Ala His Leu Asn Asp Ala Val Arg Arg Ala
            180                 185                 190

Ala Glu Glu Thr Gly Ala Thr Tyr Val Asp Phe Ser Gly Val Ser Asp
            195                 200                 205

Gly His Asp Ala Cys Glu Ala Pro Gly Thr Arg Trp Ile Glu Pro Leu
            210                 215                 220

Leu Phe Gly His Ser Leu Val Pro Val His Pro Asn Ala Leu Gly Glu
225                 230                 235                 240

Arg Arg Met Ala Glu His Thr
                245

<210> SEQ ID NO 58
<211> LENGTH: 247
<212> TYPE: PRT
<213> ORGANISM: Streptomyces coelicolor

<400> SEQUENCE: 58

Tyr Val Ala Leu Gly Asp Ser Tyr Ser Ala Gly Ser Gly Val Leu Pro
1               5                   10                  15

Val Asp Pro Ala Asn Leu Leu Cys Leu Arg Ser Thr Ala Asn Tyr Pro
            20                  25                  30

His Val Ile Ala Asp Thr Thr Gly Ala Arg Leu Thr Asp Val Thr Cys
        35                  40                  45

Gly Ala Ala Gln Thr Ala Asp Phe Thr Arg Ala Gln Tyr Pro Gly Val
    50                  55                  60

Ala Pro Gln Leu Asp Ala Leu Gly Thr Gly Thr Asp Leu Val Thr Leu
65                  70                  75                  80

Thr Ile Gly Gly Asn Asp Asn Ser Thr Phe Ile Asn Ala Ile Thr Ala
                85                  90                  95

Cys Gly Thr Ala Gly Val Leu Ser Gly Gly Lys Gly Ser Pro Cys Lys
            100                 105                 110

Asp Arg His Gly Thr Ser Phe Asp Asp Glu Ile Glu Ala Asn Thr Tyr
            115                 120                 125

Pro Ala Leu Lys Glu Ala Leu Leu Gly Val Arg Ala Arg Ala Pro His
            130                 135                 140

Ala Arg Val Ala Ala Leu Gly Tyr Pro Trp Ile Thr Pro Ala Thr Ala
145                 150                 155                 160

Asp Pro Ser Cys Phe Leu Lys Leu Pro Leu Ala Ala Gly Asp Val Pro
                165                 170                 175

Tyr Leu Arg Ala Ile Gln Ala His Leu Asn Asp Ala Val Arg Arg Ala
            180                 185                 190

Ala Glu Glu Thr Gly Ala Thr Tyr Val Asp Phe Ser Gly Val Ser Asp
            195                 200                 205

Gly His Asp Ala Cys Glu Ala Pro Gly Thr Arg Trp Ile Glu Pro Leu
            210                 215                 220

Leu Phe Gly His Ser Leu Val Pro Val His Pro Asn Ala Leu Gly Glu
225                 230                 235                 240

Arg Arg Met Ala Glu His Thr
                245
```

<210> SEQ ID NO 59
<211> LENGTH: 198
<212> TYPE: PRT
<213> ORGANISM: Saccharomyces cerevisiae

<400> SEQUENCE: 59

Phe Leu Leu Phe Gly Asp Ser Ile Thr Glu Phe Ala Phe Asn Thr Arg
1               5                   10                  15

Pro Ile Glu Asp Gly Lys Asp Gln Tyr Ala Leu Gly Ala Ala Leu Val
            20                  25                  30

Asn Glu Tyr Thr Arg Lys Met Asp Ile Leu Gln Arg Gly Phe Lys Gly
        35                  40                  45

Tyr Thr Ser Arg Trp Ala Leu Lys Ile Leu Pro Glu Ile Leu Lys His
    50                  55                  60

Glu Ser Asn Ile Val Met Ala Thr Ile Phe Leu Gly Ala Asn Asp Ala
65                  70                  75                  80

Cys Ser Ala Gly Pro Gln Ser Val Pro Leu Pro Glu Phe Ile Asp Asn
                85                  90                  95

Ile Arg Gln Met Val Ser Leu Met Lys Ser Tyr His Ile Arg Pro Ile
            100                 105                 110

Ile Ile Gly Pro Gly Leu Val Asp Arg Glu Lys Trp Glu Lys Glu Lys
        115                 120                 125

Ser Glu Glu Ile Ala Leu Gly Tyr Phe Arg Thr Asn Glu Asn Phe Ala
    130                 135                 140

Ile Tyr Ser Asp Ala Leu Ala Lys Leu Ala Asn Glu Glu Lys Val Pro
145                 150                 155                 160

Phe Val Ala Leu Asn Lys Ala Phe Gln Gln Glu Gly Gly Asp Ala Trp
                165                 170                 175

Gln Gln Leu Leu Thr Asp Gly Leu His Phe Ser Gly Lys Gly Tyr Lys
            180                 185                 190

Ile Phe His Asp Glu Leu
        195

<210> SEQ ID NO 60
<211> LENGTH: 317
<212> TYPE: PRT
<213> ORGANISM: Aeromonas salmonicida

<400> SEQUENCE: 60

Ala Asp Thr Arg Pro Ala Phe Ser Arg Ile Val Met Phe Gly Asp Ser
1               5                   10                  15

Leu Ser Asp Thr Gly Lys Met Tyr Ser Lys Met Arg Gly Tyr Leu Pro
            20                  25                  30

Ser Ser Pro Pro Tyr Tyr Glu Gly Arg Phe Ser Asn Gly Pro Val Trp
        35                  40                  45

Leu Glu Gln Leu Thr Lys Gln Phe Pro Gly Leu Thr Ile Ala Asn Glu
    50                  55                  60

Ala Glu Gly Gly Ala Thr Ala Val Ala Tyr Asn Lys Ile Ser Trp Asn
65                  70                  75                  80

Pro Lys Tyr Gln Val Ile Asn Asn Leu Asp Tyr Glu Val Thr Gln Phe
                85                  90                  95

Leu Gln Lys Asp Ser Phe Lys Pro Asp Asp Leu Val Ile Leu Trp Val
            100                 105                 110

Gly Ala Asn Asp Tyr Leu Ala Tyr Gly Trp Asn Thr Glu Gln Asp Ala
        115                 120                 125

Lys Arg Val Arg Asp Ala Ile Ser Asp Ala Ala Asn Arg Met Val Leu

```
    130                 135                 140

Asn Gly Ala Lys Gln Ile Leu Leu Phe Asn Leu Pro Asp Leu Gly Gln
145                 150                 155                 160

Asn Pro Ser Ala Arg Ser Gln Lys Val Val Glu Ala Val Ser His Val
                165                 170                 175

Ser Ala Tyr His Asn Lys Leu Leu Leu Asn Leu Ala Arg Gln Leu Ala
            180                 185                 190

Pro Thr Gly Met Val Lys Leu Phe Glu Ile Asp Lys Gln Phe Ala Glu
        195                 200                 205

Met Leu Arg Asp Pro Gln Asn Phe Gly Leu Ser Asp Val Glu Asn Pro
    210                 215                 220

Cys Tyr Asp Gly Gly Tyr Val Trp Lys Pro Phe Ala Thr Arg Ser Val
225                 230                 235                 240

Ser Thr Asp Arg Gln Leu Ser Ala Phe Ser Pro Gln Glu Arg Leu Ala
                245                 250                 255

Ile Ala Gly Asn Pro Leu Leu Ala Gln Ala Val Ala Ser Pro Met Ala
            260                 265                 270

Arg Arg Ser Ala Ser Pro Leu Asn Cys Glu Gly Lys Met Phe Trp Asp
        275                 280                 285

Gln Val His Pro Thr Thr Val Val His Ala Ala Leu Ser Glu Arg Ala
    290                 295                 300

Ala Thr Phe Ile Glu Thr Gln Tyr Glu Phe Leu Ala His
305                 310                 315

<210> SEQ ID NO 61
<211> LENGTH: 320
<212> TYPE: PRT
<213> ORGANISM: Ralstonia solanacearum

<400> SEQUENCE: 61

Gln Ser Gly Asn Pro Asn Val Ala Lys Val Gln Arg Met Val Val Phe
  1               5                  10                  15

Gly Asp Ser Leu Ser Asp Ile Gly Thr Tyr Thr Pro Val Ala Gln Ala
            20                  25                  30

Val Gly Gly Gly Lys Phe Thr Thr Asn Pro Gly Pro Ile Trp Ala Glu
        35                  40                  45

Thr Val Ala Ala Gln Leu Gly Val Thr Leu Thr Pro Ala Val Met Gly
     50                  55                  60

Tyr Ala Thr Ser Val Gln Asn Cys Pro Lys Ala Gly Cys Phe Asp Tyr
 65                  70                  75                  80

Ala Gln Gly Gly Ser Arg Val Thr Asp Pro Asn Gly Ile Gly His Asn
                 85                  90                  95

Gly Gly Ala Gly Ala Leu Thr Tyr Pro Val Gln Gln Gln Leu Ala Asn
            100                 105                 110

Phe Tyr Ala Ala Ser Asn Asn Thr Phe Asn Gly Asn Asn Asp Val Val
        115                 120                 125

Phe Val Leu Ala Gly Ser Asn Asp Ile Phe Phe Trp Thr Thr Ala Ala
    130                 135                 140

Ala Thr Ser Gly Ser Gly Val Thr Pro Ala Ile Ala Thr Ala Gln Val
145                 150                 155                 160

Gln Gln Ala Ala Thr Asp Leu Val Gly Tyr Val Lys Asp Met Ile Ala
                165                 170                 175

Lys Gly Ala Thr Gln Val Tyr Val Phe Asn Leu Pro Asp Ser Ser Leu
            180                 185                 190

Thr Pro Asp Gly Val Ala Ser Gly Thr Thr Gly Gln Ala Leu Leu His
```

```
                195                 200                 205
Ala Leu Val Gly Thr Phe Asn Thr Thr Leu Gln Ser Gly Leu Ala Gly
            210                 215                 220

Thr Ser Ala Arg Ile Ile Asp Phe Asn Ala Gln Leu Thr Ala Ala Ile
225                 230                 235                 240

Gln Asn Gly Ala Ser Phe Gly Phe Ala Asn Thr Ser Ala Arg Ala Cys
                245                 250                 255

Asp Ala Thr Lys Ile Asn Ala Leu Val Pro Ser Ala Gly Gly Ser Ser
            260                 265                 270

Leu Phe Cys Ser Ala Asn Thr Leu Val Ala Ser Gly Ala Asp Gln Ser
            275                 280                 285

Tyr Leu Phe Ala Asp Gly Val His Pro Thr Thr Ala Gly His Arg Leu
            290                 295                 300

Ile Ala Ser Asn Val Leu Ala Arg Leu Leu Ala Asp Asn Val Ala His
305                 310                 315                 320

<210> SEQ ID NO 62
<211> LENGTH: 226
<212> TYPE: PRT
<213> ORGANISM: Streptomyces rimosus

<400> SEQUENCE: 62

Tyr Val Ala Leu Gly Asp Ser Tyr Ser Ser Gly Val Gly Ala Gly Ser
1               5                   10                  15

Tyr Asp Ser Ser Ser Gly Ser Cys Lys Arg Ser Thr Lys Ser Tyr Pro
            20                  25                  30

Ala Leu Trp Ala Ala Ser His Thr Gly Thr Arg Phe Asn Phe Thr Ala
        35                  40                  45

Cys Ser Gly Ala Arg Thr Gly Asp Val Leu Ala Lys Gln Leu Thr Pro
    50                  55                  60

Val Asn Ser Gly Thr Asp Leu Val Ser Ile Thr Ile Gly Gly Asn Asp
65                  70                  75                  80

Ala Gly Phe Ala Asp Thr Met Thr Thr Cys Asn Leu Gln Gly Glu Ser
                85                  90                  95

Ala Cys Leu Ala Arg Ile Ala Lys Ala Arg Ala Tyr Ile Gln Gln Thr
            100                 105                 110

Leu Pro Ala Gln Leu Asp Gln Val Tyr Asp Ala Ile Asp Ser Arg Ala
        115                 120                 125

Pro Ala Ala Gln Val Val Leu Gly Tyr Pro Arg Phe Tyr Lys Leu
130                 135                 140

Gly Gly Ser Cys Ala Val Gly Leu Ser Glu Lys Ser Arg Ala Ala Ile
145                 150                 155                 160

Asn Ala Ala Ala Asp Asp Ile Asn Ala Val Thr Ala Lys Arg Ala Ala
                165                 170                 175

Asp His Gly Phe Ala Phe Gly Asp Val Asn Thr Thr Phe Ala Gly His
            180                 185                 190

Glu Leu Cys Ser Gly Ala Pro Trp Leu His Ser Val Thr Leu Pro Val
        195                 200                 205

Glu Asn Ser Tyr His Pro Thr Ala Asn Gly Gln Ser Lys Gly Tyr Leu
    210                 215                 220

Pro Val
225

<210> SEQ ID NO 63
<211> LENGTH: 182
<212> TYPE: PRT
```

<213> ORGANISM: Streptomyces coelicolor

<400> SEQUENCE: 63

```
Tyr Val Ala Val Gly Asp Ser Phe Thr Glu Gly Val Gly Asp Pro Gly
 1               5                  10                  15

Pro Asp Gly Ala Phe Val Gly Trp Ala Asp Arg Leu Ala Val Leu Leu
            20                  25                  30

Ala Asp Arg Arg Pro Glu Gly Asp Phe Thr Tyr Thr Asn Leu Ala Val
        35                  40                  45

Arg Gly Arg Leu Leu Asp Gln Ile Val Ala Glu Gln Val Pro Arg Val
    50                  55                  60

Val Gly Leu Ala Pro Asp Leu Val Ser Phe Ala Ala Gly Gly Asn Asp
65                  70                  75                  80

Ile Ile Arg Pro Gly Thr Asp Pro Asp Glu Val Ala Glu Arg Phe Glu
                85                  90                  95

Leu Ala Val Ala Ala Leu Thr Ala Ala Ala Gly Thr Val Leu Val Thr
            100                 105                 110

Thr Gly Phe Asp Thr Arg Gly Val Pro Val Leu Lys His Leu Arg Gly
        115                 120                 125

Lys Ile Ala Thr Tyr Asn Gly His Val Arg Ala Ile Ala Asp Arg Tyr
    130                 135                 140

Gly Cys Pro Val Leu Asp Leu Trp Ser Leu Arg Ser Val Gln Asp Arg
145                 150                 155                 160

Arg Ala Trp Asp Ala Asp Arg Leu His Leu Ser Pro Glu Gly His Thr
                165                 170                 175

Arg Val Ala Leu Arg Ala
            180
```

<210> SEQ ID NO 64
<211> LENGTH: 179
<212> TYPE: PRT
<213> ORGANISM: Streptomyces coelicolor

<400> SEQUENCE: 64

```
Leu Val Ala Val Gly Asp Ser Phe Thr Glu Gly Met Ser Asp Leu Leu
 1               5                  10                  15

Pro Asp Gly Ser Tyr Arg Gly Trp Ala Asp Leu Leu Ala Thr Arg Met
            20                  25                  30

Ala Ala Arg Ser Pro Gly Phe Arg Tyr Ala Asn Leu Ala Val Arg Gly
        35                  40                  45

Lys Leu Ile Gly Gln Ile Val Asp Glu Gln Val Asp Val Ala Ala Ala
    50                  55                  60

Met Gly Ala Asp Val Ile Thr Leu Val Gly Gly Leu Asn Asp Thr Leu
65                  70                  75                  80

Arg Pro Lys Cys Asp Met Ala Arg Val Arg Asp Leu Leu Thr Gln Ala
                85                  90                  95

Val Glu Arg Leu Ala Pro His Cys Glu Gln Leu Val Leu Met Arg Ser
            100                 105                 110

Pro Gly Arg Gln Gly Pro Val Leu Glu Arg Phe Arg Pro Arg Met Glu
        115                 120                 125

Ala Leu Phe Ala Val Ile Asp Asp Leu Ala Gly Arg His Gly Ala Val
    130                 135                 140

Val Val Asp Leu Tyr Gly Ala Gln Ser Leu Ala Asp Pro Arg Met Trp
145                 150                 155                 160

Asp Val Asp Arg Leu His Leu Thr Ala Glu Gly His Arg Arg Val Ala
                165                 170                 175
```

Glu Ala Val

<210> SEQ ID NO 65
<211> LENGTH: 203
<212> TYPE: PRT
<213> ORGANISM: Streptomyces coelicolor

<400> SEQUENCE: 65

Val Val Ala Phe Gly Asp Ser Ile Thr Asp Gly Ala Arg Ser Gln Ser
1               5                   10                  15

Asp Ala Asn His Arg Trp Thr Asp Val Leu Ala Ala Arg Leu His Glu
            20                  25                  30

Ala Ala Gly Asp Gly Arg Asp Thr Pro Arg Tyr Ser Val Val Asn Glu
        35                  40                  45

Gly Ile Ser Gly Asn Arg Leu Leu Thr Ser Arg Pro Gly Arg Pro Ala
    50                  55                  60

Asp Asn Pro Ser Gly Leu Ser Arg Phe Gln Arg Asp Val Leu Glu Arg
65                  70                  75                  80

Thr Asn Val Lys Ala Val Val Val Leu Gly Val Asn Asp Val Leu
                85                  90                  95

Asn Ser Pro Glu Leu Ala Asp Arg Asp Ala Ile Leu Thr Gly Leu Arg
                100                 105                 110

Thr Leu Val Asp Arg Ala His Ala Arg Gly Leu Arg Val Val Gly Ala
            115                 120                 125

Thr Ile Thr Pro Phe Gly Gly Tyr Gly Gly Tyr Thr Glu Ala Arg Glu
        130                 135                 140

Thr Met Arg Gln Glu Val Asn Glu Glu Ile Arg Ser Gly Arg Val Phe
145                 150                 155                 160

Asp Thr Val Val Asp Phe Asp Lys Ala Leu Arg Asp Pro Tyr Asp Pro
                165                 170                 175

Arg Arg Met Arg Ser Asp Tyr Ser Asp Ser Gly Asp His Leu His Pro Gly
            180                 185                 190

Asp Lys Gly Tyr Ala Arg Met Gly Ala Val Ile
        195                 200

<210> SEQ ID NO 66
<211> LENGTH: 188
<212> TYPE: PRT
<213> ORGANISM: Streptomyces coelicolor

<400> SEQUENCE: 66

Leu Met Met Leu Gly Asp Ser Thr Ala Ala Gly Gln Gly Val His Arg
1               5                   10                  15

Ala Gly Gln Thr Pro Gly Ala Leu Leu Ala Ser Gly Leu Ala Ala Val
            20                  25                  30

Ala Glu Arg Pro Val Arg Leu Gly Ser Val Ala Gln Pro Gly Ala Cys
        35                  40                  45

Ser Asp Asp Leu Asp Arg Gln Val Ala Leu Val Leu Ala Glu Pro Asp
    50                  55                  60

Arg Val Pro Asp Ile Cys Val Ile Met Val Gly Ala Asn Asp Val Thr
65                  70                  75                  80

His Arg Met Pro Ala Thr Arg Ser Val Arg His Leu Ser Ser Ala Val
                85                  90                  95

Arg Arg Leu Arg Thr Ala Gly Ala Glu Val Val Val Gly Thr Cys Pro
                100                 105                 110

Asp Leu Gly Thr Ile Glu Arg Val Arg Gln Pro Leu Arg Trp Leu Ala

```
                    115                 120                 125
Arg Arg Ala Ser Arg Gln Leu Ala Ala Ala Gln Thr Ile Gly Ala Val
    130                 135                 140

Glu Gln Gly Gly Arg Thr Val Ser Leu Gly Asp Leu Leu Gly Pro Glu
145                 150                 155                 160

Phe Ala Gln Asn Pro Arg Glu Leu Phe Gly Pro Asp Asn Tyr His Pro
                165                 170                 175

Ser Ala Glu Gly Tyr Ala Thr Ala Met Ala Val
                180                 185

<210> SEQ ID NO 67
<211> LENGTH: 231
<212> TYPE: PRT
<213> ORGANISM: Streptomyces coelicolor

<400> SEQUENCE: 67

Val Ala Ala Val Gly Asp Ser Ile Thr Arg Gly Phe Asp Ala Cys Ala
1               5                   10                  15

Val Leu Ser Asp Cys Pro Glu Val Ser Trp Ala Thr Gly Ser Ser Ala
            20                  25                  30

Lys Val Asp Ser Leu Ala Val Arg Leu Leu Gly Lys Ala Asp Ala Ala
        35                  40                  45

Glu His Ser Trp Asn Tyr Ala Val Thr Gly Ala Arg Met Ala Asp Leu
    50                  55                  60

Thr Ala Gln Val Thr Arg Ala Ala Gln Arg Glu Pro Glu Leu Val Ala
65                  70                  75                  80

Val Met Ala Gly Ala Asn Asp Ala Cys Arg Ser Thr Thr Ser Ala Met
                85                  90                  95

Thr Pro Val Ala Asp Phe Arg Ala Gln Phe Glu Ala Met Ala Thr
            100                 105                 110

Leu Arg Lys Lys Leu Pro Lys Ala Gln Val Tyr Val Ser Ser Ile Pro
        115                 120                 125

Asp Leu Lys Arg Leu Trp Ser Gln Gly Arg Thr Asn Pro Leu Gly Lys
    130                 135                 140

Gln Val Trp Lys Leu Gly Leu Cys Pro Ser Met Leu Gly Asp Ala Asp
145                 150                 155                 160

Ser Leu Asp Ser Ala Ala Thr Leu Arg Arg Asn Thr Val Arg Asp Arg
                165                 170                 175

Val Ala Asp Tyr Asn Glu Val Leu Arg Glu Val Cys Ala Lys Asp Arg
            180                 185                 190

Arg Cys Arg Ser Asp Asp Gly Ala Val His Glu Phe Arg Phe Gly Thr
        195                 200                 205

Asp Gln Leu Ser His Trp Asp Trp Phe His Pro Ser Val Asp Gly Gln
    210                 215                 220

Ala Arg Leu Ala Glu Ile Ala
225                 230

<210> SEQ ID NO 68
<211> LENGTH: 295
<212> TYPE: PRT
<213> ORGANISM: Aeromonas hydrophila

<400> SEQUENCE: 68

Ile Val Met Phe Gly Asp Ser Leu Ser Asp Thr Gly Lys Met Tyr Ser
1               5                   10                  15

Lys Met Arg Gly Tyr Leu Pro Ser Ser Pro Tyr Tyr Glu Gly Arg
            20                  25                  30
```

```
Phe Ser Asn Gly Pro Val Trp Leu Glu Gln Leu Thr Asn Glu Phe Pro
        35                  40                  45

Gly Leu Thr Ile Ala Asn Glu Ala Glu Gly Gly Pro Thr Ala Val Ala
    50                  55                  60

Tyr Asn Lys Ile Ser Trp Asn Pro Lys Tyr Gln Val Ile Asn Asn Leu
65                  70                  75                  80

Asp Tyr Glu Val Thr Gln Phe Leu Gln Lys Asp Ser Phe Lys Pro Asp
                85                  90                  95

Asp Leu Val Ile Leu Trp Val Gly Ala Asn Asp Tyr Leu Ala Tyr Gly
                100                 105                 110

Trp Asn Thr Glu Gln Asp Ala Lys Arg Val Arg Asp Ala Ile Ser Asp
            115                 120                 125

Ala Ala Asn Arg Met Val Leu Asn Gly Ala Lys Glu Ile Leu Leu Phe
        130                 135                 140

Asn Leu Pro Asp Leu Gly Gln Asn Pro Ser Ala Arg Ser Gln Lys Val
145                 150                 155                 160

Val Glu Ala Ala Ser His Val Ser Ala Tyr His Asn Gln Leu Leu Leu
                165                 170                 175

Asn Leu Ala Arg Gln Leu Ala Pro Thr Gly Met Val Lys Leu Phe Glu
            180                 185                 190

Ile Asp Lys Gln Phe Ala Glu Met Leu Arg Asp Pro Gln Asn Phe Gly
        195                 200                 205

Leu Ser Asp Gln Arg Asn Ala Cys Tyr Gly Gly Ser Tyr Val Trp Lys
    210                 215                 220

Pro Phe Ala Ser Arg Ser Ala Ser Thr Asp Ser Gln Leu Ser Ala Phe
225                 230                 235                 240

Asn Pro Gln Glu Arg Leu Ala Ile Ala Gly Asn Pro Leu Leu Ala Gln
                245                 250                 255

Ala Val Ala Ser Pro Met Ala Ala Arg Ser Ala Ser Thr Leu Asn Cys
            260                 265                 270

Glu Gly Lys Met Phe Trp Asp Gln Val His Pro Thr Thr Val Val His
        275                 280                 285

Ala Ala Leu Ser Glu Pro Ala
        290                 295

<210> SEQ ID NO 69
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
agcatatgaa aaaatggttt gtttgtttat tgggg                              35

<210> SEQ ID NO 70
<211> LENGTH: 367
<212> TYPE: PRT
<213> ORGANISM: Artificial Sequence
<220> FEATURE:
<223> OTHER INFORMATION: Description of Artificial Sequence: Synthetic
      Pfam00657.11 consensus sequence

<400> SEQUENCE: 70

Ile Val Ala Phe Gly Asp Ser Leu Thr Asp Gly Gly Gly Ala Tyr Tyr
1               5                   10                  15

Gly Asp Ser Asp Gly Gly Gly Trp Gly Ala Gly Leu Ala Asp Arg Leu
```

```
                    20                  25                  30
Thr Ser Leu Ala Arg Leu Arg Ala Arg Gly Arg Gly Val Asp Val Phe
            35                  40                  45

Asn Arg Gly Ile Ser Gly Arg Thr Ser Asp Gly Arg Leu Val Val Asp
        50                  55                  60

Ala Arg Leu Val Ala Thr Leu Leu Phe Leu Ala Gln Phe Leu Gly Leu
65                  70                  75                  80

Asn Leu Pro Pro Tyr Leu Ser Gly Asp Phe Leu Arg Gly Ala Asn Phe
                85                  90                  95

Ala Ser Ala Gly Ala Thr Ile Leu Gly Thr Ser Leu Ile Pro Phe Leu
            100                 105                 110

Asn Ile Gln Val Gln Phe Lys Asp Phe Lys Ser Lys Val Leu Glu Leu
            115                 120                 125

Arg Gln Ala Leu Gly Leu Leu Gln Glu Leu Leu Arg Leu Val Pro Val
            130                 135                 140

Leu Asp Ala Lys Ser Pro Asp Leu Val Thr Ile Met Ile Gly Thr Asn
145                 150                 155                 160

Asp Leu Ile Thr Val Ala Lys Phe Gly Pro Lys Ser Thr Lys Ser Asp
                165                 170                 175

Arg Asn Val Ser Val Pro Glu Phe Arg Asp Asn Leu Arg Lys Leu Ile
                180                 185                 190

Lys Arg Leu Arg Ser Ala Asn Gly Ala Arg Ile Ile Ile Leu Ile Thr
            195                 200                 205

Leu Val Leu Leu Asn Leu Pro Leu Pro Leu Gly Cys Leu Pro Gln Lys
            210                 215                 220

Leu Ala Leu Ala Leu Ala Ser Ser Lys Asn Val Asp Ala Thr Gly Cys
225                 230                 235                 240

Leu Glu Arg Leu Asn Glu Ala Val Ala Asp Tyr Asn Glu Ala Leu Arg
                245                 250                 255

Glu Leu Ala Glu Ile Glu Lys Leu Gln Ala Gln Leu Arg Lys Asp Gly
                260                 265                 270

Leu Pro Asp Leu Lys Glu Ala Asn Val Pro Tyr Val Asp Leu Tyr Ser
            275                 280                 285

Ile Phe Gln Asp Leu Asp Gly Ile Gln Asn Pro Ser Ala Tyr Val Tyr
            290                 295                 300

Gly Phe Glu Glu Thr Lys Ala Cys Cys Gly Tyr Gly Gly Arg Tyr Asn
305                 310                 315                 320

Tyr Asn Arg Val Cys Gly Asn Ala Gly Leu Cys Lys Val Thr Ala Lys
                325                 330                 335

Ala Cys Asp Ala Ser Ser Tyr Leu Leu Ala Thr Leu Phe Trp Asp Gly
            340                 345                 350

Phe His Pro Ser Glu Lys Gly Tyr Lys Ala Val Ala Glu Ala Leu
            355                 360                 365
```